US012662653B2

(12) United States Patent
Nankervis et al.

(10) Patent No.: US 12,662,653 B2
(45) Date of Patent: Jun. 23, 2026

(54) CELL EXPANSION

(71) Applicant: Terumo BCT, Inc., Lakewood, CO (US)

(72) Inventors: Brian J. Nankervis, Golden, CO (US); Mark E. Jones, Littleton, CO (US); Domicinda M. Hill, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 601 days.

(21) Appl. No.: 18/105,280

(22) Filed: Feb. 3, 2023

(65) Prior Publication Data

US 2023/0340385 A1      Oct. 26, 2023

Related U.S. Application Data

(60) Division of application No. 16/112,498, filed on Aug. 24, 2018, now Pat. No. 11,624,046, which is a
(Continued)

(51) Int. Cl.
*C12M 3/02*      (2006.01)
*C12M 1/00*      (2006.01)
(Continued)

(52) U.S. Cl.
CPC .............. *C12M 3/02* (2013.01); *C12M 25/10* (2013.01); *C12M 25/16* (2013.01); *C12M 27/10* (2013.01);
(Continued)

(58) Field of Classification Search
CPC ........ C12M 3/02; C12M 29/04; C12M 29/10; C12M 29/14; C12M 27/16; C12M 27/10; C12M 41/48; C12N 5/0636
(Continued)

(56) References Cited

U.S. PATENT DOCUMENTS

| | | | |
|---|---|---|---|
| 2,997,077 | A | 8/1961 | Rodrigues |
| 3,013,435 | A | 12/1961 | Rodrigues |

(Continued)

FOREIGN PATENT DOCUMENTS

| | | | |
|---|---|---|---|
| CA | 1016332 | A | 8/1977 |
| DE | 4007703 | A1 | 9/1991 |

(Continued)

OTHER PUBLICATIONS

Abumiya, et al at National Cardiovascular Center Research Institute in Japan, suggest that subjecting human umbilical vein endothelial cells (HUVECs) to laminar shear stress for a period of 8 hours increased the relative expression of VEGFR-2 mRNA (Ateriosclerosis, Thrombosis, and Vascular Biology, 2002).
(Continued)

*Primary Examiner* — Michael L Hobbs
*Assistant Examiner* — Lenora A Abel
(74) *Attorney, Agent, or Firm* — Harness, Dickey & Pierce, P.L.C.

(57)      ABSTRACT

Embodiments described herein generally provide for expanding cells in a cell expansion system. The cells may be grown in a bioreactor, and the cells may be activated by an activator (e.g., a soluble activator complex). Nutrient and gas exchange capabilities of a closed, automated cell expansion system may allow cells to be seeded at reduced cell seeding densities, for example. Parameters of the cell growth environment may be manipulated to load the cells into a particular position in the bioreactor for the efficient exchange of nutrients and gases. System parameters may be adjusted to shear any cell colonies that may form during the expansion phase. Metabolic concentrations may be controlled to improve cell growth and viability. Cell residence in the bioreactor may be controlled. In embodiments, the cells may include T cells. In further embodiments, the cells
(Continued)

may include T cell subpopulations, including regulatory T cells (Tregs), helper, naïve, memory, or effector, for example.

20 Claims, 46 Drawing Sheets

Related U.S. Application Data continuation-in-part of application No. 15/943,536, filed on Apr. 2, 2018, now Pat. No. 11,702,634, and a continuation-in-part of application No. 15/943,619, filed on Apr. 2, 2018, now Pat. No. 11,629,332.

(60) Provisional application No. 62/647,361, filed on Mar. 23, 2018, provisional application No. 62/549,871, filed on Aug. 24, 2017, provisional application No. 62/549,884, filed on Aug. 24, 2017, provisional application No. 62/479,760, filed on Mar. 31, 2017, provisional application No. 62/479,788, filed on Mar. 31, 2017, provisional application No. 62/479,721, filed on Mar. 31, 2017.

(51) Int. Cl.
| | |
|---|---|
| *C12M 1/12* | (2006.01) |
| *C12M 1/36* | (2006.01) |
| *C12M 3/04* | (2006.01) |
| *C12M 3/06* | (2006.01) |
| *C12N 5/0783* | (2010.01) |

(52) U.S. Cl.
CPC ............ *C12M 27/16* (2013.01); *C12M 29/04* (2013.01); *C12M 29/10* (2013.01); *C12M 29/14* (2013.01); *C12M 41/48* (2013.01); *C12N 5/0636* (2013.01)

(58) Field of Classification Search
USPC ...................................................... 435/297.2
See application file for complete search history.

(56) References Cited

U.S. PATENT DOCUMENTS

| | | | |
|---|---|---|---|
| 3,067,915 A | 12/1962 | Shapiro et al. |
| 3,191,807 A | 6/1965 | Rodrigues |
| 3,283,727 A | 11/1966 | Rodrigues |
| 3,701,717 A | 10/1972 | Ingvorsen |
| 4,173,415 A | 11/1979 | Wyatt |
| 4,301,010 A | 11/1981 | Eddleman et al. |
| 4,301,118 A | 11/1981 | Eddleman et al. |
| 4,412,990 A | 11/1983 | Lundblad et al. |
| 4,418,691 A | 12/1983 | Yannas et al. |
| 4,439,901 A | 4/1984 | Eddleman |
| 4,478,829 A | 10/1984 | Landaburu et al. |
| 4,486,188 A | 12/1984 | Altshuler et al. |
| 4,509,695 A | 4/1985 | Bessman |
| 4,585,654 A | 4/1986 | Landaburu et al. |
| 4,618,586 A | 10/1986 | Walker |
| 4,629,686 A | 12/1986 | Gruenberg |
| 4,670,544 A | 6/1987 | Schwinn et al. |
| 4,727,059 A | 2/1988 | Binder et al. |
| 4,828,706 A | 5/1989 | Eddleman |
| 4,897,358 A | 1/1990 | Carrasco |
| 4,960,521 A | 10/1990 | Keller |
| 4,988,623 A | 1/1991 | Schwarz et al. |
| 5,015,585 A | 5/1991 | Robinson |
| 5,019,054 A | 5/1991 | Clement et al. |
| 5,126,238 A | 6/1992 | Gebhard et al. |
| 5,130,141 A | 7/1992 | Law et al. |
| 5,149,544 A | 9/1992 | Gentile et al. |
| 5,169,930 A | 12/1992 | Ruoslahti et al. |
| 5,192,553 A | 3/1993 | Boyse et al. |
| 5,197,985 A | 3/1993 | Caplan et al. |
| 5,202,254 A | 4/1993 | Amiot et al. |
| 5,225,346 A | 7/1993 | Matsumiya et al. |
| 5,226,914 A | 7/1993 | Caplan et al. |
| 5,240,614 A | 8/1993 | Ofsthun et al. |
| 5,240,861 A | 8/1993 | Bieri |
| 5,283,058 A | 2/1994 | Faustman |
| 5,310,676 A | 5/1994 | Johansson et al. |
| 5,324,428 A | 6/1994 | Flaherty |
| 5,342,752 A | 8/1994 | Platz et al. |
| 5,422,197 A | 6/1995 | Zito |
| 5,436,151 A | 7/1995 | McGlave et al. |
| 5,437,994 A | 8/1995 | Emerson et al. |
| 5,439,757 A | 8/1995 | Zito |
| 5,459,069 A | 10/1995 | Palsson et al. |
| 5,460,964 A | 10/1995 | McGlave et al. |
| H1509 H | 12/1995 | Eran et al. |
| 5,478,739 A | 12/1995 | Slivka et al. |
| 5,486,359 A | 1/1996 | Caplan et al. |
| 5,496,659 A | 3/1996 | Zito |
| 5,507,949 A | 4/1996 | Ho |
| 5,512,180 A | 4/1996 | Ho |
| 5,527,467 A | 6/1996 | Ofsthun et al. |
| 5,543,316 A | 8/1996 | Zawadzka et al. |
| 5,545,492 A | 8/1996 | Zito |
| 5,549,674 A | 8/1996 | Humes et al. |
| 5,571,720 A | 11/1996 | Grandics et al. |
| 5,591,625 A | 1/1997 | Gerson et al. |
| 5,593,580 A | 1/1997 | Kopf |
| 5,595,909 A | 1/1997 | Hu et al. |
| 5,599,703 A | 2/1997 | Davis et al. |
| 5,605,822 A | 2/1997 | Emerson et al. |
| 5,605,829 A | 2/1997 | McGlave et al. |
| 5,605,835 A | 2/1997 | Hu et al. |
| 5,622,857 A | 4/1997 | Goffe |
| 5,626,731 A | 5/1997 | Cooley et al. |
| 5,627,070 A | 5/1997 | Gruenberg |
| 5,635,386 A | 6/1997 | Palsson et al. |
| 5,635,387 A | 6/1997 | Fei et al. |
| 5,643,736 A | 7/1997 | Bruder et al. |
| 5,646,043 A | 7/1997 | Emerson et al. |
| 5,654,186 A | 8/1997 | Cerami et al. |
| 5,656,421 A | 8/1997 | Gebhard et al. |
| 5,658,995 A | 8/1997 | Kohn et al. |
| 5,667,985 A | 9/1997 | O'Leary et al. |
| 5,670,147 A | 9/1997 | Emerson et al. |
| 5,674,750 A | 10/1997 | Kraus et al. |
| 5,684,712 A | 11/1997 | Goffe et al. |
| 5,686,289 A | 11/1997 | Humes et al. |
| 5,695,989 A | 12/1997 | Kalamasz |
| 5,700,289 A | 12/1997 | Breitbart et al. |
| 5,705,534 A | 1/1998 | D'Agostino et al. |
| 5,707,859 A | 1/1998 | Miller et al. |
| 5,712,163 A | 1/1998 | Parenteau et al. |
| 5,728,581 A | 3/1998 | Schwartz et al. |
| 5,733,541 A | 3/1998 | Taichman et al. |
| 5,733,542 A | 3/1998 | Haynesworth et al. |
| 5,736,396 A | 4/1998 | Bruder et al. |
| 5,744,347 A | 4/1998 | Wagner et al. |
| 5,750,651 A | 5/1998 | Oppermann et al. |
| 5,753,506 A | 5/1998 | Johe |
| 5,763,197 A | 6/1998 | Tsukamoto et al. |
| 5,763,266 A | 6/1998 | Palsson et al. |
| 5,766,944 A | 6/1998 | Ruiz |
| 5,772,994 A | 6/1998 | Ildstad et al. |
| 5,783,075 A | 7/1998 | Eddleman et al. |
| 5,783,216 A | 7/1998 | Faustman |
| 5,785,912 A | 7/1998 | Cooley et al. |
| 5,804,446 A | 9/1998 | Cerami et al. |
| 5,806,529 A | 9/1998 | Reisner et al. |
| 5,807,686 A | 9/1998 | Wagner et al. |
| 5,811,094 A | 9/1998 | Caplan et al. |
| 5,811,397 A | 9/1998 | Francavilla et al. |
| 5,817,773 A | 10/1998 | Wilson et al. |
| 5,821,218 A | 10/1998 | Toback et al. |
| 5,827,735 A | 10/1998 | Young et al. |
| 5,827,740 A | 10/1998 | Pittenger |
| 5,830,921 A | 11/1998 | Cooley et al. |
| 5,833,979 A | 11/1998 | Schinstine et al. |

(56)                References Cited

U.S. PATENT DOCUMENTS

| 5,837,258 | A | 11/1998 | Grotendorst |
| 5,837,539 | A | 11/1998 | Caplan et al. |
| 5,840,502 | A | 11/1998 | Van Vlasselaer |
| 5,840,576 | A | 11/1998 | Schinstine et al. |
| 5,840,580 | A | 11/1998 | Terstappen et al. |
| 5,842,477 | A | 12/1998 | Naughton et al. |
| 5,843,633 | A | 12/1998 | Yin et al. |
| 5,846,796 | A | 12/1998 | Cerami et al. |
| 5,853,247 | A | 12/1998 | Shroyer |
| 5,853,717 | A | 12/1998 | Schinstine et al. |
| 5,855,608 | A | 1/1999 | Brekke et al. |
| 5,855,613 | A | 1/1999 | Antanavich et al. |
| 5,855,619 | A | 1/1999 | Caplan et al. |
| 5,858,747 | A | 1/1999 | Schinstine et al. |
| 5,858,782 | A | 1/1999 | Long et al. |
| 5,861,315 | A | 1/1999 | Nakahata |
| 5,866,115 | A | 2/1999 | Kanz et al. |
| 5,866,420 | A | 2/1999 | Talbot et al. |
| 5,868,930 | A | 2/1999 | Kopf |
| 5,882,295 | A | 3/1999 | Kope |
| 5,882,918 | A | 3/1999 | Goffe |
| 5,882,929 | A | 3/1999 | Fofonoff et al. |
| 5,888,807 | A | 3/1999 | Palsson et al. |
| 5,902,741 | A | 5/1999 | Purchio et al. |
| 5,906,827 | A | 5/1999 | Khouri et al. |
| 5,906,934 | A | 5/1999 | Grande et al. |
| 5,908,782 | A | 6/1999 | Marshak et al. |
| 5,908,784 | A | 6/1999 | Johnstone et al. |
| 5,912,177 | A | 6/1999 | Turner et al. |
| 5,914,108 | A | 6/1999 | Tsukamoto et al. |
| 5,922,597 | A | 7/1999 | Verfaillie et al. |
| 5,922,847 | A | 7/1999 | Broudy et al. |
| 5,925,567 | A | 7/1999 | Kraus et al. |
| 5,928,945 | A | 7/1999 | Seliktar et al. |
| 5,935,849 | A | 8/1999 | Schinstine et al. |
| 5,938,929 | A | 8/1999 | Shimagaki et al. |
| 5,939,323 | A | 8/1999 | Valentini et al. |
| 5,942,225 | A | 8/1999 | Bruder et al. |
| 5,955,353 | A | 9/1999 | Amiot |
| 5,958,763 | A | 9/1999 | Goffe |
| 5,965,436 | A | 10/1999 | Thiede et al. |
| 5,972,703 | A | 10/1999 | Long et al. |
| 5,980,795 | A | 11/1999 | Klotzer et al. |
| 5,981,211 | A | 11/1999 | Hu et al. |
| 5,981,708 | A | 11/1999 | Lawman et al. |
| 5,998,184 | A | 12/1999 | Shi |
| 6,001,585 | A | 12/1999 | Gramer |
| 6,001,643 | A | 12/1999 | Spaulding |
| 6,001,647 | A | 12/1999 | Peck et al. |
| 6,004,743 | A | 12/1999 | Kenyon et al. |
| 6,010,696 | A | 1/2000 | Caplan et al. |
| 6,015,554 | A | 1/2000 | Galy |
| 6,022,540 | A | 2/2000 | Bruder et al. |
| 6,022,742 | A | 2/2000 | Kopf |
| 6,022,743 | A | 2/2000 | Naughton et al. |
| 6,027,743 | A | 2/2000 | Khouri et al. |
| 6,030,836 | A | 2/2000 | Thiede et al. |
| 6,040,180 | A | 3/2000 | Johe |
| 6,045,818 | A | 4/2000 | Cima et al. |
| 6,048,721 | A | 4/2000 | Armstrong et al. |
| 6,048,727 | A | 4/2000 | Kopf |
| 6,049,026 | A | 4/2000 | Muschler |
| 6,054,121 | A | 4/2000 | Cerami et al. |
| 6,060,270 | A | 5/2000 | Humes |
| 6,066,317 | A | 5/2000 | Yang et al. |
| 6,071,691 | A | 6/2000 | Hoekstra et al. |
| 6,074,366 | A | 6/2000 | Rogers et al. |
| 6,082,364 | A | 7/2000 | Balian et al. |
| 6,083,747 | A | 7/2000 | Wong et al. |
| 6,086,643 | A | 7/2000 | Clark et al. |
| 6,087,113 | A | 7/2000 | Caplan et al. |
| 6,096,537 | A | 8/2000 | Chappel |
| 6,103,117 | A | 8/2000 | Shimagaki et al. |
| 6,103,522 | A | 8/2000 | Torok-Storb et al. |
| 6,110,176 | A | 8/2000 | Shapira |
| 6,110,482 | A | 8/2000 | Khouri et al. |
| 6,114,307 | A | 9/2000 | Jaspers et al. |
| 6,117,985 | A | 9/2000 | Thomas et al. |
| 6,120,491 | A | 9/2000 | Kohn et al. |
| 6,127,141 | A | 10/2000 | Kopf |
| 6,129,911 | A | 10/2000 | Faris |
| 6,143,293 | A | 11/2000 | Weiss et al. |
| 6,146,360 | A | 11/2000 | Rogers et al. |
| 6,146,888 | A | 11/2000 | Smith et al. |
| 6,149,902 | A | 11/2000 | Artavanis-Tsakonas et al. |
| 6,149,906 | A | 11/2000 | Mosca |
| 6,150,164 | A | 11/2000 | Humes |
| 6,152,964 | A | 11/2000 | Van Blitterswijk et al. |
| 6,162,643 | A | 12/2000 | Wille, Jr. |
| 6,165,225 | A | 12/2000 | Antanavich et al. |
| 6,165,785 | A | 12/2000 | Ogle et al. |
| 6,174,333 | B1 | 1/2001 | Kadiyala et al. |
| 6,174,526 | B1 | 1/2001 | Cerami et al. |
| 6,174,666 | B1 | 1/2001 | Pavlakis et al. |
| 6,179,871 | B1 | 1/2001 | Halpern |
| 6,197,325 | B1 | 3/2001 | MacPhee et al. |
| 6,197,575 | B1 | 3/2001 | Griffith et al. |
| 6,200,606 | B1 | 3/2001 | Peterson et al. |
| 6,214,369 | B1 | 4/2001 | Grande et al. |
| 6,214,574 | B1 | 4/2001 | Kopf |
| 6,224,860 | B1 | 5/2001 | Brown |
| 6,225,119 | B1 | 5/2001 | Qasba et al. |
| 6,225,368 | B1 | 5/2001 | D'Agostino et al. |
| 6,228,117 | B1 | 5/2001 | De Bruijn et al. |
| 6,228,607 | B1 | 5/2001 | Kersten et al. |
| 6,238,908 | B1 | 5/2001 | Armstrong et al. |
| 6,239,157 | B1 | 5/2001 | Mbalaviele |
| 6,242,252 | B1 | 6/2001 | Reid et al. |
| 6,248,319 | B1 | 6/2001 | Zsebo et al. |
| 6,248,587 | B1 | 6/2001 | Rodgers et al. |
| 6,255,112 | B1 | 7/2001 | Thiede et al. |
| 6,258,597 | B1 | 7/2001 | Bachovchin et al. |
| 6,258,778 | B1 | 7/2001 | Rodgers et al. |
| 6,261,549 | B1 | 7/2001 | Fernandez et al. |
| 6,280,718 | B1 | 8/2001 | Kaufman et al. |
| 6,280,724 | B1 | 8/2001 | Moore |
| 6,281,012 | B1 | 8/2001 | McIntosh et al. |
| 6,281,195 | B1 | 8/2001 | Rueger et al. |
| 6,287,864 | B1 | 9/2001 | Bagnis et al. |
| 6,291,249 | B1 | 9/2001 | Mahant et al. |
| 6,297,213 | B1 | 10/2001 | Oppermann et al. |
| 6,299,650 | B1 | 10/2001 | Van Blitterswijk et al. |
| 6,306,424 | B1 | 10/2001 | Vyakamam et al. |
| 6,306,575 | B1 | 10/2001 | Thomas et al. |
| 6,322,784 | B1 | 11/2001 | Pittenger et al. |
| 6,322,786 | B1 | 11/2001 | Anderson |
| 6,326,198 | B1 | 12/2001 | Emerson et al. |
| 6,326,201 | B1 | 12/2001 | Fung et al. |
| 6,328,765 | B1 | 12/2001 | Hardwick et al. |
| 6,328,960 | B1 | 12/2001 | McIntosh et al. |
| 6,333,029 | B1 | 12/2001 | Vyakamam et al. |
| 6,335,195 | B1 | 1/2002 | Rodgers et al. |
| 6,338,942 | B2 | 1/2002 | Kraus et al. |
| 6,340,592 | B1 | 1/2002 | Stringer |
| 6,342,370 | B1 | 1/2002 | Connolly et al. |
| 6,355,239 | B1 | 3/2002 | Bruder et al. |
| 6,358,252 | B1 | 3/2002 | Shapira |
| 6,361,997 | B1 | 3/2002 | Huss |
| 6,365,149 | B2 | 4/2002 | Vyakarnam et al. |
| 6,368,636 | B1 | 4/2002 | McIntosh et al. |
| 6,372,210 | B2 | 4/2002 | Brown |
| 6,372,244 | B1 | 4/2002 | Antanavich et al. |
| 6,372,494 | B1 | 4/2002 | Naughton et al. |
| 6,372,892 | B1 | 4/2002 | Ballinger et al. |
| 6,376,742 | B1 | 4/2002 | Zdrahala et al. |
| 6,379,953 | B1 | 4/2002 | Bruder et al. |
| 6,387,367 | B1 | 5/2002 | Davis-Sproul et al. |
| 6,387,369 | B1 | 5/2002 | Pittenger et al. |
| 6,387,693 | B2 | 5/2002 | Rieser et al. |
| 6,387,964 | B1 | 5/2002 | D'Agostino et al. |
| 6,392,118 | B1 | 5/2002 | Hammang et al. |
| 6,394,812 | B1 | 5/2002 | Sullivan et al. |
| 6,399,580 | B1 | 6/2002 | Elias et al. |
| 6,410,320 | B1 | 6/2002 | Humes |

(56) References Cited

U.S. PATENT DOCUMENTS

| | | |
|---|---|---|
| 6,414,219 B1 | 7/2002 | Denhardt et al. |
| 6,416,496 B1 | 7/2002 | Rogers et al. |
| 6,417,205 B1 | 7/2002 | Cooke et al. |
| 6,419,829 B2 | 7/2002 | Ho et al. |
| 6,420,138 B1 | 7/2002 | Gentz et al. |
| 6,423,681 B1 | 7/2002 | Barasch et al. |
| 6,426,332 B1 | 7/2002 | Rueger et al. |
| 6,428,802 B1 | 8/2002 | Atala |
| 6,429,012 B1 | 8/2002 | Kraus et al. |
| 6,429,013 B1 | 8/2002 | Halvorsen et al. |
| 6,432,653 B1 | 8/2002 | Okarma |
| 6,432,711 B1 | 8/2002 | Dinsmore et al. |
| 6,440,407 B1 | 8/2002 | Bauer et al. |
| 6,440,734 B1 | 8/2002 | Pykett et al. |
| 6,451,562 B1 | 9/2002 | Ruben et al. |
| 6,454,811 B1 | 9/2002 | Sherwood et al. |
| 6,455,678 B1 | 9/2002 | Yin et al. |
| 6,458,585 B1 | 10/2002 | Vachula et al. |
| 6,458,589 B1 | 10/2002 | Rambhatla et al. |
| 6,461,495 B1 | 10/2002 | Morrissey et al. |
| 6,461,853 B1 | 10/2002 | Zhu |
| 6,464,983 B1 | 10/2002 | Grotendorst |
| 6,465,205 B2 | 10/2002 | Hicks, Jr. |
| 6,465,247 B1 | 10/2002 | Weissman et al. |
| 6,465,249 B2 | 10/2002 | Reya et al. |
| 6,468,794 B1 | 10/2002 | Uchida et al. |
| 6,472,200 B1 | 10/2002 | Mitrani |
| 6,475,481 B2 | 11/2002 | Talmadge |
| 6,479,064 B1 | 11/2002 | Atala |
| 6,482,231 B1 | 11/2002 | Abatangelo et al. |
| 6,482,411 B1 | 11/2002 | Ahuja et al. |
| 6,482,645 B2 | 11/2002 | Atala |
| 6,482,926 B1 | 11/2002 | Thomas et al. |
| 6,488,925 B2 | 12/2002 | Ruben et al. |
| 6,491,918 B1 | 12/2002 | Thomas et al. |
| 6,495,129 B1 | 12/2002 | Li et al. |
| 6,495,364 B2 | 12/2002 | Hammang et al. |
| 6,497,875 B1 | 12/2002 | Sorrell et al. |
| 6,498,034 B1 | 12/2002 | Strobl |
| 6,506,574 B1 | 1/2003 | Rambhatla et al. |
| 6,511,510 B1 | 1/2003 | de Bruijn et al. |
| 6,511,767 B1 | 1/2003 | Calver et al. |
| 6,511,958 B1 | 1/2003 | Atkinson et al. |
| 6,514,514 B1 | 2/2003 | Atkinson et al. |
| 6,524,452 B1 | 2/2003 | Clark et al. |
| 6,528,052 B1 | 3/2003 | Smith et al. |
| 6,528,245 B2 | 3/2003 | Sanchez-Ramos et al. |
| 6,531,445 B1 | 3/2003 | Cohen et al. |
| 6,534,084 B1 | 3/2003 | Vyakamam et al. |
| 6,537,807 B1 | 3/2003 | Smith et al. |
| 6,541,024 B1 | 4/2003 | Kadiyala et al. |
| 6,541,249 B2 | 4/2003 | Wager et al. |
| 6,544,506 B2 | 4/2003 | Reisner |
| 6,548,734 B1 | 4/2003 | Glimcher et al. |
| 6,555,324 B1 | 4/2003 | Olweus et al. |
| 6,555,374 B1 | 4/2003 | Gimble et al. |
| 6,559,119 B1 | 5/2003 | Burgess et al. |
| 6,562,616 B1 | 5/2003 | Toner et al. |
| 6,565,843 B1 | 5/2003 | Cohen et al. |
| 6,569,421 B2 | 5/2003 | Hodges |
| 6,569,427 B1 | 5/2003 | Boyse et al. |
| 6,569,428 B1 | 5/2003 | Isner et al. |
| 6,569,654 B2 | 5/2003 | Shastri et al. |
| 6,576,188 B1 | 6/2003 | Rose et al. |
| 6,576,428 B1 | 6/2003 | Assenmacher et al. |
| 6,576,464 B2 | 6/2003 | Gold et al. |
| 6,576,465 B1 | 6/2003 | Long |
| 6,582,471 B1 | 6/2003 | Bittmann et al. |
| 6,582,955 B2 | 6/2003 | Martinez et al. |
| 6,586,192 B1 | 7/2003 | Peschle et al. |
| 6,589,728 B2 | 7/2003 | Csete et al. |
| 6,589,786 B1 | 7/2003 | Mangano et al. |
| 6,596,274 B1 | 7/2003 | Abatangelo et al. |
| 6,599,300 B2 | 7/2003 | Vibe-Hansen et al. |
| 6,599,520 B2 | 7/2003 | Scarborough et al. |
| 6,610,535 B1 | 8/2003 | Lu et al. |
| 6,613,798 B1 | 9/2003 | Porter et al. |
| 6,616,912 B2 | 9/2003 | Eddleman et al. |
| 6,617,070 B1 | 9/2003 | Morrissey et al. |
| 6,617,152 B2 | 9/2003 | Bryhan et al. |
| 6,617,159 B1 | 9/2003 | Cancedda et al. |
| 6,623,749 B2 | 9/2003 | Williams et al. |
| 6,623,942 B2 | 9/2003 | Ruben et al. |
| 6,624,108 B1 | 9/2003 | Clark et al. |
| 6,626,950 B2 | 9/2003 | Brown et al. |
| 6,627,191 B1 | 9/2003 | Bartelmez et al. |
| 6,632,425 B1 | 10/2003 | Li et al. |
| 6,632,620 B1 | 10/2003 | Makarovskiy |
| 6,632,934 B1 | 10/2003 | Moreadith et al. |
| 6,638,765 B1 | 10/2003 | Rosenberg |
| 6,642,048 B2 | 11/2003 | Xu et al. |
| 6,642,049 B1 | 11/2003 | Chute et al. |
| 6,642,201 B1 | 11/2003 | Khavinson et al. |
| 6,645,489 B2 | 11/2003 | Pykett et al. |
| 6,645,727 B2 | 11/2003 | Thomas et al. |
| 6,645,763 B2 | 11/2003 | Kobayashi et al. |
| 6,649,189 B2 | 11/2003 | Talmadge et al. |
| 6,649,595 B2 | 11/2003 | Clackson et al. |
| 6,649,631 B1 | 11/2003 | Orme et al. |
| 6,653,105 B2 | 11/2003 | Triglia et al. |
| 6,653,134 B2 | 11/2003 | Prockop et al. |
| 6,660,523 B2 | 12/2003 | Blom et al. |
| 6,662,805 B2 | 12/2003 | Frondoza et al. |
| 6,667,034 B2 | 12/2003 | Palsson et al. |
| 6,667,176 B1 | 12/2003 | Funk et al. |
| 6,670,169 B1 | 12/2003 | Schob et al. |
| 6,670,175 B2 | 12/2003 | Wang et al. |
| 6,673,603 B2 | 1/2004 | Baetge et al. |
| 6,673,606 B1 | 1/2004 | Tennekoon et al. |
| 6,677,306 B1 | 1/2004 | Veis et al. |
| 6,683,192 B2 | 1/2004 | Baxter et al. |
| 6,685,936 B2 | 2/2004 | McIntosh et al. |
| 6,685,971 B2 | 2/2004 | Xu |
| 6,686,198 B1 | 2/2004 | Melton et al. |
| 6,696,575 B2 | 2/2004 | Schmidt et al. |
| 6,699,716 B2 | 3/2004 | Sullivan et al. |
| 6,703,017 B1 | 3/2004 | Peck et al. |
| 6,703,209 B1 | 3/2004 | Baetscher et al. |
| 6,706,293 B2 | 3/2004 | Quintanilla Almagro et al. |
| 6,709,864 B1 | 3/2004 | Pittenger et al. |
| 6,712,850 B2 | 3/2004 | Vyakarnam et al. |
| 6,719,969 B1 | 4/2004 | Hogaboam et al. |
| 6,719,970 B1 | 4/2004 | Costantino et al. |
| 6,720,340 B1 | 4/2004 | Cooke et al. |
| 6,730,314 B2 | 5/2004 | Jeschke et al. |
| 6,730,315 B2 | 5/2004 | Usala et al. |
| 6,730,510 B2 | 5/2004 | Roos et al. |
| 6,733,746 B2 | 5/2004 | Daley et al. |
| 6,734,000 B2 | 5/2004 | Chin et al. |
| 6,740,493 B1 | 5/2004 | Long et al. |
| 6,759,039 B2 | 7/2004 | Tsang et al. |
| 6,759,245 B1 | 7/2004 | Toner et al. |
| 6,761,883 B2 | 7/2004 | Weissman et al. |
| 6,761,887 B1 | 7/2004 | Kavalkovich et al. |
| 6,767,699 B2 | 7/2004 | Polo et al. |
| 6,767,737 B1 | 7/2004 | Wilson et al. |
| 6,767,738 B1 | 7/2004 | Gage et al. |
| 6,767,740 B2 | 7/2004 | Sramek et al. |
| 6,770,478 B2 | 8/2004 | Crowe et al. |
| 6,777,227 B2 | 8/2004 | Ricci et al. |
| 6,777,231 B1 | 8/2004 | Katz et al. |
| 6,780,612 B1 | 8/2004 | Ford et al. |
| 6,787,355 B1 | 9/2004 | Miller et al. |
| 6,790,455 B2 | 9/2004 | Chu et al. |
| 6,793,939 B2 | 9/2004 | Badylak |
| 6,797,269 B2 | 9/2004 | Mosca et al. |
| 6,797,514 B2 | 9/2004 | Berenson et al. |
| 6,800,480 B1 | 10/2004 | Bodnar et al. |
| 6,802,971 B2 | 10/2004 | Gorsuch et al. |
| 6,805,860 B1 | 10/2004 | Alt |
| 6,809,117 B2 | 10/2004 | Enikolopov et al. |
| 6,811,773 B1 | 11/2004 | Gentz et al. |
| 6,811,776 B2 | 11/2004 | Kale et al. |
| 6,814,961 B1 | 11/2004 | Jensen et al. |

(56) References Cited

U.S. PATENT DOCUMENTS

| | | |
|---|---|---|
| 6,821,513 B1 | 11/2004 | Fleming |
| 6,821,790 B2 | 11/2004 | Mahant et al. |
| 6,828,145 B2 | 12/2004 | Avital et al. |
| 6,833,269 B2 | 12/2004 | Carpenter |
| 6,835,377 B2 | 12/2004 | Goldberg et al. |
| 6,835,566 B2 | 12/2004 | Smith et al. |
| 6,838,284 B2 | 1/2005 | de Bruijn et al. |
| 6,841,150 B2 | 1/2005 | Halvorsen et al. |
| 6,841,151 B2 | 1/2005 | Stringer |
| 6,841,294 B1 | 1/2005 | Morrissey et al. |
| 6,841,355 B2 | 1/2005 | Livant |
| 6,841,386 B2 | 1/2005 | Kraus et al. |
| 6,841,542 B2 | 1/2005 | Bartelmez et al. |
| 6,844,011 B1 | 1/2005 | Faustman |
| 6,849,051 B2 | 2/2005 | Sramek et al. |
| 6,849,255 B2 | 2/2005 | Gazit et al. |
| 6,849,454 B2 | 2/2005 | Kelly et al. |
| 6,849,662 B2 | 2/2005 | Enikolopov et al. |
| 6,852,308 B2 | 2/2005 | Kohn et al. |
| 6,852,321 B2 | 2/2005 | Colucci et al. |
| 6,852,533 B1 | 2/2005 | Rafii et al. |
| 6,855,242 B1 | 2/2005 | Comninellis et al. |
| 6,855,542 B2 | 2/2005 | DiMilla et al. |
| 6,863,900 B2 | 3/2005 | Kadiyala et al. |
| 6,866,843 B2 | 3/2005 | Habener et al. |
| 6,872,389 B1 | 3/2005 | Faris |
| 6,875,430 B2 | 4/2005 | McIntosh et al. |
| 6,887,600 B2 | 5/2005 | Morrissey et al. |
| 6,887,704 B2 | 5/2005 | Peled et al. |
| 6,908,763 B1 | 6/2005 | Akashi et al. |
| 6,911,201 B1 | 6/2005 | Merchav et al. |
| 6,914,279 B2 | 7/2005 | Lu et al. |
| 6,939,955 B2 | 9/2005 | Rameshwar |
| 6,965,018 B2 | 11/2005 | Mikesell et al. |
| 6,979,321 B2 | 12/2005 | Geis et al. |
| 6,988,004 B2 | 1/2006 | Kanno et al. |
| 7,008,394 B2 | 3/2006 | Geise et al. |
| 7,015,037 B1 | 3/2006 | Furcht et al. |
| 7,029,666 B2 | 4/2006 | Bruder et al. |
| 7,033,339 B1 | 4/2006 | Lynn |
| 7,045,098 B2 | 5/2006 | Stephens |
| 7,052,517 B2 | 5/2006 | Murphy et al. |
| 7,056,493 B2 | 6/2006 | Kohn et al. |
| 7,118,672 B2 | 10/2006 | Husain et al. |
| 7,122,178 B1 | 10/2006 | Simmons et al. |
| 7,160,719 B2 | 1/2007 | Nyberg |
| 7,169,295 B2 | 1/2007 | Husain et al. |
| 7,172,696 B1 | 2/2007 | Martinez et al. |
| 7,175,763 B2 | 2/2007 | Husain et al. |
| 7,192,776 B2 | 3/2007 | Stephens |
| 7,195,711 B2 | 3/2007 | Gorsuch et al. |
| 7,250,154 B2 | 7/2007 | Kohn et al. |
| 7,271,234 B2 | 9/2007 | Kohn et al. |
| 7,294,259 B2 | 11/2007 | Cote et al. |
| 7,300,571 B2 | 11/2007 | Cote et al. |
| 7,303,676 B2 | 12/2007 | Husain et al. |
| 7,303,677 B2 | 12/2007 | Cote et al. |
| 7,341,062 B2 | 3/2008 | Chachques et al. |
| 7,358,001 B2 | 4/2008 | Morrissey et al. |
| 7,361,493 B1 | 4/2008 | Hammond et al. |
| 7,368,169 B2 | 5/2008 | Kohn et al. |
| 7,378,271 B2 | 5/2008 | Bader |
| 7,399,872 B2 | 7/2008 | Webster et al. |
| 7,416,884 B2 | 8/2008 | Gemmiti et al. |
| 7,425,440 B2 | 9/2008 | Malinge et al. |
| 7,435,586 B2 | 10/2008 | Bartlett et al. |
| 7,438,902 B2 | 10/2008 | Habener et al. |
| 7,439,057 B2 | 10/2008 | Frangos et al. |
| 7,452,529 B2 | 11/2008 | Brown, Jr. et al. |
| 7,491,388 B1 | 2/2009 | McIntosh et al. |
| 7,494,811 B2 | 2/2009 | Wolfinbarger, Jr. et al. |
| 7,514,074 B2 | 4/2009 | Pittenger et al. |
| 7,514,075 B2 | 4/2009 | Hedrick et al. |
| 7,524,676 B2 | 4/2009 | Reiter et al. |
| 7,534,609 B2 | 5/2009 | Merchav et al. |
| 7,572,374 B2 | 8/2009 | Gorsuch et al. |
| 7,579,179 B2 | 8/2009 | Bryhan et al. |
| 7,585,412 B2 | 9/2009 | Gorsuch et al. |
| 7,588,938 B2 | 9/2009 | Ma |
| 7,598,075 B2 | 10/2009 | Smith et al. |
| 7,608,447 B2 | 10/2009 | Cohen et al. |
| 7,659,118 B2 | 2/2010 | Furcht et al. |
| 7,678,573 B2 | 3/2010 | Merchav et al. |
| 7,682,823 B1 | 3/2010 | Runyon |
| 7,722,896 B2 | 5/2010 | Kohn et al. |
| D620,732 S | 8/2010 | Andrews |
| 7,838,122 B2 | 11/2010 | Kohn et al. |
| 7,838,289 B2 | 11/2010 | Furcht et al. |
| 7,892,829 B2 | 2/2011 | Pittenger et al. |
| 7,919,307 B2 | 4/2011 | Klaus et al. |
| 7,927,587 B2 | 4/2011 | Blazer et al. |
| 7,989,851 B2 | 8/2011 | Lu et al. |
| 8,008,528 B2 | 8/2011 | Kohn et al. |
| 8,034,365 B2 | 10/2011 | Baluca |
| 8,075,881 B2 | 12/2011 | Verfaillie et al. |
| 8,147,824 B2 | 4/2012 | Maziarz et al. |
| 8,147,863 B2 | 4/2012 | Kohn et al. |
| 8,158,120 B2 | 4/2012 | Pittenger et al. |
| 8,158,121 B2 | 4/2012 | Pittenger et al. |
| 8,252,280 B1 | 8/2012 | Verfaillie et al. |
| 8,252,887 B2 | 8/2012 | Bolikal et al. |
| 8,288,159 B2 | 10/2012 | Warren et al. |
| 8,288,590 B2 | 10/2012 | Kohn et al. |
| 8,298,823 B2 | 10/2012 | Warren et al. |
| 8,361,453 B2 | 1/2013 | Uhrich et al. |
| 8,377,683 B2 | 2/2013 | Lu et al. |
| 8,383,397 B2 | 2/2013 | Wojciechowski et al. |
| 8,383,806 B2 | 2/2013 | Rameshwar |
| 8,399,245 B2 | 3/2013 | Leuthaeuser et al. |
| 8,415,449 B2 | 4/2013 | Kohn et al. |
| 8,435,781 B2 | 5/2013 | Kodama |
| 8,461,289 B2 | 6/2013 | Kohn et al. |
| 8,476,399 B2 | 7/2013 | Bolikal et al. |
| 8,486,621 B2 | 7/2013 | Luo et al. |
| 8,486,695 B2 | 7/2013 | Danilkovitch et al. |
| 8,492,140 B2 | 7/2013 | Smith et al. |
| 8,492,150 B2 | 7/2013 | Parker et al. |
| 8,524,496 B2 | 9/2013 | Meiron et al. |
| 8,529,888 B2 | 9/2013 | Meiron et al. |
| 8,540,499 B2 | 9/2013 | Page et al. |
| 8,551,511 B2 | 10/2013 | Brandom et al. |
| 8,580,249 B2 | 11/2013 | Blazar et al. |
| 8,678,638 B2 | 3/2014 | Wong |
| 8,852,570 B2 | 10/2014 | Pittenger et al. |
| 8,852,571 B2 | 10/2014 | Pittenger et al. |
| 8,852,572 B2 | 10/2014 | Pittenger et al. |
| 8,852,573 B2 | 10/2014 | Pittenger et al. |
| 8,852,574 B2 | 10/2014 | Pittenger et al. |
| 8,852,575 B2 | 10/2014 | Pittenger et al. |
| 9,109,193 B2 | 8/2015 | Galliher et al. |
| 9,220,810 B2 | 12/2015 | Ma et al. |
| 9,441,195 B2 | 9/2016 | Wojciechowski et al. |
| 9,534,198 B2 | 1/2017 | Page et al. |
| 9,732,313 B2 | 8/2017 | Hirschel et al. |
| 10,093,956 B2 | 10/2018 | Hirschel et al. |
| 10,494,421 B2 | 12/2019 | Castillo |
| 11,118,151 B2 * | 9/2021 | Ferrie ................... C12M 23/44 |
| 2001/0017188 A1 | 8/2001 | Cooley et al. |
| 2001/0020086 A1 | 9/2001 | Hubbell et al. |
| 2001/0021516 A1 | 9/2001 | Wei et al. |
| 2001/0029046 A1 | 10/2001 | Beaulieu |
| 2001/0033834 A1 | 10/2001 | Wilkison et al. |
| 2001/0036663 A1 | 11/2001 | Kraus et al. |
| 2001/0041687 A1 | 11/2001 | Mruk |
| 2001/0044413 A1 | 11/2001 | Pierce et al. |
| 2001/0049139 A1 | 12/2001 | Lagasse et al. |
| 2002/0015724 A1 | 2/2002 | Yang et al. |
| 2002/0018804 A1 | 2/2002 | Austin et al. |
| 2002/0028510 A1 | 3/2002 | Sanberg et al. |
| 2002/0031757 A1 | 3/2002 | Ohgushi et al. |
| 2002/0037278 A1 | 3/2002 | Ueno et al. |
| 2002/0045260 A1 | 4/2002 | Hung et al. |
| 2002/0064869 A1 | 5/2002 | Ebner et al. |
| 2002/0076400 A1 | 6/2002 | Katz et al. |

(56) References Cited

U.S. PATENT DOCUMENTS

| | | |
|---|---|---|
| 2002/0077687 A1 | 6/2002 | Ahn |
| 2002/0082698 A1 | 6/2002 | Parenteau et al. |
| 2002/0116054 A1 | 8/2002 | Lundell et al. |
| 2002/0128581 A1 | 9/2002 | Vishnoi et al. |
| 2002/0128582 A1 | 9/2002 | Farrell et al. |
| 2002/0128583 A1 | 9/2002 | Min et al. |
| 2002/0128584 A1 | 9/2002 | Brown et al. |
| 2002/0130100 A1 | 9/2002 | Smith |
| 2002/0132343 A1 | 9/2002 | Lum |
| 2002/0139743 A1 | 10/2002 | Critz et al. |
| 2002/0142457 A1 | 10/2002 | Umezawa et al. |
| 2002/0146678 A1 | 10/2002 | Benvenisty |
| 2002/0146817 A1 | 10/2002 | Cannon et al. |
| 2002/0150989 A1 | 10/2002 | Greene et al. |
| 2002/0151056 A1 | 10/2002 | Sasai et al. |
| 2002/0159981 A1 | 10/2002 | Peled et al. |
| 2002/0160032 A1 | 10/2002 | Long et al. |
| 2002/0160510 A1 | 10/2002 | Hariri |
| 2002/0168765 A1 | 11/2002 | Prockop et al. |
| 2002/0169408 A1 | 11/2002 | Beretta et al. |
| 2002/0182241 A1 | 12/2002 | Borenstein et al. |
| 2002/0182664 A1 | 12/2002 | Dolecek et al. |
| 2002/0188962 A1 | 12/2002 | Denhardt et al. |
| 2002/0197240 A1 | 12/2002 | Chiu |
| 2003/0021850 A1 | 1/2003 | Xu |
| 2003/0022390 A1 | 1/2003 | Stephens |
| 2003/0027330 A1 | 2/2003 | Lanza et al. |
| 2003/0027331 A1 | 2/2003 | Yan et al. |
| 2003/0032143 A1 | 2/2003 | Neff et al. |
| 2003/0036168 A1 | 2/2003 | Ni et al. |
| 2003/0040113 A1 | 2/2003 | Mizuno et al. |
| 2003/0049236 A1 | 3/2003 | Kassem et al. |
| 2003/0054331 A1 | 3/2003 | Fraser et al. |
| 2003/0059851 A1 | 3/2003 | Smith |
| 2003/0059939 A1 | 3/2003 | Page et al. |
| 2003/0078345 A1 | 4/2003 | Morrisey |
| 2003/0082795 A1 | 5/2003 | Shuler et al. |
| 2003/0086915 A1 | 5/2003 | Rader et al. |
| 2003/0089471 A1 | 5/2003 | Gehr et al. |
| 2003/0092101 A1 | 5/2003 | Ni et al. |
| 2003/0101465 A1 | 5/2003 | Lawman et al. |
| 2003/0103957 A1 | 6/2003 | McKerracher |
| 2003/0104568 A1 | 6/2003 | Lee |
| 2003/0113813 A1 | 6/2003 | Heidaran et al. |
| 2003/0113910 A1 | 6/2003 | Levanduski |
| 2003/0124091 A1 | 7/2003 | Tuse et al. |
| 2003/0124721 A1 | 7/2003 | Cheatham et al. |
| 2003/0130593 A1 | 7/2003 | Gonzalez |
| 2003/0133918 A1 | 7/2003 | Sherley |
| 2003/0138950 A1 | 7/2003 | McAllister et al. |
| 2003/0143727 A1 | 7/2003 | Chang |
| 2003/0148152 A1 | 8/2003 | Morrisey |
| 2003/0149011 A1 | 8/2003 | Ackerman et al. |
| 2003/0152558 A1 | 8/2003 | Luft et al. |
| 2003/0157078 A1 | 8/2003 | Hall et al. |
| 2003/0157709 A1 | 8/2003 | DiMilla et al. |
| 2003/0161817 A1 | 8/2003 | Young et al. |
| 2003/0166272 A1 | 9/2003 | Abuljadayel |
| 2003/0170214 A1 | 9/2003 | Bader |
| 2003/0180296 A1 | 9/2003 | Salcedo et al. |
| 2003/0185817 A1 | 10/2003 | Thomas et al. |
| 2003/0202938 A1 | 10/2003 | Rameshwar |
| 2003/0203483 A1 | 10/2003 | Seshi |
| 2003/0204323 A1 | 10/2003 | Morrisey |
| 2003/0211602 A1 | 11/2003 | Atala |
| 2003/0211603 A1 | 11/2003 | Earp et al. |
| 2003/0216718 A1 | 11/2003 | Hamblin et al. |
| 2003/0219898 A1 | 11/2003 | Sugaya et al. |
| 2003/0223968 A1 | 12/2003 | Yang |
| 2003/0224420 A1 | 12/2003 | Hellerstein et al. |
| 2003/0224510 A1 | 12/2003 | Yamaguchi et al. |
| 2003/0225010 A1 | 12/2003 | Rameshwar |
| 2003/0232432 A1 | 12/2003 | Bhat |
| 2003/0232752 A1 | 12/2003 | Freeman et al. |
| 2003/0235909 A1 | 12/2003 | Hariri et al. |
| 2004/0009158 A1 | 1/2004 | Sands et al. |
| 2004/0009589 A1 | 1/2004 | Levenberg et al. |
| 2004/0010231 A1 | 1/2004 | Leonhardt et al. |
| 2004/0014209 A1 | 1/2004 | Lassar et al. |
| 2004/0018174 A1 | 1/2004 | Palasis |
| 2004/0018617 A1 | 1/2004 | Hwang |
| 2004/0023324 A1 | 2/2004 | Sakano et al. |
| 2004/0023370 A1 | 2/2004 | Yu et al. |
| 2004/0033214 A1 | 2/2004 | Young et al. |
| 2004/0033599 A1 | 2/2004 | Rosenberg |
| 2004/0037811 A1 | 2/2004 | Penn et al. |
| 2004/0037815 A1 | 2/2004 | Clarke et al. |
| 2004/0038316 A1 | 2/2004 | Kaiser et al. |
| 2004/0053869 A1 | 3/2004 | Andrews et al. |
| 2004/0062753 A1 | 4/2004 | Rezania et al. |
| 2004/0063205 A1 | 4/2004 | Xu |
| 2004/0067585 A1 | 4/2004 | Wang et al. |
| 2004/0071668 A1 | 4/2004 | Bays et al. |
| 2004/0072259 A1 | 4/2004 | Scadden et al. |
| 2004/0077079 A1 | 4/2004 | Storgaard et al. |
| 2004/0079248 A1 | 4/2004 | Mayer et al. |
| 2004/0087016 A1 | 5/2004 | Keating et al. |
| 2004/0091936 A1 | 5/2004 | West |
| 2004/0096476 A1 | 5/2004 | Uhrich et al. |
| 2004/0097408 A1 | 5/2004 | Leder et al. |
| 2004/0101959 A1 | 5/2004 | Marko et al. |
| 2004/0107453 A1 | 6/2004 | Furcht et al. |
| 2004/0110286 A1 | 6/2004 | Bhatia |
| 2004/0115804 A1 | 6/2004 | Fu et al. |
| 2004/0115806 A1 | 6/2004 | Fu |
| 2004/0120932 A1 | 6/2004 | Zahner |
| 2004/0121461 A1 | 6/2004 | Honmou et al. |
| 2004/0121464 A1 | 6/2004 | Rathjen et al. |
| 2004/0126405 A1 | 7/2004 | Sahatjian et al. |
| 2004/0128077 A1 | 7/2004 | Koebler et al. |
| 2004/0131601 A1 | 7/2004 | Epstein et al. |
| 2004/0132184 A1 | 7/2004 | Dennis et al. |
| 2004/0136967 A1 | 7/2004 | Weiss et al. |
| 2004/0137612 A1 | 7/2004 | Baksh |
| 2004/0137613 A1 | 7/2004 | Vacanti et al. |
| 2004/0143174 A1 | 7/2004 | Brubaker |
| 2004/0143863 A1 | 7/2004 | Li et al. |
| 2004/0151700 A1 | 8/2004 | Harlan et al. |
| 2004/0151701 A1 | 8/2004 | Kim et al. |
| 2004/0151706 A1 | 8/2004 | Shakhov et al. |
| 2004/0151729 A1 | 8/2004 | Michalopoulos et al. |
| 2004/0152190 A1 | 8/2004 | Sumita |
| 2004/0161419 A1 | 8/2004 | Strom et al. |
| 2004/0171533 A1 | 9/2004 | Zehentner et al. |
| 2004/0180347 A1 | 9/2004 | Stanton et al. |
| 2004/0191902 A1 | 9/2004 | Hambor et al. |
| 2004/0197310 A1 | 10/2004 | Sanberg et al. |
| 2004/0197375 A1 | 10/2004 | Rezania et al. |
| 2004/0208786 A1 | 10/2004 | Kevy et al. |
| 2004/0214275 A1 | 10/2004 | Soejima et al. |
| 2004/0219134 A1 | 11/2004 | Naughton et al. |
| 2004/0219136 A1 | 11/2004 | Hariri |
| 2004/0219563 A1 | 11/2004 | West et al. |
| 2004/0224403 A1 | 11/2004 | Bhatia |
| 2004/0229351 A1 | 11/2004 | Rodriguez et al. |
| 2004/0234972 A1 | 11/2004 | Owens et al. |
| 2004/0235158 A1 | 11/2004 | Bartlett et al. |
| 2004/0235160 A1 | 11/2004 | Nishikawa et al. |
| 2004/0235166 A1 | 11/2004 | Prockop et al. |
| 2004/0242469 A1 | 12/2004 | Lee et al. |
| 2004/0258669 A1 | 12/2004 | Dzau et al. |
| 2004/0259242 A1 | 12/2004 | Malinge et al. |
| 2004/0259254 A1 | 12/2004 | Honmou et al. |
| 2004/0260058 A1 | 12/2004 | Scheek et al. |
| 2004/0260318 A1 | 12/2004 | Hunter et al. |
| 2004/0265996 A1 | 12/2004 | Schwarz et al. |
| 2005/0002914 A1 | 1/2005 | Rosen et al. |
| 2005/0003460 A1 | 1/2005 | Nilsson et al. |
| 2005/0003527 A1 | 1/2005 | Lang et al. |
| 2005/0003534 A1 | 1/2005 | Huberman et al. |
| 2005/0008624 A1 | 1/2005 | Peled et al. |
| 2005/0008626 A1 | 1/2005 | Fraser et al. |
| 2005/0009178 A1 | 1/2005 | Yost et al. |
| 2005/0009179 A1 | 1/2005 | Gemmiti et al. |

(56) References Cited

U.S. PATENT DOCUMENTS

| | | |
|---|---|---|
| 2005/0009181 A1 | 1/2005 | Black et al. |
| 2005/0013804 A1 | 1/2005 | Kato et al. |
| 2005/0014252 A1 | 1/2005 | Chu et al. |
| 2005/0014253 A1 | 1/2005 | Ehmann et al. |
| 2005/0014254 A1 | 1/2005 | Kruse |
| 2005/0014255 A1 | 1/2005 | Tang et al. |
| 2005/0019801 A1 | 1/2005 | Rubin et al. |
| 2005/0019908 A1 | 1/2005 | Hariri |
| 2005/0019910 A1 | 1/2005 | Takagi et al. |
| 2005/0019911 A1 | 1/2005 | Gronthos et al. |
| 2005/0026836 A1 | 2/2005 | Dack et al. |
| 2005/0031587 A1 | 2/2005 | Tsutsui et al. |
| 2005/0031595 A1 | 2/2005 | Peled et al. |
| 2005/0031598 A1 | 2/2005 | Levenberg et al. |
| 2005/0032122 A1 | 2/2005 | Twang et al. |
| 2005/0032207 A1 | 2/2005 | Wobus et al. |
| 2005/0032209 A1 | 2/2005 | Messina et al. |
| 2005/0032218 A1 | 2/2005 | Gerlach |
| 2005/0036980 A1 | 2/2005 | Chaney et al. |
| 2005/0037488 A1 | 2/2005 | Mitalipova et al. |
| 2005/0037490 A1 | 2/2005 | Rosenberg et al. |
| 2005/0037492 A1 | 2/2005 | Xu et al. |
| 2005/0037493 A1 | 2/2005 | Mandalam et al. |
| 2005/0037949 A1 | 2/2005 | O'Brien et al. |
| 2005/0106119 A1 | 5/2005 | Brandom et al. |
| 2005/0106127 A1 | 5/2005 | Kraus et al. |
| 2005/0112447 A1 | 5/2005 | Fletcher et al. |
| 2005/0112762 A1 | 5/2005 | Hart et al. |
| 2005/0118712 A1 | 6/2005 | Tsai et al. |
| 2005/0130297 A1 | 6/2005 | Sarem et al. |
| 2005/0136093 A1 | 6/2005 | Denk |
| 2005/0137517 A1 | 6/2005 | Blickhan et al. |
| 2005/0142162 A1 | 6/2005 | Hunter et al. |
| 2005/0149157 A1 | 7/2005 | Hunter et al. |
| 2005/0152946 A1 | 7/2005 | Hunter et al. |
| 2005/0158289 A1 | 7/2005 | Simmons et al. |
| 2005/0172340 A1 | 8/2005 | Logvinov et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0180957 A1 | 8/2005 | Scharp et al. |
| 2005/0181502 A1 | 8/2005 | Furcht et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0186671 A1 | 8/2005 | Cannon et al. |
| 2005/0187140 A1 | 8/2005 | Hunter et al. |
| 2005/0196421 A1 | 9/2005 | Hunter et al. |
| 2005/0208095 A1 | 9/2005 | Hunter et al. |
| 2005/0244963 A1 | 11/2005 | Teplyashin |
| 2005/0249731 A1 | 11/2005 | Aslan et al. |
| 2005/0255118 A1 | 11/2005 | Wehner |
| 2005/0261674 A1 | 11/2005 | Nobis et al. |
| 2005/0277577 A1 | 12/2005 | Hunter et al. |
| 2005/0281790 A1 | 12/2005 | Simmons et al. |
| 2005/0282733 A1 | 12/2005 | Prins et al. |
| 2005/0283844 A1 | 12/2005 | Furcht et al. |
| 2006/0002900 A1 | 1/2006 | Binder et al. |
| 2006/0008452 A1 | 1/2006 | Simmons et al. |
| 2006/0019389 A1 | 1/2006 | Yayon et al. |
| 2006/0054941 A1 | 3/2006 | Lu et al. |
| 2006/0083720 A1 | 4/2006 | Fraser et al. |
| 2006/0099198 A1 | 5/2006 | Thomson et al. |
| 2006/0166364 A1 | 7/2006 | Senesac |
| 2006/0172008 A1 | 8/2006 | Yayon et al. |
| 2006/0193840 A1 | 8/2006 | Gronthos et al. |
| 2006/0228798 A1 | 10/2006 | Verfaillie et al. |
| 2006/0239909 A1 | 10/2006 | Anderson et al. |
| 2006/0258586 A1 | 11/2006 | Sheppard et al. |
| 2006/0258933 A1 | 11/2006 | Ellis et al. |
| 2006/0259998 A1 | 11/2006 | Brumbley et al. |
| 2006/0280748 A1 | 12/2006 | Buckheit |
| 2006/0286077 A1 | 12/2006 | Gronthos et al. |
| 2007/0005148 A1 | 1/2007 | Barofsky et al. |
| 2007/0011752 A1 | 1/2007 | Paleyanda |
| 2007/0042462 A1 | 2/2007 | Hildinger |
| 2007/0065938 A1 | 3/2007 | Gronthos et al. |
| 2007/0105222 A1 | 5/2007 | Wolfinbarger et al. |
| 2007/0116612 A1 | 5/2007 | Williamson |
| 2007/0117180 A1 | 5/2007 | Morikawa et al. |
| 2007/0123996 A1 | 5/2007 | Sugaya et al. |
| 2007/0166834 A1 | 7/2007 | Williamson et al. |
| 2007/0178071 A1 | 8/2007 | Westenfelder |
| 2007/0196421 A1 | 8/2007 | Hunter et al. |
| 2007/0197957 A1 | 8/2007 | Hunter et al. |
| 2007/0198063 A1 | 8/2007 | Hunter et al. |
| 2007/0202485 A1 | 8/2007 | Nees et al. |
| 2007/0203330 A1 | 8/2007 | Kretschmar et al. |
| 2007/0208134 A1 | 9/2007 | Hunter et al. |
| 2007/0258943 A1 | 11/2007 | Penn et al. |
| 2007/0274970 A1 | 11/2007 | Gordon et al. |
| 2007/0275457 A1 | 11/2007 | Granchelli et al. |
| 2007/0295651 A1 | 12/2007 | Martinez et al. |
| 2007/0298015 A1 | 12/2007 | Beer et al. |
| 2008/0003663 A1 | 1/2008 | Bryhan et al. |
| 2008/0009458 A1 | 1/2008 | Dornan et al. |
| 2008/0032398 A1 | 2/2008 | Cannon et al. |
| 2008/0050770 A1 | 2/2008 | Zhang et al. |
| 2008/0063600 A1 | 3/2008 | Aguzzi et al. |
| 2008/0064649 A1 | 3/2008 | Rameshwar |
| 2008/0069807 A1 | 3/2008 | Jy et al. |
| 2008/0095676 A1 | 4/2008 | Andretta |
| 2008/0095690 A1 | 4/2008 | Liu |
| 2008/0103412 A1 | 5/2008 | Chin |
| 2008/0110827 A1 | 5/2008 | Cote et al. |
| 2008/0113426 A1 | 5/2008 | Smith et al. |
| 2008/0113440 A1 | 5/2008 | Gurney et al. |
| 2008/0153077 A1 | 6/2008 | Henry |
| 2008/0160597 A1 | 7/2008 | van der Heiden et al. |
| 2008/0166808 A1 | 7/2008 | Nyberg |
| 2008/0181879 A1 | 7/2008 | Catelas et al. |
| 2008/0190857 A1 | 8/2008 | Beretta et al. |
| 2008/0194017 A1 | 8/2008 | Esser et al. |
| 2008/0206831 A1 | 8/2008 | Coffey et al. |
| 2008/0220524 A1 | 9/2008 | Noll et al. |
| 2008/0220526 A1 | 9/2008 | Ellison et al. |
| 2008/0221443 A1 | 9/2008 | Ritchie et al. |
| 2008/0227189 A1 | 9/2008 | Bader |
| 2008/0268165 A1 | 10/2008 | Fekety et al. |
| 2008/0306095 A1 | 12/2008 | Crawford |
| 2009/0004738 A1 | 1/2009 | Merchav et al. |
| 2009/0011399 A1 | 1/2009 | Fischer |
| 2009/0047289 A1 | 2/2009 | Denhardt et al. |
| 2009/0074728 A1 | 3/2009 | Gronthos et al. |
| 2009/0075881 A1 | 3/2009 | Catelas et al. |
| 2009/0076481 A1 | 3/2009 | Stegmann et al. |
| 2009/0081770 A1 | 3/2009 | Srienc et al. |
| 2009/0081797 A1 | 3/2009 | Fadeev et al. |
| 2009/0092608 A1 | 4/2009 | Ni et al. |
| 2009/0098103 A1 | 4/2009 | Madison et al. |
| 2009/0098645 A1 | 4/2009 | Fang et al. |
| 2009/0100944 A1 | 4/2009 | Newby |
| 2009/0104163 A1 | 4/2009 | Deans et al. |
| 2009/0104692 A1 | 4/2009 | Bartfeld et al. |
| 2009/0104699 A1 | 4/2009 | Newby et al. |
| 2009/0118161 A1 | 5/2009 | Cruz |
| 2009/0181087 A1 | 7/2009 | Kraus et al. |
| 2009/0183581 A1 | 7/2009 | Wilkinson et al. |
| 2009/0191627 A1 | 7/2009 | Fadeev et al. |
| 2009/0191632 A1 | 7/2009 | Fadeev et al. |
| 2009/0191634 A1 | 7/2009 | Martin et al. |
| 2009/0203065 A1 | 8/2009 | Gehman et al. |
| 2009/0203129 A1 | 8/2009 | Furcht et al. |
| 2009/0203130 A1 | 8/2009 | Furcht et al. |
| 2009/0214382 A1 | 8/2009 | Burgess et al. |
| 2009/0214481 A1 | 8/2009 | Muhs et al. |
| 2009/0214652 A1 | 8/2009 | Hunter et al. |
| 2009/0215022 A1 | 8/2009 | Page et al. |
| 2009/0227024 A1 | 9/2009 | Baker et al. |
| 2009/0227027 A1 | 9/2009 | Baker et al. |
| 2009/0233334 A1 | 9/2009 | Hildinger et al. |
| 2009/0233353 A1 | 9/2009 | Furcht et al. |
| 2009/0233354 A1 | 9/2009 | Furcht et al. |

(56) References Cited

U.S. PATENT DOCUMENTS

| | | |
|---|---|---|
| 2009/0258379 A1 | 10/2009 | Klein et al. |
| 2009/0269841 A1 | 10/2009 | Wojciechowski et al. |
| 2009/0270725 A1 | 10/2009 | Leimbach et al. |
| 2009/0280153 A1 | 11/2009 | Hunter et al. |
| 2009/0280565 A1 | 11/2009 | Jolicoeur et al. |
| 2009/0291890 A1 | 11/2009 | Madison et al. |
| 2010/0009409 A1 | 1/2010 | Hubbell et al. |
| 2010/0021954 A1 | 1/2010 | Deshayes et al. |
| 2010/0021990 A1 | 1/2010 | Edwards et al. |
| 2010/0028311 A1 | 2/2010 | Motlagh et al. |
| 2010/0075410 A1 | 3/2010 | Desai et al. |
| 2010/0086481 A1 | 4/2010 | Baird et al. |
| 2010/0092536 A1 | 4/2010 | Hunter et al. |
| 2010/0093607 A1 | 4/2010 | Dickneite |
| 2010/0111910 A1 | 5/2010 | Rakoczy |
| 2010/0129376 A1 | 5/2010 | Denhardt et al. |
| 2010/0129912 A1 | 5/2010 | Su et al. |
| 2010/0136091 A1 | 6/2010 | Moghe et al. |
| 2010/0144634 A1 | 6/2010 | Zheng et al. |
| 2010/0183561 A1 | 7/2010 | Sakthivel et al. |
| 2010/0183585 A1 | 7/2010 | Van Zant et al. |
| 2010/0203020 A1 | 8/2010 | Ghosh |
| 2010/0230203 A1 | 9/2010 | Karayianni |
| 2010/0248366 A1 | 9/2010 | Fadeev et al. |
| 2010/0278933 A1 | 11/2010 | Sayeski et al. |
| 2010/0285453 A1 | 11/2010 | Goodrich |
| 2010/0285590 A1 | 11/2010 | Verfaillie et al. |
| 2010/0291180 A1 | 11/2010 | Uhrich |
| 2010/0291181 A1 | 11/2010 | Uhrich et al. |
| 2010/0297234 A1 | 11/2010 | Sugino et al. |
| 2010/0304427 A1 | 12/2010 | Faris et al. |
| 2010/0304482 A1 | 12/2010 | Deshayes et al. |
| 2010/0310524 A1 | 12/2010 | Bechor et al. |
| 2010/0316446 A1 | 12/2010 | Runyon |
| 2011/0085746 A1 | 4/2011 | Wong et al. |
| 2011/0111498 A1 | 5/2011 | Oh et al. |
| 2011/0129447 A1 | 6/2011 | Meretzki et al. |
| 2011/0129486 A1 | 6/2011 | Meiron |
| 2011/0143433 A1 | 6/2011 | Oh et al. |
| 2011/0159584 A1 | 6/2011 | Gibbons et al. |
| 2011/0171182 A1 | 7/2011 | Abelman |
| 2011/0171659 A1 | 7/2011 | Furcht et al. |
| 2011/0177595 A1 | 7/2011 | Furcht et al. |
| 2011/0212493 A1 | 9/2011 | Hirschel et al. |
| 2011/0256108 A1 | 10/2011 | Meiron et al. |
| 2011/0256160 A1 | 10/2011 | Meiron et al. |
| 2011/0293583 A1 | 12/2011 | Aberman |
| 2012/0028352 A1 | 2/2012 | Oh et al. |
| 2012/0051976 A1 | 3/2012 | Lu et al. |
| 2012/0058554 A1 | 3/2012 | Deshayes et al. |
| 2012/0064047 A1 | 3/2012 | Verfaillie et al. |
| 2012/0064583 A1 | 3/2012 | Edwards et al. |
| 2012/0118919 A1 | 5/2012 | Cianciolo |
| 2012/0122220 A1 | 5/2012 | Merchav et al. |
| 2012/0135043 A1 | 5/2012 | Maziarz et al. |
| 2012/0145580 A1 | 6/2012 | Paruit et al. |
| 2012/0156779 A1 | 6/2012 | Anneren et al. |
| 2012/0178885 A1 | 7/2012 | Kohn et al. |
| 2012/0189713 A1 | 7/2012 | Kohn et al. |
| 2012/0208039 A1 | 8/2012 | Barbaroux et al. |
| 2012/0219531 A1 | 8/2012 | Oh et al. |
| 2012/0219737 A1 | 8/2012 | Sugino et al. |
| 2012/0226013 A1 | 9/2012 | Kohn et al. |
| 2012/0231519 A1 | 9/2012 | Bushman et al. |
| 2012/0237557 A1 | 9/2012 | Lewitus et al. |
| 2012/0295352 A1 | 11/2012 | Antwiler |
| 2012/0308531 A1 | 12/2012 | Pinxteren et al. |
| 2012/0315696 A1 | 12/2012 | Luitjens et al. |
| 2013/0004465 A1 | 1/2013 | Aberman |
| 2013/0039892 A1 | 2/2013 | Aberman |
| 2013/0058907 A1 | 3/2013 | Wojciechowski et al. |
| 2013/0059383 A1 | 3/2013 | Dijkhuizen Borgart et al. |
| 2013/0101561 A1 | 4/2013 | Sabaawy |
| 2013/0143313 A1 | 6/2013 | Niazi |
| 2013/0157353 A1 | 6/2013 | Dijkhuizen Borgart et al. |
| 2013/0259843 A1 | 10/2013 | Duda et al. |
| 2013/0319575 A1 | 12/2013 | Mendyk |
| 2013/0323213 A1 | 12/2013 | Meiron et al. |
| 2013/0337558 A1 | 12/2013 | Meiron et al. |
| 2014/0004553 A1 | 1/2014 | Parker et al. |
| 2014/0017209 A1 | 1/2014 | Aberman et al. |
| 2014/0030805 A1 | 1/2014 | Kasuto et al. |
| 2014/0051162 A1 | 2/2014 | Nankervis |
| 2014/0051167 A1 | 2/2014 | Nankervis et al. |
| 2014/0112893 A1 | 4/2014 | Tom et al. |
| 2014/0186937 A1 | 7/2014 | Smith et al. |
| 2014/0193895 A1 | 7/2014 | Smith et al. |
| 2014/0193911 A1 | 7/2014 | Newby et al. |
| 2014/0242039 A1 | 8/2014 | Meiron et al. |
| 2014/0248244 A1 | 9/2014 | Danilkovitch et al. |
| 2014/0315300 A1 | 10/2014 | Oh et al. |
| 2014/0342448 A1 | 11/2014 | Nagels |
| 2015/0004693 A1 | 1/2015 | Danilkovitch et al. |
| 2015/0104431 A1 | 4/2015 | Pittenger et al. |
| 2015/0111252 A1 | 4/2015 | Hirschel et al. |
| 2015/0125138 A1 | 5/2015 | Kamieli et al. |
| 2015/0175950 A1 | 6/2015 | Hirschel et al. |
| 2015/0225685 A1 | 8/2015 | Hirschel et al. |
| 2015/0247122 A1 | 9/2015 | Tom et al. |
| 2015/0259749 A1 | 9/2015 | Santos et al. |
| 2016/0333314 A1 | 11/2016 | Nguyen et al. |
| 2016/0362650 A1 | 12/2016 | Wojciechowski et al. |
| 2016/0362652 A1 | 12/2016 | Page et al. |
| 2018/0010082 A1 | 1/2018 | Jaques et al. |
| 2018/0030398 A1 | 2/2018 | Castillo |
| 2018/0155668 A1 | 6/2018 | Hirschel et al. |
| 2019/0194628 A1 | 6/2019 | Rao et al. |
| 2022/0135921 A1* | 5/2022 | Sowwan ............... C12M 29/18<br>435/395 |

FOREIGN PATENT DOCUMENTS

| | | |
|---|---|---|
| DE | 10244859 A1 | 4/2004 |
| DE | 10327988 A1 | 7/2004 |
| DE | 102012200939 A1 | 7/2013 |
| EP | 750938 A1 | 1/1997 |
| EP | 906415 A1 | 4/1999 |
| EP | 959980 A1 | 12/1999 |
| EP | 1007631 A1 | 6/2000 |
| EP | 1028737 A1 | 8/2000 |
| EP | 1028991 A1 | 8/2000 |
| EP | 1066052 A2 | 1/2001 |
| EP | 1066060 A2 | 1/2001 |
| EP | 1084230 A2 | 3/2001 |
| EP | 1147176 A1 | 10/2001 |
| EP | 1220611 A1 | 7/2002 |
| EP | 1223956 A1 | 7/2002 |
| EP | 1325953 A1 | 7/2003 |
| EP | 1437404 A1 | 7/2004 |
| EP | 1437406 A2 | 7/2004 |
| EP | 1447443 A1 | 8/2004 |
| EP | 1452594 A1 | 9/2004 |
| EP | 1062321 B1 | 12/2004 |
| EP | 1484080 A1 | 12/2004 |
| EP | 1498478 A1 | 1/2005 |
| EP | 1036057 B1 | 10/2005 |
| EP | 1605044 A2 | 12/2005 |
| EP | 1756262 A1 | 2/2007 |
| EP | 1771737 A1 | 4/2007 |
| EP | 1882030 A1 | 1/2008 |
| EP | 1908490 A1 | 4/2008 |
| EP | 1971679 A2 | 9/2008 |
| EP | 1991668 A2 | 11/2008 |
| EP | 2027247 A2 | 2/2009 |
| EP | 2200622 A1 | 6/2010 |
| EP | 2208782 A2 | 7/2010 |
| EP | 2264145 A1 | 12/2010 |
| EP | 2303293 A1 | 4/2011 |
| EP | 2311938 A1 | 4/2011 |
| EP | 2331957 A1 | 6/2011 |
| EP | 2334310 A2 | 6/2011 |
| EP | 2334783 A2 | 6/2011 |
| EP | 2361968 A1 | 8/2011 |
| EP | 2366775 A1 | 9/2011 |

(56) References Cited

FOREIGN PATENT DOCUMENTS

| | | | |
|---|---|---|---|
| EP | 2465922 | A2 | 6/2012 |
| EP | 2548951 | A1 | 1/2013 |
| EP | 2561066 | A1 | 2/2013 |
| EP | 2575831 | A1 | 4/2013 |
| EP | 2591789 | A2 | 5/2013 |
| EP | 2624845 | A2 | 8/2013 |
| EP | 2626417 | A1 | 8/2013 |
| EP | 2641606 | A1 | 9/2013 |
| EP | 2689008 | A1 | 1/2014 |
| EP | 2694639 | A1 | 2/2014 |
| EP | 2697362 | A2 | 2/2014 |
| EP | 2739720 | A1 | 6/2014 |
| EP | 2807246 | A1 | 12/2014 |
| GB | 1414671 | A | 11/1975 |
| GB | 2297980 | A | 8/1996 |
| GB | 2360789 | A | 10/2001 |
| HU | 3285 | U | 5/2007 |
| JP | 2003/052360 | A | 2/2003 |
| JP | 5548207 | B2 | 7/2014 |
| JP | 2016-536998 | A | 12/2016 |
| MY | 115206 | A | 4/2003 |
| WO | 9013306 | A2 | 11/1990 |
| WO | 9105238 | A1 | 4/1991 |
| WO | 9106641 | A1 | 5/1991 |
| WO | 9109194 | A1 | 6/1991 |
| WO | 94/25571 | A1 | 11/1994 |
| WO | 96/29395 | A1 | 9/1996 |
| WO | 96/39035 | A1 | 12/1996 |
| WO | 97/05826 | A1 | 2/1997 |
| WO | 97/29792 | A1 | 8/1997 |
| WO | 97/39104 | A1 | 10/1997 |
| WO | 1997-040137 | A1 | 10/1997 |
| WO | 98/31403 | A1 | 7/1998 |
| WO | 98/51317 | A1 | 11/1998 |
| WO | 98/51785 | A1 | 11/1998 |
| WO | 99/05180 | A1 | 2/1999 |
| WO | 99/24391 | A1 | 5/1999 |
| WO | 99/24490 | A1 | 5/1999 |
| WO | 99/27167 | A1 | 6/1999 |
| WO | 99/49015 | A2 | 9/1999 |
| WO | 00/06704 | A2 | 2/2000 |
| WO | 0009018 | A1 | 2/2000 |
| WO | 00/16420 | A1 | 3/2000 |
| WO | 00/17326 | A1 | 3/2000 |
| WO | 00/29002 | A2 | 5/2000 |
| WO | 0032225 | A1 | 6/2000 |
| WO | 00/44058 | A2 | 7/2000 |
| WO | 0054651 | A2 | 9/2000 |
| WO | 0056405 | A2 | 9/2000 |
| WO | 00/59933 | A2 | 10/2000 |
| WO | 00/69449 | A2 | 11/2000 |
| WO | 00/75196 | A1 | 12/2000 |
| WO | 00/77236 | A2 | 12/2000 |
| WO | 2001/000783 | A2 | 1/2001 |
| WO | 2001/011011 | A2 | 2/2001 |
| WO | 2001/018174 | A2 | 3/2001 |
| WO | 2001/021766 | A2 | 3/2001 |
| WO | 2001/025402 | A1 | 4/2001 |
| WO | 2001/029189 | A2 | 4/2001 |
| WO | 0122810 | A2 | 4/2001 |
| WO | 2001/034167 | A1 | 5/2001 |
| WO | 2001/049851 | A1 | 7/2001 |
| WO | 2001/054706 | A2 | 8/2001 |
| WO | 2001-094541 | A2 | 12/2001 |
| WO | 2002/042422 | A2 | 5/2002 |
| WO | 2002/057430 | A2 | 7/2002 |
| WO | 2002/092794 | A2 | 11/2002 |
| WO | 2002/101385 | A1 | 12/2002 |
| WO | 2003/010303 | A1 | 2/2003 |
| WO | 2003/014313 | A2 | 2/2003 |
| WO | 2003/016916 | A1 | 2/2003 |
| WO | 2003/023018 | A2 | 3/2003 |
| WO | 2003/023019 | A1 | 3/2003 |
| WO | 2003/025167 | A2 | 3/2003 |
| WO | 2003/029402 | A2 | 4/2003 |
| WO | 2003/040336 | A2 | 5/2003 |
| WO | 2003/042405 | A2 | 5/2003 |
| WO | 2003/046161 | A2 | 6/2003 |
| WO | 2003/055989 | A2 | 7/2003 |
| WO | 2003/061685 | A1 | 7/2003 |
| WO | 2003/061686 | A1 | 7/2003 |
| WO | 2003/068961 | A2 | 8/2003 |
| WO | 2003/072064 | A2 | 9/2003 |
| WO | 2003/078609 | A1 | 9/2003 |
| WO | 2003/078967 | A2 | 9/2003 |
| WO | 2003/080816 | A2 | 10/2003 |
| WO | 2003/082145 | A2 | 10/2003 |
| WO | 2003/085099 | A2 | 10/2003 |
| WO | 2003/089631 | A1 | 10/2003 |
| WO | 2003/091398 | A2 | 11/2003 |
| WO | 2003/095631 | A1 | 11/2003 |
| WO | 2004/001697 | A1 | 12/2003 |
| WO | 2004/012226 | A2 | 2/2004 |
| WO | 2004/016779 | A1 | 2/2004 |
| WO | 2004/018526 | A1 | 3/2004 |
| WO | 2004/018655 | A2 | 3/2004 |
| WO | 2004/026115 | A2 | 4/2004 |
| WO | 2004/029231 | A1 | 4/2004 |
| WO | 2004/042023 | A2 | 5/2004 |
| WO | 2004/042033 | A2 | 5/2004 |
| WO | 2004/042040 | A1 | 5/2004 |
| WO | 2004/044127 | A2 | 5/2004 |
| WO | 2004/044158 | A2 | 5/2004 |
| WO | 2004/046304 | A1 | 6/2004 |
| WO | 2004/050826 | A2 | 6/2004 |
| WO | 2004/053096 | A2 | 6/2004 |
| WO | 2004/055155 | A2 | 7/2004 |
| WO | 2004/056186 | A1 | 7/2004 |
| WO | 2004/065616 | A2 | 8/2004 |
| WO | 2004/069172 | A2 | 8/2004 |
| WO | 2004/070013 | A2 | 8/2004 |
| WO | 2004/072264 | A2 | 8/2004 |
| WO | 2004/073633 | A2 | 9/2004 |
| WO | 2004/074464 | A1 | 9/2004 |
| WO | 2004/076642 | A2 | 9/2004 |
| WO | 2004/076653 | A1 | 9/2004 |
| WO | 2004/087870 | A2 | 10/2004 |
| WO | 2004/094588 | A2 | 11/2004 |
| WO | 2004/096975 | A2 | 11/2004 |
| WO | 2004/104166 | A2 | 12/2004 |
| WO | 2004/106499 | A1 | 12/2004 |
| WO | 2004/113513 | A2 | 12/2004 |
| WO | 2005/001033 | A2 | 1/2005 |
| WO | 2005/001081 | A1 | 1/2005 |
| WO | 2005/003320 | A2 | 1/2005 |
| WO | 2005/007799 | A2 | 1/2005 |
| WO | 2005/010172 | A2 | 2/2005 |
| WO | 2005/011524 | A1 | 2/2005 |
| WO | 2005/012480 | A2 | 2/2005 |
| WO | 2005/012510 | A1 | 2/2005 |
| WO | 2005/012512 | A1 | 2/2005 |
| WO | 05014775 | A2 | 2/2005 |
| WO | 2005/028433 | A2 | 3/2005 |
| WO | 05044972 | A2 | 5/2005 |
| WO | 2005/056747 | A2 | 6/2005 |
| WO | 05051316 | A2 | 6/2005 |
| WO | 2005/063303 | A1 | 7/2005 |
| WO | 2005/075636 | A1 | 8/2005 |
| WO | 2005/107760 | A1 | 11/2005 |
| WO | 2006/009291 | A1 | 1/2006 |
| WO | 2006/032075 | A1 | 3/2006 |
| WO | 2006/032092 | A1 | 3/2006 |
| WO | 2006/108229 | A1 | 10/2006 |
| WO | 2006/113881 | A2 | 10/2006 |
| WO | 2006/121445 | A2 | 11/2006 |
| WO | 06124021 | A1 | 11/2006 |
| WO | 06129312 | A2 | 12/2006 |
| WO | 2007/115367 | A1 | 10/2007 |
| WO | 2007/115368 | A1 | 10/2007 |
| WO | 2008/006168 | A1 | 1/2008 |
| WO | 2008/011664 | A1 | 1/2008 |
| WO | 2008/017128 | A1 | 2/2008 |
| WO | 2008/028241 | A1 | 3/2008 |
| WO | 08040812 | A1 | 4/2008 |

(56)    References Cited

FOREIGN PATENT DOCUMENTS

| WO | 2008/116261 A1 | 10/2008 |
|----|----------------|---------|
| WO | 2008/149129 A1 | 12/2008 |
| WO | 2009/026635 A1 | 3/2009 |
| WO | 09058146 A1 | 5/2009 |
| WO | 09080054 A1 | 7/2009 |
| WO | 09081408 A2 | 7/2009 |
| WO | 2009/140452 A2 | 11/2009 |
| WO | 09132457 A1 | 11/2009 |
| WO | 2009/144720 A1 | 12/2009 |
| WO | 10005527 A1 | 1/2010 |
| WO | 2010/019886 A1 | 2/2010 |
| WO | 10014253 A2 | 2/2010 |
| WO | 10019997 A1 | 2/2010 |
| WO | 2010/026573 A1 | 3/2010 |
| WO | 2010/026574 A2 | 3/2010 |
| WO | 2010/026575 A2 | 3/2010 |
| WO | 2010/036760 A1 | 4/2010 |
| WO | 2010/059487 A1 | 5/2010 |
| WO | 10061377 A2 | 6/2010 |
| WO | 10068710 A2 | 6/2010 |
| WO | 10071826 A2 | 6/2010 |
| WO | 10083385 A2 | 7/2010 |
| WO | 10111255 A1 | 9/2010 |
| WO | 10119036 A1 | 10/2010 |
| WO | 10123594 A2 | 10/2010 |
| WO | 2011/025445 A1 | 3/2011 |
| WO | 2011/132087 A1 | 10/2011 |
| WO | 2011/147967 A1 | 12/2011 |
| WO | 2012/072924 A1 | 6/2012 |
| WO | 2012/127320 A1 | 9/2012 |
| WO | 2012/138968 A1 | 10/2012 |
| WO | 2012/140519 A2 | 10/2012 |
| WO | 2012/171026 A2 | 12/2012 |
| WO | 2012/171030 A2 | 12/2012 |
| WO | 2013/110651 A1 | 8/2013 |
| WO | 2014/037862 A1 | 3/2014 |
| WO | 2014/037863 A1 | 3/2014 |
| WO | 2014/068508 A2 | 5/2014 |
| WO | 2014/128306 A1 | 8/2014 |
| WO | 2014/128634 A1 | 8/2014 |
| WO | 2014/131846 A1 | 9/2014 |
| WO | 2014/141111 A1 | 9/2014 |
| WO | 2015/004609 A2 | 1/2015 |
| WO | 2015/073918 A1 | 5/2015 |
| WO | 2015/118148 A1 | 8/2015 |
| WO | 2015/118149 A1 | 8/2015 |
| WO | 2015/131143 A1 | 9/2015 |
| WO | 2016-183350 A1 | 11/2016 |
| WO | 2017/072201 A2 | 5/2017 |

OTHER PUBLICATIONS

Afzali B, Edozie FC, Fazekasova H, Scotta C, Mitchell PJ, Canavan JB, Kordasti SY, Chana PS, Ellis R, Lord GM, John S, Hilton R, Lechler RI, Lombardi G. Comparison of regulatory T cells in hemodialysis patients and healthy controls: implications for cell therapy in transplantation. Clin J Am Soc Nephrol. 2013;8(8):1396-405.

Akram, Khondoker M., et al. "Mesenchymal stem cells promote alveolar epithelial cell wound repair in vitro through distinct migratory and paracrine mechanisms." Respiratory research 14.1 (2013): 1-16.

Alberts B, Johnson A, Lewis J, et al. Molecular Biology of the Cell. 4th edition. New York: Garland Science; 2002. Fibroblasts and Their Transformations: The Connective-Tissue Cell Family. Available from: https://www.ncbi.nlm.nih.gov/books/NBK26889.

Alenazi, Noof A., et al. "Modified polyether-sulfone membrane: A mini review." Designed monomers and polymers 20.1 (2017): 532-546.

Almeida L, Lochner M, Berod L, Sparwasser T. Metabolic pathways in T cell activation and lineage differentiation. Semin Immunol. 2016;28(5):514-524.

Amy Putnam, Todd M. Brusko, Michael R. Lee, Weihong Liu, Gregory L. Szot, Taumoha Ghosh, Mark A. Atkinson, and Jeffrey A. Bluestone. Expansion of human regulatory T-Cells from patients with Type 1 Diabetes. Diabetes, 58: 652-662, 2009.

Anurathapan et al., "Engineered T cells for cancer treatment," Cytotherapy, vol. 16, pp. 713-733, 2014.

Aronowski J, Samways E, Strong R, Rhoades HM, Grotta JC. An alternative method for the quantitation of neuronal damage after experimental middle cerebral artery occlusion in rats: Analysis of behavioral deficit. Journal of cerebral blood flow and metabolism : official journal of the International Society of Cerebral Blood Flow and Metabolism. 1996;16:705-713.

Arrigoni, Chiara, et al. "Rotating versus perfusion bioreactor for the culture of engineered vascular constructs based on hyaluronic acid." Biotechnology and bioengineering 100.5 (2008): 988-997.

Azar, Toni, Jody Sharp, and David Lawson. "Heart rates of male and female Sprague-Dawley and spontaneously hypertensive rats housed singly or in groups." Journal of the American Association for Laboratory Animal Science 50.2 (2011): 175-184.

Baecher-Allan, Clare, et al. "CD4+ CD25high regulatory cells in human peripheral blood." The Journal of Immunology 167.3 (2001): 1245-1253.

Bai/Delaney (Nohla Therapeutics) showed that expanding Cord Blood-derived CD34+CD38-CD45RA-HSPCs in a biodegradable zwitterionic hydrogel with a rNotch ligand cocktail for 24 days mitigated HSPC differentiation and promoted self-renewal of lymphoid and myeloid cell phenotypes in an NSG mouse model (Nature Medicine, 2019).

Ballas CB, Zielske SP, Gerson SL (2002) Adult bone marrow stem cells for cell and gene therapies: implications for greater use. J Cell Biochem Suppl 38: 20-28.

Ballke C, Gran E, Baekkevold ES, Jahnsen FL. Characterization of Regulatory T-Cell Markers in CD4+ T Cells of the Upper Airway Mucosa. PLoS One. 2016;11(2):e0148826.

Baraniak PR, McDevitt TC (2010) Stem cell paracrine actions and tissue regeneration. Regen Med 5(1): 121-143.

Barckhausen C, Rice B, Baila S, et al. (2016) GMP-Compliant Expansion of Clinical-Grade Human Mesenchymal Stromal/Stem Cells Using a Closed Hollow Fiber Bioreactor. Methods Mol Biol 1416: 389-412.

Barker et al. "CD34+ Cell Content of 126 341 Cord Blood Units in the US Inventory: Implications for Transplantation and Banking," blood Advances, vol. 3, No. 8, pp. 1267-1271, Apr. 23, 2019.

Bazarian JJ, Cernak I, Noble-Haeusslein L, Potolicchio S, Temkin N. Long-term neurologic outcomes after traumatic brain injury. The Journal of head trauma rehabilitation. 2009;24:439-451.

Bending D, Pesenacker AM, Ursu S, Wu Q, Lom H, Thirugnanabalan B, Wedderburn LR. Hypomethylation at the regulatory T cell-specific demethylated region in CD25hi T cells is decoupled from FOXP3 expression at the inflamed site in childhood arthritis. J Immunol. 2014;193(6):2699-708.

Berendse M, Grounds MD, Lloyd CM (2003) Myoblast structure affects subsequent skeletal myotube morphology and sarcomere assembly. Exp Cell Res 291(2): 435-450.

Bernard, A., Payton, Mark 1995. "Fermentation and Growth of Escherichia coli for Optimal Protein Production", John Wiley & Sons. Current Protocols in Protein Science (1995) 5.3.1-5.3.18.

Berney SM, Schaan T, Wolf RE, van der Heyde H, Atkinson TP. CD2 (OKT11) augments CD3-mediated intracellular signaling events in human T lymphocytes. J Investig Med. 2000;48(2):102-9.

Bioheart Clinical Trial Clinica 1302 Apr. 18, 2008.

Biomolecular and Cellular Interactions with the Hollow Fiber Membrane Currently Used in the Quantum® Cell Expansion System. 12th NJ Symposium on Biomaterials Science, Oct. 6-7, 2014, New Brunswick, NJ.

Blache C, Chauvin JM, Marie-Cardine A, Contentin N, Pommier P, Dedreux I, Francois S, Jacquot S, Bastit D, Boyer O. Reduced frequency of regulatory T cells in peripheral blood stem cell compared to bone marrow transplantations. Biol Blood Marrow Transplant. 2010;16(3):430-4.

Bluestone et al. Type 1 diabetes immunotherapy using polyclonal regulatory T cells. Science Translational Medicine 7(315):1-34, 2015.

(56)         References Cited

OTHER PUBLICATIONS

Bluestone JA, Tang Q. Treg cells-the next frontier of cell therapy. Science. 2018;362(6411):154-155.

Blum S, Moore AN, Adams F, Dash PK. A mitogen-activated protein kinase cascade in the ca1/ca2 subfield of the dorsal hippocampus is essential for long-term spatial memory. The Journal of neuroscience : the official journal of the Society for Neuroscience. 1999;19:3535-3544.

Boitano, Anthony E., et al. "Aryl hydrocarbon receptor antagonists promote the expansion of human hematopoietic stem cells." Science 329.5997 (2010): 1345-1348.

Bojun Li et al. Heparin-induced conformation changes of fibronectin within the extracellular matrix promote hMSC osteogenic differentiation. Biomaterials Science 3: 73-84, 2015.

Boquest AC, Shahdadfar A, Brinchmann JE, Collas P. Isolation of Stromal Stem Cells from Human Adipose Tissue. Methods Mol Biol. 2006;325:35-46. doi: 10.1385/1-59745-005-7:35. PMID: 16761717.

Borden, M. and Longo, M., "Dissolution Behavior of Lipid Monolayer-Coated, Air-Filled Microbubbles: Effect of Lipid Hydrophobic Chain Length," Langmuir, vol. 18, pp. 9225-9233, 2002.

Bourke, Sharon L., and Joachim Kohn. "Polymers derived from the amino acid L-tyrosine: polycarbonates, polyarylates and copolymers with poly (ethylene glycol)." Advanced drug delivery reviews 55.4 (2003): 447-466.

Brand, K. and Hermfisse, U., "Aerobic Glycolysis by Proliferating Cells: a Protective Strategy against Reactive Oxygen Species," The FASEB Journal, vol. 11, pp. 388-395, Apr. 1997.

Brentjens et al., "CD19-Targeted T Cells Rapidly Induce Molecular Remission in Adults with Chemotherapy-Refractory Acute Lympohblastic Leukemia," Science Translational Medicine, vol. 5, Issue 177, pp. 1-9, Mar. 20, 2013.

Brentjens et al., "Safety and Persistance of Adoptively Transferred Autologous CD19-Target T Cells in Patients with Relapsed or Chemotherapy Refractory B-Cell Leukemias," Blood, vol. 118, No. 18, pp. 4817-4828, Nov. 3, 2011.

Brunstein C, Miller J, Cao Q, McKenna D, Hippen K, Curtsinger J, DeFor T, Levine B, June C, Rubinstein P, McGlave P, Blazar B, Wagner J. Infusion of ex vivo expanded T regulatory cells in adults transplanted with umbilical cord blood: safety profile and detection kinetics. Blood 2011; 117(3):1061-1070.

C. H. Weaver, et al. An Analysis of Engraftment Kinetics as a function of the CD34 Content of the Peripheral Blood Progenitor Cell Collections in 692 Patients After the Administration of Myeloblative Chemotherapy. Blood 86(10):3691-3969, 1995.

Cano, Àngels, Cristina Minguillón, and Cristina Palet. "Immobilization of endo-1, 4-β-xylanase on polysulfone acrylate membranes: Synthesis and characterization." Journal of membrane science 280. 1-2 (2006): 383-388.

Carswell, K. and Papoutsakis, E. "Culture of Human T Cells in Stirred Bioreactors for Cellular Immunotherapy Applications: Shear, Proliferation, and the IL-2 Receptor," Biotechnology and Bioengineering, vol. 68, No. 3, pp. 329-338, May 5, 2000.

Celeste Nelson et al., Emergent patterns of growth controlled by multicellular form and mechanics, (in Christopher Chen's Lab demonstrated, in separate experiments, that curved surfaces with a radius of curvature (200?m) that is greater than the cell diameter and surfaces that have undulating special patterning (depressions) increase the patterned growth of ECs [PNAS 102(33): 11594-11599, 2005].

Chapman NM, Chi H. mTOR signaling, Tregs and immune modulation. Immunotherapy. 2014;6(12):1295-311.

Chaudhry A, Samstein RM, Treuting P, Liang Y, Pils MC, Heinrich JM, Jack RS, Wunderlich FT, Bruning JC, Muller W, Rudensky AY. Interleukin-10 signaling in regulatory T cells is required for suppression of Th17 cell-mediated inflammation. Immunity. 2011;34(4):566-78.

Chen, C. and Broden, M., "The Role of Poly(theylene glycol) Brush Architecture in Complement Activation on Targeted Microbubble Surfaces," Biomaterials, vol. 32, No. 27, pp. 6579-6587, Jun. 17, 2011.

Choi W, Kwon SJ, Jin HJ, et al. (2017) Optimization of culture conditions for rapid clinical-scale expansion of human umbilical cord blood-derived mesenchymal stem cells. Clin Transl Med 6(1): 38.

Chullikana A, Majumdar AS, Gottipamula S, et al. (2015) Randomized, double-blind, phase I/II study of intravenous allogeneic mesenchymal stromal cells in acute myocardial infarction. Cytotherapy 17(3): 250-261.

Coeshott C, Vang B, Jones M, Nankervis B. Large-scale expansion and characterization of CD3(+) T-cells in the Quantum((R)) Cell Expansion System. J Transl Med. 2019;17(1):258.

Coombes JL, Robinson NJ, Maloy KJ, Uhlig HH, Powrie F. Regulatory T cells and intestinal homeostasis. Immunol Rev. 2005;204:184-94.

Coquillard C. mTOR Signaling in Regulatory T cell Differentiation and Expansion. SOJ Immunology. 2015;3(1):1-10.

Hogstedt, Benkt, Anita Karlsson, and Anders Holmen. "Frequency and size distribution of micronuclei in lymphocytes stimulated with phytohemagglutinin and pokeweed mitogen in workers exposed to piperazine." Hereditas 109.(1988): 139-142.

Hollyman et al., "Manufacturing Validation of Biologicall Functional T Cells Targeted to CD19 Antigen for Autologous Adoptive Cell Therapy," J Immunother, vol. 32, No. 2, pp. 169-180, Feb.-Mar. 2009.

http://www.ucdenver.edu/academics/colleges/medicalschool/centers/cancercenter/Research/sharedresources/AnimalImaging/smal-lanimalimaging/Pages/MRI.aspx.

SCT Webinar "Volume Reduction technology for Large Scale Harvest or Post-thaw Manipulation of Cellular Therapeutics". Feb. 8, 2012, 60 pages.

Itkin, Tomer, and Tsvee Lapidot. "SDF-1 keeps HSC quiescent at home." Blood, The Journal of the American Society of Hematology 117.2 (2011): 373-374.

Iwashima, Shigejiro, et al. "Novel culture system of mesenchymal stromal cells from human subcutaneous adipose tissue." Stem cells and development 18.4 (2009): 533-544.

Jang, Eugene, et al. "Syndecan-4 proteoliposomes enhance fibroblast growth factor-2 (FGF-2)-induced proliferation, migration, and neovascularization of ischemic muscle." Proceedings of the National Academy of Sciences 109.5 (2012): 1679-1684.

Jarocha D, Stangel-Wojcikiewicz K, Basta A, Majka M (2014) Efficient myoblast expansion for regenerative medicine use. Int J Mol Med 34(1): 83-91.

Jo CH, Lee YG, Shin WH, et al. (2014) Intra-articular injection of mesenchymal stem cells for the treatment of osteoarthritis of the knee: a proof-of-concept clinical trial. Stem Cells 32(5): 1254-1266.

Johansson, Ulrika, et al. "Pancreatic islet survival and engraftment is promoted by culture on functionalized spider silk matrices." PloS one 10.6 (2015): e0130169.

John Carvell, et al. Monitoring Live Biomass in Disposable Bioreactors, BioProcess International 14(3)s, Mar. 2016.

John Nicolette, et al (Abbott Laboratories). In Vitro Micronucleus Screening of Pharmaceutical Candidates by Flow Cyto9metry in Chinese Hamster V79 Cells, Environmental and Molecular Mutagenesis 00:000-000, 2010.

John P. Carvell and Jason E. Dowd. On-line measurements and control of viable cell density in cell culture manufacturing processes using radio frequency impedance. Cytotechnology 50: 35-48, 2006.

Johnson, Patrick A., et al. "Interplay of anionic charge, poly (ethylene glycol), and iodinated tyrosine incorporation within tyrosine? derived polycarbonates: Effects on vascular smooth muscle cell adhesion, proliferation, and motility." Journal of Biomedical Materials Research Part A: An Official Journal of The Society for Biomaterials, The Japanese Society for Biomaterials, and The Australian Society for Biomaterials and the Korean Society for Biomaterials 93.2 (2010): 505-514.

Johnston LC, Su X, Maguire-Zeiss K, Horovitz K, Ankoudinova I, Guschin D, Hadaczek P, Federoff HJ, Bankiewicz K, Forsayeth J. Human interleukin-10 gene transfer is protective in a rat model of Parkinson's disease. Mol Ther. 2008;16(8):1392-9.

Jones M, Varella-Garcia M, Skokan M, et al. (2013) Genetic stability of bone marrow-derived human mesenchymal stromal cells in the Quantum System. Cytotherapy 15(11): 1323-1339.

(56) References Cited

OTHER PUBLICATIONS

Jones2016ISCT 2016 Poster 69.

Joy, Abraham, et al. "Control of surface chemistry, substrate stiffness, and cell function in a novel terpolymer methacrylate library." Langmuir 27.5 (2011): 1891-1899.

Kalamasz et al., "Optimization of Human T-Cell Expansion Ex Vivo Using Magnetic Beads Conjugated with Anti-CD3 and Anti-CD28 Antibodies," J Immunother, vol. 27, No. 5, pp. 405-418, Sep.-Oct. 2004.

Klapper et al., "Single-Pass, Closed-System Rapid Expansion of Lymphocyte Cultures for Adoptive Cell Therapy," Journal of Immunological Methods, 345, pp. 90-99, Apr. 21, 2009.

Klein, Elias, Eva Eichholz, and Don H. Yeager. "Affinity membranes prepared from hydrophilic coatings on microporous polysulfone hollow fibers." Journal of membrane science 90.1-2 (1994): 69-80.

Korpanty et al., "Tageting Vascular Enothelium with Avidin Microbubbles," Ultrasound in Medicine and Biology, vol. 31, No. 9, pp. 1279-1283, May 24, 2005.

Krauss et al., "Signaling Takes a Breath—New Quantitative Perspectives on Bioenergetics and Signal Transduction," Immunity, vol. 15, pp. 497-502, Oct. 2001.

Kulikov, A. V., et al. "Application of multipotent mesenchymal stromal cells from human adipose tissue for compensation of neurological deficiency induced by 3-nitropropionic acid in rats." Bulletin of experimental biology and medicine 145.4 (2008): 514-519.

Kumar P, Marinelarena A, Raghunathan D, Ragothaman VK, Saini S, Bhattacharya P, Fan J, Epstein AL, Maker AV, Prabhakar BS. Critical role of OX40 signaling in the TCR-independent phase of human and murine thymic Treg generation. Cell Mol Immunol. 2019; 16(2):138-153.

Kwan, J. and Borden, M., "Lipid Monolayer Collapse and Microbubble Stability," Advances in Colloid and Interface Science, vols. 183-184, pp. 82-99, Aug. 21, 2012.

Lee et al., "Continued Antigen Stimulation Is Not Required During CD4+ T Cell Clonal Expansion," The Journal of Immunology, 168, pp. 1682-1689, 2002.

Lee, Jae W., et al. "Allogeneic human mesenchymal stem cells for treatment of E. coli endotoxin-induced acute lung injury in the ex vivo perfused human lung." Proceedings of the national academy of Sciences 106.38 (2009): 16357-16362.

Levine, B., "T Lymphocyte Engineering ex vivo for Cancer and Infectious Disease," Expert Opinion on Biological Therapy, vol. 4, No. 4, pp. 475-489, 2008.

Lum et al., "Ultrasound Radiation Force Enables Targeted Deposition of Model Drug Carriers Loaded on Microbubbles," Journal of Controlled Release, 111, pp. 128-134, 2006.

M. R. Koller, et al. Clinical-scale human umbilical cord blood cell expansion in a novel automated perfusion culture system. Bone Marrow Transplantion 21:653-663, 1998.

Malin, Stephen F., et al. "Noninvasive prediction of glucose by near-infrared diffuse reflectance spectroscopy." (1999): 1651-1658.

Malone et al., "Characterization of Human Tumor-Infiltrating Lymphocytes Expanded in Hollow-Fiber Bioreactors for Immunotherapy of Cancer," Cancer Biotherapy & Radiopharmaceuticals, vol. 16, No. 5, pp. 381-390, 2001.

Mao AS, Mooney DJ (2015) Regenerative medicine: current therapies and future directions. Proc Natl Acad Sci USA 112(47): 14452-14459.

Marek-Trzonkowska, Natalia, et al. "Administration of CD4+ CD25highCD127-regulatory T cells preserves β-cell function in type 1 diabetes in children." Diabetes care 35.9 (2012): 1817-1820.

Maria Streltsova, Dean Lee (Nationwide Children's Hospital, OSU, Columbus, OH) et al (Int'l Journal of Molecular Sciences, 2019).

Markgraf CG, Clifton GL, Aguirre M, Chaney SF, Knox-Du Bois C, Kennon K, Verma N. Injury severity and sensitivity to treatment after controlled cortical impact in rats. Journal of neurotrauma. 2001;18:175-186.

Mathew et al. A Phase I Clinical Trials I with Ex Vivo Expanded Recipient Regulatory T cells in Living Donor Kidney Transplants. Nature, Scientific Reports 8:7428 (1-12), 2018.

Matthay, Michael A., et al. "Therapeutic potential of mesenchymal stem cells for severe acute lung injury." Chest 138.4 (2010): 965-972.

Maynard CL, Harrington LE, Janowski KM, Oliver JR, Zindl CL, Rudensky AY, Weaver CT. Regulatory T cells expressing interleukin 10 develop from Foxp3+ and Foxp3-precursor cells in the absence of interleukin 10. Nat Immunol. 2007;8(9):931-41.

McKenna DH, Jr., Sumstad D, Kadidlo DM, et al. Optimization of cGMP purification and expansion of umbilical cord blood-derived T-regulatory cells in support of first-in-human clinical trials. Cytotherapy 2017;19:250-62.

McLimans W, Kinetics of Gas Diffusion in Mammalian Cell Culture Systems. Biotechnology and Bioengineering 1968; 10:725-740.

McMurtrey, Richard J. "Analytic models of oxygen and nutrient diffusion, metabolism dynamics, and architecture optimization in three-dimensional tissue constructs with applications and insights in cerebral organoids." Tissue Engineering Part C: Methods 22.3 (2016): 221-249.

Menge, Tyler, et al. "Mesenchymal stem cells regulate blood-brain barrier integrity through TIMP3 release after traumatic brain injury." Science translational medicine 4.161 (2012): 161ra150-161ra150.

Miska J, Lee-Chang C, Rashidi A, Muroski ME, Chang AL, Lopez-Rosas A, Zhang P, Panek WK, Cordero A, Han Y, Ahmed AU, Chandel NS, Lesniak MS. HIF-1alpha Is a Metabolic Switch between Glycolytic-Driven Migration and Oxidative Phosphorylation-Driven Immunosuppression of Tregs in Glioblastoma. Cell Rep. 2019;27(1):226-237 e4.

Miyara M, Yoshioka Y, Kitoh A, Shima T, Wing K, Niwa A, Parizot C, Taflin C, Heike T, Valeyre D, Mathian A, Nakahata T, Yamaguchi T, Nomura T, Ono M, Amoura Z, Gorochov G, Sakaguchi S. Functional delineation and differentiation dynamics of human CD4+ T cells expressing the FoxP3 transcription factor. Immunity. 2009;30(6):899-911.

Murugappan, G., et al. "Human hematopoietic progenitor cells grow faster under rotational laminar flows." Biotechnology progress 26.5 (2010): 1465-1473.

Nankervis B, Jones M, Vang B et al. (2018) Optimizing T Cell Expansion in a Hollow-Fiber Bioreactor. Curr Stem Cell Rep. Advanced online publication. https://doi.org/10.1007/s40778-018-0116-x.

Nankervis, Brian, et al. "Optimizing T cell expansion in a hollow-fiber bioreactor." Current Stem Cell Reports 4.1 (2018): 46-51.

Nedoszytko B, Lange M, Sokolowska-Wojdylo M, Renke J, Trzonkowski P, Sobjanek M, Szczerkowska-Dobosz A, Niedoszytko M, Gorska A, Romantowski J, Czarny J, Skokowski J, Kalinowski L, Nowicki R. The role of regulatory T cells and genes involved in their differentiation in pathogenesis of selected inflammatory and neoplastic skin diseases. Part II: The Treg role in skin diseases pathogenesis. Postepy Dermatol Alergol. 2017;34(5):405-417.

Nehlin JO, Just M, Rustan AC (2011) Human myotubes from myoblast cultures undergoing senescence exhibit defects in glucose and lipid metabolism. Biogerontology 12: 349-365.

Unknown author, "New Victories for Adult Stem Cell Research," New York, Feb. 6, 2007.

Newton R, Priyadharshini B, Turka LA. Immunometabolism of regulatory T cells. Nat Immunol. 2016;17(6):618-25.

Ng TH, Britton GJ, Hill EV, Verhagen J, Burton BR, Wraith DC. Regulation of adaptive immunity; the role of interleukin-10. Front Immunol. 2013;4:129.

Nikolaychik, V. V., M. M. Samet, and P. I. Lelkes. "A New, Cryoprecipitate Based Coating For Improved Endothelial Cell Attachment And Growth On Medical Grade Artificial Surfaces." ASAIO Journal (American Society for Artificial Internal Organs: 1992) 40.3 (1994): M846-52.

Nish SA, Schenten D, Wunderlich FT, Pope SD, Gao Y, Hoshi N, Yu S, Yan X, Lee HK, Pasman L, Brodsky I, Yordy B, Zhao H, Bruning J, Medzhitov R. T cell-intrinsic role of IL-6 signaling in primary and memory responses. Elife. 2014;3: e01949.

(56)             References Cited

OTHER PUBLICATIONS

Niwayama, Jun, et al. "Analysis of hemodynamics during blood purification therapy using a newly developed noninvasive continuous monitoring method." Therapeutic Apheresis and Dialysis 10.4 (2006): 380-386.

Nugent, Helen M., et al. "Adventitial endothelial implants reduce matrix metalloproteinase-2 expression and increase luminal diameter in porcine arteriovenous grafts." Journal of vascular surgery 46.3 (2007): 548-556.

Okano et al (Tokyo Women's Medical College, Japan) demonstrated the recovery of endothelial cells and hepatocytes from plasma-treated polystyrene dishes grafted with PNIAAm (Journal of Biomedical Materials Research, 1993).

Onishi Y, Fehervari Z, Yamaguchi T, Sakaguchi S. Foxp3+ natural regulatory T cells preferentially form aggregates on dendritic cells in vitro and actively inhibit their maturation. Proc Natl Acad Sci U S A. 2008;105(29):10113-8.

Onyszchuk G, LeVine SM, Brooks WM, Berman NE. Post-acute pathological changes in the thalamus and internal capsule in aged mice following controlled cortical impact injury: A magnetic resonance imaging, iron histochemical, and glial immunohistochemical study. Neuroscience letters. 2009;452:204-208.

Pacella I, Procaccini C, Focaccetti C, Miacci S, Timperi E, Faicchia D, Severa M, Rizzo F, Coccia EM, Bonacina F, Mitro N, Norata GD, Rossetti G, Ranzani V, Pagani M, Giorda E, Wei Y, Matarese G, Barnaba V, Piconese S. Fatty acid metabolism complements glycolysis in the selective regulatory T cell expansion during tumor growth. Proc Natl Acad Sci U S A. 2018;115(28):E6546-E6555.

Parhi, Purnendu, Avantika Golas, and Erwin A. Vogler. "Role Of Proteins And Water In The Initial Attachment Of Mammalian Cells To Biomedical Surfaces: A Review." Journal of Adhesion Science and Technology 24.5 (2010):853-888.

Pati S, Gerber MH, Menge TD, Wataha KA, Zhao Y, Baumgartner JA, Zhao J, Letourneau PA, Huby MP, Baer LA, Salsbury JR, Kozar RA, Wade CE, Walker PA, Dash PK, Cox CS, Jr., Doursout MF, Holcomb JB. Bone marrow derived mesenchymal stem cells inhibit inflammation and preserve vascular endothelial integrity in the lungs after hemorrhagic shock. PloS one. 2011;6:e25171.

Pati S, Khakoo AY, Zhao J, Jimenez F, Gerber MH, Harting M, Redell JB, Grill R, Matsuo Y, Guha S, Cox CS, Reitz MS, Holcomb JB, Dash PK. Human mesenchymal stem cells inhibit vascular permeability by modulating vascular endothelial cadherin/beta-catenin signaling. Stem cells and development. 2011;20:89-101.

Peters JH, Preijers FW, Woestenenk R, Hilbrands LB, Koenen HJ, Joosten I. Clinical grade Treg: GMP isolation, improvement of purity by CD127 Depletion, Treg expansion, and Treg cryopreservation. PLoS One. 2008;3(9):e3161.

Peters, R.; Jones, M.; Brecheisen, M.; Startz, T.; Vang, B.; Nankervis, B.; Frank, N.; Nguyen, K. (2012) TerumoBCT. https://www.terumobct.com/location/north-america/products-and-services/Pages/Quantum-Materials.aspx.

Porter CM, Horvath-Arcidiacono JA, Singh AK, Horvath KA, Bloom ET, Mohiuddin MM. Characterization and expansion of baboon CD34+CD25+ Treg cells for potential use in a non-human primate xenotransplantation model. Xenotransplantation. 2007;14(4):298-308.

Povsic TJ, O'Connor CM, Henry T, et al. (2011) A double-blind, randomized, controlled, multicenter study to assess the safety and cardiovascular effects of skeletal myoblast implantation by catheter delivery in patients with chronic heart failure after myocardial infarction. Am Heart J 162(4): 654-662.

Prockop, Darwin J., Carl A. Gregory, and Jeffery L. Spees. "One strategy for cell and gene therapy: harnessing the power of adult stem cells to repair tissues." Proceedings of the National Academy of Sciences 100.suppl_1 (2003):11917-11923.

Q. L. Hao, et al. A functional comparison of CD34+ CD38= cells in cord blood and bone marrow. Blood 86:3745-3753, 1995.

Rahmahwati, Nurlaela, Deana Wahyuningrum, and Anita Alni. "The Synthesis Of Polyethersulfone (PES) Derivatives For The Immobilization Of Lipase Enzyme." Key Engineering Materials. vol. 811. Trans Tech Publications Ltd, 2019.

Rey-Jurado, Emma, et al. "Assessing the importance of domestic vaccine manufacturing centers: an overview of immunization programs, vaccine manufacture, and distribution." Frontiers in immunology 9 (2018): 26.

Roballo KC, Dhungana S, Z. J, Oakey J, Bushman J. Localized delivery of immunosuppressive regulatory T cells to peripheral nerve allografts promotes regeneration of branched segmental defects. Biomaterials. 2019;209:1-9.

Rodrigues, C., Fernandes, T., Diogo, M., Lobato da Silva, C., Cabral, J. Stem Cell Cultivation in Bioreactors. 2011. Biotechnology Advances v. 29, pp. 815-829.

Ronco C1, Levin N, Brendolan A, Nalesso F, Cruz D, Ocampo C, Kuang D, Bonello M, De Cal M, Corradi V, Ricci Z. Flow distribution analysis by helical scanning in polysulfone hemodialyzers: effects of fiber structure and design on flow patterns and solute clearances. Hemodial Int. Oct. 2006; 10(4):380-8.

Ronco, C., Brendolan, A., Crepaldi, C., Todighiero, M., Scabardi, M. Blood and Dialysate Flow Distributions in Hollow-Fiber Hemodialyzers Analyzed by Computerized Helical Scanning Technique. 2002. Journal of the American Society of Nephrology. V. 13, pp. S53-S61.

Rosenblum MD, Way SS, Abbas AK. Regulatory T cell memory. Nat Rev Immunol. 2016;16(2):90-101.

Rubtsov YP, Rasmussen JP, Chi EY, Fontenot J, Castelli L, Ye X, Treuting P, Siewe L, Roers A, Henderson WR, Jr., Muller W, Rudensky AY. Regulatory T cell-derived interleukin-10 limits inflammation at environmental interfaces. Immunity. 2008;28(4):546-58.

Rudensky, Alexander Y. "Regulatory T cells and Foxp3." Immunological reviews 241.1 (2011): 260-268.

Ryu, Min-Hyung, and Mark Gomelsky. "Near-infrared light responsive synthetic c-di-GMP module for optogenetic applications." ACS synthetic biology 3.11 (2014): 802-810.

S. Koestenbauer, et al. Protocols for Hematopoietic Stem Cell Expansion from Umbilical Cord Blood. Cell Transplantation 18: 1059-1068, 2009.

S. L. Smith, et al. Expansion of neutrophil precursors and progenitors in suspension cultures of CD34+ cells enriched from human bone marrow. Experimental Hematology 21:870-877, 1993.

Safinia N, Grageda N, Scotta C, Thirkell S, Fry LJ, Vaikunthanathan T, Lechler RI, Lombardi G. Cell Therapy in Organ Transplantation: Our Experience on the Clinical Translation of Regulatory T Cells. Front Immunol. 2018;9:354.

Sahay A, Scobie KN, Hill AS, O'Carroll CM, Kheirbek MA, Burghardt NS, Fenton AA, Dranovsky A, Hen R. Increasing adult hippocampal neurogenesis is sufficient to improve pattern separation. Nature. 2011;472:466-470.

Sakaguchi S, Sakaguchi N, Asano M, Itoh M, Toda M. Immunologic self-tolerance maintained by activated T cells expressing IL-2 receptor alpha-chains (CD25). Breakdown of a single mechanism of self-tolerance causes various autoimmune diseases. J Immunol. 1995;155(3):1151-64.

Sakaguchi S, Sakaguchi N, Shimizu J, Yamazaki S, Sakihama T, Itoh M, Kuniyasu Y, Nomura T, Toda M, Takahashi T. Immunologic tolerance maintained by CD25+ CD4+ regulatory T cells: their common role in controlling autoimmunity, tumor immunity, and transplantation tolerance. Immunol Rev. 2001;182:18-32.

Schild, Howard G. "Poly (N-isopropylacrylamide): experiment, theory and application." Progress in polymer science 17.2 (1992): 163-249.

Schmitz R, Alessio A, Kina P. The Physics of PET/CT scanners. Imaging Research Laboratory, Department of Radiology, University of Washington http://depts.washington.edu/imreslab/education/Physics%20of%20PET.pdf, 2013, 16 pages.

Schwartz RH. T cell anergy. Annu Rev Immunol. 2003;21:305-34.

Shevkoplyas et al., "The Force Acting on a Superparamagnetic Bead due to an Applied Magnetic Field," Lab on a Chip, 7, pp. 1294-1302, 2007.

Shimazu Y, Shimazu Y, Hishizawa M, Hamaguchi M, Nagai Y, Sugino N, Fujii S, Kawahara M, Kadowaki N, Nishikawa H, Sakaguchi S, Takaori-Kondo A. Hypomethylation of the Treg-

(56)     References Cited

OTHER PUBLICATIONS

Specific Demethylated Region in FOXP3 Is a Hallmark of the Regulatory T-cell Subtype in Adult T-cell Leukemia. Cancer Immunol Res. 2016;4(2):136-45.

Shimizu et all., "Fabrication of Pulsatile Cardiac Tissue Grafts Using a Novel 3-Dimensional Cell Sheet Manipulation Technique and Temperature-Responsive Cell Culture Surfaces," Circulation Research, vol. 90, Feb. 22, 2022, e40-e48, pp. 1-9.

Sigma-Aldrich Cheimcals Mitomycin C (M4287) MSDS, v4.4, Jul. 7, 2011.

Sirsi, S. and Borden, M., "Microbubble Composition, Properties, and Biomedical Applications," Bubble Science, Engineering & Technolology, vol. 1, No. 1-2, pp. 3-17, 2009.

Smith C, Okern G, Rehan S, et al. Ex vivo expansion of human T cells for adoptive immunotherapy using the novel Xeno-free CTS Immune Cell Serum Replacement. Clinical & Translational Immunology 2015;4:e31.

Somerville et al., "Clinical Scale Rapid Expansion of Lymphocytes for Adoptive Cell Transfer Therapy in the WAVE® Bioreactor," Journal of Translational Medicine, vol. 10, No. 69, pp. 1-11, 2012.

Somerville, R. and Dudley, M., "Bioreactors Get Personal," OncoImmunology, vol. 1, No. 8, pp. 1435-1437, Nov. 2012.

Spectrum Labs KrosFlo Research IIi TFF System, 2013, Spectrum Laboratories, Inc., 4 pages.

Stafano Tiziani, et al. Metabolomic Profiling of Drug Response in Acute Myeloid Leukaemia Cell lines. PLOSone 4(1):e4251 (Jan. 22, 2009).

Creed JA, DiLeonardi AM, Fox DP, Tessler AR, Raghupathi R. Concussive brain trauma in the mouse results in acute cognitive deficits and sustained impairment of axonal function. Journal of neurotrauma. 2011;28:547-563.

Cuchiara, Maude L., et al. "Covalent immobilization of stem cell factor and stromal derived factor 1a for in vitro culture of hematopoietic progenitor cells." Acta biomaterialia 9.12 (2013): 9258-9269.

Da Silva, Ricardo MP, Joao F. Mano, and Rui L. Reis. "Smart thermoresponsive coatings and surfaces for tissue engineering: switching cell-material boundaries." Trends in Biotechnology 25.12 (2007): 577-583.

Dash PK, Hochner B, Kandel ER. Injection of the camp-responsive element into the nucleus of aplysia sensory neurons blocks long-term facilitation. Nature. 1990;345:718-721.

Dash PK, Johnson D, Clark J, Orsi SA, Zhang M, Zhao J, Grill RJ, Moore AN, Pati S. Involvement of the glycogen synthase kinase-3 signaling pathway in tbi pathology and neurocognitive outcome. PloS one. 2011;6:e24648.

Dash PK, Mach SA, Blum S, Moore AN. Intrahippocampal wortmannin infusion enhances long-term spatial and contextual memories. Learn Mem. 2002;9:167-177.

Dash PK, Orsi SA, Zhang M, Grill RJ, Pati S, Zhao J, Moore AN. Valproate administered after traumatic brain injury provides neuroprotection and improves cognitive function in rats. PloS one. 2010;5:e11383.

Dash PK, Zhao J, Orsi SA, Zhang M, Moore AN. Sulforaphane improves cognitive function administered following traumatic brain injury. Neuroscience letters. 2009;460:103-107.

Davila et al., "Efficacy and Toxicity Management of 19-28z CAR T Cell Therapy in B cell Acute Lymphoblastic Leukemia," Science Translational Medicine, vol. 6, No. 224, pp. 1-10, Feb. 19, 2014.

Dejana E, Orsenigo F, Lampugnani MG. The role of adherens junctions and ve-cadherin in the control of vascular permeability. Journal of cell science. 2008;121:2115-2122.

Dejana E, Spagnuolo R, Bazzoni G. Interendothelial junctions and their role in the control of angiogenesis, vascular permeability and leukocyte transmigration. Thrombosis and haemostasis. 2001;86:308-315.

Dejana E, Tournier-Lasserve E, Weinstein BM. The control of vascular integrity by endothelial cell junctions: Molecular basis and pathological implications. Developmental cell. 2009;16:209-221.

Del Pino A, Ligero G, Lopez MB, et al. (2015) Morphology, cell viability, karyotype, expression of surface markers and plasticity of three primary cell line cultures before and after the cryostorage in LN2 and GN2. Cryobiology 70(1): 1-8.

Delaney, Colleen, et al. "Notch-mediated expansion of human cord blood progenitor cells capable of rapid myeloid reconstitution." Nature medicine 16.2 (2010): 232-236.

Ding, Zhongli, Guohua Chen, and Allan S. Hoffman. "Synthesis and purification of thermally sensitive oligomer? enzyme conjugates of poly (N-isopropylacrylamide)? trypsin." Bioconjugate chemistry 7.1 (1996): 121-125.

Dixon CE, Clifton GL, Lighthall JW, Yaghmai AA, Hayes RL. A controlled cortical impact model of traumatic brain injury in the rat. Journal of neuroscience methods. 1991;39:253-262.

Dominici M, Le Blanc K, Mueller I, et al. (2006) Minimal criteria for defining multipotent mesenchymal stromal cells. The International Society for Cellular Therapy position statement. Cytotherapy 8(4): 315-317.

Durrani S, Konoplyannikov M, Ashraf M, Haider KH (2010) Skeletal myoblasts for cardiac repair. Regen Med 5(6): 919-932.

Esensten JH, Muller YD, Bluestone JA, Tang Q. Regulatory T-cell therapy for autoimmune and autoinflammatory diseases: The next frontier. J Allergy Clin Immunol. 2018;142(6):1710-1718.

Fakin R, Hamacher J, Gugger M, Gazdhar A, Moser H, Schmid RA. Prolonged amelioration of acute lung allograft rejection by sequential overexpression of human interleukin-10 and hepatocyte growth factor in rats. Exp Lung Res. 2011;37(9):555-62.

Fedorov et al., "PD-1- and CTLA-4-Based Inhibitory Chimeric Antigen Receptors (iCARs) Divert Off-Target Immunotherapy Responses," Science Translational Medicine, vol. 5, No. 215, pp. 1-12, Dec. 11, 2013.

Ferreira LMR, Muller YD, Bluestone JA, Tang Q. Next-generation regulatory T cell therapy. Nat Rev Drug Discov. 2019;18(10):749-769.

Fischbach, Michael A., Jeffrey A. Bluestone, and Wendell A. Lim. "Cell-based therapeutics: the next pillar of medicine." Science translational medicine 5.179 (2013): 179ps7-179ps7.

Fisk, Nicholas M., et al. "Can routine commercial cord blood banking be scientifically and ethically justified?." PLoS medicine 2.2 (2005): e44.

Forbes Jun. 23, 2014 article "Will this man cure cancer?".

Fowler DH. Rapamycin-resistant effector T-cell therapy. Immunol Rev. 2014;257(1):210-25.

Fraser H, Safinia N, Grageda N, Thirkell S, Lowe K, Fry LJ, Scotta C, Hope A, Fisher C, Hilton R, Game D, Harden P, Bushell A, Wood K, Lechler RI, Lombardi G. A Rapamycin-Based GMP-Compatible Process for the Isolation and Expansion of Regulatory T Cells for Clinical Trials. Mol Ther Methods Clin Dev. 2018;8:198-209.

Frauwirth KA, Riley JL, Harris MH, Parry RV, Rathmell JC, Plas DR, Elstrom RL, June CH, Thompson CB. The CD28 signaling pathway regulates glucose metabolism. Immunity. 2002;16(6):769-77.

Fuchs A, Gliwinski M, Grageda N, Spiering R, Abbas AK, Appel S, Bacchetta R, Battaglia M, Berglund D, Blazar B, Bluestone JA, Bornhauser M, Ten Brinke A, Brusko TM, Cools N, Cuturi MC, Geissler E, Giannoukakis N, Golab K, Hafler DA, van Ham SM, Hester J et al. Minimum Information about T Regulatory Cells: A Step toward Reproducibility and Standardization. Front Immunol. 2017;8:1844.

G0211: Study for Gamma Irradiation of Bioreactor Membranes, undated, author unknown, 3 pages.

Galgani M, De Rosa V, La Cava A, Matarese G. Role of Metabolism in the Immunobiology of Regulatory T Cells. J Immunol. 2016;197(7):2567-75.

Garlie, Nina K., et al. "T cells coactivated with immobilized anti-CD3 and anti-CD28 as potential immunotherapy for cancer." Journal of immunotherapy (Hagerstown, Md.: 1997) 22.4 (1999): 336-345.

Gedaly R, De Stefano F, Turcios L, Hill M, Hidalgo G, Mitov MI, Alstott MC, Butterfield DA, Mitchell HC, Hart J, Al-Attar A, Jennings CD, Marti F. mTOR Inhibitor Everolimus in Regulatory T Cell Expansion for Clinical Application in Transplantation. Transplantation. 2019;103(4):705-715.

(56)　　　　　　References Cited

OTHER PUBLICATIONS

Gimble, Jeffrey M., Adam J. Katz, and Bruce A. Bunnell. "Adipose-derived stem cells for regenerative medicine." Circulation research 100.9 (2007): 1249-1260.

Gingras AC, Raught B, Sonenberg N. Regulation of translation initiation by FRAP/mTOR. Genes Dev. 2001;15(7):807-26.

Godin, Michel, et al. "Measuring the mass, density, and size of particles and cells using a suspended microchannel resonator." Applied physics letters 91.12 (2007): 123121.

Golab K, Leveson-Gower D, Wang XJ, Grzanka J, Marek-Trzonkowska N, Krzystyniak A, Millis JM, Trzonkowski P, Witkowski P. Challenges in cryopreservation of regulatory T cells (Tregs) for clinical therapeutic applications. Int Immunopharmacol. 2013;16(3):371-5.

Goldring CE, Duffy PA, Benvenisty N, Andrews PW, Ben-David U, Eakins R, French N, Hanley NA, Kelly L, Kitteringham NR, Kurth J, Ladenheim D, Laverty H, McBlane J, Narayanan G, Patel S, Reinhardt J, Rossi A, Sharpe M, Park BK. Assessing the safety of stem cell therapeutics. Cell stem cell. 2011;8:618-628.

Griesche, Nadine, et al. "A simple modification of the separation method reduces heterogeneity of adipose-derived stem cells." cells tissues organs 192.2 (2010): 106-115.

Gutcher I, Donkor MK, Ma Q, Rudensky AY, Flavell RA, Li MO. Autocrine transforming growth factor-beta1 promotes in vivo Th17 cell differentiation. Immunity. 2011;34(3):396-408.

Haack-Sorensen M, Follin B, Juhl M, et al. (2016) Culture expansion of adipose derived stromal cells. A closed automated Quantum Cell Expansion System compared with manual flask-based culture. J Transl Med 14(1): 319.

Hall ED, Sullivan PG, Gibson TR, Pavel KM, Thompson BM, Scheff SW. Spatial and temporal characteristics of neurodegeneration after controlled cortical impact in mice: More than a focal brain injury. Journal of neurotrauma. 2005;22:252-265.

Hami et al., "GMP Production and Testing of Xcellerated T Cells for the Treatment of Patients with CLL," Cytotherapy, pp. 554-562, 2004.

Hamm RJ, Dixon CE, Gbadebo DM, Singha AK, Jenkins LW, Lyeth BG, Hayes RL. Cognitive deficits following traumatic brain injury produced by controlled cortical impact. Journal of neurotrauma. 1992;9:11-20.

Hanley PJ, Mei Z, Durett AG, et al. (2014) Efficient manufacturing of therapeutic mesenchymal stromal cells with the use of the Quantum Cell Expansion System. Cytotherapy 16(8): 1048-1058.

Harimoto, Masami, et al. "Novel approach for achieving double-layered cell sheets co-culture: overlaying endothelial cell sheets onto monolayer hepatocytes utilizing temperature-responsive culture dishes." Journal of Biomedical Materials Research: An Official Journal of The Society for Biomaterials, The Japanese Society for Biomaterials, and The Australian Society for Biomaterials and the Korean Society for Biomaterials 62.3 (2002): 464-470.

He N, Fan W, Henriquez B, Yu RT, Atkins AR, Liddle C, Zheng Y, Downes M, Evans RM. Metabolic control of regulatory T cell (Treg) survival and function by Lkb1. Proc Natl Acad Sci U S A. 2017;114(47):12542-12547.

He X, Landman S, Bauland SC, van den Dolder J, Koenen HJ, Joosten I. A TNFR2-Agonist Facilitates High Purity Expansion of Human Low Purity Treg Cells. PLoS One. 2016;11(5):e0156311.

Heskins, Michael, and James E. Guillet. "Solution properties of poly (N-isopropylacrylamide)." Journal of Macromolecular Science—Chemistry 2.8 (1968): 1441-1455.

Hill JA, Feuerer M, Tash K, Haxhinasto S, Perez J, Melamed R, Mathis D, Benoist C. Foxp3 transcription-factor-dependent and -independent regulation of the regulatory T cell transcriptional signature. Immunity. 2007;27(5):786-800.

Unknown Author, StAR_Abstract, 2014, 1 page.

Startz et al May 2016 TBCT T-cell White Paper.

Startz, T., et al. "Maturation of dendritic cells from CD14+ monocytes in an automated functionally closed hollow fiber bioreactor system." Cytotherapy 16.4 (2014): S29.

Steven M. Bryce, et al (Litron Laboratories). In vitro micronucleus assay scored by flow cytometry provides a comprehensive evaluation of cytogenetic damage and cytotoxicity. Mutation Research 630(1-2): 78-91, 2007.

Steven M. Bryce, et al (Novartis Pharma AG, Johnson & Johnson Pharmaceutical Research, GlaxoSmithKline). Interlaboratory evaluation of a flow cytometric, high content in vitro micronucleus assay. Genetic Toxicology and Environmental Mutagenesis 650: 181-195, 2008.

Stuart, Martien A. Cohen, et al. "Emerging applications of stimuli-responsive polymer materials." Nature materials 9.2 (2010): 101-113.

Su LF, Del Alcazar D, Stelekati E, Wherry EJ, Davis MM. Antigen exposure shapes the ratio between antigen-specific Tregs and conventional T cells in human peripheral blood. Proc Natl Acad Sci U S A. 2016;113(41):E6192-E6198.

Takezawa, Toshiaki, Yuichi Mori, and Katsutoshi Yoshizato. "Cell culture on a thermo-responsive polymer surface." Bio/technology 8.9 (1990): 854-856.

The effect of rocking rate and angle on T cell cultures grown in Xuri™ Cell Expansion Systems, Aug. 2014, GE Healthcare UK Limited, 4 pages.

Trzonkowski et al., "Ex Vivo Expansion of CD4+ CD25+ T Regulatory Cells for Immunosuppressive Therapy," Cytometry Part A, 75A, pp. 175-188, 2009.

Trzonkowski, Piotr, et al. "First-in-man clinical results of the treatment of patients with graft versus host disease with human ex vivo expanded CD4+ CD25+ CD127? T regulatory cells." Clinical immunology 133.1 (2009): 22-26.

Tsvetkov, Ts, et al. "Isolation and cryopreservation of human peripheral blood monocytes." Cryobiology 23.6 (1986): 531-536.

Underwood, P. Anne, et al. "Effects of base material, plasma proteins and FGF2 on endothelial cell adhesion and growth." Journal of Biomaterials Science, Polymer Edition 13.8 (2002): 845-862.

Urbich, et al from the Goethe-Universität, demonstrated that human endothelial cells increased VEGFR-2 mRNA expression when exposed to 5-15 dynes/cm2 of constant shear force for a period of 6-24 hours (FEBS, 2002).

Van der Net JB, Bushell A, Wood KJ, Harden PN. Regulatory T cells: first steps of clinical application in solid organ transplantation. Transpl Int. 2016;29(1):3-11.

Van der Windt GJ, Pearce EL. Metabolic switching and fuel choice during T-cell differentiation and memory development. Immunol Rev. 2012;249(1):27-42.

Vera et al., "Accelerated Production of Antigen-Specific T-Cells for Pre-Clinical and Clinical Applications Using Gas-Permeable Rapid Expansion Cultureware (G-Rex)," J Immunother, vol. 33, No. 3, pp. 305-315, Apr. 2010.

Villa, Alma Y. Camacho, et al. "CD133+ CD34+ and CD133+ CD38+ blood progenitor cells as predictors of platelet engraftment in patients undergoing autologous peripheral blood stem cell transplantation." Transfusion and Apheresis Science 46.3 (2012): 239-244.

Visser EP1, Disselhorst JA, Brom M, Laverman P, Gotthardt M, Oyen WJ, Boerman OC. Spatial resolution and sensitivity of the Inveon small-animal PET scanner. J Nucl Med. Jan. 2009;50(1):139-47.

Von Laer, D., et al. "Loss of CD38 antigen on CD34+ CD38+ cells during short-term culture." Leukemia 14.5 (2000): 947-948.

Wagner Jr, John E., et al. "Phase I/II trial of StemRegenin-1 expanded umbilical cord blood hematopoietic stem cells supports testing as a stand-alone graft." Cell stem cell 18.1 (2016): 144-155.

Walker, Peter A., et al. "Direct intrathecal implantation of mesenchymal stromal cells leads to enhanced neuroprotection via an NF? B-mediated increase in interleukin-6 production." Stem cells and development 19.6 (2010): 867-876.

Wang R, Dillon CP, Shi LZ, Milasta S, Carter R, Finkelstein D, McCormick LL, Fitzgerald P, Chi H, Munger J, Green DR. The transcription factor Myc controls metabolic reprogramming upon T lymphocyte activation. Immunity. 2011;35 (6):871-82.

(56) References Cited

OTHER PUBLICATIONS

Wang, Jiamian, John A. Jansen, and Fang Yang. "Electrospraying: possibilities and challenges of engineering carriers for biomedical applications—a mini review." Frontiers in Chemistry 7 (2019): 258.

Ward H, Vigues S, Poole S, Bristow AF. The rat interleukin 10 receptor: cloning and sequencing of cDNA coding for the alpha-chain protein sequence, and demonstration by western blotting of expression in the rat brain. Cytokine. 2001;15(5):237-40.

Wawman, Rebecca Ellen, Helen Bartlett, and Ye Htun Oo. "Regulatory T cell metabolism in the hepatic microenvironment." Frontiers in immunology 8 (2018): 1889.

Weber et al., "White Paper on Adoptive Cell Therapy for Cancer with Tumor-Infiltrating Lymphocytes: A Report of the CTEP Subcommittee on Adoptive Cell Therapy," Clinical Cancer Research, vol. 17, No. 7, pp. 1664-1673, Apr. 1, 2011.

Weiss RA, Weiss MA, Beasley KL, Munavalli G (2007) Autologous cultured fibroblast injection for facial contour deformities: a prospective, placebo-controlled, Phase III clinical trial. Dermatol Surg 33(3): 263-268.

Widdel, F. 2010. "Theory and measurement of bacterial growth" http://www.mpi-bremen.de/Binaries/Binary13037/Wachstumsversuch.pdf.

Yamada, Noriko, et al. "Thermo? responsive polymeric surfaces; control of attachment and detachment of cultured cells." Die Makromolekulare Chemie, Rapid Communications 11.11 (1990): 571-576.

Yang, Hee Seok, et al. "Suspension culture of mammalian cells using thermosensitive microcarrier that allows cell detachment without proteolytic enzyme treatment." Cell transplantation 19.9 (2010): 1123-1132.

Yi, Zhuan, et al. "A readily modified polyethersulfone with amino-substituted groups: its amphiphilic copolymer synthesis and membrane application." Polymer 53.2 (2012): 350-358.

Yoshinari, Masao, et al. "Effect of cold plasma-surface modification on surface wettability and initial cell attachment." International Journal of Biomedical and Biological Engineering 3.10 (2009): 507-511.

Zappasodi et al., "The Effect Of Artificial Antigen-Presenting Cells with Preclustered Anit-CD28/-CD3/LFA-1 Monoclonal Antibodies on the Induction of ex vivo Expansion of Functional Human Antitumor T Cells," Haematologica, vol. 93, No. 10, pp. 1523-1534, 2008.

Zemmour D, Zilionis R, Kiner E, Klein AM, Mathis D, Benoist C. Publisher Correction: Single-cell gene expression reveals a landscape of regulatory T cell phenotypes shaped by the TCR. Nat Immunol. 2018;19(6):645.

Zeng B, Kwak-Kim J, Liu Y, Liao AH. Treg cells are negatively correlated with increased memory B cells in pre-eclampsia while maintaining suppressive function on autologous B-cell proliferation. Am J Reprod Immunol. 2013;70(6):454-63.

Zheng, et al at the University of Iowa have shown that the differential effects of pulsatile blood flow and cyclic stretch are an important growth stimulus (American Journal of Physiology—Heart and Circulatory Physiology, 2008).

Anamelechi, Charles C., et al. "Streptavidin binding and endothelial cell adhesion to biotinylated fibronectin." Langmuir 23.25 (2007): 12583-12588.

Barker, Juliet N., et al. "CD34+ cell content of 126 341 cord blood units in the US inventory: implications for transplantation and banking." Blood advances 3.8 (2019): 1267-1271.

Bluestone, Jeffrey A., et al. "Type 1 diabetes immunotherapy using polyclonal regulatory T cells." Science translational medicine 7.315 (2015): 315ra189-315ra189.

Claudio G. Brunstein, Jeffrey S. Miller, Qing Cao, Daivd H. McKenna, Keli L. Hippen, Julie Curtsinger, Todd Defor, Bruce L. Levine, Carl H. June, Pablo Rubinstein, Philip B. McGlave, Bruce R. Blazar, and John E. Wagner. Infusion of ex vivo expanded T regulatory cells in adults transplanted with umbilical cord blood: safety profile and detection kinetics. Blood, 117(3): 1061-1070, 2010.

Lang, Julie, et al. "Generation of hematopoietic humanized mice in the newborn BALB/c-Rag2nullIl12r?null mouse model: a multivariable optimization approach." Clinical Immunology 140.1 (2011): 102-116.

Kim, Do-Hyung, et al. "mTOR interacts with raptor to form a nutrient-sensitive complex that signals to the cell growth machinery." Cell 110.2 (2002): 163-175.

Kishore M, Cheung KCP, Fu H, Bonacina F, Wang G, Coe D, Ward EJ, Colamatteo A, Jangani M, Baragetti A, Matarese G, Smith DM, Haas R, Mauro C, Wraith DC, Okkenhaug K, Catapano AL, De Rosa V, Norata GD, Marelli-Berg FM. Regulatory T Cell Migration Is Dependent on Glucokinase-Mediated Glycolysis. Immunity. 2017;47(5):875-889 e10.

Klysz D, Tai X, Robert PA, Craveiro M, Cretenet G, Oburoglu L, Mongellaz C, Floess S, Fritz V, Matias MI, Yong C, Surh N, Marie JC, Huehn J, Zimmermann V, Kinet S, Dardalhon V, Taylor N. Glutamine-dependent alpha-ketoglutarate production regulates the balance between T helper 1 cell and regulatory T cell generation. Sci Signal. 2015;8(396):ra97.

Lampugnani MG, Caveda L, Breviario F, Del Maschio A, Dejana E. Endothelial cell-to-cell junctions. Structural characteristics and functional role in the regulation of vascular permeability and leukocyte extravasation. Bailliere's clinical haematology. 1993;6:539-558.

Lataillade, Jean-Jacques, et al. "Chemokine SDF-1 enhances circulating CD34+ cell proliferation in synergy with cytokines: possible role in progenitor survival." Blood, The Journal of the American Society of Hematology 95.3 (2000): 756-768.

Lindstein, Tullia, et al. "Regulation of lymphokine messenger RNA stability by a surface-mediated T cell activation pathway." Science 244.4902 (1989): 339-343.

Liotta, Francesco, et al. "Frequency of regulatory T cells in peripheral blood and in tumour? infiltrating lymphocytes correlates with poor prognosis in renal cell carcinoma." BJU international 107.9 (2011): 1500-1506.

Liu W, Putnam AL, Xu-Yu Z, Szot GL, Lee MR, Zhu S, Gottlieb PA, Kapranov P, Gingeras TR, Fazekas de St Groth B, Clayberger C, Soper DM, Ziegler SF, Bluestone JA. CD127 expression inversely correlates with FoxP3 and suppressive function of human CD4+ T reg cells. J Exp Med. 2006;203(7):1701-1711.

Mathew, James M., et al. "A phase I clinical trial with ex vivo expanded recipient regulatory T cells in living donor kidney transplants." Scientific reports 8.1 (2018): 1-12.

Ueda, Ryosuke, et al. "Interaction of natural killer cells with neutrophils exerts a significant antitumor immunity in hematopoietic stem cell transplantation recipients." Cancer medicine 5.1 (2015): 49-60.

Jin, H., and J. Bae. "Neuropeptide Y regulates the hematopoietic stem cell microenvironment and prevents nerve injury in the bone marrow." 22nd Annual ISCT Meeting (2016): S29.

Bai, Tao, et al. "Expansion of primitive human hematopoietic stem cells by culture in a zwitterionic hydrogel." Nature medicine 25.10 (2019): 1566-1575.

Horwitz, Mitchell E., et al. "Phase I/II study of stem-cell transplantation using a single cord blood unit expanded ex vivo with nicotinamide." Journal of Clinical Oncology 37.5 (2019): 367-373.

Lee III, Daniel W., et al. "Long-term outcomes following CD19 CAR T cell therapy for B-ALL are superior in patients receiving a fludarabine/cyclophosphamide preparative regimen and post-CAR hematopoietic stem cell transplantation." Blood 128.22 (2016): 218.

Goh, Celeste, Sowmya Narayanan, and Young S. Hahn. "Myeloid-derived suppressor cells: the dark knight or the joker in viral infections?." Immunological reviews 255.1 (2013): 210-221.

Pati, Shibani, and Todd E. Rasmussen. "Cellular therapies in trauma and critical care medicine: Looking towards the future." PLoS Medicine 14.7 (2017): e1002343.

Pati, Shibani, et al. "Lyophilized plasma attenuates vascular permeability, inflammation and lung injury in hemorrhagic shock." PLoS one 13.2 (2018): e0192363.

Celeste Nelson et al in Christopher Chen's Lab demonstrated, in separate experiments, that curved surfaces with a radius of curvature (200?m) that is greater than the cell diameter and surfaces that have undulating special patterning (depressions) increase the patterned growth of ECs [PNAS 102(33): 11594-11599, 2005].

(56) References Cited

OTHER PUBLICATIONS

Streltsova et al., "Recurrent Stimulation of Natural Killer Cell Clones with K562 Expressing Membrane-Bound Interleukin-21 Affects Their Phenotype, Interferon-y Production, and Lifespan," International Journal of Molecular Sciences, vol. 20, No. 443, 2019, pp. 1-18.

* cited by examiner

~1018

Table 1:  Feed Cells Task, Example IC Pump Rates (mL/min)

1020

| Day 0-4 1024 | Day 5 1030 | Day 6 1036 | Day 7 1042 |
|---|---|---|---|
| IC Inlet $Q_1$ @ 0.1 1026 | IC Inlet $Q_1$ @ 0.2 1032 | IC Inlet $Q_1$ @ 0.3 1038 | IC Inlet $Q_1$ @ 0.4 1044 |
| IC Circ $Q_2$ @ -0.1 1028 | IC Circ $Q_2$ @ -0.2 1034 | IC Circ $Q_2$ @ -0.3 1040 | IC Circ $Q_2$ @ -0.4 1046 |

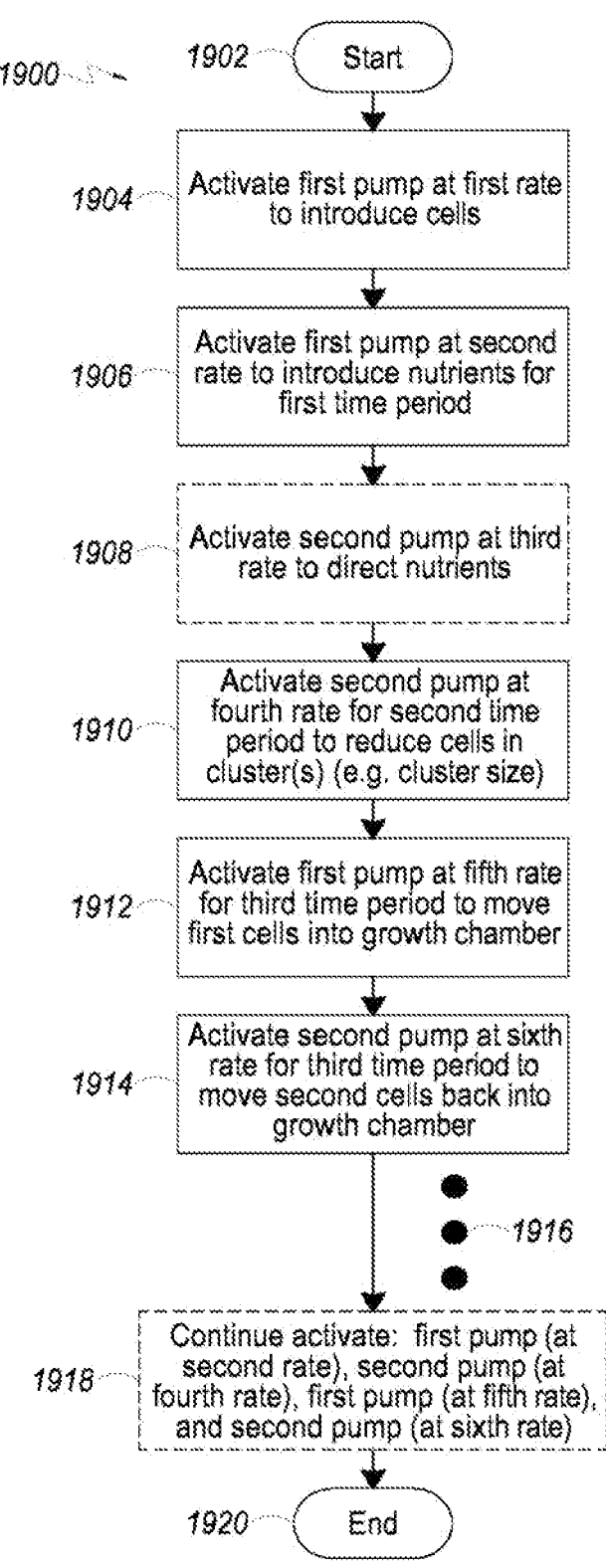

*1900*

*1902*  Start

*1904* Activate first pump at first rate to introduce cells

*1906* Activate first pump at second rate to introduce nutrients for first time period

*1908* Activate second pump at third rate to direct nutrients

*1910* Activate second pump at fourth rate for second time period to reduce cells in cluster(s) (e.g. cluster size)

*1912* Activate first pump at fifth rate for third time period to move first cells into growth chamber

*1914* Activate second pump at sixth rate for third time period to move second cells back into growth chamber

*1916*

*1918* Continue activate: first pump (at second rate), second pump (at fourth rate), first pump (at fifth rate), and second pump (at sixth rate)

*1920*  End

FIG. 19A

T-Cell Phenotype 2nd Protocol
CD4/CD8

| | CD4+ | | CD8+ |

*FIG. 32*

CELL EXPANSION

CROSS-REFERENCE TO RELATED APPLICATIONS

This application is a divisional of, and claims priority to and the benefit of, U.S. patent application Ser. No. 16/112, 498, entitled "CELL EXPANSION," filed on Aug. 24, 2018, which is a continuation-in-part of, and claims priority to and the benefit of, U.S. patent application Ser. No. 15/943,619, entitled "CELL EXPANSION," filed on Apr. 2, 2018, and U.S. patent application Ser. No. 15/943,536, entitled "EXPANDING CELLS IN A BIOREACTOR," filed on Apr. 2, 2018, and both of which claim priority to and the benefit of, the following applications: U.S. Provisional Application Ser. No. 62/479,721, filed on Mar. 31, 2017, and entitled, "Expanding Cells;" U.S. Provisional Application Ser. No. 62/479,760, filed on Mar. 31, 2017, and entitled "Cell Expansion;" U.S. Provisional Application Ser. No. 62/479, 788, filed on Mar. 31, 2017, and entitled, "Expanding Cells in a Bioreactor;" U.S. Provisional Application Ser. No. 62/549,871, filed on Aug. 24, 2017, and entitled, "Expansion of Cells;" and U.S. Provisional Application Ser. No. 62/647, 361, filed on Mar. 23, 2018, and entitled, "Expansion of Cells." This application also claims priority to U.S. Provisional Patent Application Ser. No. 62/549,884, entitled "CELL EXPANSION," filed on Aug. 24, 2017. The disclosures of all of the above-identified applications are hereby incorporated by reference in their entireties as if set forth herein in full for all that they teach and for all purposes.

BACKGROUND

Cell Expansion Systems (CESs) are used to expand and differentiate cells. Cell expansion systems may be used to expand, e.g., grow, a variety of adherent and suspension cells. Cells, of both adherent and non-adherent type, may be grown in a bioreactor in a cell expansion system.

SUMMARY

Embodiments of the present disclosure generally relate to expanding cells in a call expansion system (CES). Such expansion may occur through the use of a bioreactor or cell growth chamber, according to embodiments. In an embodiment, such reactor or cell growth chamber may comprise a hollow fiber membrane. Such hollow fiber membrane may include an extracapillary (EC) space and an intracapillary ace. A cell expansion system may expand a variety of cell types. Embodiments may provide for adherent or non-adherent cells to be grown or expanded in the cell expansion system. Non-adherent, or suspension, cells which may be expanded in the system may include T cells, or T lymphocytes, for example. In embodiments, one or more subpopulations or subsets of T cells may be grown. For example, embodiments may provide methods and systems for expanding T cells, some non-limiting examples including, effector T cells such as human effector T cells, heiper T cells such as human helper T cells, naïve T cells such as human naïve T cells, memory T cells such as human memory T cells and/or regulatory T cells (Tregs) such as human regulatory T cells (hTregs).

In embodiments, methods and systems may be provided for expanding cells in a closed, automated cell expansion system. In an embodiment, such cell expansion system may include a bioreactor or cell growth chamber. In further embodiments, such bioreactor or cell growth chamber may comprise a hollow fiber membrane.

For example, non-adherent calls, e.g., T cells such as Treg cells, may be introduced into a hollow fiber bioreactor, in which the hollow fiber bioreactor comprises a plurality of hollow fibers. According to an embodiment, the cells may be exposed to a stimulator or activator to stimulate or activate the expansion of the cells in the hollow fiber bioreactor.

A closed, automated cell expansion system comprising a bioreactor or cell growth chamber may comprise numerous capabilities, such as nutrient and gas exchange capabilities. Such capabilities may allow cells to be seeded at reduced cell seeding densities as compared to cell seeding densities used in culture flasks or other static culture methods. Embodiments provide for parameters of the cell growth environment to be manipulated to load or introduce cells into a position in the bioreactor for the efficient exchange or delivery of nutrients and gases to the growing calls. In embodiments, communication between the cells may also be promoted. For example, in an embodiment, a centralization, or centering, of cells in the bioreactor may increase cell density to promote communication such as chemical signaling, between cells.

Embodiments also may provide for system parameters to be managed to control cell residence in the bioreactor or cell growth chamber. By controlling cell residence in the bioreactor during the cell growth phase, for example, the system may provide for an efficient gas and nutrient exchange to expanding cells. In embodiments, a bioreactor may be designed to provide gas exchange, and, in some embodiments, nutrient exchange, to growing cells. In an example embodiment, a bioreactor comprising a semi-permeable hollow fiber membrane provides gas and nutrient exchange through the semi permeable hollow fiber membrane. The semi-permeable hollow fibers of the bioreactor allow essential nutrients (e.g., glucose and/or cell growth formulated media) to reach the cells and metabolic waste products (e.g., lactate) to exit the system via diffusion through the walls of the hollow fibers. However, according to embodiments, cells residing in the headers of the bioreactor or in other areas outside the hollow fibers may not receive proper gas exchange and nutrient exchange, which may result in cell aggregation and death. Embodiments therefore relate to providing methods to retain cell populations, e.g., non-adherent cell populations, in the hollow fibers of the bioreactor when feeding the cells. Such retaining of the cells in the bioreactor may also promote cell-to-cell communications because with more cells in the bioreactor itself, cell densities may increase and cell-to-cell communications may therefore improve.

Additional embodiments may provide for system features to be harnessed to shear any cell colonies, micro-colonies, or cell clusters that may form during the expansion phase of cell growth. For example, an embodiment provides for, after a period of expansion, the shearing of groups of cells, e.g., colonies, micro-colonies, or clusters, through a bioreactor hollow fiber membrane. Such shearing may reduce the number of cells in the micro-colony, colony, or cluster, in which a micro-colony, colony, or cluster may be a group of one or more attached cells. In embodiments, the clusters may also include beads used to activate expansion of the cells. Embodiments may provide a protocol to shear any colonies by circulating the suspension cell culture through, for example, the hollow fiber intracapillary (IC) loop (e.g., with hollow fibers of 215 μm inner diameter) during the expansion phase of growth. In embodiments, a colony, micro-colony, or cluster of cells may be sheared to reduce a size of the colony, micro-colony, or cluster of cells. In an embodiment, a colony, micro-colony, of cluster of cells may be sheared to provide a single cell uniform suspension and improve cell growth/viability. Such capabilities may contribute to the continuous perfusion growth of the cells, e.g., T cells such as Tregs.

Embodiments of the present disclosure further relate to growing cells using a combination of features for cell expansion. For example, in an embodiment, cells may be seeded at a reduced seeding density as compared to a cell seeding density used in culture flasks or other static culture methods. For example, in some embodiments, the volume of fluid used to seed the cells may include from about $1\times10^4$ cells/mL to about $1\times10^6$ cell/mL, such as on the order of $10^5$ cells/mL. In other embodiments, the volume of fluid used to seed the cells may include less than about $1\times10^6$ cells/mt. In some embodiments, the total number of cells seeded may be from about $10\times10^6$ to about $50\times10^6$ cells. In other embodiments, the total number of cells seeded may be less than $50\times10^6$ cells. According to embodiments, the cells may be loaded, or introduced, into a desired position in a bioreactor, e.g., hollow fiber bioreactor, in the cell expansion system. In an embodiment, cells may be exposed to an activator to activate expansion of the cells in the hollow fiber bioreactor, for example. Any colonies or clusters of cells that may form during cell expansion may be sheared by circulating the cells to cause the cells to incur a shear stress and/or shear force, for example, according to an embodiment. Such shear stress and/or shear force may cause one or more cells to break apart from a cell colony, for example. To provide proper gas and nutrient exchange to growing cell populations, further embodiments provide for retaining cell populations, e.g., suspension cell populations, inside the hollow fibers of the bioreactor during the feeding of the cells, for example, By centralizing and/or retaining cells in the hollow fibers of the bioreactor during the cell growth phase, cell densities may increase and cell-to-cell communications may improve. Reduced cell seeding densities, as compared to static cultures, may therefore be used.

Embodiments further provide for a cell expansion system for expanding cells, in which such system may include, for example, a hollow fiber bioreactor comprising an inlet port and an outlet port; a first fluid flow path having at least opposing ends, in which a first opposing end of the first fluid flow path is fluidly associated with an inlet port of the bioreactor, and a second end of the first fluid flow path is fluidly associated with an outlet port of the bioreactor, wherein the first fluid flow path is fluidly associated with an intracapillary portion of the bioreactor; a fluid inlet path fluidly associated with the first fluid flow path; and a first fluid circulation path fluidly associated with the first fluid flow path and the intracapillary portion of the bioreactor.

Embodiments further provide for the cell expansion system to include a processor for executing instructions to perform methods described and/or illustrated herein. For example, embodiments of the present disclosure provide for implementing such expansion of ceils through the use of one or more protocols or casks for use with a cell expansion system. For example, such protocols or tasks may include pre-programmed protocols or tasks. In embodiments, a pre-programmed, default, or otherwise previously saved task may be selected by a user or system operator to perform a specific function by the cell expansion system. In other embodiments, such protocols or tasks may include custom or user-defined protocols or tasks. For example, through a user interface (UI) and one or more graphical user interface (GUI) elements, a custom or user-defined protocol or task may be created. A task may comprise one or more steps.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

This summary is included to provide a selection of concepts in a simplified form, in which such concepts are further described below in the Detailed Description. This Summary is not intended to be used in any way to limit the claimed subject matter's scope. Features, including equivalents and variations thereof, may be included in addition to those provided herein.

BRIEF DESCRIPTION OF THE DRAWINGS

Embodiments of the present disclosure may be described by referencing the accompanying figures. In the figures, like numerals refer to like items. In the figures, dashed lines may be used to indicate that an element(s) may be optional.

FIG. 10B illustrates a table with example pump rates that may be used in a cell expansion system, in accordance with embodiments of the present disclosure.

FIG. 19A illustrates a flow diagram depicting the operational characteristics of a process for operating pumps to expand cells, in accordance with embodiments of the present disclosure.

FIG. 32 illustrates a bar graph depicting cell phenotypes, in accordance with embodiments of the present disclosure.

DETAILED DESCRIPTION

Figure 1A:
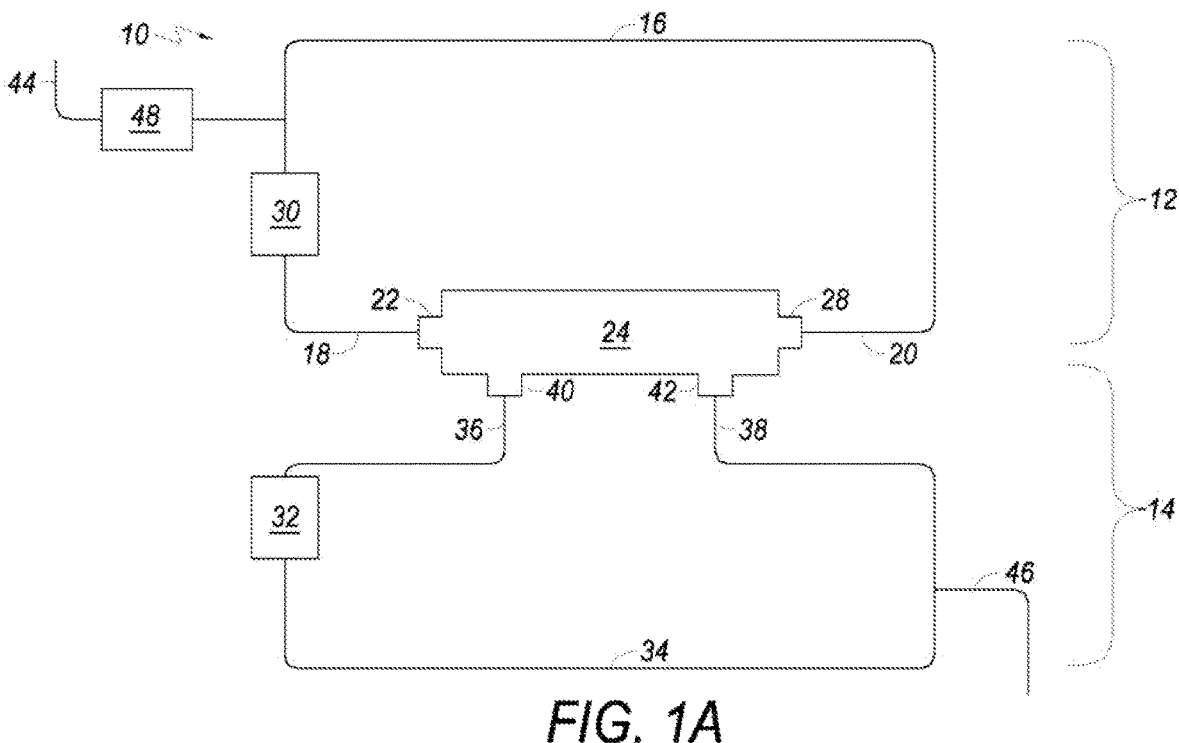
FIG. 1A depicts an embodiment of a cell expansion system (CES).

The following Detailed Description provides a discussion of illustrative embodiments with reference to the accompanying drawings. The inclusion of specific embodiments herein should not be construed as limiting or restricting the present disclosure. Further, while language specific to features, acts, and/or structures, for example, may be used in describing embodiments herein, the claims are not limited to the features, acts, and/or structures described. A person of skill in the art will appreciate that other embodiments, including improvements, are within the spirit and scope of the present disclosure. Further, any alternatives or additions, including any listed as separate embodiments, may be used or incorporated with an other embodiments herein described.

Embodiments of the present disclosure are generally directed to systems and methods for expanding cells in a cell expansion system (CES). Such expansion may occur through the use of a bioreactor or cell growth chamber, according to embodiments. In an embodiment, such bioreactor or cell growth chamber may comprise a hollow fiber membrane. Such hollow fiber membrane may include a plurality of hollow fibers and may include an extracapillary (EC) and/or intracapillary (IC) space. Embodiments may provide for adherent or non-adherent cells to be grown or expanded in the cell expansion system. For example, non-adherent or suspension cells, such as T cells, or T lymphocytes, may be expanded in the system. In embodiments, one or more subpopulations or subsets of T cells may be grown. For example, embodiments may provide methods and systems for expanding effector, helper, memory, naïve, and/or regulatory T cells (Tregs) (e.g., human regulatory T cells (hTregs)).

In embodiments, methods and systems may be provided for expanding cells in a closed, automated cell expansion system. In an embodiment, such cell expansion system may include a bioreactor or cell growth chamber. In further embodiments, such bioreactor of cell growth chamber may comprise a hollow fiber membrane. The capabilities of such system, such as nutrient and gas exchange capabilities, may allow cells to be seeded at reduced cell seeding densities. Embodiments provide for parameters of the cell growth environment to be manipulated to load or introduce cells into a position in the bioreactor for the efficient exchange of nutrients and gases to the growing cells. For example, in an embodiment, the centralization of cells in the bioreactor may increase cell density.

In embodiments, non-adherent cell populations, e.g., T cells such as Treg cells, may be introduced or loaded into a hollow fiber bioreactor, in which the hollow fiber bioreactor may comprise a plurality of hollow fibers. In embodiments, the cells may be exposed to an activator to activate the expansion of the cells in the hollow fiber bioreactor. In an embodiment, a plurality of cells may be introduced into a cell expansion system using a "load cells centrally without circulation" task, for example. Such task may be performed on Day 0 and on Days 4-8, according to an example embodiment. Other days may be used in other embodiments. In embodiments, such loading of cells task may result in the centralization of cells in the bioreactor to increase cell density. In other embodiments, the cells may be located in other portions or regions of the bioreactor to increase cell density. In embodiments, by positioning the cells in a first position, e.g., about a central region, of the bioreactor, the cells may receive an efficient exchange of nutrients and gases.

In embodiments, a relatively small number of initial cells may be seeded, as compared to the number of cells used with static culture methods. In embodiments, using a cell expansion system, cells, e.g., T cells, may be expanded from an initial number of cells that is less than about $100\times10^6$ cells, less than about $90\times10^6$ cells, less than about $80\times10^6$ cells, less than about $70\times10^6$ cells, less than about $60\times10^6$ cells, less than about $50\times10^6$ cells, less than about $40\times10^6$ cells, less than about $30\times10^6$ cells, or even less than about $20\times10^6$ cells. In other embodiments, the initial number of cells may be greater than about $80\times10^6$ cells, greater than about $90\times10^6$ cells, greater than about $10\times10^6$ cells, or even greater than about $20\times10^6$. In some embodiments, the cells that are initially seeded may comprise peripheral blood mononuclear cells (PBMC). The cells may be isolated from a volume of peripheral blood or a leukapheresis product. In these embodiments, the initial number of cells, may refer to the number of PBMC's, isolated from a volume of peripheral blood. In embodiments, lower initial cell seeding numbers may be used due to the system's overall efficiency in delivering nutrients to the culture environment, for example. In other embodiments, one or more of the steps used during expansion in combination with the system's overall efficiency in delivering nutrients to the culture environment may allow lower initial cell seeding numbers to be used. In other embodiments, from between about $1\times10^6$ to about $500\times10^6$ cells may be seeded.

In embodiments, a reduced cell seeding density, as compared to cell seeding densities used with static culture methods, may be used. In an embodiment using a cell expansion system, cells, e.g. Tregs or Treg cells, may be expanded from a cell seeding density of about $2.54\times10^6$ cells/ml to about $3.69\times10^6$ cells/mL. In other embodiments, the cell seeding density may be less than about $1\times10^6$ cells/mL. In addition, a Treg cell inoculum may be prepared from a cell seeding density of about $1.0\times10^6$ cells/mL. Other methods, e.g., static Treg cell culture methods, may use a cell seeding density of about $1.0\times10^6$ Treg cells/mL for in vitro expansion. In an embodiment, lower cell seeding densities may be used due to the system's overall efficiency in delivering nutrients to the culture environment, for example. In other embodiments, one or more of the steps used during expansion in combination with the system's overall efficiency in delivering nutrients to the culture environment may allow lower initial cell seeding densities to be used.

In embodiments, an automated cell, e.g., T cells such as Tregs, expansion may be performed using activator complex. For example, in some embodiments, beads for the stimulation of cells, may be used, for example. Beads that may be functionalized with antibodies may be used. The antibodies may activate the proliferation of the T cells. One example of beads that may be used include DYNABEADS® beads available from Thermo Fisher Scientific, Waltham, Massachusetts. The beads in some embodiments may be functionalized with antibodies on their surface, some non-limiting examples of the antibodies include: anti-CD2, anti-CD3, anti-CD4, anti-CD8, anti-CD28, anti-CD34, and combinations thereof. In embodiments, the beads may be used in the presence of 100 IU/mL of the cytokine IL-2. In other embodiments, cells, e.g., T cells such as Tregs, may be expanded without the use of a bead-based stimulation. In one embodiment, cell expansion may be performed using the Stem Cell Technologies soluble ImmunoCult™ Human CD3/CD28/CD2 T Cell Activator to activate and expand Treg cells in the presence of 200 IU/mL of the cytokine IL-2 with an automated cell expansion system. Using a soluble activator complex may reduce costs for stimulation over the cost of a bead based protocol, for example. Other types of activators may be used in other embodiments. Further, other types of cytokines or other growth factors may be used in other embodiments.

Embodiments also may provide for system parameters to be adjusted or managed to control cell residence in the bioreactor or cell growth chamber. By controlling cell residence in the bioreactor hollow fibers during the cell growth phase, for example, the system may provide for an efficient gas and nutrient exchange to expanding cells. In embodiments, a bioreactor may be designed to provide gas exchange, and, in some embodiments, nutrient exchange, to growing cells. In an example embodiment, a bioreactor comprising a semi-permeable hollow fiber membrane may provide gas and nutrient exchange through the semi-permeable hollow fiber membrane. In embodiments, methods for providing media constituents, such as various cytokines, proteins, etc., for example, to growing cells which cannot pass through the membrane may use a fluid inlet to the side of the bioreactor, e.g., intracapillary (IC) side, where cells are growing. However, even low, decreased, or reduced, e.g., minimum, inlet flow rates (0.1 mL/min, for example) may result in cells collecting in the outlet header of the bioreactor, according to embodiments. Cells residing in the headers of the bioreactor may not receive proper gas exchange and nutrient exchange, which may result in cell death and aggregation.

Embodiments relate to providing methods to retain cells, e.g., non-adherent cell populations, in the bioreactor when feeding the cells using an inlet, e.g., IC inlet, flow. While embodiments herein may refer to cells being on the IC side of the membrane when feeding, for example, other embodiments may provide for the cells to be on the EC side of the membrane, in which cells may be contained within a first circulation path and/or a second circulation path, according to embodiments. In embodiments, a feeding method may provide for pumping a first volume of fluid, e.g., media or cell growth formulated media, into a first port of the bioreactor at a first volumetric flow rate, volume flow rate, fluid flow rate, flow rate, rate of fluid flow, or volume velocity, for example. Volumetric flow rate, volume flow rare, fluid flow rate, flow rate, rate of fluid flow, or volume velocity, for example, may be used interchangeably. In some embodiments, flow rate may be a vector having both a speed and a direction. A second volume of the fluid may be pumped into a second port of the bioreactor at a second volumetric flow rate, volume flow rate, fluid flow rate, flow rate, rate of fluid flow, or volume velocity. In embodiments, such volumetric flow rate, volume flow rate, fluid flow rate, flow rate, rate of fluid flow, or volume velocity, may be controlled by one or more pump rate(s) and/or pump flow rate(s), for example. A pump rate may produce, cause, or affect a volumetric flow rate or flow rate of a fluid upon which the pump may act. As used herein, a pump rate may be described in embodiments as the volumetric flow rate or fluid flow rate produced, caused, or affected by the pump.

In embodiments, the second flow rate of the fluid into the bioreactor may be opposite the direction of the first flow rate of the fluid into the bioreactor. For example, FIGS. 5B and 5C illustrate example operational configurations showing flow rates and flow directions that may be used with a cell expansion system, such as CES 500 (e.g., FIGS. 5B, & 5C), in accordance with embodiments of the present disclosure. In embodiments, cell expansion system pumps, e.g., IC pumps, may be used to control cell residence in the bioreactor. In embodiments, cells may be lost from the bioreactor into the IC circulation path or IC loop, for example, during the expansion phase of growth. In embodiments, cells in the bioreactor that are closer to IC inlet port, for example, may receive the freshest growth media, whereas, cells in the portion of the IC circulation path outside of the bioreactor, for example, may essentially be receiving expended or conditioned media which may affect their glycolytic metabolism. In addition, cells in the bioreactor may receive mixed gas ($O_2$, $CO_2$, $N_2$) input from the gas transfer module (GTM) by diffusion from the EC loop circulation, whereas cells in the portion of the IC circulation path outside of the bioreactor may not, according to embodiments.

In embodiments, reducing the loss of cells from a hollow fiber membrane (HFM) bioreactor may be accomplished by matching, or closely or substantially marching, the IC circulation pump rate to the IC inlet pump rate, but in the opposite direction, during feeding. For example, an IC inlet pump rate of +0.1 mL/min may be matched, or closely or substantially matched, to a complementary IC circulation pump rate of −0.1 mL/min in order to maintain cells in the bioreactor during the growth phase of the cell culture which may be Days 4-7, in embodiments. This pump adjustment may counteract the forces associated with the loss of cells from the IC outlet port, in accordance with embodiments. In other embodiments, other pump rates may be used. For example, in other embodiments, the pump rates may be different. In embodiments, other pumps or additional pumps may be used. In an embodiment, fewer pumps may be used. Further, other time periods may be used in other embodiments.

In embodiments, the metabolic activity of the cell population may affect feeding parameters. For example, cell culture lactate values may be maintained at or below a predefined level. In an embodiment, cell culture lactate values may be maintained at or below about 7 mmol/L, for example. In other embodiments, cell culture lactate values may be maintained at of below about 30 mmol/L, at or below about 25 mmol/L, at or below about 20 mmol/L, at or below about 15 mmol/L, or even at or below about 10 mmol/L. In embodiments, by using a cell expansion system graphical user interface (GUI) to control a rate(s) of media addition, lactate metabolic waste product from glycolysis may be maintained at or below a predefined value, during the expansion of cells, e.g., T cells such as regulatory T cells. In other embodiments, rate(s) of media addition, for example, and/or other settings may be controlled to maintain, or attempt to maintain, the lactate levels ≤about 5 mmol/L, for example, to improve cell growth and viability. Other concentrations may be used in other embodiments.

Additional embodiments may provide for system features to be harnessed to shear any cell colonies, micro-colonies, or cell clusters that may form during the expansion phase. For example, an embodiment provides for the shearing of colonies, e.g., micro-colonies, of cells through a bioreactor hollow fiber membrane to reduce the number of cells in the micro-colony, colony, or cluster, in which a micro-colony, colony, or cluster may be a group of one or more attached cells. In embodiments, a cell expansion system (CES) bioreactor architecture may be used to shear cell, e.g., T cells such as Tregs, micro-colonies. In embodiments, as cells, e.g., T cells such as Tregs, grow, they may tend to form micro-colonies that may limit the diffusion of nutrients to the cell(s) in the center of the colony. This may lead to adverse effects such as necrosis during cell culture. Embodiments may provide a protocol to shear the colonies by circulating the suspension cell culture through, for example, the hollow fiber Intracapillary (IC) loop (e.g., with hollow fibers of about 215 μm inner diameter) during the expansion phase of growth. In embodiments, a colony, micro-colony, or cluster of cells may be sheared to reduce a size of the colony, micro-colony, or cluster of cells. In an embodiment, a colony or cluster of cells may be sheared to provide a single cell suspension and create cell growth/viability. In embodiments, such capabilities may contribute to the continuous perfusion growth of the cells, e.g., T cells such as Tregs. In some embodiments, the microcolonies may also form with beads that may be used to activate cell expansion. In these embodiments, the shearing of microcolonies may also break up any aggregates of cells, beads, or combinations thereof that may form as the cells are expanded.

In embodiments, a therapeutic dose of cells, e.g., T cells such as Tregs, may be expanded in, and harvested from, a cell expansion system. In embodiments, the number of cells at harvest may be from about $1\times10^6$ cells to about $1\times10^{10}$ cells, such as on the order of $1\times10^9$ cells. In one embodiment, the number of harvested cells may be from about $1\times10^8$ to about $1\times10^{10}$ cells, one example being between about $7.0\times10^8$ to about $1.4\times10^8$ cells. In other embodiments, the number of cells harvested may be from about $1\times10^9$ to about $100\times10^9$. In embodiments, the harvested cells may have viabilities between about 60% and about 100%. For example, the viability of the harvested cells may be above about 65% above about 70%, above about 75%, above about 80%, above about 35%, abo about 0%, or even above out 95%.

The harvested cells may express biomarkers consistent with T cells (e.g., naïve, effector, helper, memory, regulatory), in some embodiments. For example, the cells may express $CD3^+$, $CD4^+$, and/or $CD8^+$ biomarkers, in some embodiments. In embodiments, the harvested cells may include the $CD3^+$ phenotype at a frequency of between about 50% and about 100%. The harvested cells may include the $CD4^+$ phenotype at a frequency of above about 25%, above about 30%, above about 35%, above about 40%, above about 45%, above about 50%, above about 55%, or even above about 60%. In other embodiments, the cells may include the $CD8^+$ phenotype at a frequency of between about 30% to about 100%.

In other embodiments, harvested cells may express biomarkers consistent with Tregs. For example, the cells may express $CD4^+$, $CD25^+$, and/or $FoxP3^+$ biomarkers, in some embodiments. In embodiments, the harvested cells may include the CD4+CD25+ phenotype at a frequency of between about 50% and about 100%. The harvested cells may include the $CD4^+CD25^+$ phenotype at a frequency of above about 75%, above about 80%, above about 85%, above about 90%, or even above about 95%. In other embodiments, the cells may include the $CD4^+FoxP3^+$ phenotype at a frequency of between about 30% to about 100%. In some embodiments, the harvested cells may include the $CD4^+FoxP3^+$ phenotype at a frequency of above about 30%, above about 35%, above about 40%, above about 45%, above about 50%, above about 55%, above about 80%, above about 65%, or even above about 70%.

Embodiments are directed to a cell expansion system, as noted above. In embodiments, such cell expansion system is closed, in which a closed cell expansion system comprises contents that are not directly exposed to the atmosphere. Such cell expansion system may be automated. In embodiments, cells, of both adherent and non-adherent or suspension type, may be grown in a bioreactor in the cell expansion system. According to embodiments, the cell expansion system may include base media or other type of media. Methods for replenishment of media are provided for cell growth occurring in a bioreactor of the closed cell expansion system. In embodiments, the bioreactor used with such systems is a hollow fiber bioreactor. Many types of bioreactors may be used in accordance with embodiments of the present disclosure.

The system may include, in embodiments, a bioreactor that is fluidly associated with a first fluid flow path having at least opposing ends, a first opposing end of the first fluid flow path fluidly associated with a first port of a hollow fiber membrane and a second end of the first fluid flow path fluidly associated with a second port of the hollow fiber membrane. In embodiments, a hollow fiber membrane comprises a plurality of hollow fibers. The system may further include a fluid inlet path fluidly associated with the first fluid flow path, in which a plurality of cells may be introduced into the first fluid flow path through the first fluid inlet path. In some embodiments, a pump for transferring intracapillary inlet fluid from an intracapillary media bag to the first fluid flow path and a controller for controlling operation of the pump are included. The controller, in embodiments, controls the pump to transfer cells from a cell inlet bag to the first fluid flow path, for example. Another pump for circulating fluid in a first fluid circulation path may also be included, in which such pump may also include a controller for controlling operation of the pump. In an embodiment, a controller is a computing system, including a processor(s), for example. The one or more controller(s) may be configured, in embodiments, to control the one or more pump(s), such as to circulate a fluid at a flow rate within the first fluid circulation path, for example. A number of controllers may be used, e.g., a first controller, second controller, third controller, fourth controller, fifth controller, sixth controller, etc., in accordance with embodiments. Further, a number of pumps may be used, e.g., a first pump, second pump, third pump, fourth pump, fifth pump, sixth pump, etc., in accordance with embodiments of the present disclosure. In addition, while the present disclosure may refer to a media bag, a cell inlet bag, etc., multiple bags, e.g., a first media bag, a second media bag, a third media bag, a first cell inlet bag, a second cell inlet bag, a third cell inlet bag, etc., and/or other types of containers, may be used in embodiments. In other embodiments, a single media bag, a single cell inlet bag, etc., may be used. Further, additional or other fluid paths, e.g., a second fluid flow path, a second fluid inlet path, a second fluid circulation path, etc., may be included in embodiments.

In embodiments, the system is controlled by, for example: a processor coupled to the cell expansion system; a display device, in communication with the processor, and operable to display data; and a memory, in communication with and readable by the processor, and containing a series of instructions. In embodiments, when the instructions are executed by the processor, the processor receives an instruction to prime the system, for example. In response to the instruction to prime the system, the processor may execute a series of steps to prime the system and may next receive an instruction to perform an IC/EC washout, for example. In response to an instruction to load cells, for example, the processor may execute a series of steps to load the cells from a cell inlet bag, for example, into the bioreactor.

A schematic of an example cell expansion system (CES) is depicted in FIG. 1A, in accordance with embodiments of the present disclosure. CES 10 includes first fluid circulation path 12 and second fluid circulation path 14. First fluid flow path 16 has at least opposing ends 18 and 20 fluidly associated with a hollow fiber cell growth chamber 24 (also referred to herein as a "bioreactor"), according to embodiments. Specifically, opposing end 18 may be fluidly associated with a first inlet 22 of cell growth chamber 24, and opposing end 20 may be fluidly associated with first outlet 28 of cell growth chamber 24. Fluid in first circulation path 12 flows through the interior of hollow fibers 116 (see FIG. 1B) of hollow fiber membrane 117 (see FIG. 1B) disposed in cell growth chamber 24 (cell growth chambers and hollow fiber membranes are described in more detail infra). Further, first fluid flow control device 30 may be operably connected to first fluid flow path 16 and may control the flow of fluid in first circulation path 12.

Second fluid circulation path 14 includes second fluid flow path 34, cell growth chamber 24, and a second fluid flow control device 32. The second fluid flow path 34 has at least opposing ends 36 and 38, according to embodiments. Opposing ends 36 and 38 of second fluid flow path 34 may be fluidly associated with inlet port 40 and outlet port 42 respectively of cell growth chamber 24. Fluid flowing through cell growth chamber 24 may be in contact with the outside of hollow fiber membrane 117 (see FIG. 1B) in the cell growth chamber 24, in which a hollow fiber membrane comprises a plurality of hollow fibers. Second fluid circulation path 14 may be operably connected to second fluid flow control device 32.

Figure 1B:
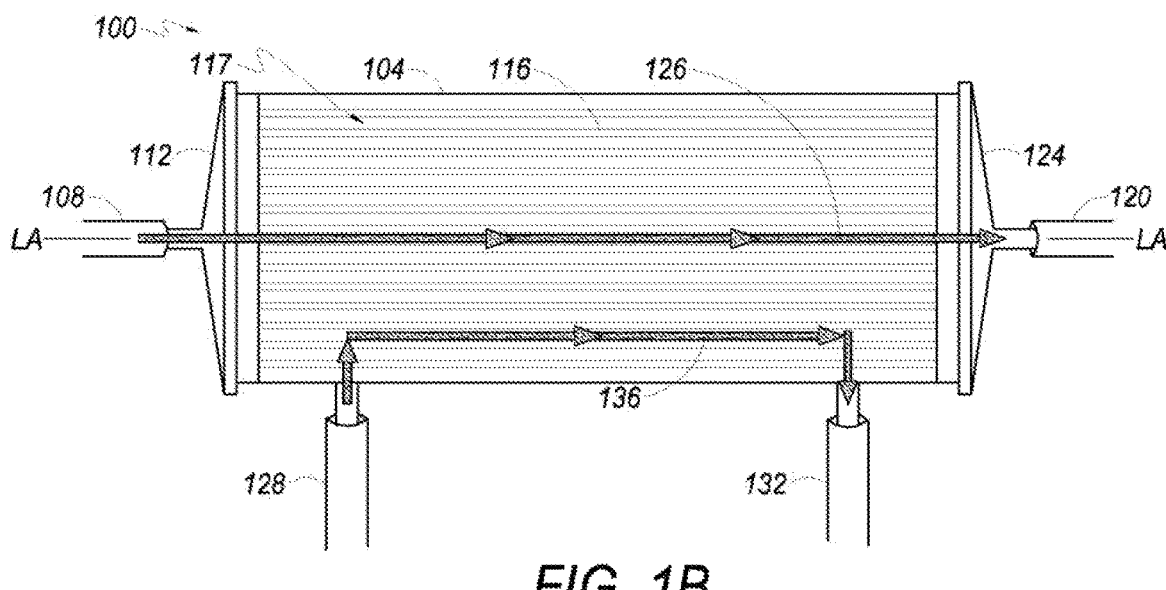
FIG. 1B illustrates a front elevation view of an embodiment of a bioreactor showing circulation paths through the bioreactor.

First and second fluid circulation paths 12 and 14 may thus be separated in cell growth chamber 24 by a hollow fiber membrane 117 (see FIG. 1B). Fluid in first fluid circulation path 12 flows through the intracapillary ("IC") space of the hollow fibers in the cell growth chamber 24. First circulation path 12 may be referred to as the "IC loop." Fluid in second circulation path 14 flows through the extracapillary ("EC") space in the cell growth chamber 24. Second fluid circulation path 14 may be referred to as the "EC loop." Fluid in first fluid circulation path 12 may flow in either a co-current or counter-current direction with respect to flow of fluid in second fluid circulation path 14, according to embodiments.

Fluid inlet path 44 may be fluidly associated with first fluid circulation path 12. Fluid inlet path 44 allows fluid into first fluid circulation path 12, while fluid outlet path 46 allows fluid to leave CES 10. Third fluid flow control device 48 may be operably associated with fluid inlet path 44. Alternatively, third fluid flow control device 48 may alternatively be associated with first outlet path 46.

Fluid flow control devices as used herein may comprise a pump, valve, clamp, or combination thereof, according to embodiments. Multiple pumps, valves, and clamps can be arranged in any combination. In various embodiments, the fluid flow control device is or includes a peristaltic pump. In embodiments, fluid circulation paths, inlet ports, and outlet ports may be constructed of tubing of any material.

Various components are referred to herein as "operably associated." As used herein, "operably associated" refers to components that are linked together in operable fashion and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g., a peristaltic pump that pumps fluids through flexible tubing by compressing the exterior of the tube).

Generally, any kind of fluid, including buffers, protein containing fluid, and cell-containing fluid, for example, can flow through the various circulations paths, inlet paths, and outlet paths. As used herein, "fluid," "media," and "fluid media" are used interchangeably.

Turning to FIG. 1B, an example of a hollow fiber cell growth chamber 100 which may be used with the present disclosure is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132.

According to embodiments of the present disclosure, fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116 comprising hollow fiber membrane 117, and cut of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber 100 via the EC inlet port 128 may be in contact with the outside of the hollow fibers 116. Small molecules (e.g., ions, water, oxygen, lactate, etc.) may diffuse through the hollow fibers 116 from the interior or IC space of the hollow fiber to the exterior or EC space, or from the EC space to the IC space. Large molecular weight molecules, such as growth factors, may be typically too large to pass through the hollow fiber membrane, and may remain in the IC space of the hollow fibers 116. The media may be replaced as needed, in embodiments. Media may also be circulated through an oxygenator or gas transfer module to exchange gasses as needed. Cells may be contained within a first circulation path and/or a second circulation path, as described below, and may be on either the IC side and/or EC side of the membrane, according to embodiments.

The material used to make the hollow fiber membrane 117 may be any biocompatible polymeric material which is capable of being made into hollow fibers. One material which may be used is a synthetic polysulfone-based material, according to an embodiment of the present disclosure.

Figure 1C:
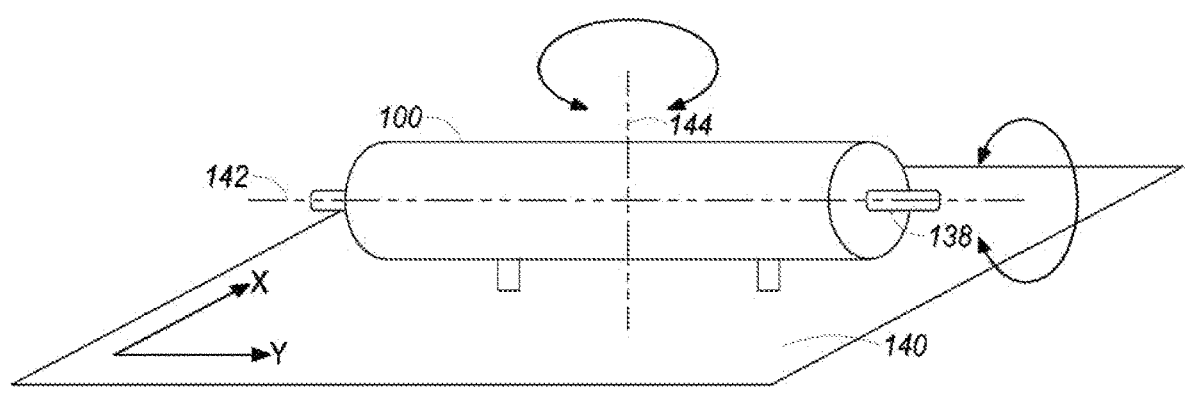
FIG. 1C depicts a rocking device for moving a cell growth chamber rotationally or laterally during operation of a cell expansion system, according to embodiments of the present disclosure.

In embodiments, the CES (such as CES 500 (see FIGS. 5A, 5B, & 5C) and/or CES 600 (see FIG. 6), for example) may include a device configured to move or "rock" the cell growth chamber relative to other components of the cell expansion system by attaching it to a rotational and/or lateral rocking device. FIG. 1C shows one such device, in which a bioreactor 100 may be rotationally connected to two rotational rocking components and to a lateral rocking component, according to an embodiment.

A first rotational rocking component 138 rotates the bioreactor 100 around central axis 142 of the bioreactor 100. Rotational rocking component 138 may be rotationally associated with bioreactor 100. In embodiments, bioreactor 100 may be rotated continuously in a single direction around central axis 142 in a clockwise or counterclockwise direction. Alternatively, bioreactor 100 may rotate in alternating fashion, first clockwise, then counterclockwise, for example, around central axis 142, according to embodiments.

The CES may also include a second rotational rocking component that rotates bioreactor 100 around rotational axis 144. Rotational axis 144 may pass through the center point of bioreactor 100 and may be normal to central axis 142. Bioreactor 100 may be rotated continuously in a single direction around rotational axis 144 in a clockwise or counterclockwise direction in embodiments. Alternatively, bioreactor 100 may be rotated around rotational axis 144 in an alternating fashion, first clockwise, then counterclockwise, for example. In various embodiments, bioreactor 100 may also be rotated around rotational axis 144 and positioned in a horizontal or vertical orientation relative to gravity.

In embodiments, lateral rocking component 140 may be laterally associated with bioreactor 100. The plane of lateral rocking component 140 moves laterally in the −x and −y directions, in embodiments. The settling of cells in the bioreactor may be reduced by movement of cell-containing media within the hollow fibers, according to embodiments.

The rotational and/or lateral movement of a rocking device may reduce the settling of cells within the device and reduce the likelihood of cells becoming trapped within a portion of the bioreactor. The rate of cells settling in the cell growth chamber is proportional to the density difference between the cells and the suspension media, according to Stokes's Law. In certain embodiments, a 180-degree rotation (fast) with a pause (having a total combined time of 30 seconds, for example) repeated as described above keeps non adherent red blood cells, for example, suspended. A minimum rotation of about 180 degrees would be preferred in an embodiment; however, one could use rotation of up to 360 degrees or greater. Different rocking components may be used separately, or may be combined in any combination. For example, a rocking component that rotates bioreactor 100 around central axis 142 may be combined with the rocking component that rotates bioreactor 100 around axis 144. Likewise, clockwise and counterclockwise rotation around different axes may be performed independently in any combination.

Figure 2:
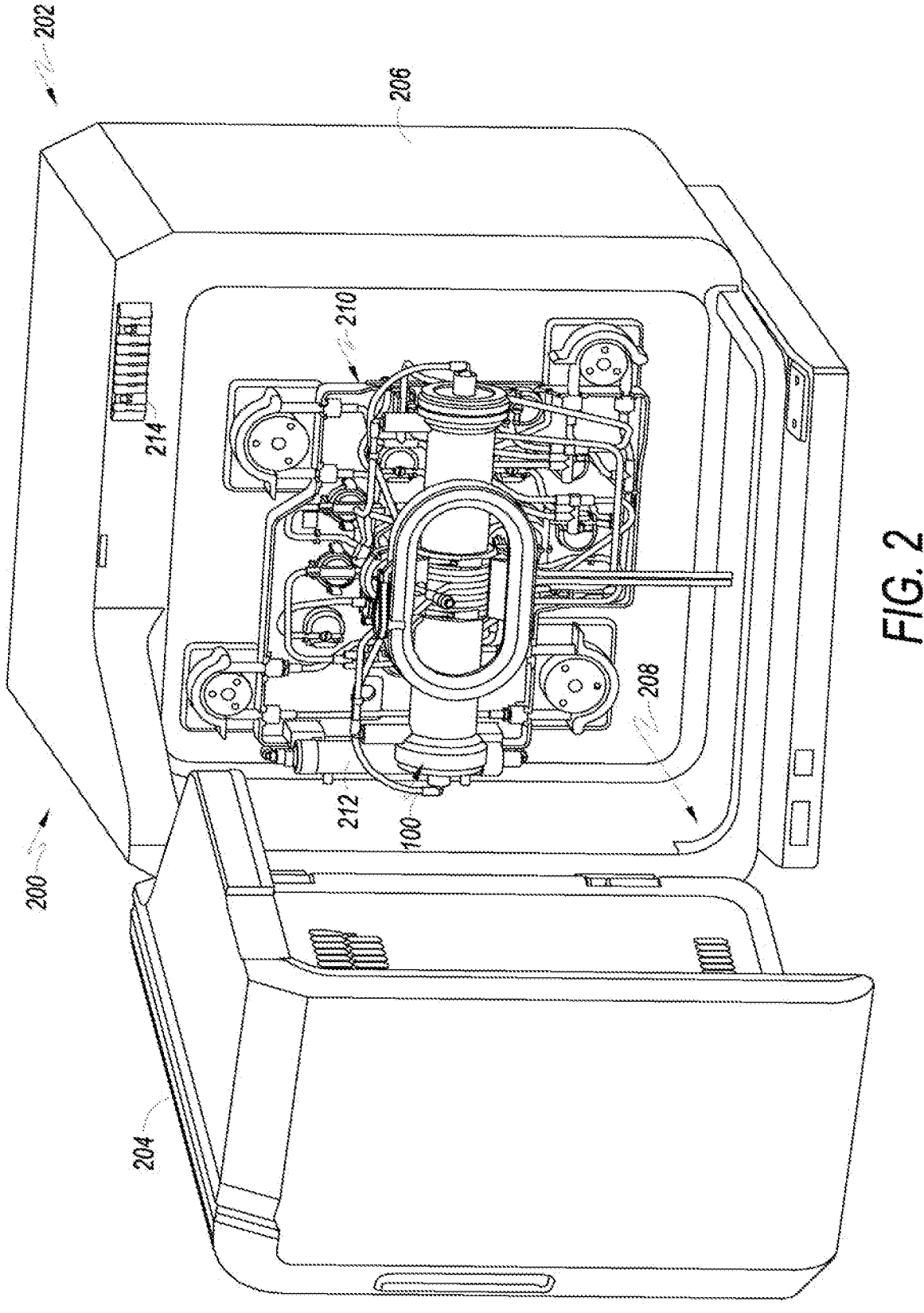
FIG. 2 illustrates a perspective view of a cell expansion system with a premounted fluid conveyance device, in accordance with embodiments of the present disclosure.

Turning to FIG. 2, an embodiment of a cell expansion system 200 with a premounted fluid conveyance assembly is shown in accordance with embodiments of t present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a premounted fluid conveyance assembly 210. The premounted fluid conveyance assembly 210 is detachably-attachable to the cell expansion machine 202 to facilitate relatively quick exchange of a new or unused premounted fluid conveyance assembly 210 at a cell expansion machine 202 for a used premounted fluid conveyance assembly 210 at the same cell expansion machine 202. A single cell expansion machine 202 may be operated to grow or expand a first set of cells using a first premounted fluid conveyance assembly 210 and, thereafter, may be used to grow or expand a second set of cells using a second premounted fluid conveyance assembly 210 without needing to be sanitized between interchanging the first premounted fluid conveyance assembly 210 for the second premounted fluid conveyance assembly 210. The premounted fluid conveyance assembly 210 includes a bioreactor 100 and an oxygenator or gas transfer module 212 (also see FIG. 4). Tubing guide slots are shown as 214 for receiving various media tubing connected to premounted fluid conveyance 210, according to embodiments.

Figure 3:
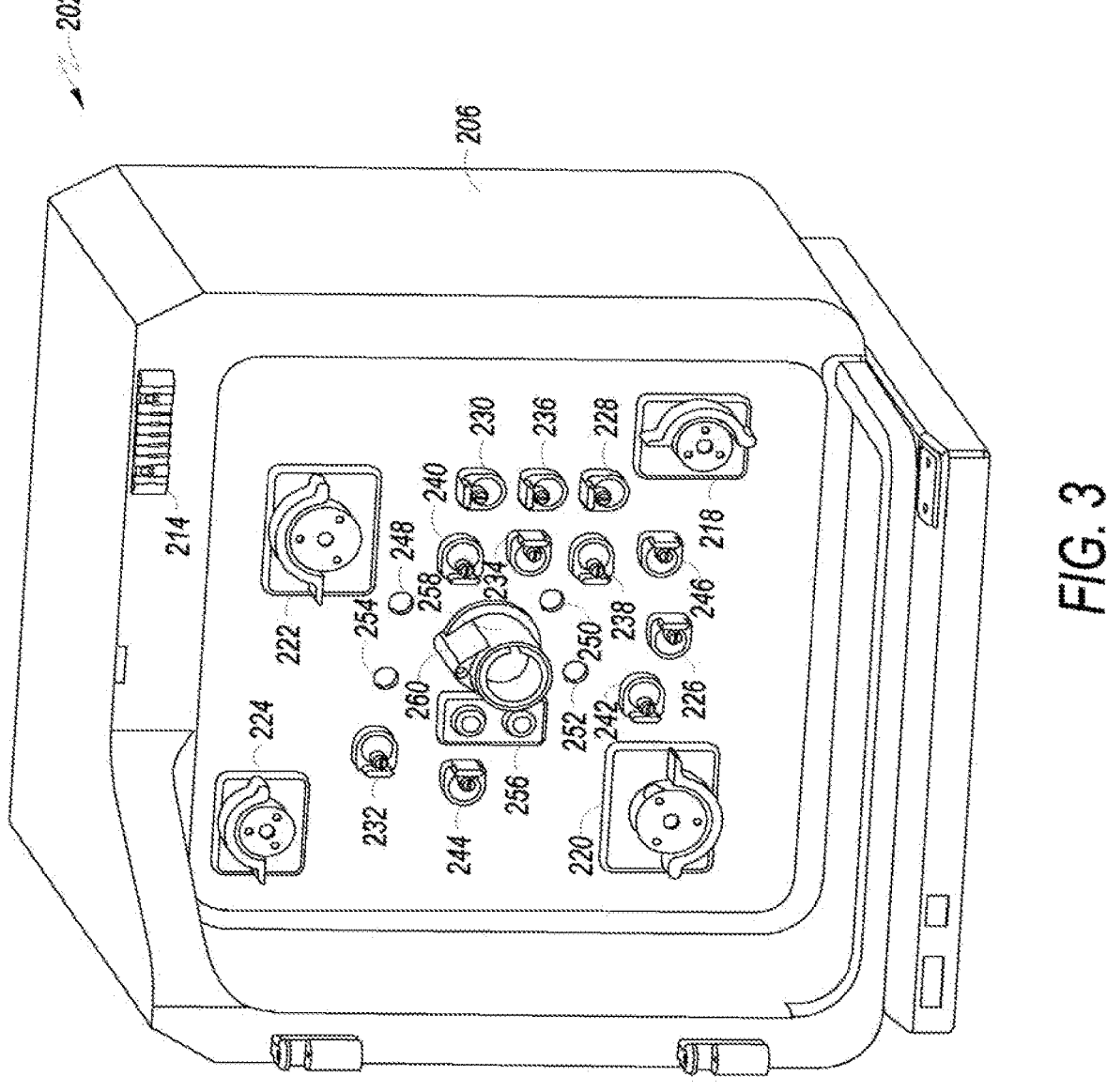
FIG. 3 depicts a perspective view of a housing of a cell expansion system, in accordance with embodiments of the present disclosure.

Next, FIG. 3 illustrates the back portion 206 of cell expansion machine 202 prior to detachably-attaching a premounted fluid conveyance assembly 210 (FIG. 2), in accordance with embodiments of the present disclosure. The closable door 204 (shown in FIG. 2) is omitted from FIG. 3. The back portion 206 of the cell expansion machine 202 includes a number of different structures for working in combination with elements of a premounted fluid conveyance assembly 210. More particularly, the back portion 206 of the cell expansion machine 202 includes a plurality of peristaltic pumps for cooperating with pump loops on the premounted fluid conveyance assembly 210, including the IC circulation pump 218, the EC circulation pump 220, the IC inlet pump 222, and the EC inlet pump 224. In addition, the back portion 206 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve

240, the IC waste or outlet valve 242, the EC waste valve 244, and the harvest valve 246. Several sensors are also associated with the back portion 206 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is an optical sensor 256 for an air removal chamber, according to an embodiment.

In accordance with embodiments, a shaft or rocker control 258 for rotating the bioreactor 100 is shown. Shaft fitting 260 associated with the shaft or rocker control 258 allows for proper alignment of a shaft access aperture, see e.g., 424 (FIG. 4) of a tubing-organizer, see e.g., 300 (FIG. 4) of a premounted conveyance assembly 210 or 400 with the back portion 206 of the cell expansion machine 202. Rotation of shaft or rocker control 258 imparts rotational movement to shaft fitting 260 and bioreactor 100. Thus, when an operator or user of the CES 200 attaches a new or unused premounted fluid conveyance assembly 400 (FIG. 4) to the cell expansion machine 202, the alignment is a relatively simple matter of properly orienting the shaft access aperture 424 (FIG. 4) of the premounted fluid conveyance assembly 210 or 400 with the shaft fitting 260.

Figure 4:
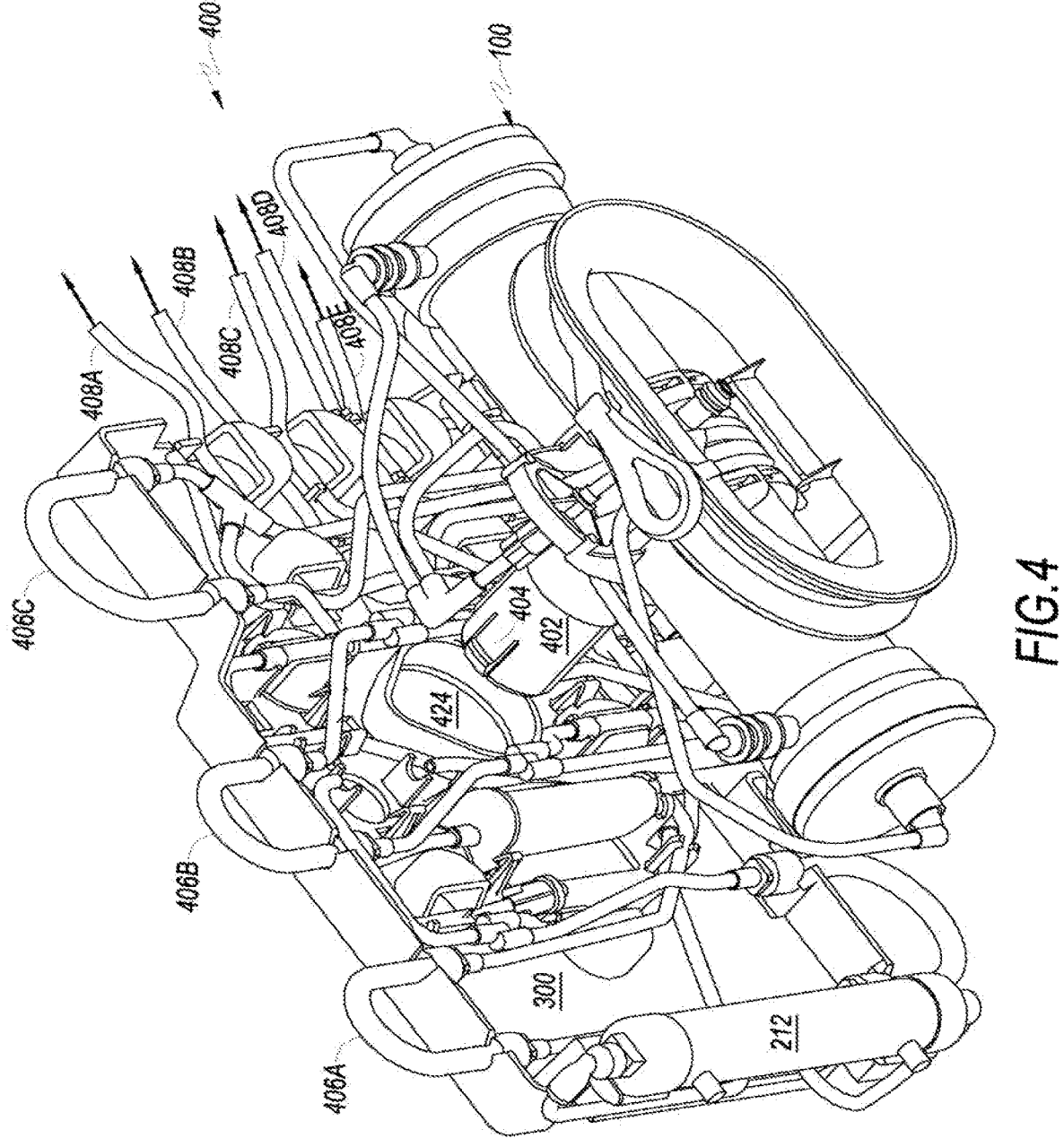
FIG. 4 illustrates a perspective view of a premounted fluid conveyance device, in accordance with embodiments of the present disclosure.

Turning to FIG. 4, a perspective view of a detachably-attachable premounted fluid conveyance assembly 400 is shown. The premounted fluid conveyance assembly 400 may be detachably-attachable to the cell expansion machine 202 (FIGS. 2 and 3) to facilitate relatively quick exchange of a new or unused premounted fluid conveyance assembly 400 at a cell expansion machine 202 for a used premounted fluid conveyance assembly 400 at the same cell expansion machine 202. As shown in FIG. 4, the bioreactor 100 may be attached to a bioreactor coupling that includes a shaft fitting 402. The shaft fitting 402 includes one of more shaft fastening mechanisms, such as a biased arm or spring member 404 for engaging a shaft, e.g., 258 (shown in FIG. 3), of the cell expansion machine 202.

According to embodiments, the premounted fluid conveyance assembly 400 includes tubing 408A, 4088, 408C, 408D, 408E, etc., and various tubing fittings to provide the fluid paths shown in FIGS. 5A, 5B, 5C, and 6, as discussed below. Pump loops 406A, 406B, and 406C may also be provided for the pump(s). In embodiments, although the various media may be provided at the site where the cell expansion machine 202 is located, the premounted fluid conveyance assembly 400 may include sufficient tubing length to extend to the exterior of the cell expansion machine 202 and to enable welded connections to tubing associated with media bag(s) or container(s), according to embodiments.

Figure 5A:
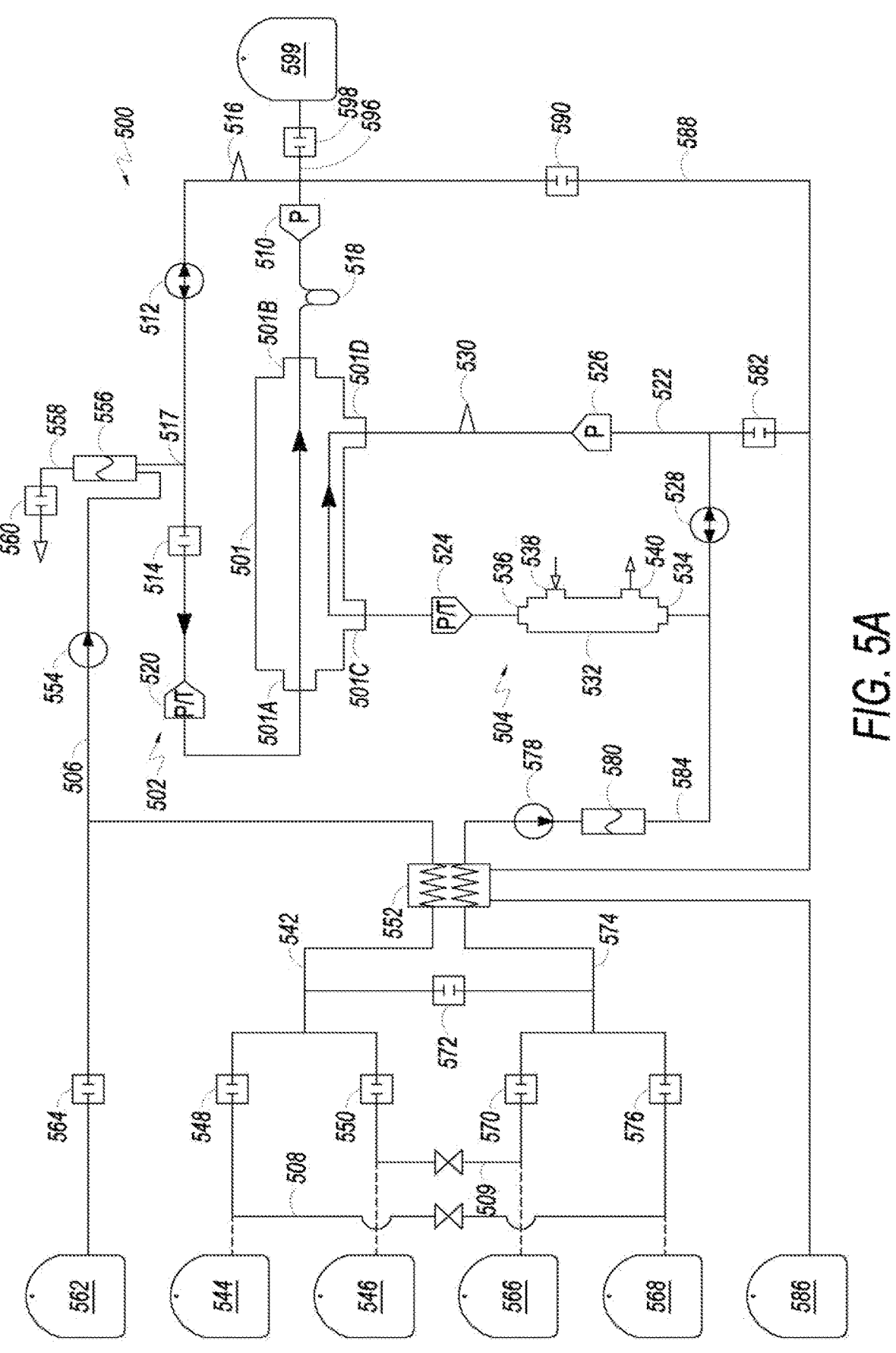
FIG. 5A depicts a schematic of a cell expansion system, including an operational configuration showing fluid movement, in accordance with an embodiment of the present disclosure.
Figure 5B:
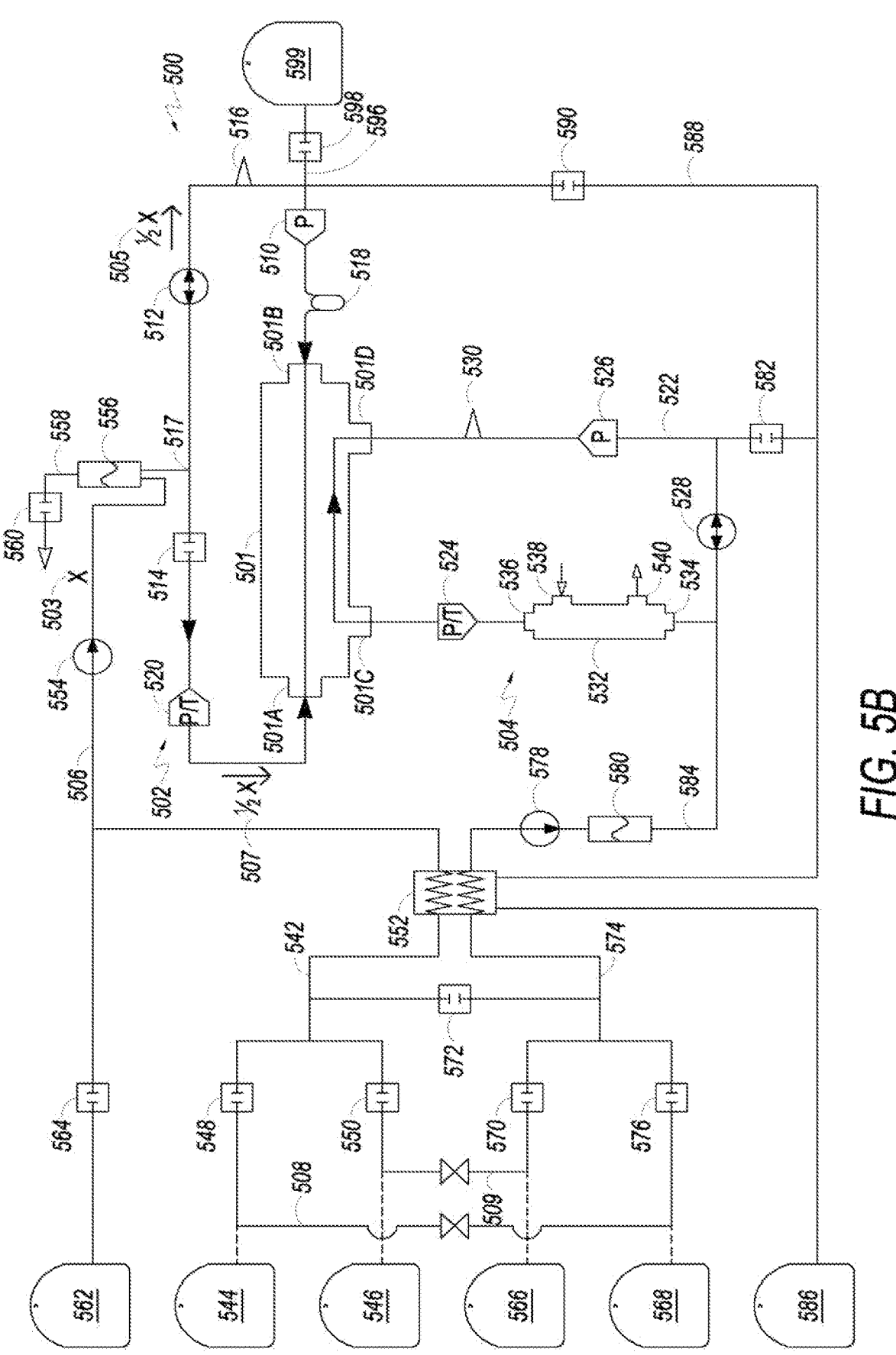
FIG. 5B depicts a schematic of a cell expansion system, including another operational configuration showing fluid movement, in accordance with an embodiment of the present disclosure.
Figure 5C:
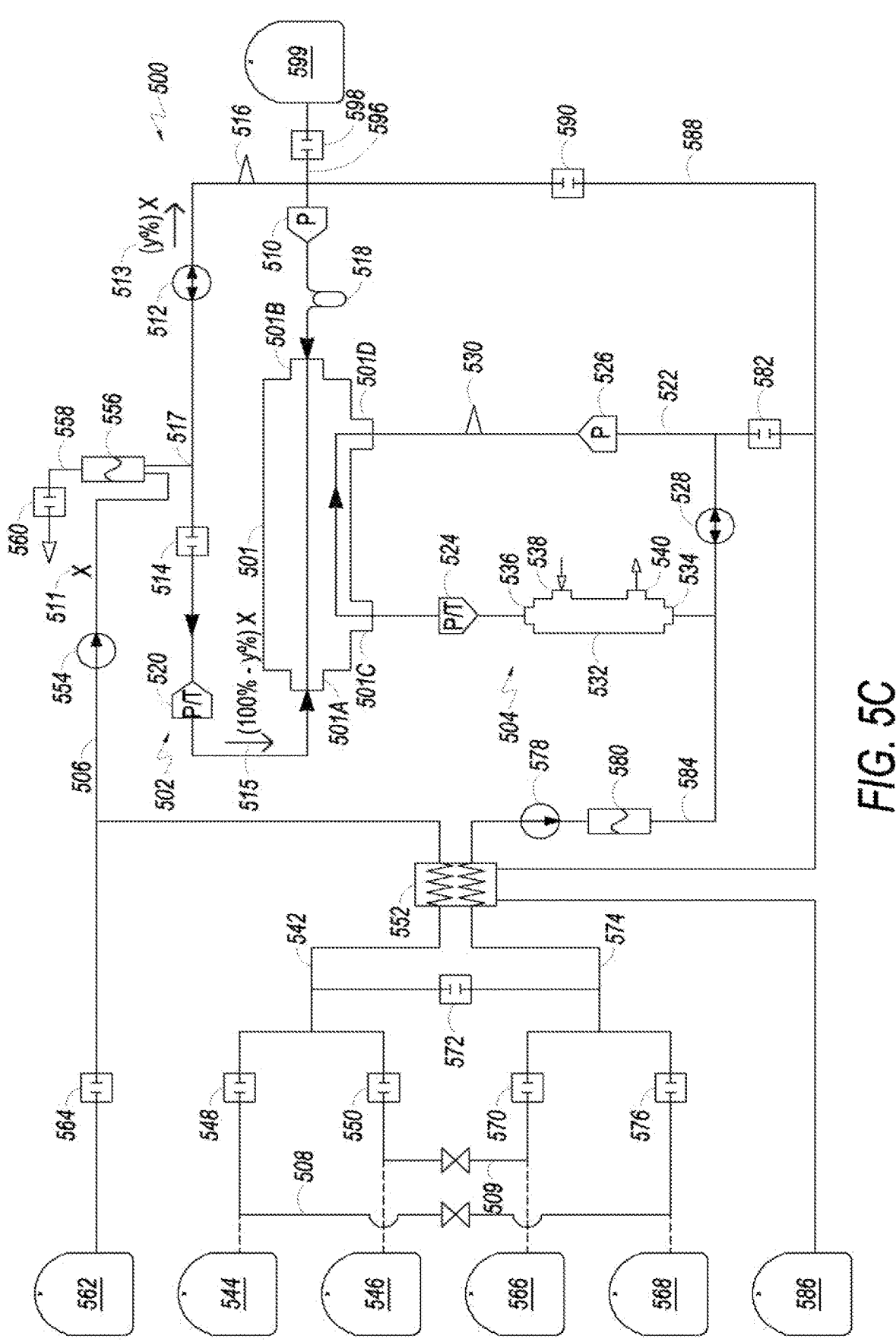
FIG. 5C depicts a schematic of a cell expansion system, including another operational configuration showing fluid movement, in accordance with an embodiment of the present disclosure.
Figure 6:
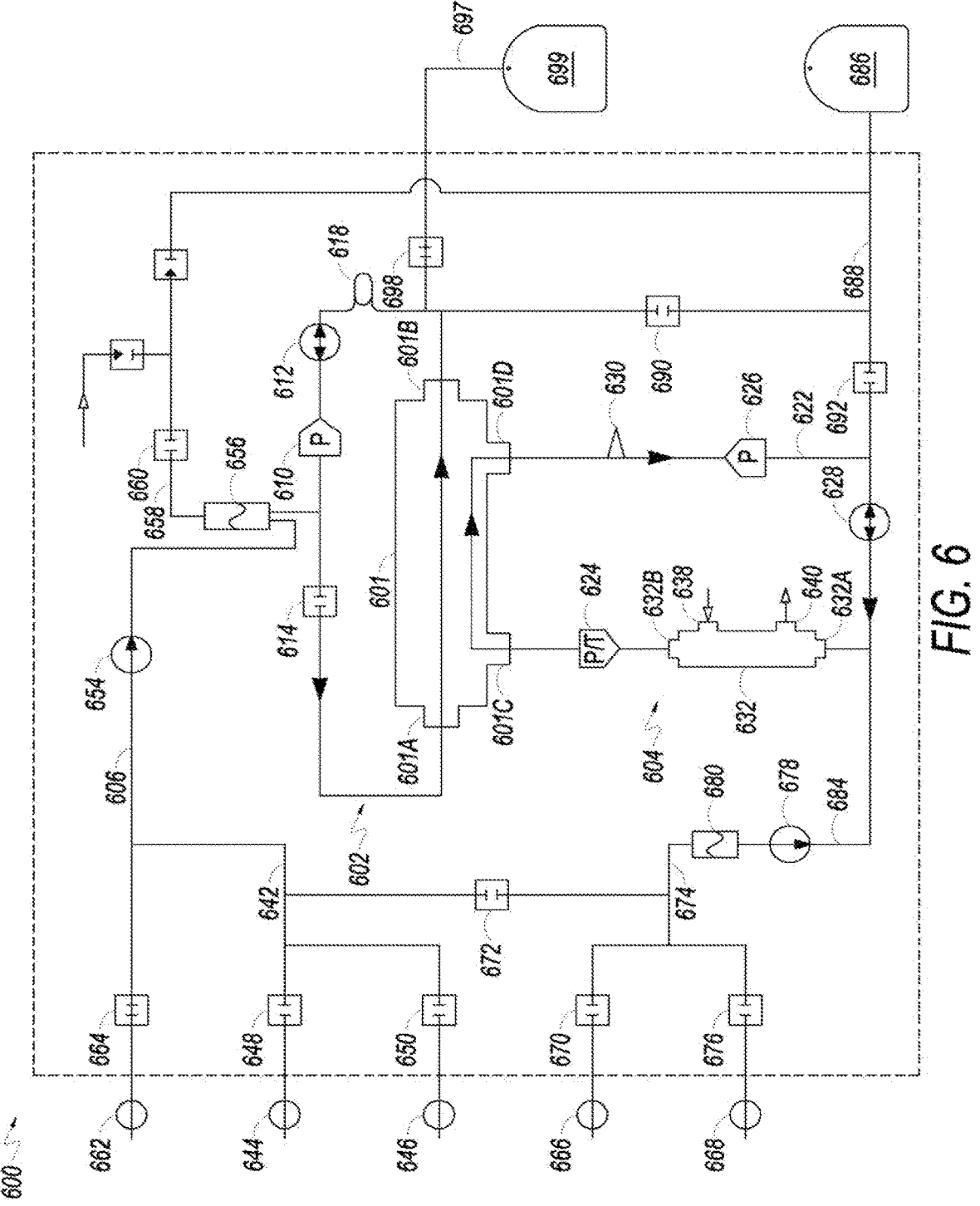
FIG. 6 illustrates a schematic of a cell expansion system, in accordance with another embodiment of the present disclosure.

Next, FIGS. 5A, 5B, and 5C illustrate schematics of embodiments of a cell expansion system 500, and FIG. 6 illustrates a schematic of another embodiment of a cell expansion system 600. In the embodiments shown in FIGS. 5A, 5B, 5C, and 6, and as described below, the cells are grown in the IC space. However, the disclosure is not limited to such examples and may in other embodiments provide for cells to be grown in the EC space.

As noted, FIGS. 5A, 5B, and 5C illustrate a CES 500. While FIGS. 5A, 5B, and 5C depict substantially similar structural components of CES 500, FIGS. 5A, 5B, and 5C illustrate possible operational configurations of fluid movement in a first fluid circulation path using the structural features of CES 500, in accordance with embodiments of the present disclosure. As shown, CES 500 includes first fluid circulation path 502 (also referred to as the "intracapillary loop" or "IC loop") and second fluid circulation path 504 (also referred to as the "extracapillary loop" or "EC loop"), according to embodiments. First fluid flow path 506 may be fluidly associated with cell growth chamber 501 to form first fluid circulation path 502. Fluid flows into cell growth chamber 501 through IC inlet port 501A, through hollow fibers in cell growth chamber 501, and exits via IC outlet port 501B. Pressure gauge 510 measures the pressure of media leaving cell growth chamber or bioreactor 501. Media flows through IC circulation pump 512 which may be used to control the rate of media flow. IC circulation pump 512 may pump the fluid in a first direction or second direction opposite the first direction. Exit port 501B may be used as an inlet in the reverse direction. For example, in a first configuration, the IC circulation pump may pump the fluid in a positive direction, in which the fluid enters the IC inlet port 501A. In a second configuration, for example, the IC circulation pump may pump the fluid in a negative direction, in which the fluid enters the IC outlet port 501B, for example.

Media entering the IC loop may enter through valve 514. As those skilled in the art will appreciate, additional valves, pressure gauges, pressure/temperature sensors, ports, and/or other devices may be placed at various locations to isolate and/or measure characteristics of the media along portions of the fluid paths. Accordingly, it is to be understood that the schematic shown represents one possible configuration for various elements of the CES 500, and modifications to the schematic shown are within the scope of the one or more present embodiments.

With regard to the IC loop 502, samples of media may be obtained from sample port 516 or sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in cell growth chamber 501 may be flushed out of cell growth chamber 501 into harvest bag 599 through valve 598 or redistributed within the hollow fibers for further growth.

Fluid in second fluid circulation path 504 enters cell growth chamber 501 via EC inlet port 501C, and leaves cell growth chamber 501 via EC outlet port 501D. Media in the EC loop 504 may be in contact with the outside of the hollow fibers in the cell growth chamber 501, thereby allowing diffusion of small molecules into and out of the hollow fibers.

Pressure/temperature gauge 524 disposed in the second fluid circulation path 504 allows the pressure and temperature of media to be measured before the media enters the EC space of the cell growth chamber 501, according to an embodiment. Pressure gauge 526 allows the pressure of media in the second fluid circulation path 504 to be measured after it leaves the cell growth chamber 501. With regard to the EC loop, samples of media may be obtained from sample port 530 or a sample coil during operation.

In embodiments, after leaving EC outlet port 501D of cell growth chamber 501, fluid in second fluid circulation path 504 passes through EC circulation pump 528 to oxygenator or gas transfer module 532. EC circulation pump 528 may also pump the fluid in opposing directions. Second fluid flow path 522 may be fluidly associated with oxygenator or gas transfer module 532 via oxygenator inlet port 534 and oxygenator outlet port 536. In operation, fluid media flows into oxygenator or gas transfer module 532 via oxygenator inlet port 534, and exits oxygenator or gas transfer module 532 via oxygenator outlet port 536. Oxygenator of gas transfer module 532 adds oxygen to, and removes bubbles from, media in the CES 500, for example. In various embodiments, media in second fluid circulation path 504 may be in equilibrium with gas entering oxygenator or gas transfer module 532. The oxygenator or gas transfer module 532 may be any appropriately sized oxygenator or gas transfer device. Air or gas flows into oxygenator or gas transfer module 532 via filter 538 and out of oxygenator or gas transfer device 532 through filter 540. Filters 538 and 540 reduce or prevent contamination of oxygenator or gas transfer module 532 and associated media. Air or gas purged from the CES 500 during portions of a priming sequence may vent to the atmosphere via the oxygenator or gas transfer module 532.

In accordance with at least one embodiment, media, including cells (from bag 562), and fluid media from bag 546 may be introduced to first fluid circulation path 502 via first fluid flow path 506. Fluid container 562 (e.g., Cell Inlet Bag or Saline Priming Fluid for priming air out of the system) may be fluidly associated with the first fluid flow path 506 and the first fluid circulation path 502 via valve 564.

Fluid containers, or media bags, 544 (e.g., Reagent) and 546 (e.g., IC Media) may be fluidly associated with either first fluid inlet path 542 via valves 548 and 550, respectively, or second fluid inlet path 574 via valves 570 and 576. First and second sterile sealable input priming paths 508 and 509 are also provided. An air removal chamber (ARC) 556 may be fluidly associated with first circulation path 502. The air removal chamber 556 may include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 500 during portions of the priming sequence or other protocols may vent to the atmosphere out air valve 560 via line 558 that may be fluidly associated with air removal chamber 556.

EC media (e.g., from bag 568) or wash solution (e.g., from bag 566) may be added to either the first or second fluid flow paths. Fluid container 566 may be fluidly associated with valve 570 that may be fluidly associated with first fluid circulation path 502 via distribution valve 572 and first fluid inlet path 542. Alternatively, fluid container 566 may be fluidly associated with second fluid circulation path 504 via second fluid inlet path 574 and EC inlet path 584 by opening valve 570 and closing distribution valve 572. Likewise, fluid container 568 may be fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing distribution valve 572.

An optional heat exchanger 552 may be provided for media reagent or wash solution introduction.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one embodiment, first and second fluid circulation paths 502 and 504 are connected to waste line 588. When valve 590 is opened, IC media may flow through waste line 588 and to waste or outlet bag 586. Likewise, when valve 582 is opened, EC media may flow through waste line 588 to waste or outlet bag 586.

In embodiments, cells may be harvested via cell harvest path 596. Here, cells from cell growth chamber 501 may be harvested by pumping the IC media containing the cells through cell harvest path 596 and valve 598 to cell harvest bag 599.

Various components of the CES 500 may be contained or housed within a machine or housing, such as cell expansion machine 202 (FIGS. 2 and 3), wherein the machine maintains cells and media, for example, at a predetermined temperature.

In the configuration depicted for CES 500 in FIG. 5A, fluid media in first fluid circulation path 502 and second fluid circulation path 504 flows through cell growth chamber 501 in the same direction (a co-current configuration), in an embodiment. The CES 500 may also be configured to flow in a counter-current conformation (not shown), in another embodiment. In the configuration shown in FIG. 5A, fluid in first fluid circulation path 502 enters the bioreactor 501 at IC inlet port 501A and exits the bioreactor 501 at IC outlet port 501B. In the configurations depicted in FIGS. 5B and 5C, fluid media in first circulation path 502 may flow in opposite or opposing directions from connection 517 such that fluid may enter IC inlet port, a first port, 501A on one end of the bioreactor, and fluid may enter IC outlet port, a second port, 501B on the opposing end of the bioreactor to retain cells in the bioreactor itself, according to embodiments. The first fluid flow path may be fluidly associated with the first fluid circulation path through connection 517. In embodiments, connection 517 may be a point or location from which the fluid may flow in opposite directions, for example, based on the direction of the IC inlet pump and the direction of the IC circulation pump. In an embodiment, connection 517 may be a T-fitting or T-coupling. In another embodiment, connection 517 may be a Y-fitting or Y-coupling. Connection 517 may be any type of fitting, coupling, fusion, pathway, tubing, etc., allowing the first fluid flow path to be fluidly associated with the first circulation path. It is to be understood that the schematics and operational configurations shown in FIGS. 5A, 5B, and 5C represent possible configurations for various elements of the cell expansion system, and modifications to the schematics and operational configurations shown are within the scope of the one or more present embodiments.

Turning to FIG. 6, a schematic of another embodiment of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with cell growth chamber 601 to form first fluid circulation path 602. Fluid flows into cell growth chamber 601 through IC inlet port 601A, through hollow fibers in cell growth chamber 601, and exits via IC outlet port 6018. Pressure sensor 610 measures the pressure of media leaving cell growth chamber 601. In addition to pressure, sensor 610 may, in embodiments, also be a temperature sensor that detects the media pressure and temperature during operation. Media flows through IC circulation pump 612 which may be used to control the rate of media flow. IC circulation pump 612 may pump the fluid in a first direction or second direction opposite the first direction. Exit port 6018 may be used as an inlet in the reverse direction. Media entering the IC loop may enter through valve 614. As those skilled in the art will appreciate, additional valves, pressure gauges, pressure/temperature sensors, ports, and/or other devices may be placed at various locations to isolate and/or measure characteristics of the media along portions of the fluid paths. Accordingly, it is to be understood that the schematic shown represents one possible configuration for various elements of the CES 600, and modifications to the schematic shown are within the scope of the one or more present embodiments.

With regard to the IC loop, samples of media may be obtained from sample coil 618 during operation. Media then returns to IC inlet port 601A to complete fluid circulation path 602. Cells grown/expanded in cell growth chamber 601 may be flushed out of cell growth chamber 601 into harvest bag 699 through valve 698 and line 697. Alternatively, when valve 698 is closed, the cells may be redistributed within chamber 601 for further growth.

Fluid in second fluid circulation path 604 enters cell growth chamber 601 via EC inlet port 601C and leaves cell growth chamber 601 via EC outlet port 601D. Media in the EC loop may be in contact with the outside of the hollow fibers in the cell growth chamber 601, thereby allowing diffusion of small molecules into and out of the hollow fibers that may be within chamber 601, according to an embodiment.

Pressure/temper sensor 624 disposed in the second fluid circulation path 604 allows the pressure and temperature of media to be measured before the media enters the EC space of the cell growth chamber 601. Sensor 626 allows the pressure and/or temperature of media in the second fluid circulation path 604 to be measured after it leaves the cell growth chamber 601. With regard to the EC loop, samples of media may be obtained from sample port 630 or a sample coil during operation.

After leaving EC outlet port 601D of cell growth chamber 601, fluid in second fluid circulation path 604 passes through EC circulation pump 628 to oxygenator or gas transfer module 632. EC circulation pump 628 may also pump the fluid in opposing directions, according to embodiments. Second fluid flow path 622 may be fluidly associated with oxygenator or gas transfer module 632 via an inlet port 632A and an outlet port. 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to, and removes bubbles from, media in the CES 600, for example. In various embodiments, media in second fluid circulation path 604 may be in equilibrium with gas entering oxygenator or gas transfer module 632. The oxygenator or gas transfer module 832 may be any appropriately sized device useful for oxygenation or gas transfer. A or gas flows into oxygenator or gas transfer module 632 via filter 638 and out of oxygenator or gas transfer device 632 through filter 640. Filters 638 and 640 reduce or prevent contamination of oxygenator of gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through cell growth chamber 601 in the same direction (a co-current configuration). The CES 600 may also be configured to flow in a counter-current conformation, according to embodiments.

In accordance with at least one embodiment, media, including cells (from a source such as a cell container, e.g., a bag) may be attached at attachment point 662, and fluid media from a media source may be attached at attachment point 646. The cells and media may be introduced into first fluid circulation path 602 via first fluid flow path 606. Attachment point 662 may be fluidly associated with the first fluid flow path 606 via valve 664, and attachment point 646 may be fluidly associated with the first fluid flow path 806 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect alt, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668, and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 and second fluid flow path 684 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing distribution valve 672.

In the IC loop, fluid may be initially advanced by the IC inlet pump 654. In the EC loop, fluid may be initially advanced by the EC inlet pump 678. An air detector 680, such as an ultrasonic sensor, may also be associated with the EC inlet path 684.

In at least one embodiment, first and second fluid circulation paths 602 and 604 are connected to waste line 688. When valve 690 is opened, IC media may flow through waste line 688 and to waste or outlet bag 686. Likewise, when valve 692 is opened, EC media may flow to waste or outlet bag 886.

After cells have been grown in cell growth chamber 601, they may be harvested via cell harvest path 697. Here, cells from cell growth chamber 601 may be harvested by pumping the IC media containing the cells through cell harvest path 697, with valve 698 open, into cell harvest bag 699.

Various components of the CES 600 may be contained or housed within a machine or housing, such as cell expansion machine 202 (FIGS. 2 and 3), wherein the machine maintains cells and media, for example, at a predetermined temperature. It is further noted that, in embodiments, components of CES 600 and CES 500 may be combined. In other embodiments, a CES may include fewer or additional components than those shown in CES 500 and/or CES 600 and still be within the scope of the present disclosure. An example of a cell expansion system that may incorporate features of the present disclosure is the Quantum® Cell Expansion System, manufactured by Terumo BCT, Inc. In Lakewood, Colorado.

It is to be understood that the schematic shown in FIG. 6 represents a possible configuration for various elements of the cell expansion system, and modifications to the schematic shown are within the scope of the one or more present embodiments.

Examples and further description of cell expansion systems are provided in U.S. Pat. No. 8,309,347 ("Cell Expansion System and Methods of Use," issued on Nov. 13, 2012) and U.S. Pat. No. 9,057,045, filed on Dec. 15, 2010, ("Method of Loading and Distributing Cells in a Bioreactor of a Cell Expansion System," issued on Jun. 16, 2015), which are hereby incorporated by reference herein in their entireties for all that they teach and for all purposes.

Figure 7:
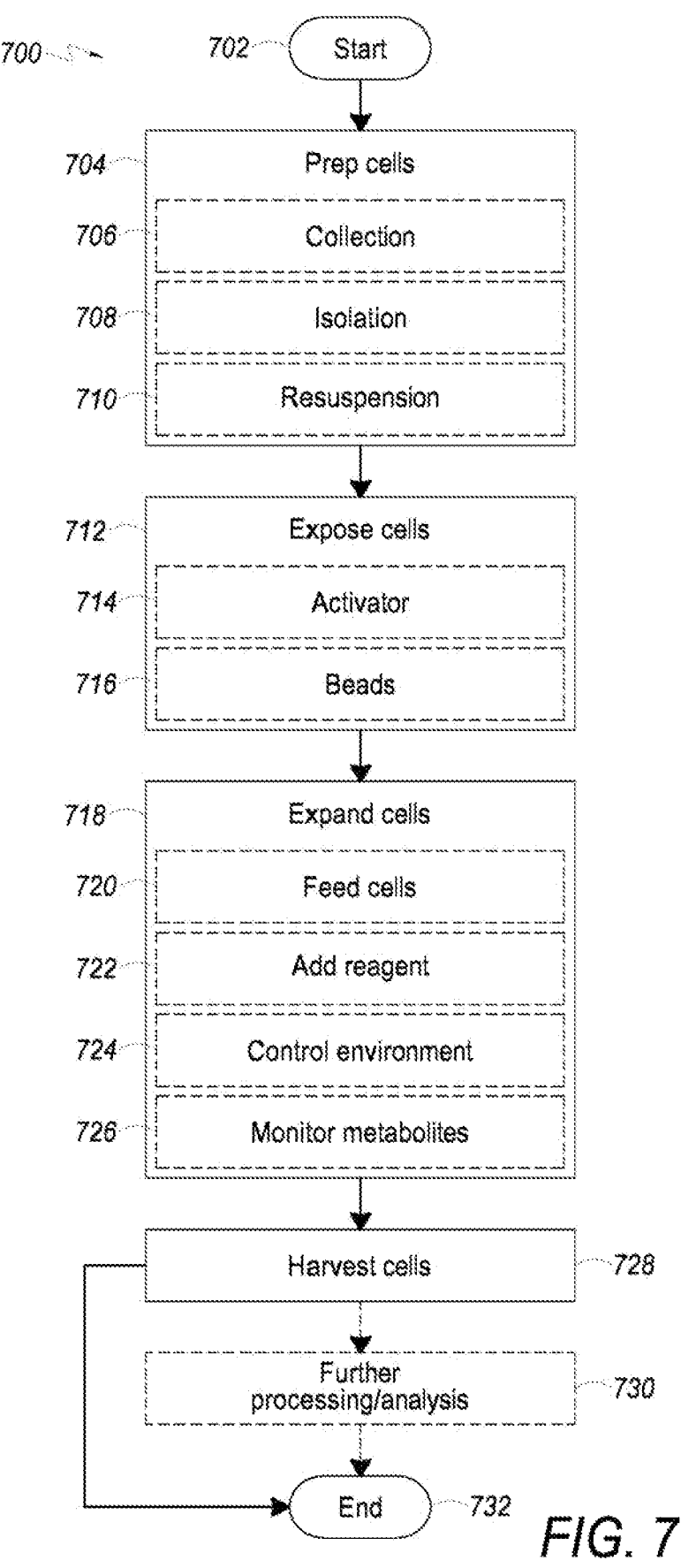
FIG. 7 depicts a flow diagram illustrating the operational characteristics of a process for expanding cells, in accordance with embodiments of the present disclosure.

While various example embodiments of a cell expansion system and methods associated therewith have been described, FIG. 7 illustrates example operational steps 700 of a process for expanding non-adherent, or suspension, cells in a cell expansion system, such as CES 500 or CES 600, in accordance with embodiments of the present disclosure.

START operation 702 is initiated, and process 700 proceeds to preparation of cells 704. In embodiments, the preparation of cells 704 may involve a number of different and optional steps. For example, the cells may be collected 706. The collection of cells 706 may involve separating and collecting the cells from a donor. In some embodiments, an apheresis procedure may be performed to collect a volume of lymphocytes from the peripheral blood of a donor, e.g. leukapheresis. The volume of lymphocytes may include the target cell population to be expanded by process 700. In other embodiments, the cell may be collected from cord blood.

After collection 706, optionally, the cells may be isolated 708 as part of the preparation 704. The volume of cells collected at step 706 may include a number of different cell types including the cells that are targeted for expansion. Optional step 708 may be performed to isolate the target cells. As one example, the target cells may be T cells, e.g., naïve, memory, helper, effector, and/or regulated. In some embodiments, the cells collected at step 706 may be isolated 708 soon after collections (e.g., they may be fresh). In other embodiments, the cells collected at 706 may be frozen for storage. In these embodiments, a thawing step may be performed prior to isolating cells as part of step 708.

In one embodiment, the T cells may be regulated T cells, e.g., T cells with phenotypes that include CD4+, CD25+, FoxP3$^+$, and/or combinations thereof. In other embodiments, the T cells may be effector, helper, memory, and/or naïve T cells, e.g., T cells with phenotypes that include CD3+, CD4+, CD8+, and/or combinations thereof. The cells may be isolated using any suitable isolation technique. For example, the cells may be isolated using immunomagnetic separation where magnetic beads functionalized with antibodies are contacted with the cells collected at 706. The functionalized beads may preferentially attach to the target cell population. A magnetic field may then be used to retain the beads with the attached target call population, while the other cells may be removed. In other embodiments, the cells may be isolated using a ficoll separation procedure. In yet other embodiments, the cells may be isolated using elutriation, such as using an ELUTRA® Cell Separation System, manufactured by Terumo BCT of Lakewood, CO.

In some embodiments, the cells may be frozen for storage after isolation step 708. In embodiments, the isolated cells may be mixed with a cryopreservative agent and stored for a period of time prior to cell expansion. These embodiments may involve a freezing step that may be performed after isolating cells at step 708.

The cells may be optionally resuspended 710 after isolation 708 (and/or thawed if previously frozen). In embodiments, the cells may be resuspended in a media that includes a number of nutrients and/or reagents that aid in maintaining the viability of the cells. In embodiments, the media may include at least serum albumin and a reagent, such as a cytokine. The cytokine may in embodiments be a recombinant human IL-2 cytokine. The media may include the cytokine at a concentrate of 200 IU/mi, in one embodiment. The media may include the cytokine at a concentrate of 100 IU/ml, in another embodiment. In yet another embodiment, the cells may be suspended in PBS with human AB serum. For example, the cells may be suspended in a fluid with PBS and 5% human AB serum. In some embodiments, such as embodiments that utilize beads as an activator, Human AB Serum may be present in all steps; including a cell loading step. Without being bound by theory, it is believed that Human serum contains LFA-3 (CD58) that may bind CD2 on T-cells, which may minimize aggregation of cells and beads.

Following the preparation of the cells 704, process 700 proceeds to expose cells 712 in order to activate the cells to expand. The cells may optionally be exposed to an activator 714 that is soluble. The activator, which may include antibody complexes, may be added to the media in which the cells are resuspended. In embodiments, the activator may be a human antibody CD3/CD28/CD2 cell activator complex. In some embodiments, the activator, may be included in the media used in the resuspension of the cells 710. Optionally, the cells may be exposed to beads 716, which may have an activator on their surface.

In embodiments, exposing the cells to the beads may involve adding a predetermined amount of beads to the resuspended cells. The beads may be added at different ratios with respect to the number of cells. For example, the beads may be added in a 1 bead:2 cell ratio. Other embodiments may provide for adding beads at different ratios, e.g., about 1 bead:about 1 cell, about 1 bead:about 2 cells, about 1 bead:about 3 cells, about 1 bead:about 4 cells, about 2 beads:about 1 cell, about 3 beads:about 1 cell, about 4 beads:about 1 cell, about 5 beads:about 1 cell, etc. The beads may have antibodies on their surface to activate the cells to expand. One example of beads that may be used include DYNABEADS® beads available from Thermo Fisher Scientific, Waltham, Massachusetts. The beads in some embodiments may be functionalized with antibodies on their surface, some non-limiting examples of the antibodies include: anti-CD2, anti-CD3; anti-CD4, anti-CD8, anti-CD28, anti-CD34 and combinations thereof.

Process 700 proceeds to expand cells 718. As part of cell expansion 718, the cells may be loaded into a cell growth chamber, e.g., a hollow fiber membrane bioreactor, where the cells are expanded. The cells may be fed 720 nutrients to promote their expansion. For example, media may be delivered into the cell growth chamber to provide the nutrients for expansion. The expansion of the cells 718 may also include adding reagents 722 periodically to the cell growth chamber to continue to promote their expansion. For example, in some embodiments, reagents (e.g., cytokines) may be added to the cell growth chamber to promote the expansion of the cells. In one embodiment, the reagent may be additional IL-2 cytokine, e.g., recombinant human IL-2 cytokine.

Also, as part of expanding the cells 718, the environment inside the cell growth chamber may be controlled 724. For example, gasses may be delivered and exchanged continuously to provide a balance of for example, carbon dioxide and oxygen to the cells expanding in the cell growth chamber. Additionally, the temperature may be controlled to be within a range optimized for cell expansion. Expansion of cells 718 may also include monitoring metabolites 726. For example, the lactate and glucose levels may be periodically monitored. A rise or fall in the metabolites may prompt changes (e.g., additional feeding, additional reagent additions, additional gas exchange, etc.) to control the environment 724 in the cell growth chamber.

Process 700 next proceeds to harvest the cells 728. Further processing of the removed cells or other analysis may optionally be performed at step 730. For example, the cells may be characterized to determine cell phenotype(s). The further processing or other analysis 730 may include performing flow cytometry, for example, to characterize cell phenotypes. Process 700 may then terminate at END operation 732. If it is not desired to perform further processing/analysis, process 700 terminates at END operation 732.

Figure 8A:
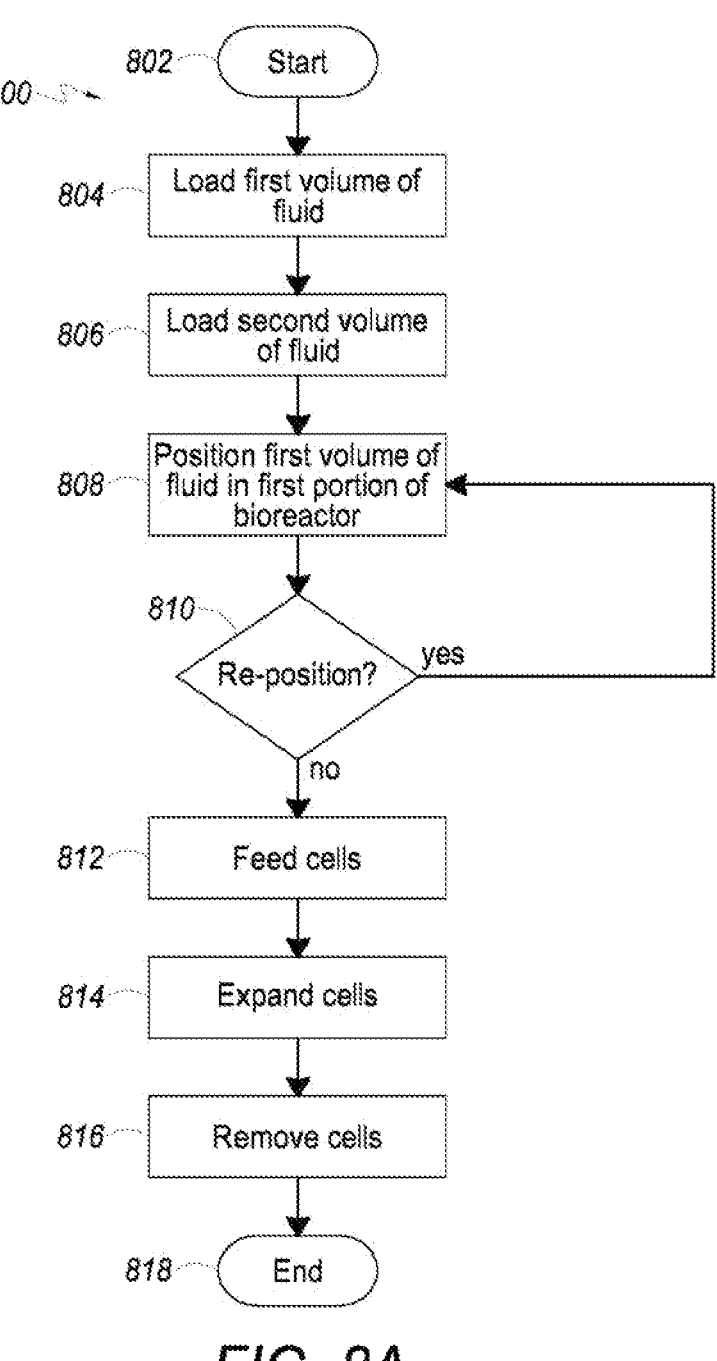
FIG. 8A illustrates a flow diagram depicting the operational characteristics of a process for expanding cells, in accordance with embodiments of the present disclosure.
Figure 8B:
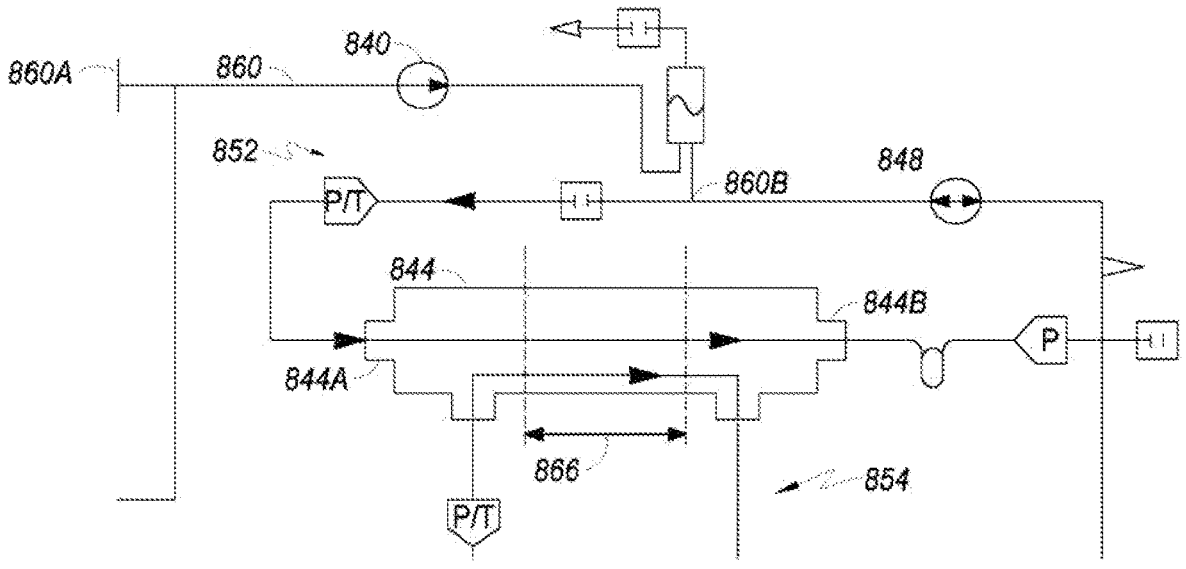
FIG. 8B depicts a schematic of a portion of a cell expansion system, in accordance with an embodiment of the present disclosure.

FIG. 8A illustrates operational steps 800 of a process, which may be used to position cells or other material (e.g., proteins, nutrients, growth factors) into a cell growth chamber according to embodiments of the present disclosure. In embodiments, the process 800 may be implemented as part of a "load cells centrally without circulation" task. Start operation 802 is initiated and process 800 proceeds to step 804, where a first volume of fluid with cells may be loaded into a cell growth chamber of a cell expansion system. In embodiments, the cells may comprise non-adherent cells, such as one or more types of T cells. In one embodiment, the plurality of cells comprises Tregs. In other embodiments, the cells may be mononuclear cells (such as PBMC's) that include a variety of T cell phenotypes. As may be appreciated, loading of the first volume of fluid with cells may be performed by components of a cell expansion system such as systems CES 500 (e.g., FIG. 5A) and CES 600 (FIG. 6), described above. FIG. 8B illustrates a portion of a cell expansion system that includes a first inlet pump 840, a first fluid flow path 860, a first fluid circulation pump 848, a first fluid circulation path 852, a cell growth chamber 844, and a second fluid circulation path 854. The first fluid flow path 860 is fluidly associated with fluid circulation path 852 through connection 860B. Embodiments may provide for the first volume of fluid with the cells to be loaded 804 through the first fluid flow path 860 utilizing the first fluid inlet pump 840 and into the first fluid circulation path 852. In embodiments, the first volume of fluid is loaded without activating the first fluid circulation pump 848.

As Illustrated in FIG. 8B, a volume of the first fluid circulation path 852 may be comprised of a number of volumes of its portions. For example, a first portion of the volume may be an intracapillary space (when the cell growth chamber is a hollow fiber membrane bioreactor) of the cell growth chamber 844. A second portion of the volume may be from connection 860B to an inlet port 844A of the cell growth chamber 844. A third portion may be from the connection 860B to an outlet port 844A of the cell growth chamber 844.

Process 800 proceeds to loading of a second volume of fluid 806. The second volume of fluid may comprise media and may be introduced into a portion of the first fluid flow path 860. In embodiments, the second volume may be a predetermined amount selected in order to position 808 the first volume into a first portion of the cell growth chamber 844. In embodiments, the first volume of fluid and the second volume of fluid may be the same. In other embodiments, the first volume of fluid and the second volume of fluid may be different. In yet other embodiments, a sum of the first volume of fluid and the second volume of fluid may be equal to a percentage of a volume of the first fluid circulation path, e.g., path 852 (FIG. 8B).

In order to position the first volume of fluid, the second volume of fluid has to be enough to push the first volume into the desired position in the cell growth chamber 844. The second volume of fluid may therefore, in embodiments, be about as large as the volume of the first fluid circulation path 852 between connection 860B and the inlet port 844A. As may be appreciated, this would push the first volume of fluid with the cells into a position within the cell growth chamber 844.

In other embodiments, the first volume of fluid (with cells) may be positioned 808 about a central region 866 of the cell growth chamber 844. In these embodiments, the second volume may be about as large a sum of the volume of the first fluid circulation path 852, between connection 860B and the inlet port 844A and the volume of the first fluid circulation path made up by the cell growth chamber 844 (e.g., the volume of the intracapillary space) that would not be occupied by the first volume of fluid when positioned in the cell growth chamber. For example, in one embodiment, the first volume of fluid (with) the cells) may be 50 mL. The cell growth chamber may have a volume of, for example, 124 mL. When the first volume is positioned around the central region 866, it will occupy the 50 ml around the central region 866, leaving 74 ml, which is on either side of the central region 866. Accordingly, 50% of 74 ml (or 37 ml) may be added to the volume between connection 860 and inlet port 844A to position the 50 ml of the first volume around the central region 866.

Positioning 808 the first volume may in embodiments, involve adding additional volumes of fluid to position the first volume with cells in the cell growth chamber. For example, if the desired position of the first volume is not achieved with the second volume, additional fluid may be added to position the first volume 808.

Process 800 proceeds to the query 810 to determine whether the first volume should be repositioned. For example, in embodiments, the first volume may be positioned closer to inlet port 844A. If it is desired to move the first volume closer to central region 866 of cell growth chamber 844, process 800 may loop back to step 808 where additional fluid may be added to the first fluid circulation path to position the first volume of fluid.

If it is determined at query 810 that the first volume does not need to be repositioned, process 800 proceeds to feeding of the cells 812. In embodiments, the cells may be fed using a media that includes a number of compounds such as glucose, proteins, growth factors, reagents, or other nutrients. In embodiments, feeding of the cells 812 may involve activating inlet pumps and circulation pumps (e.g., pumps 840 and 848) to deliver media with nutrients to the cells in the cell growth chamber 844. Some embodiments provide for the cells to be maintained in the cell growth chamber 844 during step 812, as described below. These embodiments may involve activating pumps, e.g., inlet pumps and circulation pumps (e.g., pumps 840 and 848, as described below) so that flow of fluid into the cell growth chamber 844 may be from both directions such as from the inlet port 844A and the outlet port 844B into the cell growth chamber 844.

Process 800 then proceeds to the expansion of the cells 814 where the cells may be expanded or grown. While step 814 is shown after step 812, step 814 may occur before, or simultaneous with, step 812, according to embodiments. Cells may then be removed 816 from the cell growth chamber and collected in a storage container. In embodiments, step 816 may involve a number of sub-steps. For example, the cells may be circulated by the circulation pump (e.g., pump 848) before they are collected and stored in a container. Process 800 terminates at END operation 830.

Figure 9A:
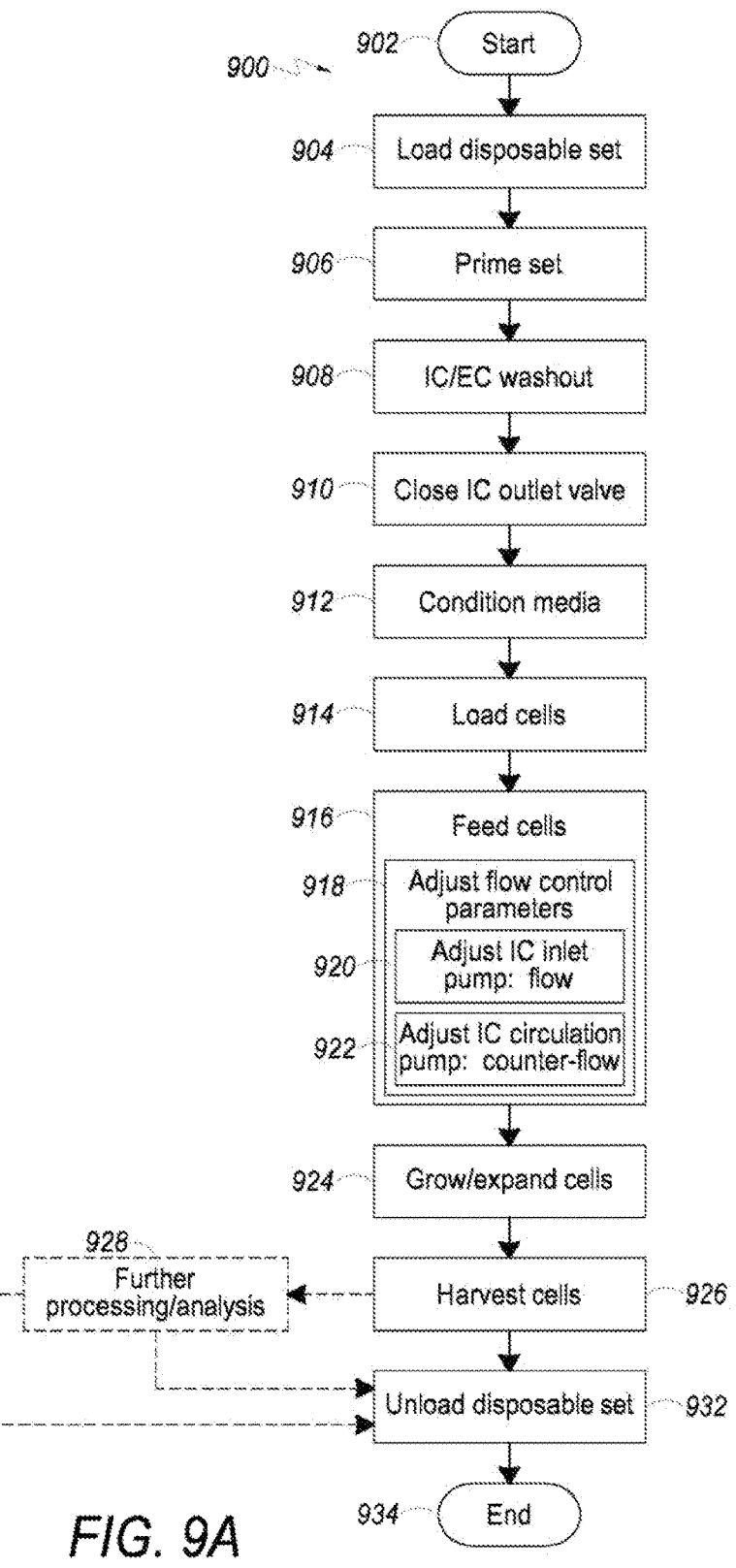
FIG. 9A depicts a flow diagram illustrating the operational characteristics of a process for expanding cells, in accordance with embodiments of the present disclosure.

Next, FIG. 9A illustrates example operational steps 900 of a process for retaining cells in a bioreactor of a cell expansion system, such as CES 500 (e.g., FIGS. 5B & 5C), in accordance with embodiments of the present disclosure. As discussed above, cells residing in the headers of the bioreactor or in the IC loop outside of the bioreactor may not receive proper gas exchange and nutrient exchange, which may result in cell aggregation and death. In an embodiment, the bioreactor provides gas exchange and nutrient exchange through the semi-permeable hollow fiber membrane. It can be important that such exchange is efficient as the surface area to volume ratio in a cell expansion system comprising a hollow fiber membrane may be significantly larger than that of other cell culturing methods (e.g., about 15 times that of cell culture flasks, for example). Such efficiency may be accomplished by minimizing the diffusion distance for media constituents able to pass the membrane surface where exchange takes place.

Figure 9B:
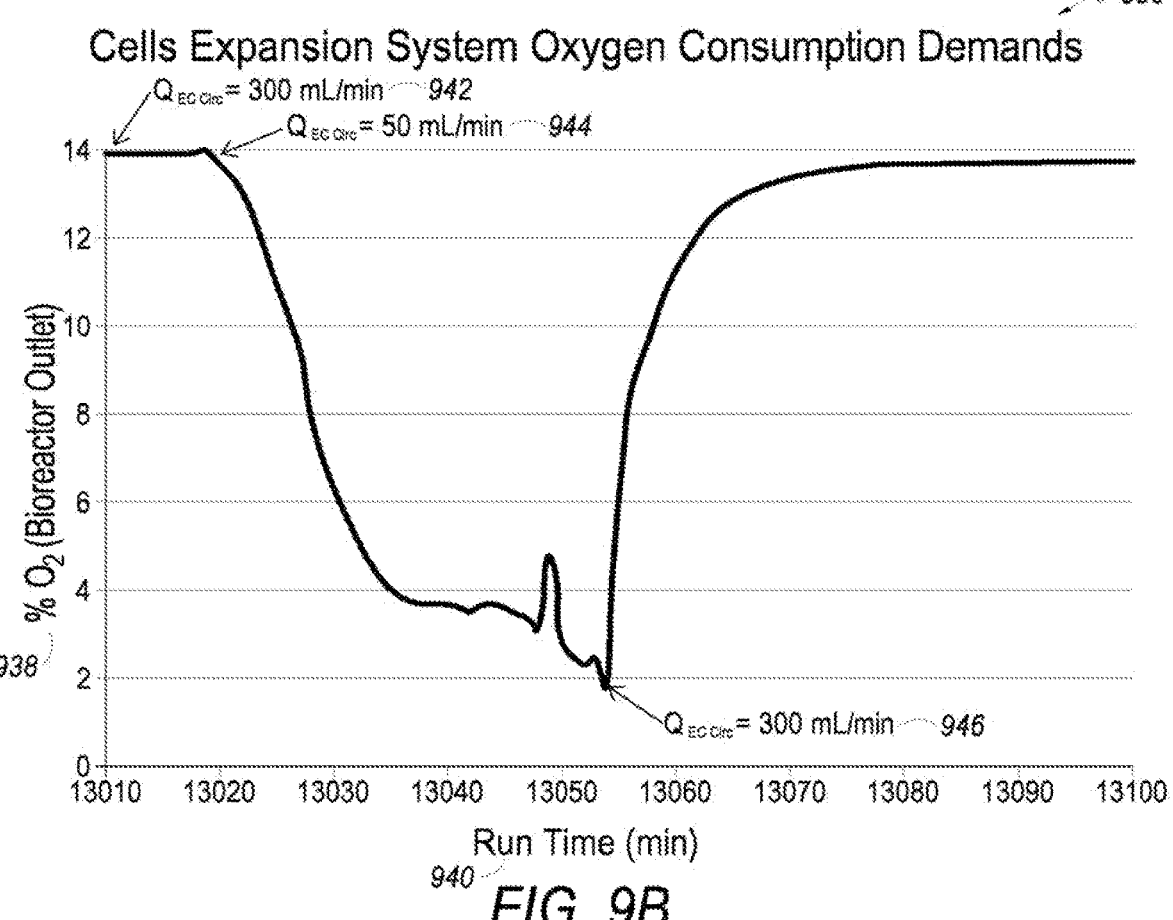
FIG. 9B illustrates a graph of oxygen consumption in a cell expansion system, in accordance with embodiments of the present disclosure.

For example, FIG. 9B illustrates a graph 936 of the oxygen consumption demands placed on a cell expansion system, such as the Quantum® Cell Expansion System during cell proliferation (approximately 3E+09 T-cells present in the bioreactor), FIG. 9B depicts the percentage (%) of oxygen ($O_2$) at the bioreactor outlet 938. For example, a sensor to measure oxygen levels may be placed at the EC outlet port of the bioreactor, according to an embodiment, in another embodiment, a sensor to measure oxygenation may be placed at the IC outlet port of the bioreactor. The percentage of $O_2$ is measured against the Run Time (e.g., In minutes) 940. To maximize the oxygen supply to the cells, the EC circulation flow rate, $Q_{IC\ Circ}$ may be set to 300 mL/min (942), according to an embodiment. FIG. 9B shows a change in oxygenation when the EC circulation rate is dropped from 300 mL/min (942) to 50 mL/min (944). For example, the cells may consume oxygen ($O_2$) in the media as the media travels across the bioreactor. Fluid at 50 mL/min (944) moves more slowly across the bioreactor than fluid at 300 mL/min (942), so there may be a longer time period or greater opportunity for the cells to strip the media of oxygen when the EC circulation rate is at 50 mL/min. The oxygenation then recovers when the EC circulation rate is taken back up to 300 mL/min (946). FIG. 9B shows a possible benefit of keeping the cells in the fibers themselves where gas transfer takes place, as opposed to in the portion of the IC circulation path outside of the bioreactor, for example, where the cells may be deprived of oxygen. It may therefore be beneficial to retain cell, e.g., non-adherent cell, populations inside the hollow fibers of the bioreactor during feeding by directing the flow of media to enter both sides of the bioreactor, e.g., the IC inlet port and the IC outlet port. In an embodiment, an equal distribution of flow to the IC inlet port and the IC outlet port may be used. In another embodiment, a larger flow to the IC inlet port as compared to the IC outlet port may be used and vice versa, depending on where it is desired to locate the cells in the bioreactor, for example.

Returning to FIG. 9A, START operation 902 is initiated and process 900 proceeds to load a disposable set or pre-mounted fluid conveyance assembly (e.g., 210 of 400) onto a cell expansion system 904. The disposable set may then be primed 906, in which the set may be primed 906 with Lonza $Ca^{2+}/Mg^{2+}$-free PBS, for example, in preparation for the loading and seeding of cells, the priming fluid may be exchanged using an IC/EC washout 908. In an embodiment, the PBS in the system may be exchanged for TexMACS GMP Base Medium, for example. In other embodiments, the base media may be Prime XV, Advanced RPMI+glutamine, RPMI 1640+glutamine, and/or IMDM+glutamine. Next, process 900 proceeds to close the IC outlet valve 910. In embodiments, the EC outlet valve may be open to allow for ultrafiltration of fluid added to the hollow fibers of a biore-actor comprising a hollow fiber membrane. The media may next be conditioned 912. Next process 900 proceeds to load cells 914, e.g., suspension or non-adherent cells, e.g., T cells such as Tregs. In an embodiment, such cells may be loaded 914 by a "load cells centrally without circulation" task. In another embodiment, such cells may be loaded 914 by a "load cells with uniform suspension" task. In other embodi-ments, other loading tasks and/or loading procedures may be used.

In an embodiment, the cells being loaded 914 may be suspended in a solution comprising media to feed the cells during and after such loading, for example. In another embodiment, such solution may comprise both media for feeding the cells and a soluble activator complex to stimu-late the cells, e.g., T cells. As noted above, the activator may in some embodiments be beads. The cells being loaded 914 may therefore also include beads with activator for stimu-lating expansion of the cells. In some embodiments, Human AB Serum may also be present. Without being bound by theory, it is believed that Human serum contains LFA-3 (CD58) that may bind CD2 on T-cells, which may minimize aggregation of cells and beads. Such loading 914 may occur on Day 0, for example.

Following the loading of cells 914, the cells may be further fed 916. During such feeding 916, it may be desired to control the cell residence in the bioreactor itself. Through the adjustment of flow control parameters 918, the cells may be retained in the bioreactor itself instead of losing cells from the bioreactor into the portion(s) of the IC loop outside of the bioreactor, for example, during the expansion phase of growth. By retaining the cells in the bioreactor, cells in the bioreactor may be closer to the IC inlet port, in which such cells may receive the freshest growth media, according to embodiments. On the other hand, cells in the IC loop may be receiving expended or conditioned media which may affect their glycolytic metabolism, for example. In addition, cells in the bioreactor may receive mixed gas (e.g., oxygen, carbon dioxide, and nitrogen) input from a gas transfer module (GTM) by diffusion from the EC loop circulation, whereas cells in her portions of the IC loop may not receive such mixed gas, according to an embodiment. It should be noted that while embodiments may provide for retaining the cells in the bioreactor itself, other embodiments may provide for maintaining the cells in any location allowing for improved nutrient delivery and/or gas exchange. Embodi-ments thus provide for the use of other locations for retain-ing cells, or controlling the residence of cells, without departing from the spirit and scope of the present disclosure.

Returning to FIG. 9A and process 900, the loss of cells from the hollow fiber membrane bioreactor may be reduced by matching, or closely or substantially matching, the IC circulation pump rate to the IC inlet pump rate, but in the opposite direction, in accordance with embodiments. The IC inlet pump 920 may be adjusted to produce a first flow rate or volumetric flow rate, and the IC circulation pump may be adjusted 922 to produce a second counter-flow rate or second counter-volumetric flow rate, in which a volumetric flow rate of fluid flow rate or rate of fluid flow or flow rate may be considered as the volume of fluid which passes per unit time (may be represented by the symbol "Q"). For example, an IC inlet pump rate of 0.1 mL/min may be matched, or closely or substantially matched, to a comple-mentary IC circulation pump rate of −0.1 mL/min to main-tain cells in the bioreactor during the growth phase of the cell culture, which may be Days 4.7, for example, in embodiments. In other embodiments, the growth phase may be Days 2-7 or Days 2-8. Such pump adjustment 918 may allow for counteracting any forces associated with a loss of cells from the IC outlet port of the bioreactor, for example.

Next, the cells may be allowed to grow or expand 924. The cells are not limited to growing or expanding at step 924, but, instead, the cells may also expand during step(s) 914, 916, 918, 920, 922, for example. Process 900 may next proceed to harvest operation 926, in which the cells may be transferred to a harvest bag(s) or container(s). The dispos-able set may then be unloaded 932 from the cell expansion system, and process 900 then terminates at END operation 934.

Alternatively, from harvest operation 926, process 900 may optionally proceed to allow for further processing/analysis 928. Such further processing 928 may include characterization of the phenotype(s), for example, of the harvested cells. From optional further processing/analysis step 928, process 900 may proceed to optionally reload any remaining cells 930. Process 900 may then proceed to unload the disposable set 932, and process 900 may then terminate at END operation 934. Alternatively, process 900 may proceed from further processing/analysis step 928 to unload disposable set 932. Process 900 may then terminate at END operation 934.

Figure 10A:
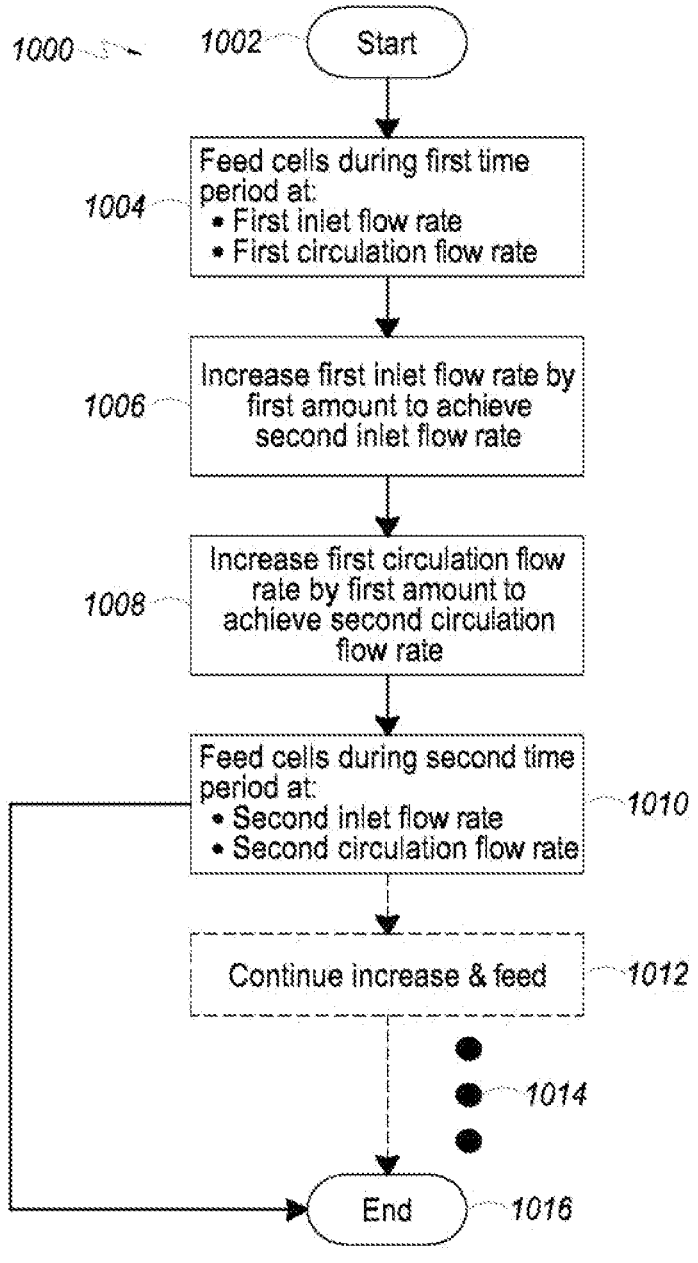
FIG. 10A illustrates a flow diagram depicting the operational characteristics of a process for expanding cells, in accordance with embodiments of the present disclosure.

Next, FIG. 10A illustrates example operational steps 1000 of a process for feeding cells that may be used with a cell expansion system, such as CES 500 (e.g., FIGS. 5B &5C), in accordance with embodiments of the present disclosure. START operation 1002 is initiated, and process 1000 pro-ceeds to load a disposable set onto the cell expansion system, prime the set, perform an IC/EC washout, condition media, and load cells, e.g., suspension or non-adherent cells, for example. Next, process 1000 proceeds to feed the cells during a first time period 1004. In embodiments, a first inlet flow rate and a first circulation flow rate may be used. As an example, a first IC inlet flow rate and a first IC circulation flow rate may be used, in which the first IC inlet flow rate may be controlled by the IC inlet pump, e.g., first pump, and the first IC circulation flow rate may be controlled by the IC circulation pump, e.g., second pump. In an example embodi-ment, the IC inlet pump (554) may cause a volumetric flow rate of 0.1 mL/min to enter the IC inlet port (501A) of the bioreactor (501) with the IC circulation pump (512) causing a complementary IC circulation volumetric flow rate or fluid flow rate of −0.1 mL/min to enter the IC outlet port (501B) of the bioreactor (501), in which the negative symbol ("−") used in −0.1 mL/min, for example, indicates a direction of the IC circulation pump (512) to cause or produce a counter-flow rate to maintain cells in the bioreactor during the growth phase of the cell culture.

During the feeding of the cells and the use of the IC pumps during feeding to control cell residence in the bioreactor through flow and counter-flow properties, the cells continue to grow and expand. As a result, the cells may demand additional media, e.g., glucose and/or cell growth formulated media, to support the expanding population. Efforts may also be made to control lactate values of the expanding cell population. In embodiments, cell culture lactate values may be maintained at or below about 20 mmol/L, at or below about 15 mmol/L, at or below about 10 mmol/L, or even at or below about 7 mmol/L. In other embodiments, rate(s) of media addition, for example, and/or other settings may be controlled to attempt to maintain the lactate levels s about 5 mmol/L, for example, to improve cell growth and viability. In yet other embodiments, rate(s) of media addition, for example, and/or other settings may be controlled to attempt to maintain the lactate levels s about 15 mmol/L, for example, to improve cell growth and viability. Other concentrations may be used in other embodiments.

In an example embodiment, an effort may be made to control lactate values at s about 7 mmol/L by concurrently increasing both the IC inlet (+) pump rate and IC circulation (−) pump rate from ±0.1 to ±0.4 mL/min within the lumen of the hollow fiber membrane over multiple time periods, e.g., days (Days 4-8), according to embodiments. For example, FIG. 10B provides a table 1018 of example IC pump rates for feeding using a "feed cells" task, for example, with a cell expansion system (e.g., CES 500). Table 1018 provides example time periods 1020, e.g., Days, versus example IC pump rates 1022 to produce volumetric flow rates to both sides of the bioreactor to maintain cells in the bioreactor. For example, Days 0-4 (1024) may use an IC inlet or input pump rate of 0.1 mL/min (1026) and an IC circulation pump rate of −0.1 mL/min (1028); Day 5 (1030) may use an IC inlet pump rate of 0.2 mL/min (1032) and an IC circulation pump rate of −0.2 mL/min (1034); Day 6 (1036) may use an IC inlet pump rate of 0.3 mL/min (1038) and an IC circulation pump rate of −0.3 mL/min (1040); and Day 7 (1042) may use an IC inlet pump rate of 0.4 mL/min (1044) and an IC circulation pump rate of −0.4 mL/min (1046). While table 1018 of FIG. 10B provides example pump rates of ±0.1 to ±0.4 mL/min for feeding the cells while retaining the cells in the bioreactor during the growth phase of the cell culture, other pump rates and resulting flow rates may be used according to embodiments without departing from the spirit and scope of the present disclosure. For example, while increments of: ±0.1 mL/min for increasing the feed flow rate are shown in this example, other increments, e.g., ±0.005 mL/min, ±0.05 mL/min, etc., may be used to increase the feed flow rate in embodiments. The time periods, e.g., Days, and pump rates in table 1018 of FIG. 10B are offered merely for illustrative purposes and are not intended to be limiting.

In another example embodiment, an effort may be made to control lactate values at ≤about 15 mmol/L by concurrently increasing both the IC inlet (+) pump rate and IC circulation (−) pump rate within the lumen of the hollow fiber membrane over a time period of cell expansion. For example, during a first time period (Days 0-2 or Days 0-4) an IC inlet or input pump rate of 0.1 mL/min and an IC circulation pump rate of −0.1 mL/min may be used. During a second time period (Days 3-7 or Days 5-8) an IC inlet or input pump rate of 0.4 mL/min and an IC circulation pump rate of −0.4 mL/min may be used. Other pump rates and resulting flow rates may be used according to embodiments without departing from the spirit and scope of the present disclosure. For example, while increments on the order of ±0.1 mL/min (e.g., ±0.1 mL/min; ±0.2 mL/min; ±0.3 mL/min, etc.) for increasing the feed flow rate are shown in this example, other order of increments, (e.g., ±0.005 mL/min, ±0.05 mL/min, etc.) may be used to increase the feed flow rate in embodiments. The time periods, e.g., Days, and pump rates are offered merely for illustrative purposes and are not intended to be limiting.

Returning to FIG. 10A, process 1000 proceeds from feeding the cells during a first time period 1004 to increasing the first inlet flow rate by a first amount to achieve a second inlet flow rate 1006. For example, as in the embodiment depicted in FIG. 10B as discussed above, the IC inlet pump rate (+) may increase from 0.1 mL/min to 0.2 mL/min to produce an IC inlet flow rate of 0.2 mL/min. Further, the IC circulation pump rate (−) may concurrently increase from −0.1 mL/min to −0.2 mL/min to produce an IC circulation flow rate of −0.2 mL/min. The first circulation flow rate is thus increased by the first amount to achieve the second circulation flow rate 1008. The cells may then be fed during a second time period at the second inlet flow rate and at the second circulation flow rate 1010 to maintain the cells in the bioreactor and outside of the headers and outside of the portion of the IC circulation path outside of the bioreactor, for example. Following the second time period of feeding 1010, process 1000 may terminate at END operation 1016 if it is not desired to continue feeding and/or expanding the cells, for example. Alternatively, pro 1000 may optionally continue to increase, or otherwise change, the feeding flow rates 1012. There may be any number of feeding time periods, as represented by ellipsis 1014. Following the desired number of feeding time periods 1014, process 1000 then terminates at END operation 1016. While FIGS. 10A and 10B and process 1000 show "Increases" in the flow rates, other adjustments to the flow rates may be made. For example, the flow rates may decrease or remain substantially the same from one feeding period to the next. Considerations, such as metabolic activity, for example, may determine how flow rates are adjusted. The "increases" in flow rates in FIGS. 10A and 10B are offered merely for illustrative purposes and are not intended to be limiting.

Figure 11A:
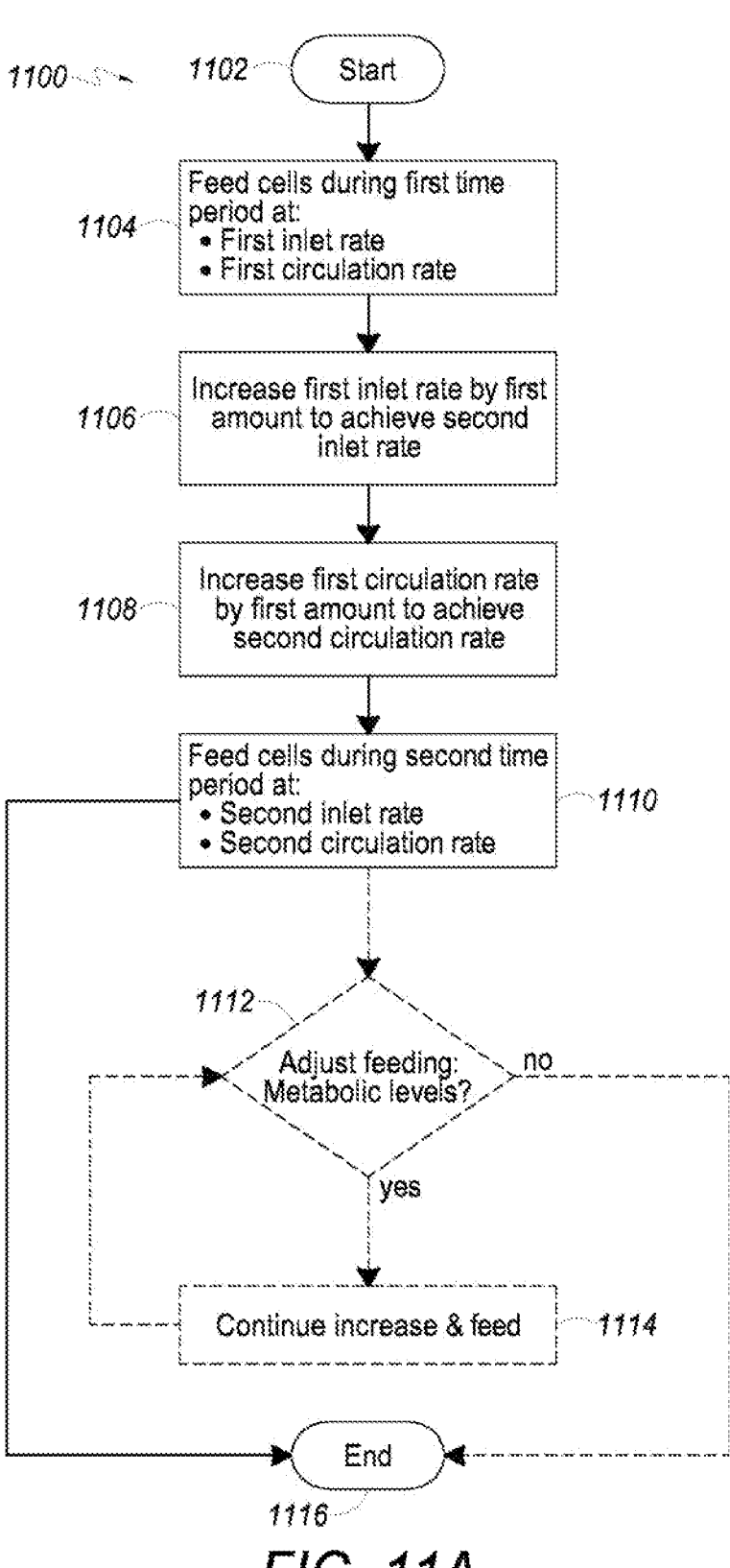
FIG. 11A depicts a flow diagram illustrating the operational characteristics of a process for expanding cells, in accordance with embodiments of the present disclosure.

Turning to FIG. 11A, example operational steps 1100 of a process for feeding cells that may be used with a cell expansion system, such as CES 500 (e.g., FIGS. 5B & 5C), are provided in accordance with embodiments of the present disclosure. START operation is initiated 1102, and process 1100 proceeds to load a disposable set onto the cell expansion system, prime the set, perform an IC/EC washout, condition media, and load cells, e.g. suspension of non-adherent cells, for example. Next, process 1100 proceeds to feed the ceils during a first time period 1104. In embodiments, a first inlet rate or flow rate and a first circulation rate or flow rate may be used. As an example, a first IC inlet flow rate and a first IC circulation flow rate may be used, in which the first IC inlet flow rate may be controlled by the IC inlet pump, e.g., first pump, and the first IC circulation flow rate may be controlled by the IC circulation pump, e.g., second pump. In an example embodiment, the IC inlet pump (554) may cause a volumetric flow rate or fluid flow rate of 0.1 mL/min to enter the IC inlet port (SOLA) of the bioreactor (501) with the IC circulation pump (512) causing a complementary IC circulation flow rate of −0.1 mL/min to enter the IC outlet port (501B) of the bioreactor (501), in which the negative symbol ("−") used in −0.1 mL/min, for example, indicates a direction of the IC circulation pump (512) to cause or produce a counter flow rate to maintain cells in the bioreactor during the growth phase of the cell culture.

During the feeding of the cells and the use of the IC pumps to control cell residence in the bioreactor through flow and counter-flow properties, the cells continue to grow and expand. As a result, the cells may demand additional media, e.g., glucose and/or cell growth formulated media, to support the expanding population. Efforts may also be made to control lactate values of the expanding cell population. In an example embodiment, an effort may be made to control lactate values at ≤about 7 mmol/L, for example, by concurrently increasing both the IC inlet (+) pump rate and IC circulation (−) pump rate from ±0.1 to ±0.4 mL/min within the lumen of the hollow fiber membrane over multiple days, e.g., Days 4-8, according to embodiments. For example, see FIG. 10B, table 1018, and the discussion above, for example pump rates for feeding. As noted, while table 1018 of FIG. 10B provides pump rates of ±0.1 to ±0.4 mL/min for feeding the cells while retaining the cells in the bioreactor during the growth phase of cell culturing, other pump rates and resulting flow rates may be used according to embodiments without departing from the spirit and scope of the present disclosure. In another example embodiment, an effort may be made to control lactate values at s about 15 mmol/L, for example, by concurrently increasing both the IC inlet (+) pump rate and IC circulation (−) pump rate within the lumen of the hollow fiber membrane over multiple days, according to embodiments. The time periods, e.g., Days, and pump rates mentioned above, and for example listed in table 1018 of FIG. 10B, are offered merely for illustrative purposes and are not intended to be limiting.

Returning to FIG. 11A, process 1100 proceeds from feeding the cells during a first time period 1104 to increasing the first inlet rate or flow rate by a first amount to achieve a second inlet rate or flow rate 1106. For example, as in the embodiment depicted in FIG. 10B as discussed above, the IC inlet pump rate (+) may increase from 0.1 mL/min to 0.2 mL/min to produce an IC inlet flow rate of 0.2 mL/min. Further, the IC circulation pump rate (−) may concurrently increase from −0.1 mL/min to −0.2 mL/min to produce an IC circulation flow rate of −0.2 mL/min. In other embodiments, the IC inlet pump rate (+) may increase from 0.1 mL/min to 0.4 mL/min to produce an IC inlet flow rate of 0.2 mL/min. Further, the IC circulation pump rate (−) may concurrently increase from −0.1 mL/min to −0.4 mL/min to produce an IC circulation flow rate of −0.4 mL/min. The first circulation rate of flow rate is thus increased by the first amount to achieve the second circulation rate or flow rate 1108. The cells may then be fed during a second time period at the second inlet rate or flow rate and at the second circulation rate or flow rate 1110 to maintain the cells in the bioreactor and outside of the headers or the portion of the IC circulation path outside of the bioreactor, for example. Following the second period of feeding 1110, process 1100 may terminate at END operation 1116 if it is not desired to continue feeding and/or expanding the cells, for example.

Alternatively, process 1100 may optionally determine whether to adjust the feeding rates or flow rates based on metabolic activity, in which process 1100 proceeds to optional query 1112 to determine whether to adjust feeding based on metabolic levels. Monitoring the glucose and/or lactate levels can facilitate the adjustment of cell expansion system media flow rates, e.g., IC media flow rate, to support cell, e.g., Treg, expansion in a bioreactor, such as a hollow fiber bioreactor, for example.

Figure 11B:
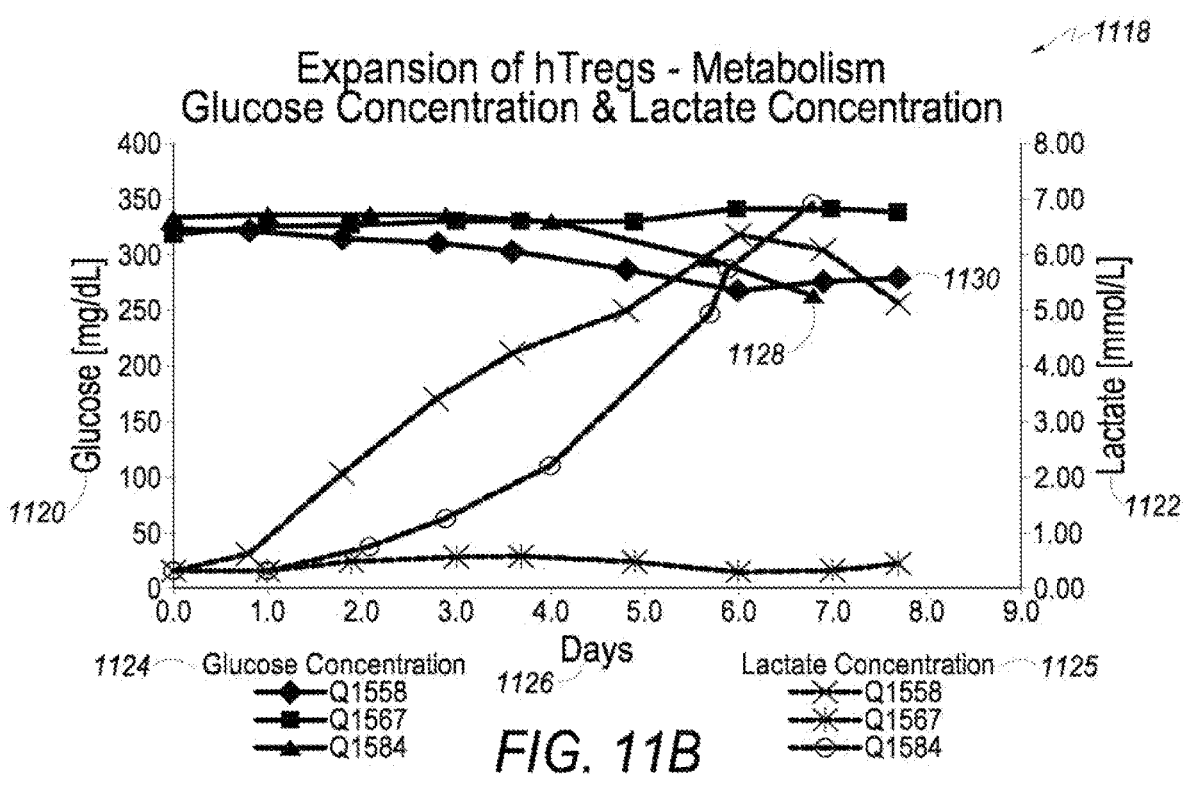
FIG. 11B illustrates a graph of the metabolism of expanding cells, in accordance with embodiments of the present disclosure.
Figure 11C:
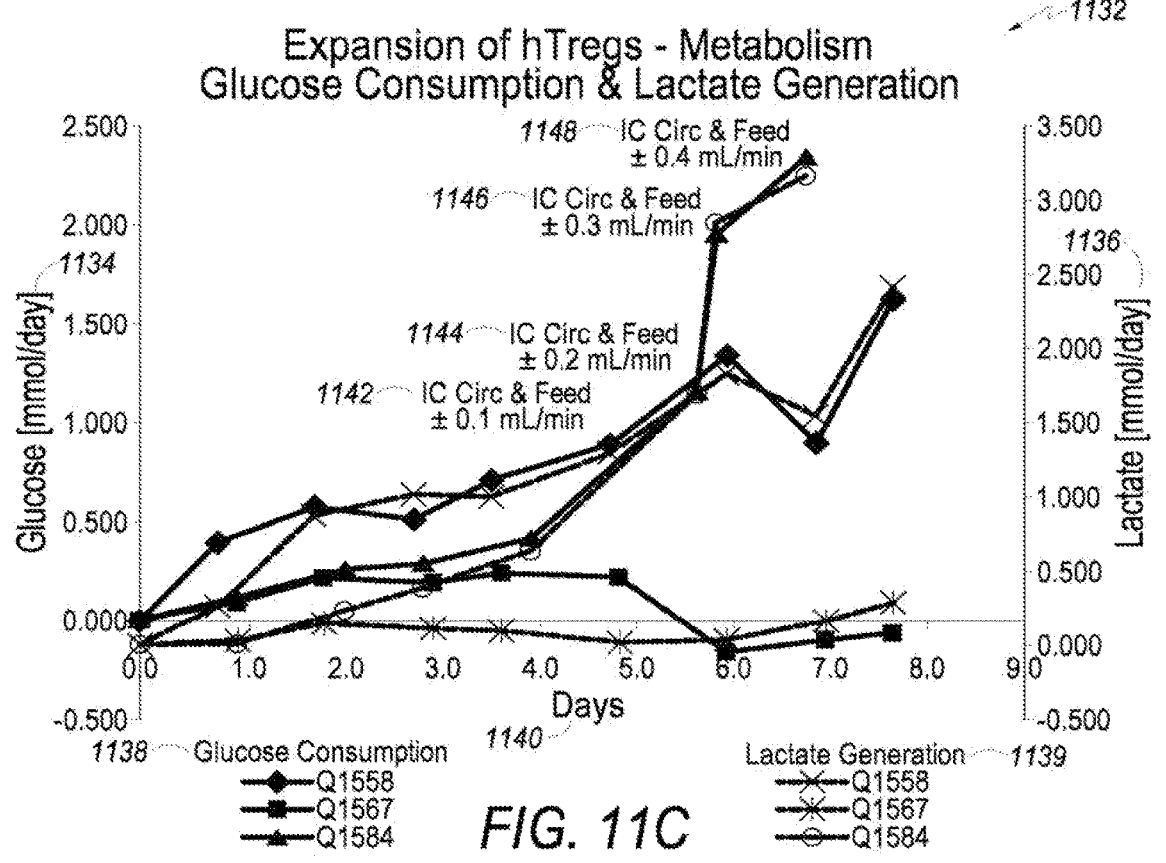
FIG. 11C illustrates a graph of the metabolism of expanding cells, in accordance with embodiments of the present disclosure.

As shown in FIGS. 11B and 11C, embodiments provide for controlling the lactate values of cell expansion runs or procedures involving the expansion of T cells, e.g., hTregs as a non-limiting example. Graphs 1118 and 1132 indicate that measurements of glucose and lactate levels may be used to adjust cell expansion system media flow rates, e.g., IC media flow rates, to support the expansion of T cells, e.g., Tregs, for ample. For example, FIG. 11B provides a graph 1118 showing the metabolisms of expanding hTregs, in which such cell expansion may occur in a cell expansion system, such as the Quantum® Cell Expansion System. The glucose concentration (mg/dL) 1120 and lactate concentration (mmol/L) 1122 are shown for various cell expansion runs 1124 and 1125 across periods of time, e.g., Days, 1126. Throughout these Treg runs 1124 and 1125, an effort may be made to control the lactate values of the expanding cell population to values s about 7 mmol/L by concurrently increasing both the IC inlet (+) pump rate and IC circulation pump rate from ±0.1 to ±0.4 mL/min, for example, within the lumen of the hollow fiber membrane over Days 4-8, for example. In other embodiments, other pump rates may be used. As shown, the lowest glucose levels during the Treg cell expansions may range from a concentration 1128 of 264 mg/dL on Day 7 (Q1584) to a concentration 1130 of 279 mg/dL on Day 8 (Q1558), according to the embodiments shown. As depicted, the base glucose concentration. In the cell growth formulated medium for runs 1124 may range from 325 mg/dL to 335 mg/dL, for example. In other embodiments, it may be desired to maintain the lactate levels s about 5 mmol/L to improve cell growth and viability. In yet other embodiments, the conditions for growth may provide for maintaining the glucose levels above a percentage of a starting concentration. For example, in some embodiments, the IC inlet (+) pump rate, IC circulation pump rate, the EC inlet (+) pump rate and/or EC circulation pump rate may be changed during the expansion to maintain the glucose concentration at greater than about 20% of the starting concentration, at greater than about 30% of the starting concentration, at greater than about 40% of the starting concentration, at greater than about 50% of the starting concentration, at greater than about 60% of the starting concentration, at greater than about 70% of the starting concentration, at greater than about 80% of the starting concentration, at greater than about 90% of the starting concentration, or even greater than about 100% of the starting concentration. In some embodiments, the glucose concentration may be maintained above 300 mg/dL. In embodiments, graphical user interface (GUI) elements may be used to control the rate of media addition and to maintain the lactate metabolic waste product from glycolysis below a defined level during the expansion of cells.

Turning to FIG. 11C, graph 1132 shows the metabolisms of expanding hTregs, in which such cell expansion may occur in a cell expansion system, such as the Quantum® Cell Expansion System. The glucose consumption (mmol/day) 1134 and lactate generation (mmol/day) 1136 are shown for various cell expansion runs 1138 and 1139 across periods of time 1140, e.g., Days. To control lactate values at ≤about 7 mmol/L, for example, concurrent increases may be made to the IC inlet (+) pump rate and IC circulation (−) pump rates from ±0.1 to ±0.4 mL/min, in an embodiment. For example, graph 1132 shows IC circulation and IC feed rates of 10.1 mL/min (1142); 10.2 mL/min (1144); 10.3 mL/min (1146); and ±0.4 mL/min (1148). Other embodiments may use other flow rates. For example, when expanding different types of cells, e.g., other T cells, other flow rates may be used. Also, in addition to the IC inlet (+) pump rate and the IC circulation (−) pump rate the EC inlet pump rate and the EC circulation rate may be used to control glucose and lactate values in some embodiments. The flow rates used and shown in FIGS. 11B and 11C are offered for purposes of illustration and are not intended to be limiting. It is noted that while positive (+) may be shown for the direction of the IC inlet pump and negative (−) may be shown for the direction of the IC circulation pump, such directions are offered for illustrative purposes only, in which such directions depend on the configurations of the pumps used.

Returning to FIG. 11A and optional query 1112, if it is not desired to measure metabolic activity and/or adjust feeding levels based on such measurement(s), process 1100 proceeds "no" to END operation 1116, and process 1100 terminates. Alternatively, where it is desired to adjust feeding levels based on metabolic activity, process 1100 proceeds "yes" to optional step 1114 to continue to increase the rate of media addition and feed the expanding cell population. While step 1114 is shown as one step, this step may involve numerous adjustments to the media addition rate, such as increasing the IC inlet flow rate, increasing the IC circulation flow rate, increasing the EC inlet flow rate, and/or increasing the EC circulation flow rate, for example. Step 1114 is shown as one step only for illustrative purposes and is not intended to be limiting. Following any adjustments to the rate of media addition, process 1100 proceeds to optional query 1112 to determine whether to continue measuring metabolic levels and/or adjust feeding. If it is not desired to continue measuring metabolic activity and/or adjusting feeding levels based on metabolic activity, process 1100 proceeds "no" to END operation 1116, and process 1100 terminates. While FIG. 11A and process 1100 show "Increases" In the rates or flow rates, other adjustments to the flow rates may be made. For example, the rates or flow rates may decrease or remain substantially the same from one feeding period to the next. The type of adjustments which may be made may depend on the metabolic activity assessment of the growing cell population. The "increases" in flow rate in FIG. 11A, for example, are offered merely for illustrative purposes and are not intended to be limiting.

Figure 12:
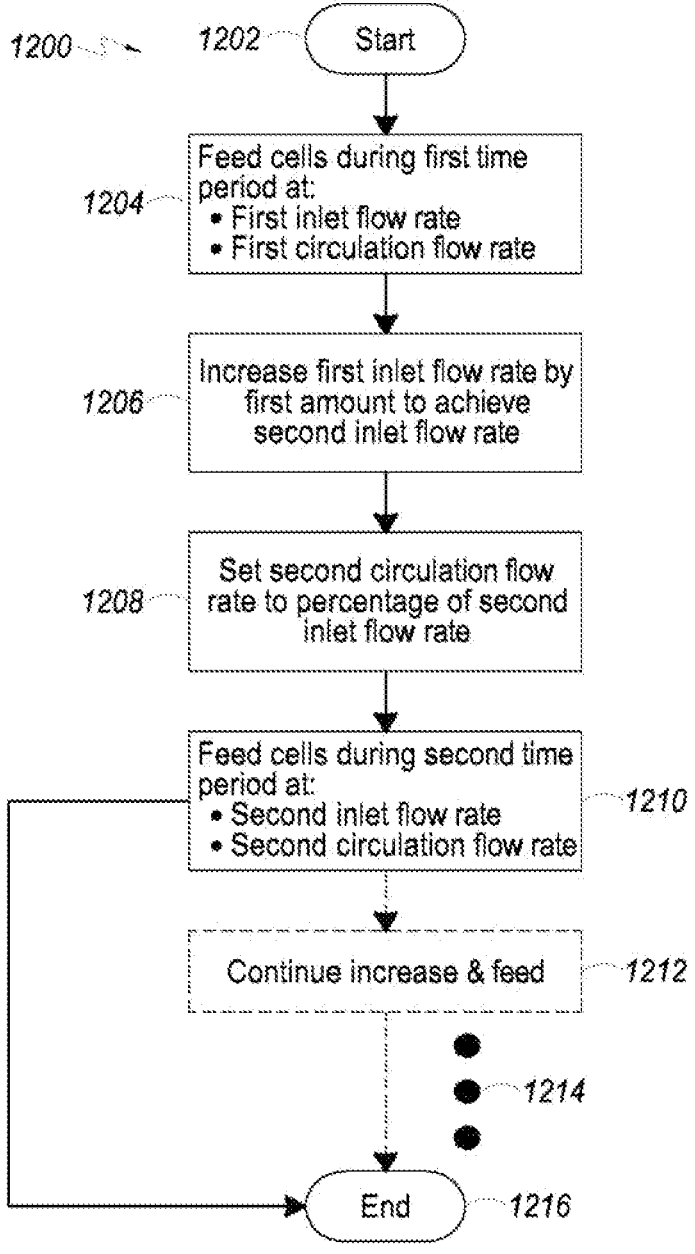
FIG. 12 illustrates a flow diagram depicting the operational characteristics of a process for expanding cells, in accordance with embodiments of the present disclosure.

Next, FIG. 12 illustrates example operational steps 1200 of a process for retaining cells in a location during feeding using a cell expansion system, such as CES 500 (e.g., FIGS. 5B &5C), in accordance with embodiments of the present disclosure. START operation 1202 is initiated, and process 1200 proceeds to load a disposable set onto the cell expansion system, prime the set, perform IC/EC washout, condition media, and load cells, e.g., suspension or non-adherent cells, for example. Next, process 1200 proceeds to feed the cells during a first time period 1204. In embodiments, a first inlet flow rate and a first circulation flow rate may be used. As an example, a first IC inlet flow rate and a first IC circulation flow rate may be used, in which the first IC inlet flow rate may be produced and controlled by the IC inlet pump, e.g., first pump, and the first IC circulation flow rate may be produced and controlled by the IC circulation pump, e.g., second pump. In an example embodiment, the first IC inlet pump (554) may cause a volumetric flow rate of 0.1 mL/min to enter the IC inlet port (501A) of the bioreactor with the IC circulation pump (512) causing a complementary IC circulation volumetric flow rate or fluid flow rate of −0.1 mL/min to enter the IC outlet port (501B) of the bioreactor (501), in which the negative symbol ("−") used in −0.1 mL/min, for example, Indicates a direction of the IC circulation pump to cause of produce a counter-flow rate to maintain cells in the bioreactor during the growth phase of the cell culture. In another embodiment, the first IC circulation flow rate may be a percentage of the first IC inlet flow rate. For example, the first IC circulation flow rate may be about fifty percent (50%) or about one-half (½), or another percentage of portion according to embodiments, of the first IC inlet flow rate.

During the feeding (and expansion) of the cells and the use of the IC pumps, for example, to control cell residence in the bioreactor through flow and counter-flow properties, the cells continue to grow and expand. As a result, the cells may demand additional media, e.g., glucose and/or cell growth formulated media, to support the expanding population. In embodiments, efforts may be made to increase the rate of media addition to feed the expanding cell population, in an example embodiment, an increase in the IC inlet pump rate (+) may cause the IC inlet flow rate to increase by a first amount to achieve a second IC inlet flow rate 1206. For example, the IC inlet flow rate may increase by a first amount of 0.1 mL/min to achieve a second IC inlet flow rate of 0.2 mL/min, according to an embodiment. Other adjustments may be made to the IC inlet flow rate according to other embodiments.

Next, the second IC circulation flow rate may be set, or adjusted of configured, to equal a percentage, or portion, or fraction of the second IC inlet flow rate 1208, according to embodiments. For example, the second IC circulation flow rate may be set, or adjusted or configured, to equal about fifty percent (50%) or about one-half (½), or another percentage or portion according to embodiments, of the value of the IC inlet flow rate, according to an embodiment. Depending on the value of the first IC circulation flow rate, an adjustment to the IC circulation pump rate (−) may cause the second IC circulation flow rate to increase, according to an embodiment. In another embodiment, an adjustment may be made to the IC circulation pump rate to produce or cause the second IC circulation flow rate to decrease such that the IC circulation flow rate may be substantially equal to a pre-defined percentage or pre-defined fraction of the second IC inlet flow rate. In yet another embodiment, no adjustment may be made to the IC circulation pump rate. For example, where the first IC inlet flow rate equals 0.3 mL/min, and the first IC circulation flow rate equals −0.1 mL/min, if the second IC inlet flow rate is increased to 0.2 mL/min, the second IC circulation flow rate may be set to $(-½)*(second$ $Q_{IC\ Inlet})$ (where $Q_{IC\ Inlet}$ is the IC inlet flow rate) or $(-½)*(0.2\ mL/min)$, which provides for a second Quo (where $C_{IC\ Circ}$ is the IC circulation flow rate) of −0.1 mL/min, and no adjustment to the IC circulation pump rate may be made to achieve such second $Q_{IC\ Circ}$.

Turning to FIGS. 5B and 5C, such figures depict operational configurations of cell expansion system 500 showing fluid movement in the first circulation path, in accordance with embodiments of the present disclosure. The configurations of FIGS. 5B and 5C show a spilt, for example, in the flow rate to the IC inlet port, e.g., first port, and to the IC cutlet port, e.g., second port, to keep the cells in the cell growth chamber or bioreactor. As discussed with respect to CES 500 above, in the IC loop or first circulation path 502, fluid may be initially advanced by the IC inlet pump 554. Such fluid may be advanced in a first direction, such as a positive direction, for example. Fluid may flow into cell growth chamber or bioreactor 501 through IC inlet port 501A, through hollow fibers in cell growth chamber or bioreactor 501, and may exit via IC outlet port 501B. Media may flow through IC circulation pump 512 which may be used to control the rate of media flow. IC circulation pump may pump the fluid in a first direction or second direction opposite the first direction. Exit port 501B may be used as an inlet in the reverse direction, for example. In an embodiment, the IC circulation pump 512 may pump the fluid in a direction opposite the direction of the IC inlet pump, for example. As an example, the direction of the IC inlet pump may be positive (+), and the direction of the IC circulation pump may be negative (−) to cause a counter-flow such that fluid may enter both sides of the bioreactor to keep the cells in the bioreactor.

In an embodiment, a first portion of fluid may branch at connection 517 to flow into the IC inlet port (501A) of the bioreactor 501. In an embodiment, the IC circulation pump 512 may operate at a pump rate that may be matched, or closely or substantially be matched, to the IC inlet pump 554 rate, but in the opposite direction, such that a second portion of fluid may branch at connection 517 to flow into the IC outlet port (501B) of the bioreactor 501. For example, an IC inlet pump rate of +0.1 mL/min may be matched, or closely or substantially be matched, to a complementary IC circulation pump rate of −0.1 mL/min to maintain cells in the bioreactor during the growth phase of the cell culture. Such pump adjustment tactic during the feeding may counteract forces associated with the loss of cells from the IC outlet port. Such type of feeding using pump adjustments to cause flow and counter-flow into the IC inlet port (501A) and IC outlet port (501B), respectively, of the bioreactor may be referred to as a modified feeding method, according to an embodiment. In another example embodiment, the IC circulation pump rate may be adjusted to cause a flow rate into the IC outlet port (501B) that may be equal to about fifty percent (50%) or about one-half (½), or another percentage or fraction in other embodiments, of the IC inlet flow rate, but in the opposite direction. For example, with an IC inlet pump rate of 0.4 mL/min, an IC circulation pump rate may be set, or configured or adjusted, to about −0.2 mL/min. Other percentages or portions may be used in other embodiments.

FIGS. 5B and 5C illustrate operational configurations showing fluid movement in CES 500, in which the flow and counter-flow rates to keep the cells in the cell growth chamber or bioreactor 501 are shown, according to embodiments. For example, such flow rates are illustrated in FIG. 5B as "X" flow rate 503; "(−½) X" flow rate 505 (where the negative symbol ("−") is an indication of direction, in which a direction of flow rate 505 is shown by the directional arrow in FIG. 5B); and "(½) X" flow rate 507, in which about %, or a first portion, of the flow rate branches at connection 517 to enter IC inlet port (501A) of bioreactor 501, and about ½, or a second portion, of the flow rate branches at connection 517 to enter the IC outlet port (501B) of bioreactor 501, according to embodiments. As shown, the sum of the first portion and the second portion may be substantially equal to the total flow rate 503, in which the total flow rate 503 is pumped by IC inlet pump 554. Depending on the flow and counter-flow rates which may be used to keep the cells in the bioreactor or cell growth chamber 501, other types of fractions of percentages of the IC inlet pump rate may be used to set, or configure or adjust, the IC circulation pump. As such, FIG. 5C illustrates such flow rates as "X" flow rate 511; "−(y %)*X" flow rate 513 (where the negative symbol ("−") is an indication of direction, in which a direction of flow rate 513 is shown by the directional arrow in FIG. 5C); and "(100%−y %)*X" flow rate 515, where "y" equals a numeric percentage, according to embodiments, in embodiments, the sum of flow rate 513 and flow rate 515 is substantially equal to flow rate 511.

In an embodiment, all, or substantially all, of the flow from the first fluid flow path 506 may flow to IC inlet port (501A) of bioreactor 501 from connection 517, for example. In another embodiment, all, or substantially all, of the flow from the first fluid flow path 506 may flow to IC outlet port (501B) of bioreactor 501 from connection 517. In yet another embodiment, a first portion of the flow from first fluid flow path 506 may flow from connection 517 to IC inlet port (501A), and a second portion of the flow from the first fluid flow path 506 may flow from connection 517 to IC outlet port (501B). In embodiments, the percentage of the IC inlet flow rate at which the IC circulation flow rate may be set may range from about 0 percent to about 100 percent. In other embodiments, the percentage may be between about 25 percent and about 75 percent. In other embodiments, the percentage may be between about 40 percent and about 60 percent. In other embodiments, the percentage may be between about 45 percent and about 55 percent. In embodiments, the percentage may be about 50 percent. It is to be understood that the operational configurations shown in FIGS. 5B and 5C represent possible configurations for various operations of the cell expansion system, and modifications to the configurations shown are within the scope of the one or more present embodiments.

Returning to FIG. 12, the cells may be fed (and continue expanding) during a second time period at the second inlet flow rate and at the second circulation flow rate 1210 to maintain the cells in the bioreactor and outside of the headers or portion of the IC circulation path outside of the bioreactor, for example. Following the second period of feeding 1210, process 1200 may terminate at END operation 1216 if it is not desired to continue feeding and/or expanding the cells, for example. Alternatively, process 1200 may optionally continue to increase, or otherwise change, the feeding flow rates 1212. There may be any number of feeding time periods, as represented by ellipsis 1214. Following the desired number of feeding time periods 1214, process 1200 may then terminate at END operation 1216. While FIG. 12 and process 1200 show "Increases" in the flow rates, other adjustments to the flow rates may be made. For example, the flow rates may decrease or remain substantially the same from one feeding period to the next. Considerations, such as metabolic activity, for example, may determine how flow rates are adjusted. The "increases" in flow rates in FIG. 12 are offered merely for illustrative purposes and are not intended to be limiting.

Figure 13:
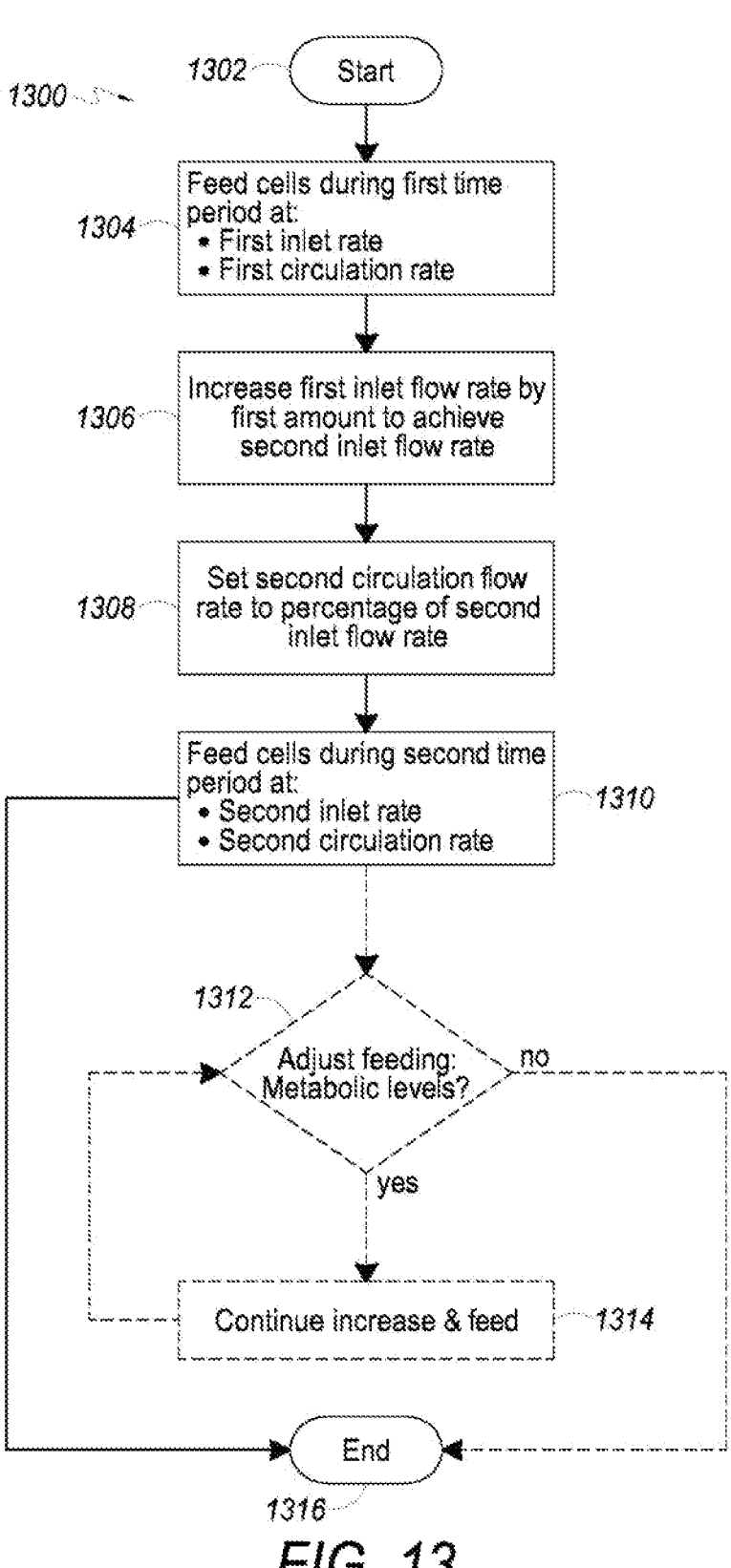
FIG. 13 depicts a flow diagram illustrating the operational characteristics of a process for expanding cells, in accordance with embodiments of the present disclosure.

Turning to FIG. 13, example operational steps 1300 of a process for feeding cells while retaining the cells in a first location, e.g., in the bioreactor, that may be used with a cell expansion system, such as CES 500 (e.g., FIGS. 5B & 5C), are provided in accordance with embodiments of the present disclosure. START operation 1302 is initiated, and process 1300 proceeds to load a disposable set onto the cell expansion system, prime the set, perform IC/EC washout, condition media, and load cells, e.g., suspension or non-adherent cells, for example. Next, process 1300 proceeds to feed the cells during a first time period 1304. In embodiments, a first inlet flow rate and a first circulation flow rate may be used. As an example, a first IC inlet flow rate and a first IC circulation flow rate may be used, in which the first IC inlet flow rate may be produced and controlled by the IC inlet pump, e.g., first pump, and the first IC circulation flow rate may be produced and controlled by the IC circulation pump, e.g., second pump. In an example embodiment, the first IC inlet pump rate may cause a volumetric flow rate of 0.1 mL/min to enter the IC inlet port of the bioreactor with a complementary IC circulation pump rate of −0.1 mL/min causing a volumetric flow rate of −0.1 mL/min to enter the IC outlet port of the bioreactor, in which the negative symbol ("−") used in −0.1 mL/min, for example, indicates a direction of the IC circulation pump (512) to cause or produce a counter-flow rate to maintain cells in the bioreactor during the growth phase of the cell culture. In another embodiment, the first IC circulation flow rate may be a percentage of fraction or portion of the first IC inlet flow rate. For example, the first IC circulation flow rate may be about fifty percent (50%) or about one-half (½), or another percentage or portion according to embodiments, of the IC inlet flow rate.

During the feeding (and expansion) of the cells and the use of the IC pumps to control cell residence in the bioreactor through flow and counter-flow properties, the cells continue to grow and expand. As a result, the calls may demand additional media, e.g., glucose and/or cell growth formulated media, to support the expanding population. In embodiments, efforts may be made to increase the rate of media addition to feed the expanding cell population. In an example embodiment, an increase in the IC inlet pump rate (+) may cause the IC inlet flow rate to increase by a first amount to achieve a second IC inlet flow rate 1306. For example, the IC inlet flow rate may be increased by a first amount of 0.1 mL/min to achieve a second IC inlet flow rate of 0.2 mL/min, according to an embodiment. Other adjustments may be made to the IC inlet flow rate according to other embodiments.

Next, the second IC circulation flow rate may be set, or configured or adjusted, to equal a percentage or portion or fraction of the second IC inlet flow rate 1308, according to embodiments. For example, the second IC circulation flow rate may be set, or configured or adjusted, to equal about fifty percent (50%) or about one-half (½), or another percentage or portion according to embodiments, of the value of the IC inlet flow rate, according to an embodiment. In an embodiment, all, or substantially all, of the flow from the first fluid flow path 506 may flow to IC inlet port (501A) of bioreactor 501 from connection 517, for example. In another embodiment, all, or substantially all, of the flow from the first fluid flow path 506 may flow to IC outlet port (501B) of bioreactor 501 from connection 517. In yet another embodiment, a first portion of the flow from first fluid flow path 506 may flow from connection 517 to IC inlet port (501A), and a second portion of the flow from the first fluid flow path 506 may flow from connection 517 to IC outlet port (501B). In embodiments, the percentage of the IC inlet flow rate at which the IC circulation flow rate may be set may range from about 0 percent to about 100 percent. In other embodiments, the percentage may be between about 25 percent and about 75 percent. In other embodiments, the percentage may be between about 40 percent and about 60 percent. In other embodiments, the percentage may be between about 45 percent and about 55 percent. In embodiments, the percentage may be about 50 percent.

Depending on the value of the first IC circulation flow rate, an adjustment to the IC circulation pump rate (−) may cause the second IC circulation flow rate to increase, according to an embodiment. In another embodiment, an adjustment may be made to the IC circulation pump rate to cause the second IC circulation flow rate to decrease such that the second IC circulation flow rate may be substantially equals to a pre-defined percentage or pre-defined fraction of the second IC inlet flow rate. In yet another embodiment, no adjustment may be made to the IC circulation pump rate. For example, where the first IC inlet flow rate equals 0.1 mL/min, and the first IC circulation flow rate equals −0.1 mL/min, if the second IC inlet flow rate is increased to 0.2 mL/min, the second IC circulation flow rate may be set to (−½)*(second $Q_{IC\ Inlet}$) of (−½)*(0.2 mL/min), which provides for a second $Q_{IC\ Circ}$ of −0.1 mL/min, and no adjustment to the IC circulation pump rate may be made to achieve such second $Q_{IC\ Circ}$ two according to an embodiment.

The cells may then be fed (and continue expanding) during a second time period at the second IC inlet flow rate and at the second IC circulation flow rate 1310 to maintain the cells in the bioreactor and outside of the headers or portion of the IC circulation path outside of the bioreactor, for example. Following the second time period of feeding 1310, process 1300 may terminate at END operation 1316 if it is not desired to continue feeding and/or expanding the cells, for example.

In embodiments, a first time period, a second time period, a third time period, a fourth time period, a fifth time period, etc. may each comprise one or more days (and/or hours and/or minutes). For example, a time period may be one (1) to fourteen (14) days, according to embodiments. However, a time period may be less than one (1) day or greater than fourteen (14) days, in other embodiments. In an embodiment, a first time period for feeding may comprise Day 0, Day 1, Day 2, Day 3, Day 4; a second time period for feeding may comprise Day 5; a third time period for feeding may comprise Day 6; and a fourth time period for feeding may comprise Day 7, for example. In another embodiment, a first time period may comprise Day 0, Day 1, and Day 2 (e.g., duration of about 3 days); a second time period may comprise Day 3, Day 4, and Day 5 (e.g., duration of about 3 days) third time period may comprise Day 6, Day 7, and Day 8 (e.g., duration of about 3 days); a fourth time period may comprise Day 9 and Day 10 (e.g., duration of about 2 days); and a fifth time period may comprise Day 11, Day 12, and Day 13 (e.g., duration of about 3 days). In yet another embodiment, a first time period may comprise Day 0, Day 1, (e.g., duration of about 2 days); a second time period may comprise Day 2, (e.g., duration of about 1 day); a third time period may comprise one half of Day 3 (e.g., duration of about 0.5 day); a fourth time period may comprise one half of Day 3 (e.g., duration of about 0.5 day) a fifth time period may comprise one half of Day 4 (e.g., duration of about 0.5 day); a sixth time period may comprise one half of Day 4 (e.g., duration of about 0.5 day); a seventh time period may comprise one half of Day 5 (e.g., duration of about 0.5 day); an eighth time period may comprise one half of Day 5 (e.g., duration of about 0.5 day); a ninth time period may comprise one half of Day 6 (e.g., duration of about 0.5 day); a tenth time period may comprise one half of Day 6 (e.g., duration of about 0.5 day); a eleventh time period may comprise one half of Day 7 (e.g., duration of about 0.5 day); and a twelfth time period may comprise one half of Day 7 (e.g., duration of about 0.5 day). Time periods may be different durations according to embodiments. Each time period may be measured in days, hours, minutes, and/or portions thereof.

Returning to FIG. 13, process 1300 may optionally continue to optional query 1312 to determine whether to adjust feeding rates of flow rates based on metabolic activity or metabolic levels. For the expansion of Tregs, for example, it may be desired to control the lactate values of the expanding cell population to values s about 7 mmol/L. Where it is desired to maintain the cell culture lactate values at or below about 7 mmol/L, for example, the rate of media addition may be controlled during the expansion of the cells, e.g., regulatory T cells. In other embodiments, it may be desired to maintain the lactate levels ≤about 5 mmol/L to improve cell growth and viability. In yet other embodiments, it may be desired to maintain the lactate levels at s about 20 mmol/L, at & about 15 mmol/L, or even at s about 10 mmol/L. In embodiments, graphical user interface (GUI) elements may be used to control the rate of media addition and to maintain the lactate metabolic waste product from glycolysis below a pre-defined level during the expansion of cells.

At optional query 1312, if it is not desired to measure metabolic activity and/or adjust feeding levels based on such measurement(s), process 1300 proceeds "no" to END operation 1316, and process 1300 terminates. Alternatively, where it is desired to adjust feeding levels based on metabolic activity, process 1300 proceeds "yes" to optional step 1314 to continue to increase the rate of media addition and feed the expanding cell population. While step 1314 is shown as one step, this step may involve numerous adjustments to the media addition rate, such as increasing the IC inlet flow rate and increasing the IC circulation flow rate, for example, Step 1314 is shown as one step only for illustrative purposes and is not intended to be limiting. Following any adjustments to the rate of media addition, process 1300 returns to optional query 1312 to determine whether to continue to measure metabolic levels and/or adjust feeding. If it is not desired to adjust feeding levels based on metabolic activity, process 1300 proceeds "no" to END operation 1316, and process 1300 terminates. While FIG. 13 and process 1300 show "increases" in the rates of flow rates, other adjustments to the flow rates may be made. For example, the rates or flow rates may decrease or remain substantially the same from one feeding period to the next. The type of adjustments which may be made may depend on the metabolic activity assessment of the growing cell population. The "increases" in flow rate in FIG. 13 are offered merely for illustrative purposes and are not intended to be limiting.

Figure 14:
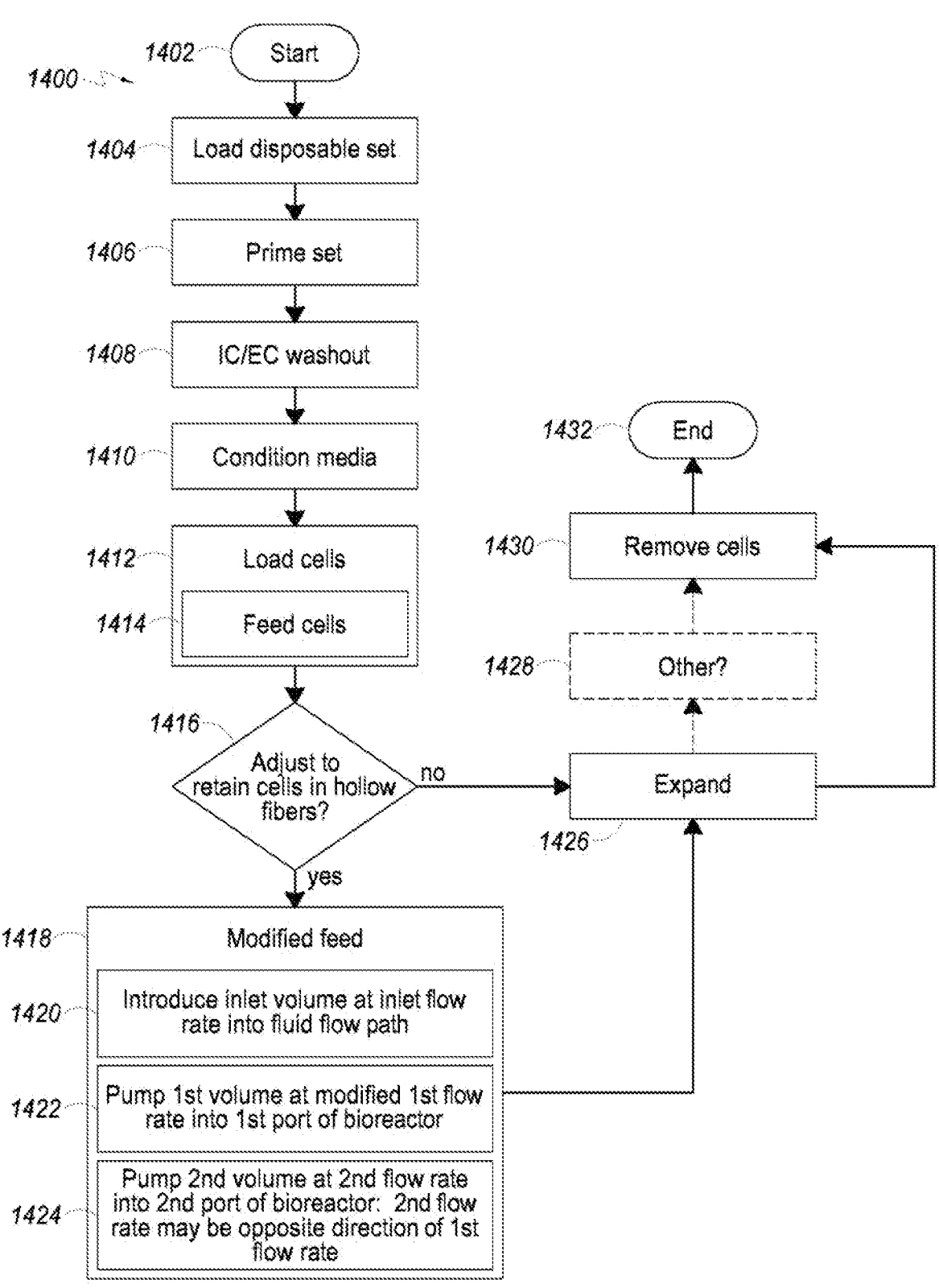
FIG. 14 illustrates a flow diagram depicting the operational characteristics of a process for expanding cells, in accordance with embodiments of the present disclosure.

Next, FIG. 14 illustrates example operational steps 1400 of a process for retaining cells during feeding that may be used with a cell expansion system, such as CES 500 (FIGS. 5B & 5C), in accordance with embodiments of the present disclosure. START operation 1402 is initiated, and process 1400 proceeds to load a disposable tubing set or premounted fluid conveyance assembly (e.g., 210 or 400) 1404 onto the cell expansion system. Next, the system may be primed 1406. In an embodiment, a user or operator, for example, may provide an instruction to the system to prime by selecting a task for priming, for example. In an embodiment, such task for priming may be a pre programmed task, for example. Next, the IC/EC washout task may be performed 1408, in which fluid on the IC circulation loop and on the EC circulation loop may be replaced, for example. The replacement volume may be determined by the number of IC volumes and EC volumes exchanged, according to an embodiment.

Next, to maintain the proper or desired gas concentration across the fibers in the bioreactor membrane, the condition media task 1410 may be executed to allow the media to reach equilibrium with the provided gas supply before cells are loaded into the bioreactor. For example, contact between the media and the gas supply provided by gas transfer module (GTM) or oxygenator may be provided by adjusting the EC circulation rate. The system may then be maintained in a proper or desired state until a user of operator, for example, is ready to load cells into the bioreactor. In an embodiment, the system may be conditioned with media, such as complete media, for example, Complete media may be any media source used for cell growth. In an embodiment, the system may be conditioned with serum-free media, for example. In an embodiment, the system may be conditioned with base media. Any type of media understood by those of skill in the art may be used.

Process 1400 next proceeds to loading cells 1412 into the bioreactor from a cell inlet bag, for example. In an embodiment, the cells in the cell inlet bag may be in solution with media to feed 1414 the cells, for example. In another embodiment, the cells in the cell inlet bag may be in solution both with media to feed 1414 the cells and with a soluble activator complex to stimulate the cells, e.g., T cells or Tregs. In embodiments, the cells may be activated using beads to stimulate expansion. In these embodiments, the beads may be mixed in the media with the cells before loading of the cells. In an embodiment, the cells (and feed solution, in embodiments) may be loaded into the bioreactor from the cell inlet bag until the bag is empty. Cells (and feed solution, in embodiments, and beads in other embodiments) may be chased from the air removal chamber to the bioreactor. In an embodiment, a "load calls with uniform suspension" task may be executed to load the cells (and feed solution, in embodiments). In another embodiment, a "load cells centrally without circulation" task may be executed to load the cells (and feed solution, in embodiments) into a specific, e.g., central, region of the bioreactor. Other loading methods and/or loading tasks may be used in accordance with embodiments.

Next, process 1400 proceeds to query 1416 to determine whether to use a modified feeding method to retain the cells, e.g., non-adherent or suspension cells, such as T cells or Tregs, in the bioreactor, e.g., hollow fiber bioreactor. For example, it may be desired to locate the cells in the bioreactor itself and out of the headers of the bioreactor of the rest of the IC loop. If it is not desired to use a modified feeding method to retain the cells in the bioreactor itself, process 1400 proceeds "no" to expand the cells 1426, in which the cells may continue to grow/expand using the media that they were initially fed with in step 1414, for example.

On the other hand, if it is desired to retain the cells in the bioreactor itself, process 1400 proceeds "yes" to modified feed 1418, in which the cells may be fed by using a flow rate into the IC inlet port (501A) of the bioreactor (501) and a flow rate into the IC outlet port (501B) of the bioreactor (501) to keep the cells in the bioreactor. In so doing, an inlet volumetric flow rate or inlet flow rate may be introduced into the first fluid flow path (506) 1420. For example, an IC inlet flow rate may be introduced into the fluid flow path (506) 1420. The IC inlet pump (554), e.g., a first peristaltic pump (in an embodiment), may operate at a pre-defined number of revolutions per minute (RPMs) to cause a pre-defined IC inlet volumetric flow rate, or IC inlet flow rate, of fluid in the first fluid flow path (506) 1420. A processor(s) and/or controller(s) may direct or control the first pump and/or second pump, for example, to operate at a pre-defined number of RPMs, according to an embodiment. Depending on the speed and direction of the IC circulation pump (512), a modified first flow rate, or first portion of the IC inlet flow rate, may enter the IC inlet port (501A), or first port, of the bioreactor (501) 1422. A pump rate of a pump may depend on the diameter of the pump or configuration of the pump, e.g., peristaltic pump. Other types of pumps may also be used, in which the pump rate may depend on the configuration of the pump used. The IC circulation pump (512), e.g., a second peristaltic pump (in an embodiment), may operate at a pre-defined number of RPMs, and in a direction opposite a direction of the first pump, to cause or produce a pre-defined IC circulation flow rate, or second flow rate, or second portion of the IC inlet flow rate, to enter the IC outlet port (501B), or second port, of the bioreactor (501) 1424. For example, embodiments may provide for about one-half (about ½), or a first portion, of the IC inlet flow rate to branch at connection 517 to enter IC inlet port (501A) of bioreactor 501, and about one-half (or ½), or a second portion, of the IC inlet flow rate to branch at connection 517 to enter the IC outlet port (501B) of bioreactor 501. As shown, the sum of the first portion and the second portion may substantially equal the IC inlet flow rate 503 (e.g., FIG. 5B), in which the IC inlet flow rate 503 may be pumped by IC inlet pump 554. Depending on the flow and counter-flow rates which may be used to keep the cells in the bioreactor or cell growth chamber 501, other types of fractions or percentages of the IC inlet pump rate may be used to set, or configure or adjust, the IC circulation pump, according to embodiments.

After feeding the cells with such flow and counter-flow properties to keep the cells in the bioreactor, process 1400 proceeds to grow/expand the cells 1426. While the expansion of cells is shown at step 1426, the cells may also grow/expand during one or more other step(s), such as 1412, 1414, 1416, 1418, 1420, 1422, 1424, for example. From expand step 1426, process 1400 proceeds to harvest or remove the cells 1430. Process 1400 may then terminate at END operation 1432. If any other steps are desired before harvest, such as continuing with a second modified feed method or other type of feeding method, process 1400 proceeds to optional "Other" step 1428, according to embodiments. From optional step 1428, process 1400 proceeds to harvest or remove the cells from the bioreactor 1430, and process 1400 may then terminate at END operation 1432.

Figure 15A:
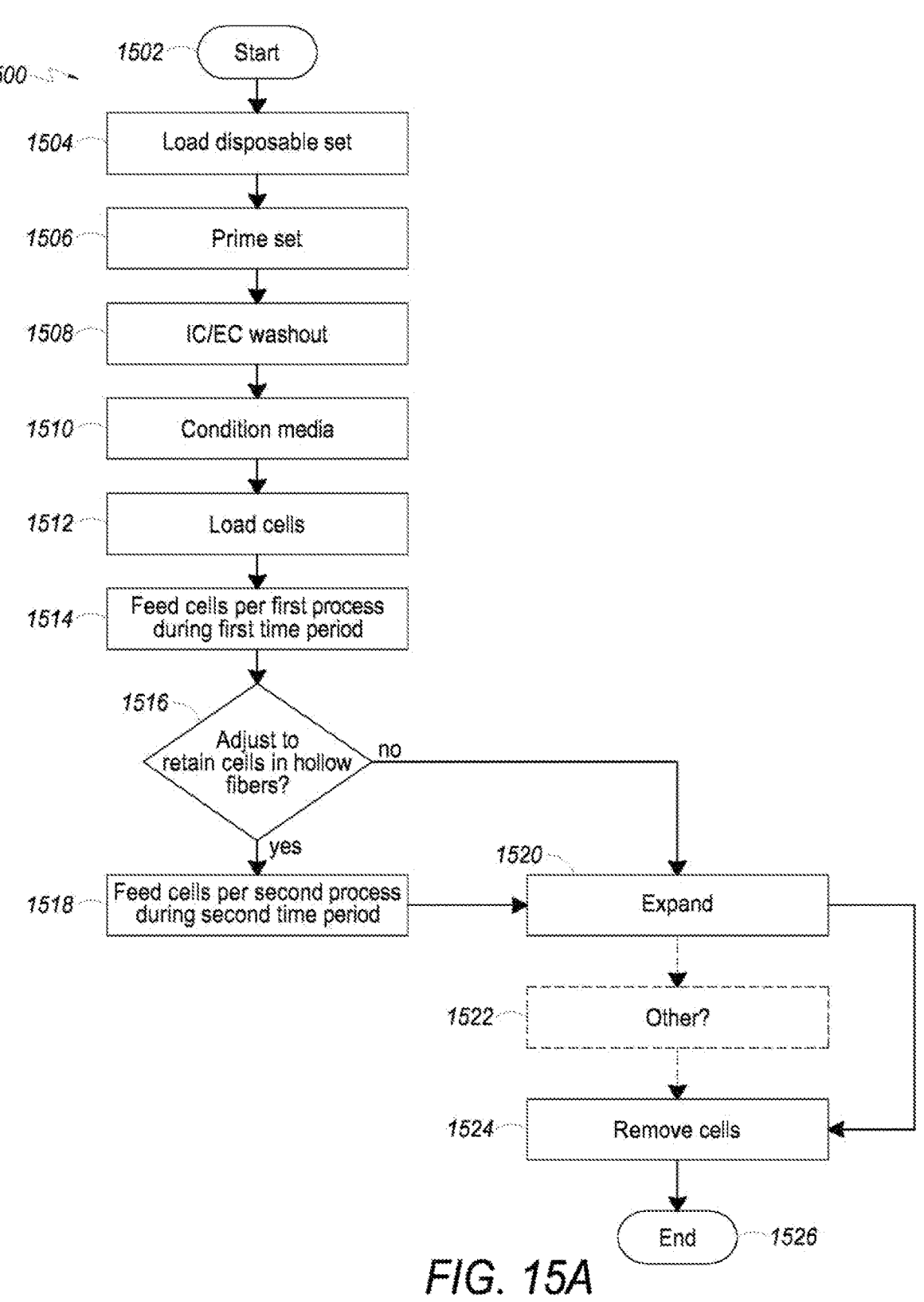
FIG. 15A illustrates a flow diagram depicting the operational characteristics of a process for expanding cells, in accordance with embodiments of the present disclosure.

Turning to FIG. 15A, example operational steps 1500 of a process for feeding cells to retain the cells in a first location, e.g., in the bioreactor itself, that may be used with a cell expansion system, such as CES 500 (e.g., FIGS. 5B & 5C), are provided in accordance with embodiments of the present disclosure. START operation 1502 is initiated, and process 1500 proceeds to load the disposable tubing set or premounted fluid conveyance assembly (e.g., 210 or 400) 1504 onto the cell expansion system. Next, the system may be primed 1506. In an embodiment, a user or operator, for example, may provide an instruction to the system to prime by selecting a task for priming, for example. In an embodiment, such task for priming may be a pre-programmed task. Next, an IC/EC washout task may be performed 1508, in which fluid on the IC circulation loop and on the EC circulation loop may be replaced, for example. The replacement volume may be determined by the number of IC volumes and EC volumes exchanged, according to an embodiment.

Next, to maintain the proper or desired gas concentration across the fibers in the bioreactor membrana, the condition media task 1510 may be executed to allow the media to reach equilibrium with the provided gas supply before cells are loaded into the bioreactor. For example, contact between the media and the gas supply provided by the gas transfer module (GTM) or oxygenator may be provided by adjusting the EC circulation rate. The system may then be maintained in a proper or desired state until a user or operator, for example, is ready to load cells into the bioreactor. In an embodiment, the system may be conditioned with media, such as complete media, for example. Complete media may be any media source used for cell growth. In an embodiment, the system may be conditioned with serum-free media, for example. In an embodiment, the system may be conditioned with base media. Any type of media understood by those of skill in the art may be used.

Process 1500 next proceeds to loading cells 1512 into the bioreactor from a cell inlet bag, for example. In an embodiment, the cells in the cell inlet bag may be in solution with media to feed the cells, for example. In another embodiment, the cells in the cell inlet bag may be in solution both with media and with a soluble activator complex to stimulate the cells, e.g. T cells such as Tregs. In embodiments, the cells may be activated using beads to stimulate expansion. In these embodiments, the beads may be mixed in the media with the cells before loading of the cells. In an embodiment, the cells may be loaded into the bioreactor from the cell inlet bag until the bag is empty. Cells (and beads if used) may be chased from the air removal chamber to the bioreactor. In an embodiment, a "load cells with uniform suspension" task may be executed to load the cells. In another embodiment, a "load cells centrally without circulation" task may be executed to load the cells into a specific, e.g., central, region of the bioreactor. Other loading methods and/or loading tasks may be used in accordance with embodiments.

Next, process 1500 proceeds to feed the cells per a first process during a first time period 1514. In an embodiment, the cells may be fed at a minimum or low feed rate, for example, where the cell population is beginning to grow/expand, and a minimum or low feed rate is able to meet the feeding demands of such population. For example, an IC inlet pump rate of +0.1 mL/min to cause or produce a first fluid flow rate of 0.1 mL/min may be used during such first time period. While this example provides for a low or minimum feed rate of 0.1 mL/min, a low or minimum feed rate may be greater than or equal to about 0.01 mL/min and less than or equal to about 0.1 mL/min, according to embodiments. In embodiments, the low or minimum feed rate may be greater than 0.1 mL/min. If it is desired to reduce the loss of cells from the hollow fiber membrane bioreactor during such first time period, the IC inlet pump rate of +0.1 mL/min may be matched, or closely or substantially matched, to a complementary IC circulation pump rate of −0.1 mL/min to maintain cells in the bioreactor during the growth phase of the cell culture. Other pump rates and resulting fluid flow rates may be used in other embodiments.

Figure 15B:
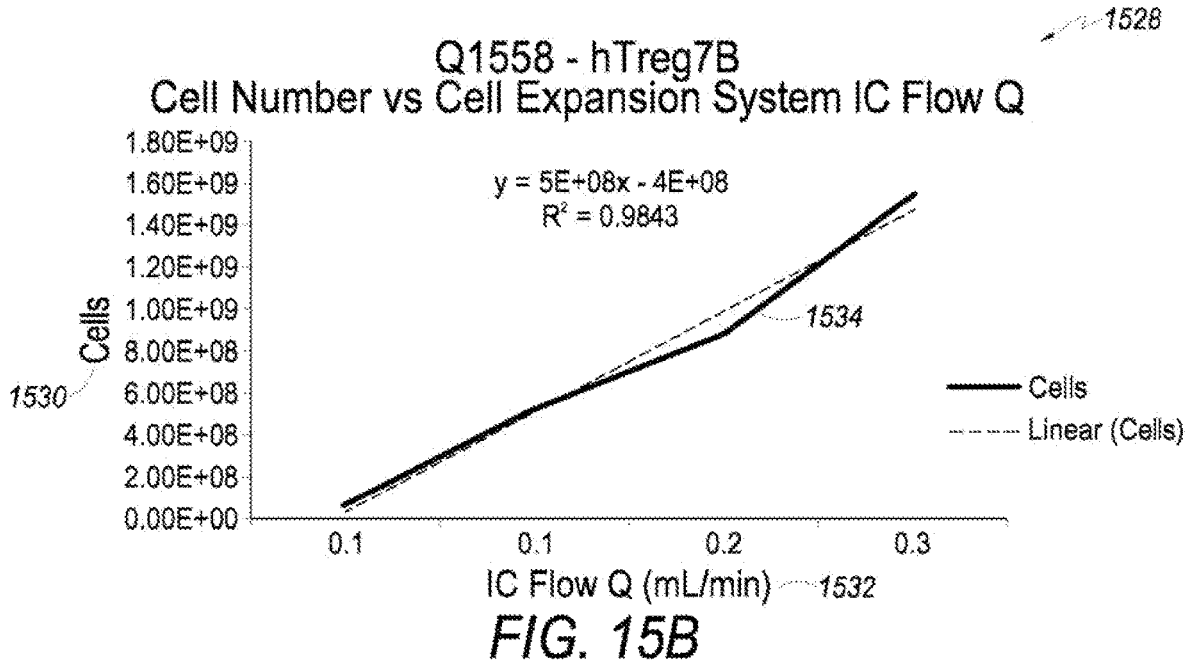
FIG. 15B illustrates a graph of cell number versus flow rate during cell expansion, in accordance with embodiments of the present disclosure.

Next, process 1500 proceeds to query 1516 to determine whether to adjust the feeding rate to retain the cells in the bioreactor itself while also accounting for a growing cell population and increasing feeding demands, according to embodiments. For example, FIG. 15B shows an increasing feed rate in response to an increasing cell population. As shown in FIG. 15B, graph 1528 shows the cell number versus the IC flow rate for a run or procedure on a cell expansion system, e.g., Quantum® Cell Expansion System. In an embodiment, the IC flow rate comprises media for feeding the cells, and may thus also be referred to as the IC media flow rate. The number of cells 1530 is shown versus the IC flow rate (mL/min) 1532. As shown, the IC flow rate increases from 0.1 mL/min to 0.2 mL/min to 0.3 mL/min with an increase in the cells and the growing feeding demands of an expanding cell population, according to an embodiment. In the embodiment shown, there may be a substantially linear relationship, as shown by line 1534, between the number of cells and the IC flow rate.

Returning to FIG. 15A and query 1516, if it is not desired to adjust the feeding rate, process 1500 proceeds "no" to expand the cells 1520, in which the cells may continue to grow/expand using the media with which they were fed during the first time period 1514, for example. While the expansion of cells is shown at step 1520, the cells may also grow/expand during one or more other step(s), such as 1512, 1514, 1516, 1518, for example. On the other hand, if it is desired to adjust the feeding rate while keeping the cells in the bioreactor, process 1500 proceeds "yes" to feed the calls per a second process during a second time period 1518. In an embodiment, such second process may involve feeding the cells at substantially the same feed rates as during the first time period, for example. In another embodiment, the second process may involve feeding the cells at different feed rates as compared to the feed rates used during the first time period. In an embodiment, the IC inlet flow rate may be increased, and the IC circulation flow rate may be set, or configured or adjusted, to equal a percentage or portion of fraction of the IC inlet flow rate. For example, the IC circulation flow rate may be set to equal about fifty percent (50%) of about one-half (½), or another percentage or portion according to embodiments, of the value of the IC inlet flow rate, according to an embodiment. Determining whether to set, configure or adjust, the IC circulation flow rate to a percentage or fraction or portion of the IC inlet flow rate may be based on the value of the IC inlet flow rate, according to an embodiment. For example, an embodiment provides for the following method to retain cells in a bioreactor when feeding the cells using IC inlet flow (where $Q_{IC\ Circ}$=IC circulation flow rate (mL/min); $Q_{IC\ Inlet}$: IC Inlet flow rate (mL/min):

$$Q_{IC\ Circ}=(-)1/2*Q_{IC\ Inlet}\text{ when }Q_{IC\ Inlet}\geq 0.2\text{ mL/min}$$

and $$Q_{IC\ Circ}=(-)Q_{IC\ Inlet}\text{ when }Q_{IC\ Inlet}=0.1\text{ mL/min.}$$

While the above equations provide for different calculations of the IC circulation flow rate based on the values of the IC inlet flow rates (e.g., 0.2 mL/min or 0.1 mL/min), other values of such IC inlet flow rate for making such determination may be used, according to other embodiments. Further, while about fifty percent (50%) or about one-half (½) is used in this example, other percentages, ratios, fractions, and/or portions may be used in accordance with embodiments. Returning to process 1500, after feeding the cells with such flow and counter-flow properties as a part of second process 1518 to keep the cells in the bioreactor, process 1500 proceeds to grow/expand the cells 1520. While the expansion of cells is shown at step 1520, the cells may also grow/expand during one or more other step(s), such as 1512, 1514, 1516, 1518, for example. From expand step 1520, process 1500 proceeds to harvest or remove the cells 1524. Process 1500 may then terminate at END operation 1526. If any other steps are desired before harvesting the cells, process 1500 proceeds to optional "Other" step 1522, according to embodiments. From optional step 1522, process 1500 proceeds to harvest or remove the cells from the bioreactor 1524, and process 1500 may then terminate at END operation 1526.

Figure 16:
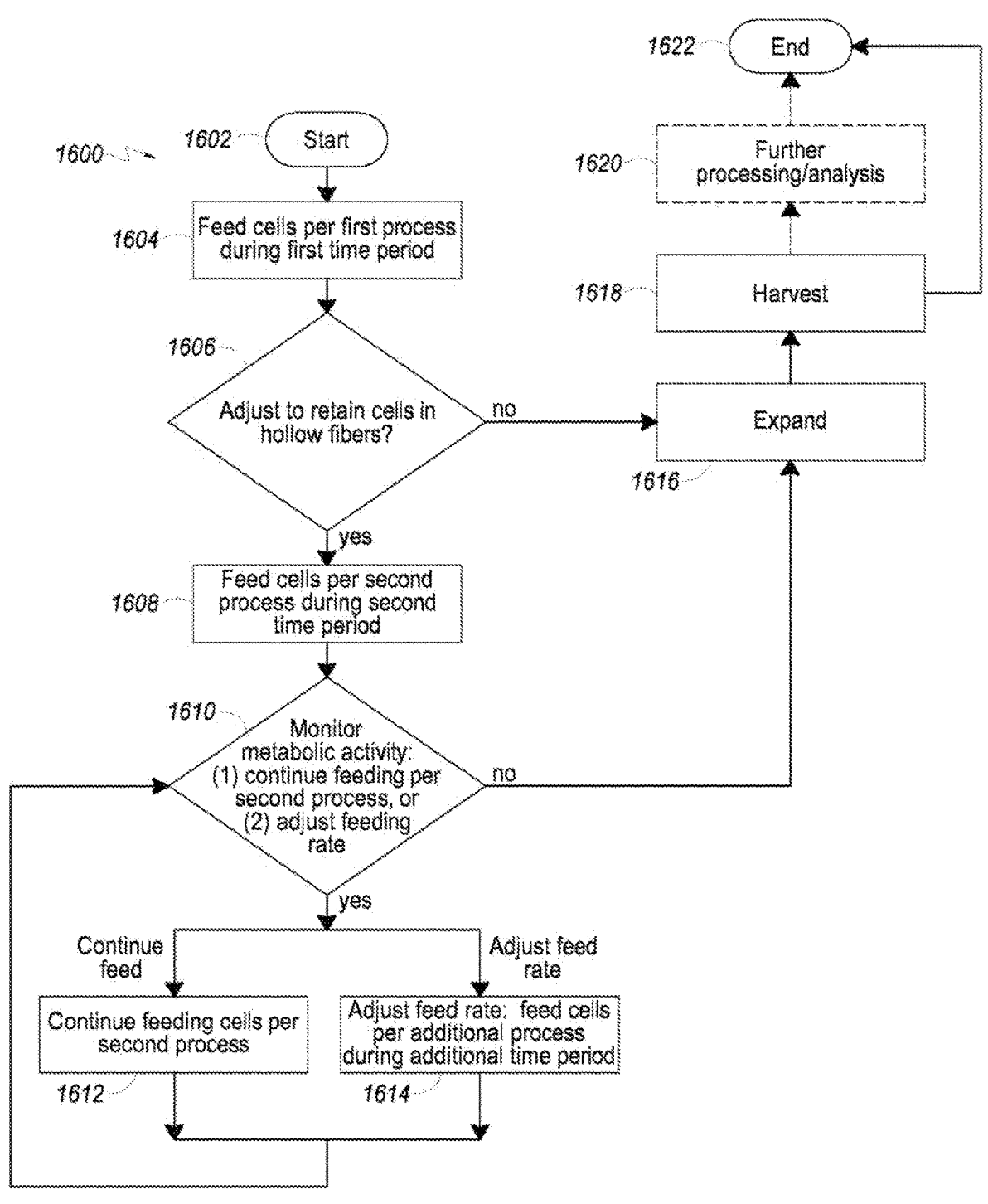
FIG. 16 depicts a flow diagram illustrating the operational characteristics of a process for expanding cells, in accordance with embodiments of the present disclosure.

Next, FIG. 16 illustrates example operational steps 1600 of a process for feeding cells that may be used with a cell expansion system, such as CES 500 (e.g., FIGS. 5B & 5C), in accordance with embodiments of the present disclosure. START operation 1602 is initiated, in which a disposable set may be loaded onto a cell expansion system, the system may be primed, IC/EC washout may be performed, media may be conditioned, and cells may be loaded, for example. Process 1600 next proceeds to feed the cells according to a first process during a first time period 1604. In an embodiment, the cells may be fed at a minimum or low feed rate, for example, where the cell population is beginning to grow/ expand, and a minimum or low feed rate is able to meet the feeding demands of such population. For example, an IC inlet pump rare of +0.1 mL/min may be used during such first time period. While this example provides for a low or minimum feed rate of 0.1 mL/min, a low or minimum feed rate may be greater than or equal to about 0.01 mL/min and less than or equal to about 0.1 mL/min, according to embodiments. In embodiments, the low or minimum feed rate may be greater than 0.1 mL/min. if it is desired to reduce the loss of cells from the hollow fiber membrane bioreactor during such first time period, the IC inlet pump rate of +0.1 mL/min may be matched, or closely or substantially matched, to a complementary IC circulation pump rate of −0.1 mL/min to maintain cells in the bioreactor during the growth phase of the cell culture.

Next, process 1600 proceeds to query 1606 to determine whether the feeding rate may be adjusted to account for a growing cell population and/or to continue efforts to keep the cells in the bioreactor. If it is desired to adjust the feeding rate to retain the cells in the bioreactor, process 1600 proceeds "yes" to feed the cells according to a second process during a second time period 1608. In an embodiment, such second process may involve feeding the cells at substantially the same feed rates as during t the first time period, for example. In another embodiment, the second process may involve feeding the cells at different feed rates as compared to the feed rates used during the first time period. In an embodiment, the IC inlet flow rate may be increased, and the IC circulation flow rate may be set, or configured or adjusted, to equal a percentage or fraction or portion of the IC inlet flow rate. For example, the IC circulation flow rate may be set to equal about fifty percent (50%) or about one-half (½), or another percentage or portion according to embodiments, of the value of the IC inlet flow rate, according to an embodiment. Determining whether to set the IC circulation flow rate to a percentage of the IC inlet flow rate may be based on the value of the IC inlet flow rate, according to an embodiment. For example, an embodiment provides for the following (where $Q_{IC\ Circ}$=IC circulation flow rate (mL/min), $Q_{IC\ Inlet}$=IC inlet flow rate (mL/min):

$$Q_{IC\ Circ}=(-)1/2*Q_{IC\ Inlet}\text{ when }Q_{IC\ Inlet}\geq 0.2\text{ mL/min}$$

and $$Q_{IC\ Circ}=(-)Q_{IC\ Inlet}\text{ when }Q_{IC\ Inlet}=0.1\text{ mL/min.}$$

While the above equations provide for different calculations of the IC circulation flow rate based on the values of the IC inlet flow rates (e.g. 0.2 mL/min or 0.1 mL/min), other values of such IC inlet flow rate for making such determination may be used, according to other embodiments. Further, while about fifty percent (50%) or about one-half (½) is used in this example, other percentages, ratios, fractions, and/or portions may be used in accordance with embodiments. Returning to process 1600, after feeding the cells with such flow and counter-flow properties as a part of second process 1608 to keep the cells in the bioreactor, process 1600 proceeds to query 1610 to determine whether to monitor of measure the metabolic activity, e.g. glucose consumption and/or lactate generation, of the growing cell population. If it is not desired to monitor the metabolic activity, process 1600 proceeds "no" to expand the cells 1616, in which the cells may continue to grow/expand using the media with which they were fed during the first time period 1604 and/or second time period 1608, for example. While the expansion of cells is shown at step 1616, the cells may also grow/expand during one or more other step(s), such as 1604, 1606, 1608, 1610, 1612, 1614, for example.

Returning to query 1610, if it is desired to monitor or measure the metabolic activity of the growing cell population, process 1600 proceeds "yes" to either continue to feed the cells per the second process or adjust the feed rate, based on the metabolic activity and/or measurements thereof. In an embodiment, monitoring the glucose and/or lactate levels may facilitate the adjustment of media flow rates, e.g., IC flow rate, to support cell, e.g., T cell such as Treg, expansion in a bioreactor, e.g., hollow fiber bioreactor. In embodiments, cell culture lactate values may be maintained below about 7 mmol/L, for example. In other embodiments, cell culture lactate values may be maintained below about 15 mmol/L, for example. In embodiments, by using a cell expansion system graphical user interface (GUI), for example, to control a rate(s) of media addition, lactate metabolic waste product from glycolysis may be maintained below about 7 mmol/L, for example, during the expansion of cells, e.g., regulatory T cells, or below about 15 mmol/L, for example, during the expansion of other types of T cells. In other embodiments, rate(s) of media addition, for example, and/or other settings may be controlled to attempt to maintain the lactate levels s about 5 mmol/L, for example, to improve cell growth and viability. In other embodiments, lactate may be maintained at or below about 30 mmol/L, at or below about 25 mmol/L, at or below about 20 mmol/L, at or below about 15 mmol/L, or even at or below about 10 mmol/L. Other concentrations may be used in other embodiments.

Depending on the metabolic measurements and the desired levels of lactate, for example, process 1600 proceeds to either continue feeding the cells according to the second process 1612 or adjusting the feed rate 1614. For example, the cells may be continued to be fed according to the second process 1612 where measurements of the metabolic activity show lactate levels ≤about 5 mmol/L, according to an embodiment, or s about 15 mmol/L, according to other embodiments. In another embodiment, the cells may be continued to be fed according to the second process 1612 where the measurements of the metabolic activity show lactate levels ≤about 7 mmol/L or ≤about 15 mmol/L, for example. From continuing to feed the cells per the second process 1612, process 1600 returns to query 1610 to continue monitoring the metabolic activity of the growing cell population.

Depending on the metabolic measurements and the desired levels thereof, process 1600 proceeds to adjust the feed rate 1614, in which the cells may be fed according to an additional process during an additional time period. Such additional process(es) and additional time period(s) may include, for example, a third process during a third time period, a fourth process during a fourth time period, a fifth process during a fifth time period, etc., according to embodiments. In an embodiment, such additional process may involve feeding the cells at substantially the same feed rates as during the first and/or second time periods, for example. In another embodiment, the additional process may involve feeding the cells at different feed rates as compared to the feed rates used during the first and/or second time periods. For example, the IC inlet flow rate may be increased, and the IC circulation flow rate may be matched, or closely or substantially matched, to the IC inlet flow rate, but in the opposite direction. In an embodiment. In another embodiment, the IC inlet flow rate may be increased, and the IC circulation flow rate may be set, or configured or adjusted, to equal a percentage or fraction or portion of the IC inlet flow rate, and in the opposite direction. While adjusting the feed rate 1614 shows an "additional" process and an "additional" time period in step 1614, any number of processes and time periods may be used to adjust the feed rate based on metabolic activity.

From adjusting the feed rate 1614, process 1600 returns to query 1610. If it is not desired to adjust, or further adjust, the feeding rate, process 1600 proceeds "no" to expand the cells 1616, in which the cells may continue to grow/expand using the media with which they were fed during the first time period 1604, second time period 1608, and/or additional time period 1614. While the expansion of cells is shown at step 1616, the cells may also grow/expand during one or more other step(s), such as step(s) 1604, 1606, 1608, 1610, 1612, 1614, for example. From expand step 1616, process 1600 proceeds to harvest or remove the cells 1618 from the bioreactor and into a harvest bag(s) or container(s), for example. Process 1800 may then terminate at END operation 1622. Alternatively, from harvest operation 1618, process 1600 may optionally proceed to allow for further processing/analysis 1620. Such optional further processing/analysis 1620 may include characterizing the phenotype(s), for example, of the harvested cells, e.g., T cells or Tregs. From optional further processing/analysis step 1620, process 1600 may then terminate at END operation 1622.

Figure 17A:
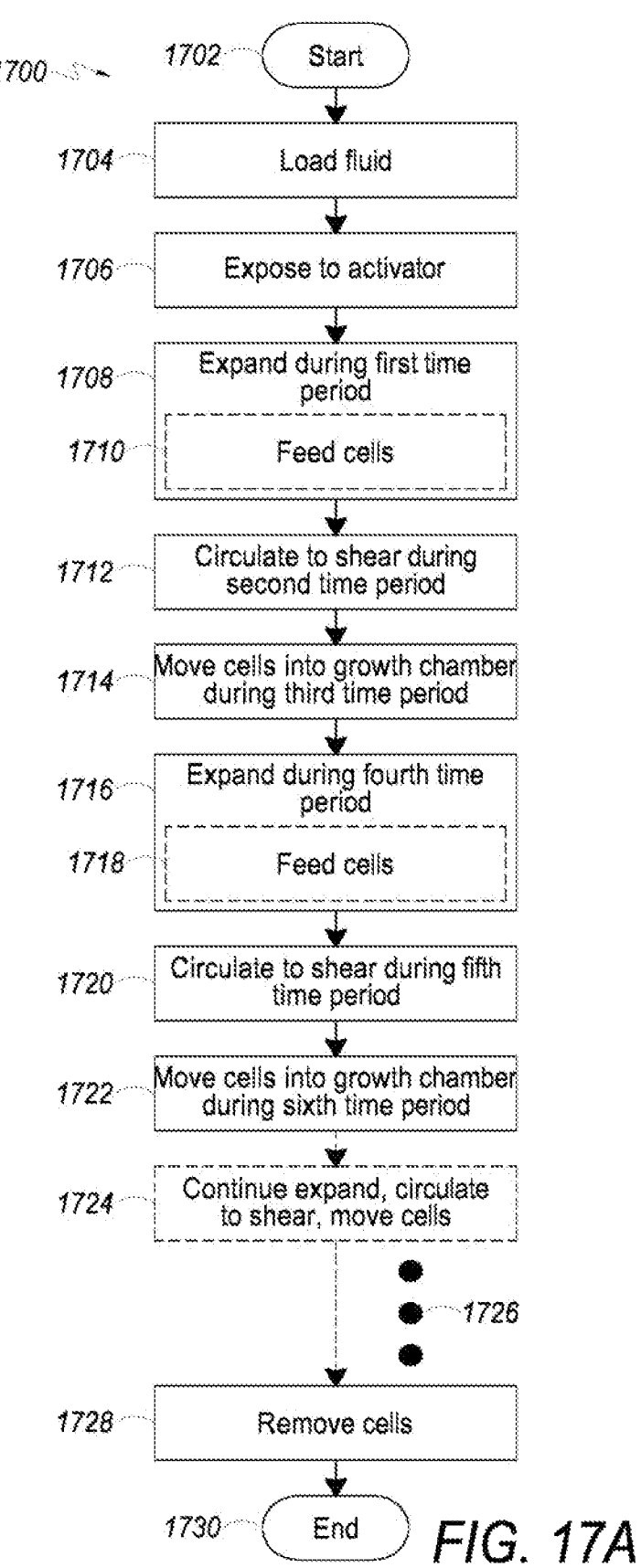
FIG. 17A depicts a flow diagram illustrating the operational characteristics of a process for expanding cells, in accordance with embodiments of the present disclosure.

FIG. 17A illustrates operational steps 1700 of a process for expanding cells that may be used with a cell expansion system in embodiments of the present disclosure. As described below, process 1700 may include steps to shear cell clusters that may form as the cells are expanded in the cell growth chamber according to embodiments of the present disclosure. The cell clusters may in embodiments also include beads that may have activator on their surface and be used to activate cell expansion. In embodiments, these steps may be implemented as part of a "modified circulation" task. START operation 1702 is initiated and process 1700 proceeds to loading fluid 1704 with cells into a cell growth chamber in a cell expansion system. In embodiments, the cells may comprise non-adherent cells, such as one or more types of T cells. In one embodiment, the cells may include Tregs. In other embodiments, the cells may include helper, effector, naïve, memory, and/or combinations thereof.

Process 1700 proceeds to exposing the cells to an activator 1706. The activator, which may include antibody complexes, may be added to the fluid loaded at step 1704. In embodiments, the activator may be a soluble human antibody CD3/CD28/CD2 cell activator complex. In other embodiments, the activator may be located on beads that are functionalized with antibodies (e.g., CD3/CD28) that activate cell expansion. The beads may be mixed with the cells. Process 1700 proceeds to expanding 1708 the cells for a first time period. Step 1708 may include feeding 1710 the cells. The cells may be fed nutrients to promote their expansion. For example, media with glucose, proteins, and reagents may be delivered into the cell growth chamber to provide nutrients for cell expansion.

The first time period for expanding 1708 the cells may be based on the time it may take for cell colonies, micro-colonies, or clusters to form. A cell colony, micro-colony, or cluster may be a group of one or more attached cells (and beads in some embodiments). In embodiments, the cells, e.g., T cells such as Tregs, may benefit from cell contact. The cell contact may stimulate signaling that promotes expansion and growth. However, after a period of expansion, the cells may attach to each other to form cell colonies, micro-colon or clusters. Without being bound by theory, it is believed that after a time period of the cells expanding 1708 the cells may form relatively large cell colonies, micro-colonies, or clusters that continue to grow. The cell colonies, micro-colonies, or clusters may create necrotic centers where nutrients (e.g., glucose), gasses (e.g., oxygen), and reagents (e.g., activator) do not reach cells in the center of the cell colonies, micro-colonies, or clusters. As a result, the conditions for cell expansion in the center of these cell colonies, micro-colonies, or clusters may be such that the expansion rate may slow (e.g., increase doubling time) or the conditions may lead to cell necrosis. In embodiments that utilize beads, the beads may also aggregate and be part of the cell colonies, micro-colonies, or clusters.

In embodiments, to allow the expansion 1708 of the cells, the first time period may be between about 5 hours and about 48 hours. In some embodiments, the first time period may be greater than about 6 hours, greater than about 12 hours, greater than about 24 hours, or even greater than about 48 hours. In other embodiments, the first time period may be less than about 72 hours, less than about 60 hours, less than about 48 hours, less than about 36 hours, less than about 24 hours, or even less than about 12 hours. After the first time period, process 1700 proceeds to circulate 1712 to shear cell colonies, micro-colonies, or clusters during a second time period. Step 1712 may be performed to reduce the size of the cell colonies, micro-colonies, or clusters. The second time period may in embodiments be less than about 120 minutes, less than about 100 minutes, less than about 80 minutes, such as between about 60 minutes and about 0.5 minutes. In some embodiments, the second time period may be between about 50 minutes and about 1 minute, such as about 4 minutes. In other embodiments, the second time period may be based on a volume of fluid introduced into the first circulation path. That is, once a volume of fluid has been introduced, the circulate 1712 to shear step may be stopped.

Figure 17B:
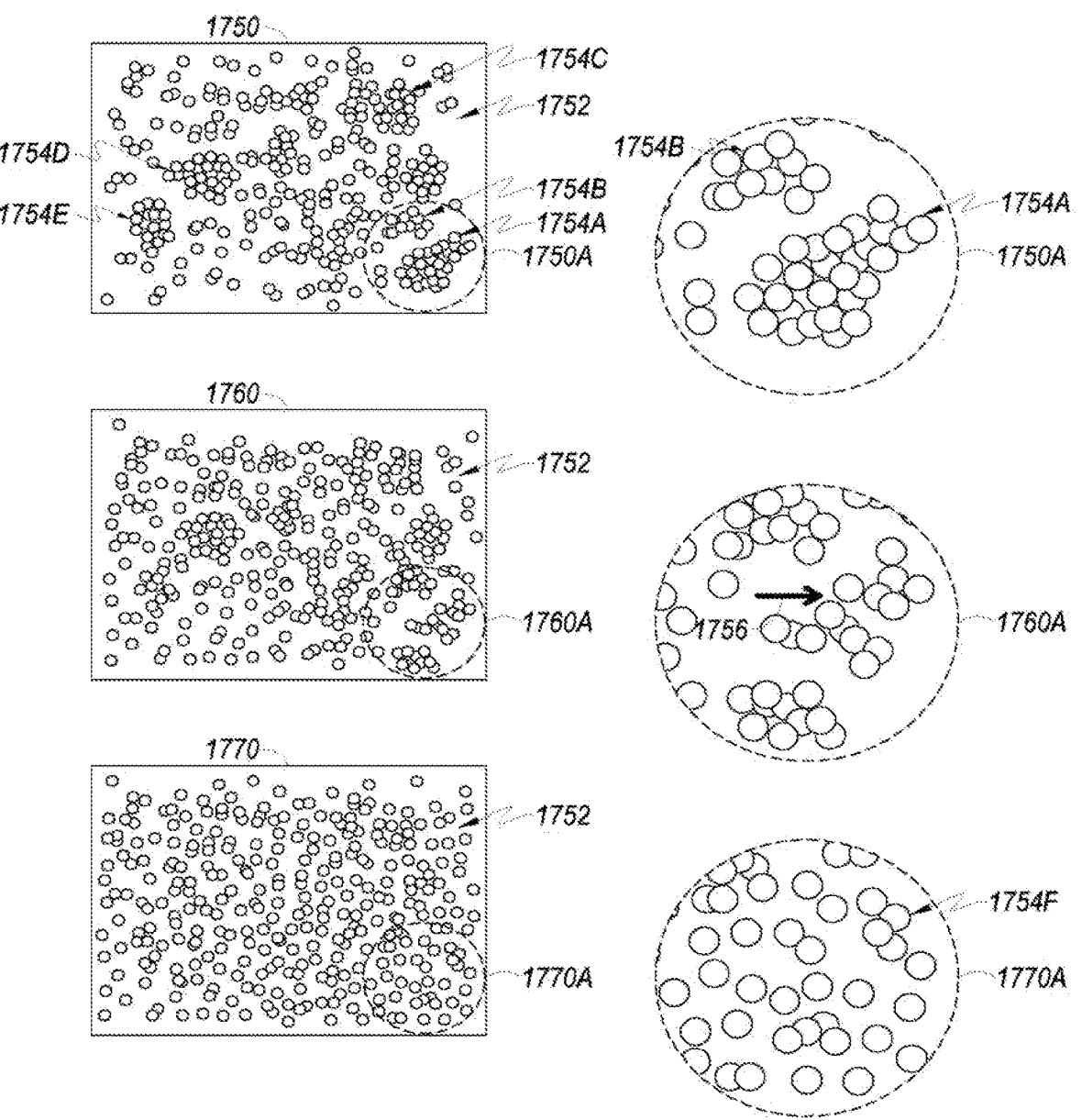
FIG. 17B depicts views of cells expanding in a cell expansion system, in accordance with embodiments of the present disclosure.

FIG. 17B Illustrates a number of views 1750, 1760, and 1770 of cells in a volume of fluid (1752) that may be expanded in a cell growth chamber as part of process 1700. For example, in some embodiments, the cell growth chamber may be a hollow fiber bioreactor. In these embodiments, views 1750, 1760, and 1770 may illustrate cells in a fiber of a hollow fiber bioreactor, for example. 1750A, 1760A, and 1770A are zoomed in portions of views 1750, 1760, and 1770, respectively. Referring to view 1750, the cells may be shown after cells have been loaded 1704, exposed to an activator, 1706 and expanded 1710 for a time period, e.g., the first time period. As illustrated in view 1750, a number of cell colonies 1754A-E have formed.

In order to reduce the number of cells in, and the size of, the cell colonies, micro-colonies, or clusters 1754A-E, step 1712 may circulate fluid and the cells through a first fluid circulation path. Without being bound by theory, it is believed that the circulation may create some force acting on the cell colonies including shear stress, as illustrated by arrow 1756 as shown in zoomed in portion 1760A. The shear stress 1756 may provide enough force to separate cells in the cell colonies. As the circulation continues, the cell colonies may begin to break up into smaller sizes, as shown in view 1760. View 1770 illustrates the cells after the circulation has been performed for the second time period. As illustrated in view 1770, the size of the cell colonies is reduced with some colonies being completely separated into individual cells. In some embodiments, the circulation to shear step 1712 may be performed until the cells and fluid comprise a single cell suspension.

In other embodiments, cell colonies, micro-colonies, or clusters of cells may remain after circulate to shear 1712. For example, colony 1754F in zoomed in portion 1770A illustrates that some colonies of a reduced size may remain after step 1712. In embodiments the cell colonies, micro-colonies, or clusters (e.g., 1754F) that remain may be between about 25 microns and about 300 microns. In other embodiments, circulate to shear may reduce the size of cell colonies, micro-colonies, or clusters (e.g., 1754F) so the call colonies, micro-colonies, or clusters may be between about 50 microns and about 250 microns. In yet other embodiments, the size of cell colonies, micro-colonies, or clusters may be between about 75 microns and about 200 microns. In some embodiments, the size of the cell colonies, micro-colonies, or clusters may be less than about 200 microns e.g., about 100 microns after a circulate to shear step.

Figure 17C:
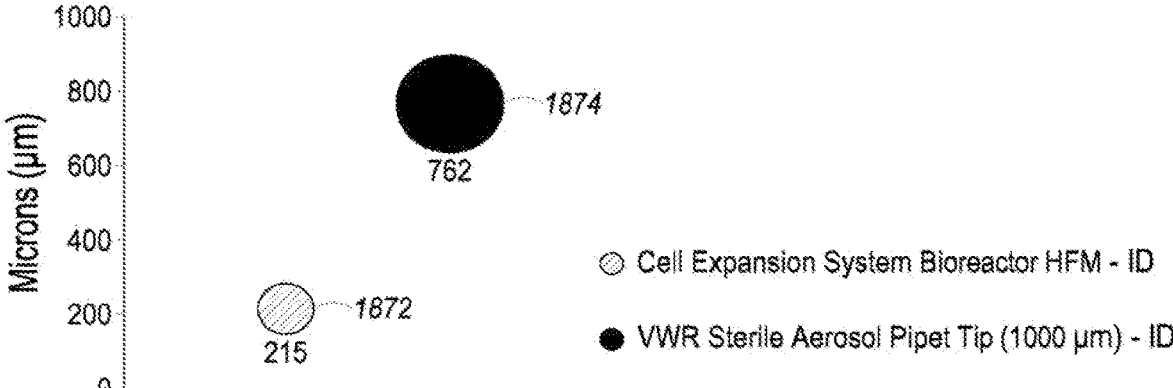
FIG. 17C illustrates a graph showing inner diameters of cell disassociation methods, in accordance with embodiments of the present disclosure.

In embodiments, the size of the remaining cell colonies, micro-colonies, or clusters may be somewhat a function of some structural features of the cell growth chamber. As mentioned above, the cell growth chamber may be a hollow fiber bioreactor with hollow fibers in some embodiments. As may be appreciated, cell colonies, micro-colonies, or clusters, as they circulate, may be affected by s tear stress each time hey contact the side walls of the hollow fiber. This contact may more efficiently reduce the size of cell colonies. When the inner diameter is larger, such as in a conventional process that may utilize a pipet to induce shear to reduce colony sizes, contact with a side wall may not occur as often. FIG. 17C illustrates differences in inner diameter size between one embodiment of a hollow fiber (e.g., 215 microns) 1772 and a pipet tip 1774 (762 microns), which may be used to disassociate attached cells in cell colonies, micro-colonies, or clusters. In embodiments, the smaller inner diameter of a hollow fiber is believed to more efficiently and effectively reduce a size of cell colonies during the circulating to shear step 1712.

The second time period for the circulate to shear 1712 may in embodiments be less than about 120 minutes, less than about 90 minutes, less than about 60 minutes, less than about 30 minutes, or even less than about 15 minutes. In some embodiments, the second time period may be between about 15 minutes and about 1 minute, such as about 4 minutes.

After the second time period, process 1700 proceeds to move cells into cell growth chamber during a third time period 1714. At step 1714 cells that are not positioned in the cell growth chamber, as a result of the circulation to shear step 1712, are moved back into the cell growth chamber during a third time period. In embodiments, this may involve activating one or more pumps to introduce fluid into a fluid circulation path. For example, fluid may be introduced from a fluid inlet path to a first fluid flow path and then into the cell growth chamber, from both an inlet port and an outlet port of the cell growth chamber. The movement of the fluid into the cell growth chamber from the inlet port and the outlet port may move cells back into the cell growth chamber.

In some embodiments, the fluid used in the step to move the cells back into the cell growth chamber 1714 may include reagents that promote cell growth. For example, in embodiments, the fluid may be media that includes glucose, proteins, or other reagents. In one embodiment, the fluid may include one or more supplements. In one embodiment, the fluid is complete media and includes a cytokine, e.g., human IL-2 cytokine supplement. The addition of the fluid may be referred to as a bolus addition. The combination of steps 1712 and 1714 may be referred to in embodiments as circulate and bolus addition.

In other embodiments, the third time period may be based on a volume of fluid introduced into the cell growth chamber during the circulate to shear step 1712. For example, in embodiments, step 1712 may be performed until about 300 ml, about 250 ml, about 200 ml, or about 150 ml, have been introduced into the fluid circulation path.

After the third time period, process 1700 proceeds to expand during a fourth time period 1716. Similar to step 1708, step 1716 may include feeding 1718 the cells. The cells may be fed nutrients to promote their expansion. For example, media with glucose, proteins, and reagents may be delivered into the cell growth chamber to provide nutrients for cell expansion.

Similar to the first time period, the fourth time period may be based on the time it may take for cell colonies to form. In embodiments, the fourth time period may be between about 5 hours and about 48 hours. In some embodiments, the fourth time period may be greater than about 6 hours, greater than about 12 hours, greater than about 24 hours, or even greater than about 48 hours. In other embodiments, the fourth time period may be less than about 72 hours, less than about 60 hours, less than about 48 hours, less than about 36 hours, less than about 24 hours, or even less than about 12 hours. Because more cells are likely in the cell growth chamber, the fourth time period may be shorter than the first time period in some embodiments. In other embodiments, the fourth time period may be the same as the first time period.

After the fourth time period, process 1700 proceeds to step 1720 to circulate to shear for a fifth time period to reduce second cell colonies. In embodiments, step 1720 may use the first circulation rate. However, in other embodiments, the circulation rate used at step 1720 may be different, either greater or less than the first circulation rate.

After the fifth time period, process 1700 proceeds to step 1722 where the cells that are not positioned in the cell growth chamber, may be moved back into the cell growth chamber during a sixth time period. Fluid may be introduced from a fluid inlet path to a first fluid flow path and into the cell growth chamber from an inlet port and an outlet port of the cell growth chamber. The movement of the fluid into the cell growth chamber from the inlet port and the outlet port may move calls back into the cell growth chamber. In some embodiments, the fluid used to move the cells back into the cell growth chamber may include reagents that promote cell growth. For example, in embodiments, the fluid may be media that includes glucose, proteins, or other reagents. In one embodiment, the fluid may include one or more supplements. In one embodiment, the fluid is complete media and includes a cytokine, e.g., human IL-2 cytokine.

The process 1700 may optionally perform the steps of expand, circulate, and move cells for an additional number of times as illustrated by optional step 1724 and ellipsis 1726. The steps of expand, circulate, and move may be performed sequentially for a period of time. For example, in some embodiments, the steps may be performed once every four days, once every three days, once every two days, daily, twice daily, or three times daily, for a period of from about two days to about twenty days (such as about 10 days, about 9 days, about 8 days, about 7 days, about 6 days, or even about 5 days). In some embodiments, the steps may be performed at varying periods of time. For example, in one embodiment, the steps may be performed after three days, and then every other day. As another example, the steps may be performed after two days and then twice daily. These are merely examples and other embodiments may utilize other periods of time.

Figure 18:
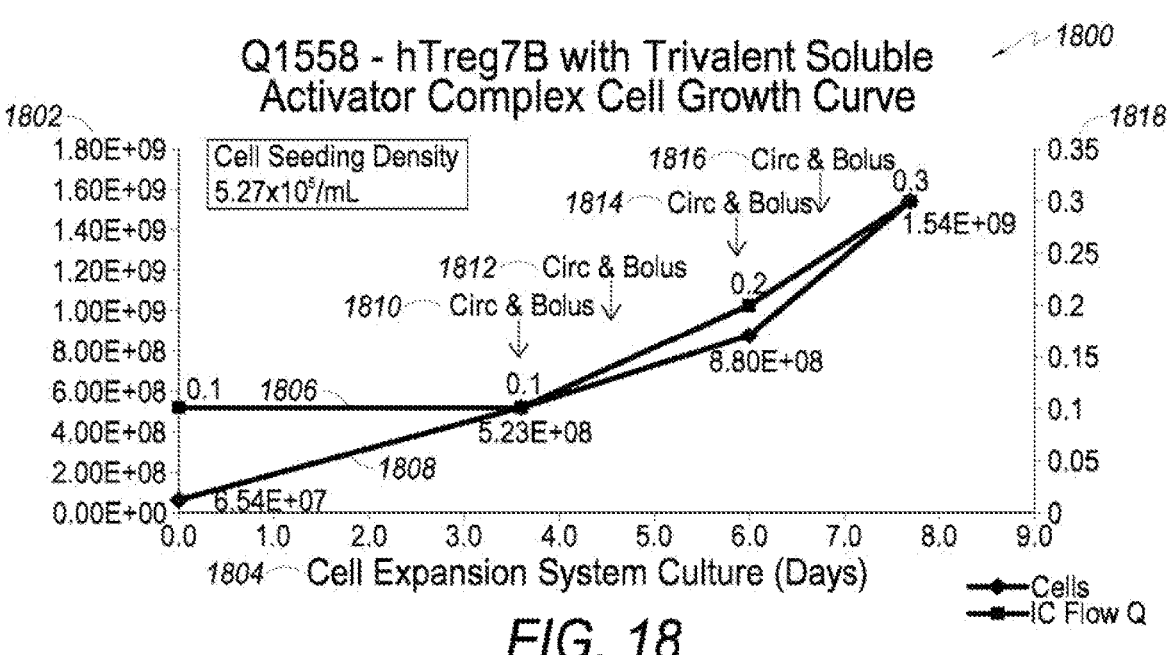
FIG. 18 illustrates a graph of cell numbers and flow rate versus culture days during cell expansion, in accordance with embodiments of the present disclosure.

For example, FIG. 18 shows a graph 1800 of performing circulation and bolus additions at different periods of time during a process of expanding cells. Curve 1808 shows the cell number 1802 versus days of cell culture 1804 on a cell expansion system, e.g., Quantum® Cell Expansion System. Curve 1806 shows IC Flow rate 1818 versus days of cell culture 1804 on a cell expansion system, e.g., Quantum® Cell Expansion System. As shown by curve 1806, the IC flow rate remains the same at 0.1 mL/min for the first three days. There is an increase in the flow rate to 0.2 mL/min at day six and an increase to 0.3 mL/min after day seven. The increase in flow rate may be in response to the increase in cell numbers as the culture days 1804 increase. Also, shown in FIG. 18, are several circulation and bolus addition steps (e.g., 1810, 1812, 1814, and 1816). There is a circulation and bolus addition 1810 performed 3.5 days after cell culture. There is another circulation and bolus addition 1812 performed after 4.5 days of cell culture. Another circulation and bolus addition is performed after 6 days of cell culture 1814, and another circulation and bolus addition after 6.5 days of cell culture 1816. As may be appreciated by looking at curves 1806 and 1808, the multiple circulation and bolus additions (1810-1816), in combination with the increasing IC flow rates, may have a positive effect on the rate of cell expansion, e.g., number of cells.

Referring back to 17A, process 1700 proceeds to remove cells 1728 from the cell growth chamber. In embodiments, this may involve harvesting the cells. Step 1728 may include additional steps such as circulation steps (e.g., 1712 and 1720) prior, or during, removal of the cells from the cell growth chamber. Process 1700 terminates at END operation 1730.

Figure 19B:
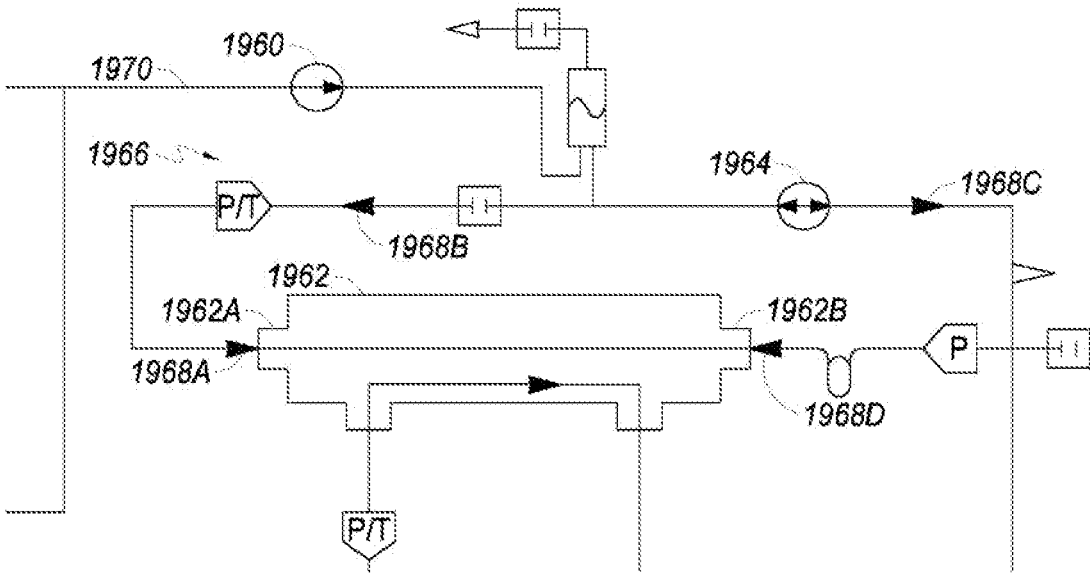
FIG. 19B depicts a schematic of a portion of a cell expansion system, in accordance with an embodiment of the present disclosure.

FIG. 19A illustrates operational steps 1900 of a process for operating pumps that may be used in a cell expansion system in embodiments of the present disclosure. As described below, process 1900 may include steps to activate pumps in a process of reducing cells (and beads if beads are used as an activator) in cell clusters that have been expanded in the cell growth chamber according to embodiments of the present disclosure. In embodiments, these steps may be implemented as part of a "modified circulation" task. In embodiments, the steps of process 1900 may be performed by a computer processor. START operation 1902 is initiated and process 1900 proceeds to step 1904, where a first pump is activated at a first flow rate to introduce a first volume of fluid including cells into the intracapillary portion of a bioreactor of a cell expansion system. In embodiments that utilize beads, the beads may be introduced with the first volume of fluid that includes the cells. In embodiments, the first pump may be an inlet pump.

After activating the first pump at the first flow rate, process 1900 proceeds to the first pump activated at a second flow rate 1906 to introduce media with nutrients into the intracapillary portion of the bioreactor for a first time period. The nutrients may include for example proteins, glucose, and other compounds that are used to feed and promote the expansion of the cells. For example, referring to FIG. 19B, a first pump 1960 may be activated at the second flow rate to introduce media into an inlet port 1962A of bioreactor 1962.

In embodiments, the first time period may be based on the time it may take for cell colonies to form. In embodiments, the first time period may be between about 5 hours and about 48 hours. In some embodiments, the first time period may be greater than about 6 hours, greater than about 12 hours, greater than about 24 hours, or even greater than about 48 hours. In other embodiments, the first time period may be less than about 72 hours, less than about 60 hours, less than about 48 hours, less than about 36 hours, less than about 24 hours, or even less than about 12 hours.

Process 1900 then proceeds to activating a second pump at a third flow rate to direct fluid into the bioreactor 1908. Optional step 1908 may be performed to activate pump 1964 to direct a portion of the fluid, introduced at step 1906, into an outlet port 19628 of the bioreactor 1962 to feed calls, for example. This may be part of a flow counter-flow feeding process for moving fluid into the bioreactor from both the IC inlet port and the IC outlet port of a bioreactor.

Figure 19C:
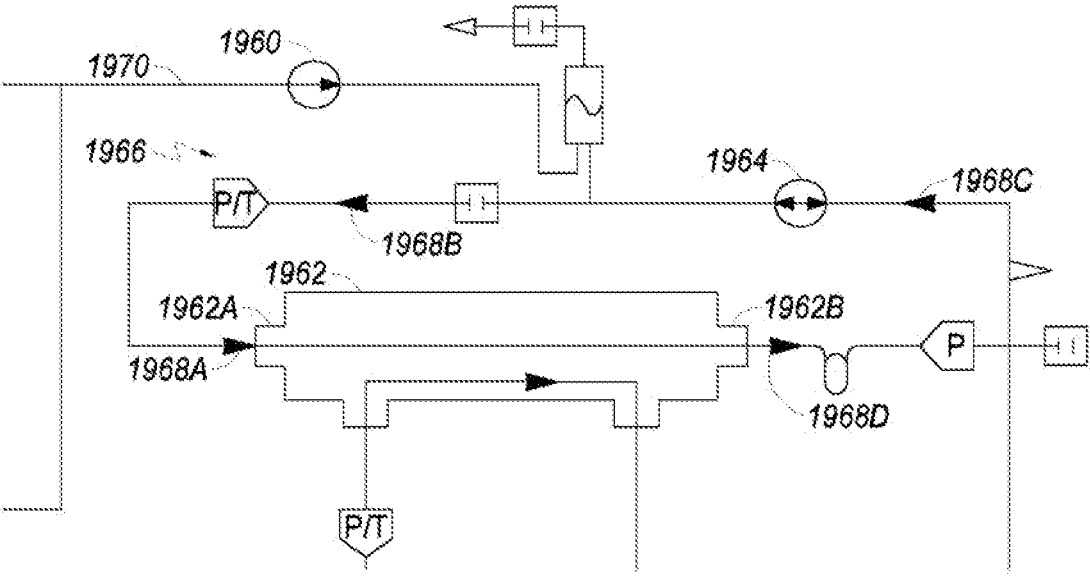
FIG. 19C depicts a schematic of a portion of a cell expansion system, in accordance with an embodiment of the present disclosure.

Process 1900 then proceeds to activating the second pump at a fourth flow rate 1910 to circulate the cells during a second time period and reduce a number of cells in a cell cluster in the bioreactor. In embodiments, the cells are circulated throughout a first fluid circulation path. Referring to FIG. 19C, second pump 1964 may be activated at step 1910 to circulate fluid through first fluid circulation path 1966, as illustrated by arrows 1968A-D.

Without being bound by theory, it is believed that after a time period the expanding cells may form cell colonies, micro-colonies, or clusters. The cell colonies may create necrotic centers where nutrients and proteins (e.g., activator) do not reach cells in the center of the colonies. As a result, the conditions for cell expansion in the center of these cell colonies, micro-colonies, or clusters may be such that the expansion rate may slow (e.g., increase doubling time) and may result in cell necrosis. In embodiments that utilize beads, the beads may also aggregate and be part of the cell colonies, micro-colonies, or clusters. Step 1910 may be performed to reduce the size of the cell colonies, micro-colonies, or clusters.

In embodiments, the fourth flow rate may be high enough to induce shearing. For example, in embodiments, the fourth flow rate may be as high as about 1000 ml/min. In other embodiments, the fourth flow rate may be between about 100 ml/min and about 600 ml/min, such as for example, 300 mL/min.

Figure 19D:
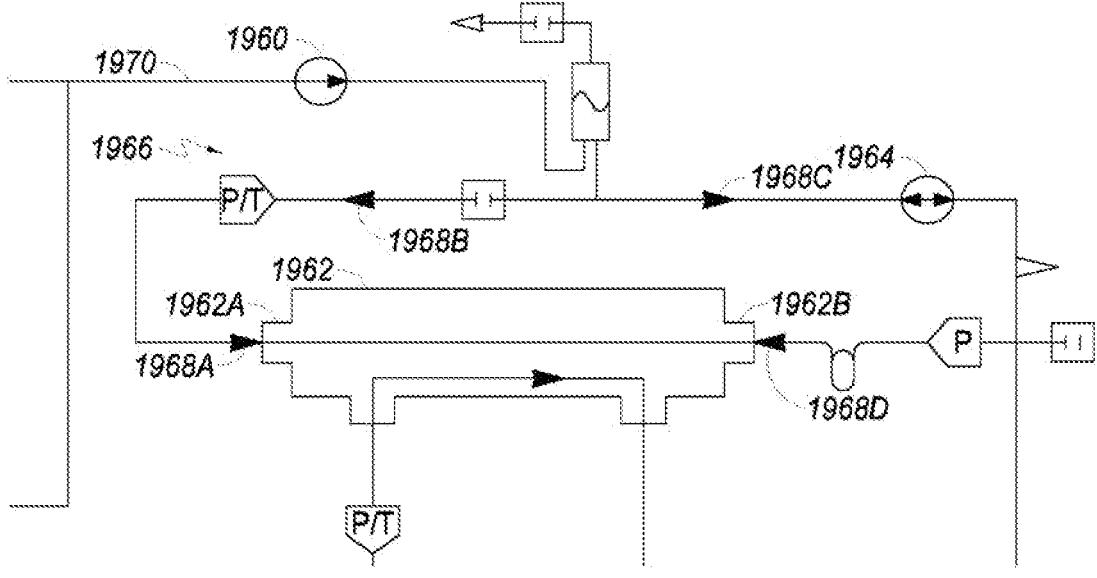
FIG. 19D depicts a schematic of a portion of a cell expansion system, in accordance with an embodiment of the present disclosure.

After the second time period, process 1900 proceeds to step 1912, where the first pump is activated at a fifth flow rate to introduce fluid through a first fluid flow path for a third time period. A first portion of the fluid introduced in the first fluid flow path may in embodiments move first cells in the first fluid flow path (that may be in the first fluid flow path because of step 1910) back into the cell growth chamber through the inlet port 1962A. Referring to FIG. 19D, pump 1960 may be activated to introduce fluid into the first fluid flow path 1970. As illustrated by arrow 1968A and 19688, fluid flows from the first fluid flow path 1970 into inlet port 1962A. This moves first cells that are outside bioreactor 1962 back into bioreactor 1962. It is believed that moving cells that are in the first fluid flow path back into the cell growth chamber improves the overall expansion of cells, since the conditions for cell growth are optimized in the cell growth chamber.

In some embodiments, the fluid introduced into the first fluid flow path at stop 1912, may include one or more materials (e.g., reagents) that promote cell expansion. For example, in embodiments, the fluid may be media that includes glucose or other nutrients for feeding the cells. In one embodiment, the fluid may include a reagent, which may comprise additional activator for continuing to activate the expansion of cells. The use of the fluid with particular reagent(s) or other materials to move the cells back into cell growth chamber, and also expose the cells to additional reagents, e.g., growth factors, proteins, etc., that promote expansion may provide improved cell expansion. In embodiments, the additional fluid used in step 1912 may be referred to as a bolus addition.

Also, after the third time period, at step 1914, the second pump may be activated at a sixth flow rate to move a second portion of the fluid introduced through the first fluid flow path, and second cells, into the cell growth chamber through the outlet port 19628. The second portion of the fluid may in embodiments move second cells in the first fluid flow path (that may be in the first fluid flow path because of step 1910) back into the cell growth chamber through the outlet port. Referring to FIG. 19D, pump 1964 may be activated to move fluid introduced into the first fluid flow path 1970 to the outlet port 1962B. As illustrated by arrow 1968C, pump 1964 moves fluid and cells in first fluid circulation path into bioreactor 1962 through outlet port 19628. As illustrated, by FIG. 19D, the sixth flow rate may be in a direction opposite the fourth flow rate (FIG. 19C). This fluid movement moves cells that are outside bioreactor 1962 back into bioreactor 1962.

In embodiments, the sixth flow rate may be less than the fifth flow rate, which as noted above moves fluid into the first fluid flow path. As may be appreciated, the fifth flow rate may result in introduction of a volume of fluid into a portion of the circulation path 1966 based on the fifth flow rate. The sixth rate may be set so that a percentage of that volume moves toward the outlet port 1962B.

In embodiments, the sixth flow rate may be set as a percentage of the fifth flow rate. For example, the sixth flow rate may be less than or equal to about 90% of the fifth flow rate. In some embodiments, the sixth flow rate may be set to less than or equal to about 80% of the fifth flow rate. In other embodiments, the sixth flow rate may be less than or equal to about 70% of the fifth flow rate. In yet other embodiments, the sixth flow rate may be less than or equal to about 60% of the fifth flow rate. In some embodiments, the sixth flow rate may be less than or equal to about 50% of the fifth flow rate.

In embodiments, the sixth flow rate is based, at least in part, on the difference between a first volume, between the second pump and the inlet port, and a second volume, between the second pump and the outlet port. Referring to FIG. 19D, portions of the first circulation path may have different volumes. For example, in one embodiment, a first volume between the second pump 1964 and the inlet port 1962A may have a first volume, and a second volume between the second pump 1964 and the outlet port 1962B may have a second volume that is different from the first, e.g., larger. In these embodiments, in order to move the cells from the circulation path back into the bioreactor, so that the cells generally reach the bioreactor at approximately the same time, the sixth flow rate may be set at least in part based on the differences in these volumes.

As may be appreciated, as fluid enters fluid circulation path 1966 from first fluid flow path 1970, the fluid moves toward inlet port 1962A at the flow rate that first pump 1960 is set. When pump 1964 is activated, it will redirect at least a portion of the fluid toward the outlet port 1962B. In embodiments, the second volume (the volume between 1964 and outlet port 1962B) may be larger than the first volume. Therefore, in order to move more fluid into the second volume, the second pump 1964 may be set at a percentage of the rate of pump 1960.

In one embodiment, at step 1912, pump 1960 may be set to 100 ml/min. In this embodiment, the second volume (from pump 1964 to outlet port 19628) may be larger than the first volume (from pump 1964 to inlet port 1962A). In order to account for the additional volume, embodiments may provide for pump 1964 to be set at 70 ml/min during step 1914. This embodiment may provide for cells to reach bioreactor 1962 during the third time period at about the same time.

In embodiments, process 1900 may optionally perform the steps of 1906-1914 a number of additional times as illustrated by ellipsis 1916 and optional step 1918. The steps of Activate: First Pump (at Second Rate) 1906, Second Pump (at Fourth Rate) 1910, First Pump (at Fifth Bare) 1912, and Second Pump (at Sixth Rate) 1914 may be continuously performed for a period of time. As noted above, the steps may be performed to feed cells, circulate cells to break up cell colonias, micro-colonias, or clusters, and move cells back into a cell growth chamber. For example, in some embodiments, the steps may be performed every three days, every two days, daily, twice daily, or three times a day, for a period of from about two days to about twenty days (such as about 10 days, about 9 days, about 8 days, about 7 days, about 6 days, or even about 5 days). In some embodiments, the steps may be performed at varying periods of time. For example, in one embodiment, the steps may be performed after three days, and then every other day. As another example, the steps may be performed after two days and then twice daily. These are merely some examples and other embodiments may utilize other periods of time. Process 1900 terminates at END operation 1920.

It is noted that in some embodiments, process 1900 may include additional steps. For example, a rocking device may be connected to the bioreactor and after the first time period (and during the second time period), when the first pump is activated at step 1910, the rocking device may be activated to rotate the bioreactor as part of circulating the cells to reduce a number of cells in a cell cluster. This is merely one example and other embodiments of process 1900 are not limited thereto.

Figure 20:
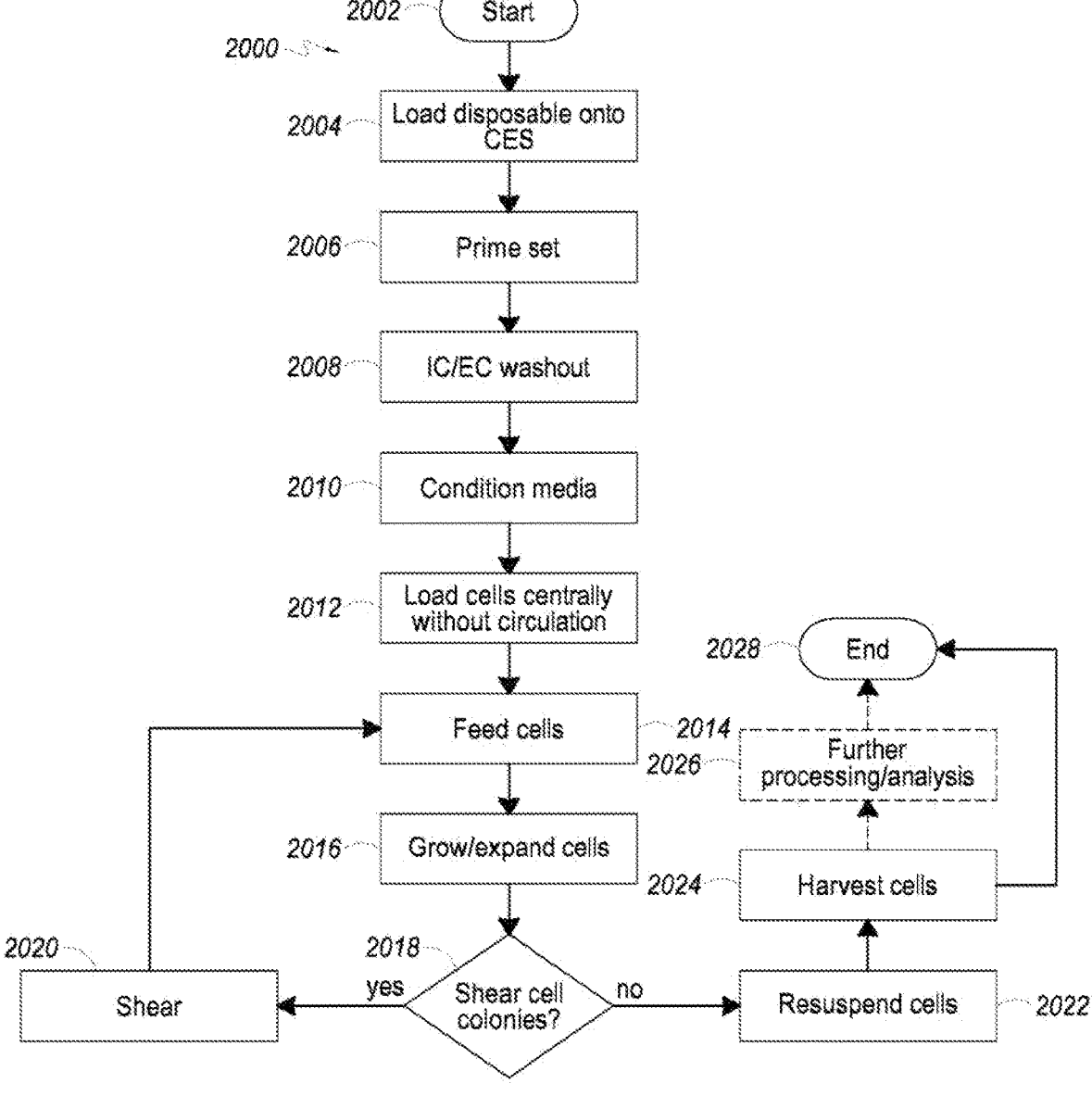
FIG. 20 illustrates a flow diagram depicting the operational characteristics of a process for expanding cells, in accordance with embodiments of the present disclosure.

FIG. 20 illustrates example operational steps 2000 of a process for expanding cells that may be used with a cell expansion system, such as CES 500 (e.g., FIG. 5A) or CES 600 (FIG. 6), in accordance with embodiments of the present disclosure. START operation 2002 is initiated, and process 2000 proceeds to load the disposable tubing set 2004 onto the cell expansion system. Next, the system may be primed 2006. In an embodiment, a user or an operator, for example, may provide an instruction to the system to prime by selecting a task for priming, for example. In an embodiment, such task for priming may be a pre-programmed task. Process 2000 then proceeds to the IC/EC Washout task 2008, in which fluid on the IC circulation loop and on the EC circulation loop is replaced. The replacement volume is determined by the number of IC Volumes and EC Volumes exchanged.

Next, to maintain the proper or desired gas concentration across the fibers in the bioreactor membrana, the condition media task 2010 may be executed to allow the media to reach equilibrium with the provided gas supply before cells are loaded into the bioreactor. For example, rapid contact between the media and the gas supply provided by the gas transfer module or oxygenator is provided by using a high EC circulation rate. The system may then be maintained in a proper or desired state until a user or operator, for example, is ready to load cells into the bioreactor. In an embodiment, the system may be conditioned with complete media, for example. Complete media may be any media source used for cell growth, in an embodiment, complete media may comprise alpha-MEM (α-MEM) and fetal bovine serum (FBS), for example. In other embodiments, complete media may include IL-2 and human serum, for example. Any type of media understood by those of skill in the art may be used.

Process 2000 next proceeds to loading cells centrally without circulation 2012 into the bioreactor from a cell inlet bag, for example. In embodiments, a "load cells centrally without circulation" task may be used, in which a first volume of fluid at a first flow rate comprising a plurality of cells may be loaded into the cell expansion system, in which the cell expansion system comprises a cell growth chamber.

A second volume of fluid at a second flow rate comprising media may then be loaded into a portion of a first fluid circulation path, for example, to position the first volume of fluid in a first portion of the cell growth chamber. In an embodiment, the first portion of the cell growth chamber of bioreactor may comprise about a central region of the bioreactor. In an embodiment, the first volume is the same as the second volume. In an embodiment, the first flow rate is the same as the second flow rate. In another embodiment, the first volume is different from the second volume. In another embodiment, the first flow rate is different from the second flow rate. In an embodiment, the sum of the first volume and the second volume may equal a percentage or proportion of the volume, e.g., total volume, of the first fluid circulation path, for example. For example, the sum of the first volume and the second volume may be about 50% of the volume, e.g., total volume, of the first fluid circulation path, for example. In an embodiment, fluid in the first fluid circulation path flows through an intracapillary (IC) space of a bioreactor or cell growth chamber. In an embodiment, fluid in a second fluid circulation path flows through an extracapillary (EC) space, for example, of a cell growth chamber or bioreactor. In an embodiment, the sum of the first volume and the second volume may be about 50%, or another percentage or proportion according to embodiments, of the volume of the intracapillary (IC) loop, for example. In an embodiment, the sum of the first volume and the second volume may be about 50%, or another percentage or proportion according to embodiments, of the volume of another fluid path, loop, etc., as applicable. Other percentages or proportions may be used, including, for example, any percentage between and including about 1% and about 100%, in accordance with embodiments.

Following the loading of the cells 2012, process 2000 next proceeds to feed the cells 2014. The cells may be grown/expanded 2016. While step 2016 is shown after step 2014, step 2016 may occur before, or simultaneous with, step 2014, according to embodiments. Next, process 2000 proceeds to query 2018 to determine whether any cell colonies, micro-colonies, or clusters have formed. A cell colony, micro-colony, or cluster may be a group of one or more attached cells, if a cell colony, micro-colony, or cluster has formed, process 2000 proceeds "yes" to shear 2020 any cell colonies, micro-colonies, or clusters. For example, after expanding a plurality of cells for a first time period, the cells may be circulated at a first circulation rate during a second time period to reduce a number of cells in a cell colony, micro-colony, or cluster. In embodiments, the circulating the cells at the first circulation rate may cause the cell colony to incur a shear stress, in which one or more cells in the cell colony may break apart from the cell colony. In an embodiment, reducing the number of cells in the cell colony, micro-colony, or cluster may provide a single cell suspension, for example. In embodiments, circulating the cells to shear any colony, micro-colony, or cluster 2020 may be used every two (2) days, for example, during cell culture to maintain uniform cell density and nutrient diffusion. Other time periods may also be used according to embodiments. In an embodiment, such shearing of any micro-colonies, colonies, or clusters may begin on or after Day 4, for example. In some embodiments, the shearing may be performed after three days, and then every other day. As another example, the steps may be performed after two days and then twice daily. Other days or time periods on which to begin such shearing may be used according to embodiments. Following shearing 2020, process 2000 may next return to feed cells 2014.

If it is determined at query 2018 not to shear any cell colonies or clusters, or if none exist, for example, process 2000 proceeds "no" to resuspend cells 2022. In embodiments, circulating the cells may be used to uniformly resuspend those cells that may be loosely adhered during culture, in embodiments, step 2022 may include circulating the cells to uniformly resuspend those cells that may be loosely adhered prior to initiating a harvest task, or other task to remove cells from the bioreactor. Following the resuspension of the cells 2022, process 2000 next proceeds to harvest the cells 2024. Further processing of the removed cells or other analysis may optionally be performed at step 2026, and process 2000 may then terminate at END operation 2028. If it is not desired to perform further processing/ analysis, process 2000 terminates at END operation 2030.

Figure 21:
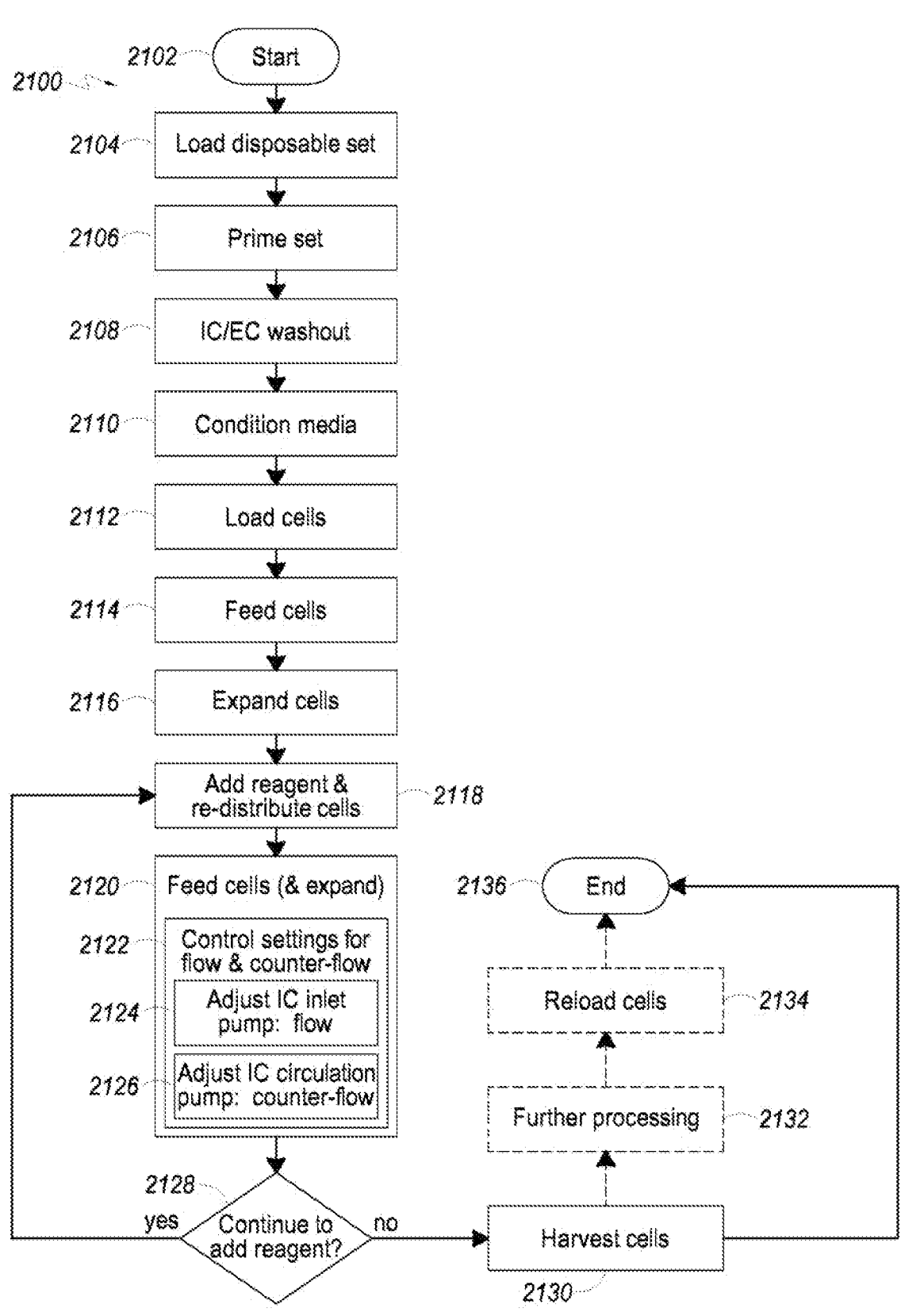
FIG. 21 depicts a flow diagram illustrating the operational characteristics of a process for expanding cells, in accordance with embodiments of the present disclosure.
Figure 22:
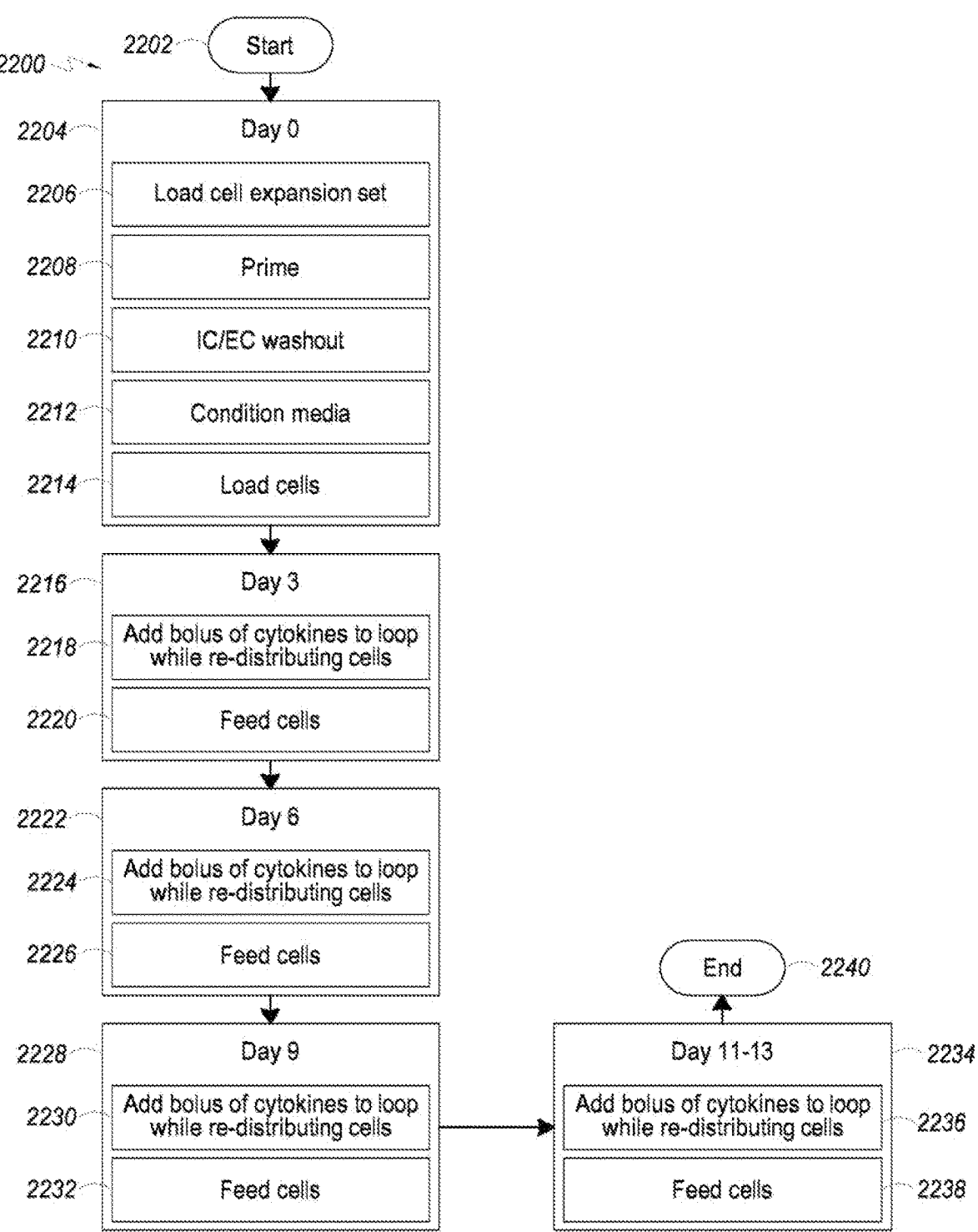
FIG. 22 illustrates a flow diagram depicting the operational characteristics of a process for expanding cells, in accordance with embodiments of the present disclosure.
Figure 23:
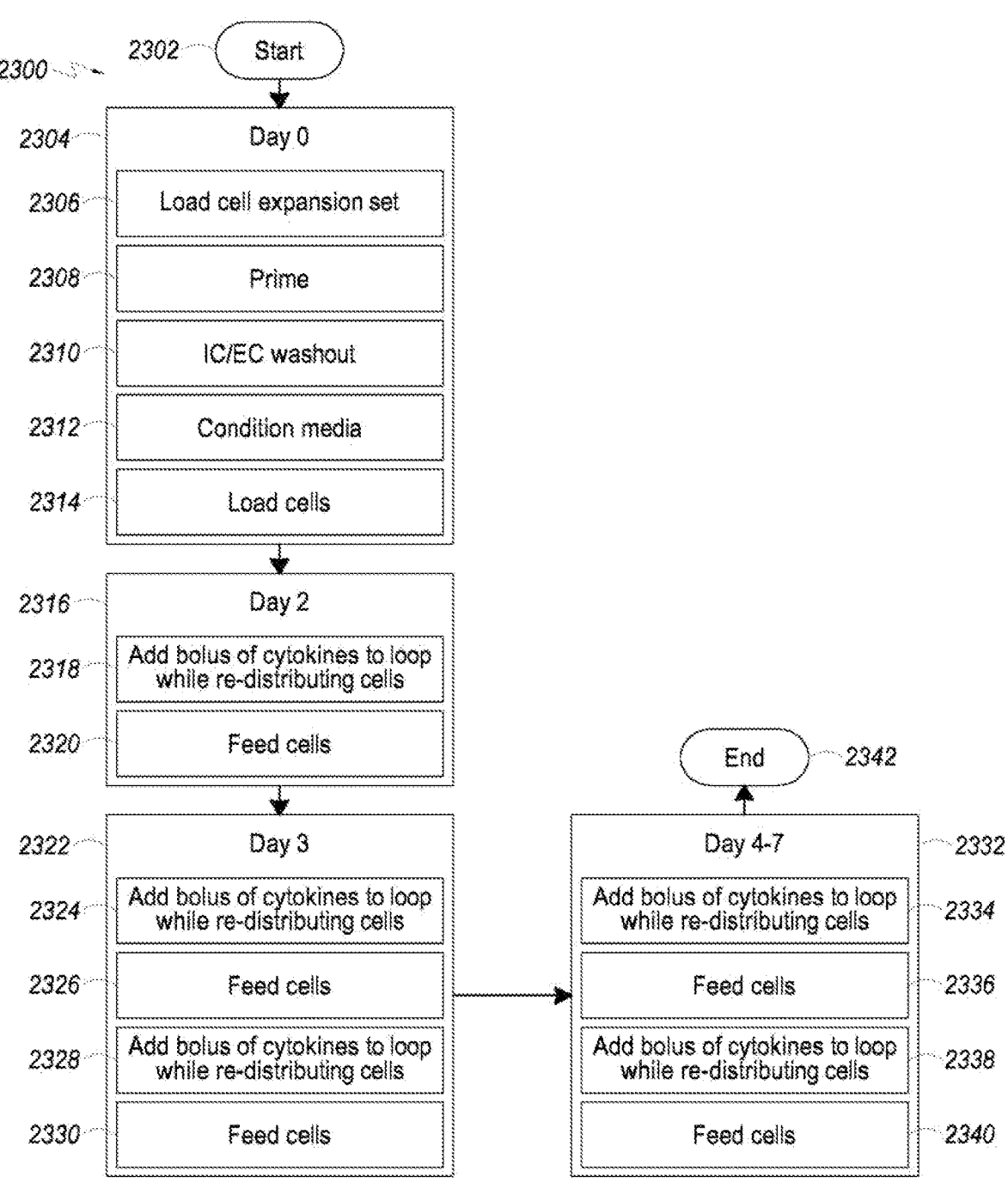
FIG. 23 illustrates a flow diagram depicting the operational characteristics of a process for expanding cells, in accordance with embodiments of the present disclosure.
Figure 24:
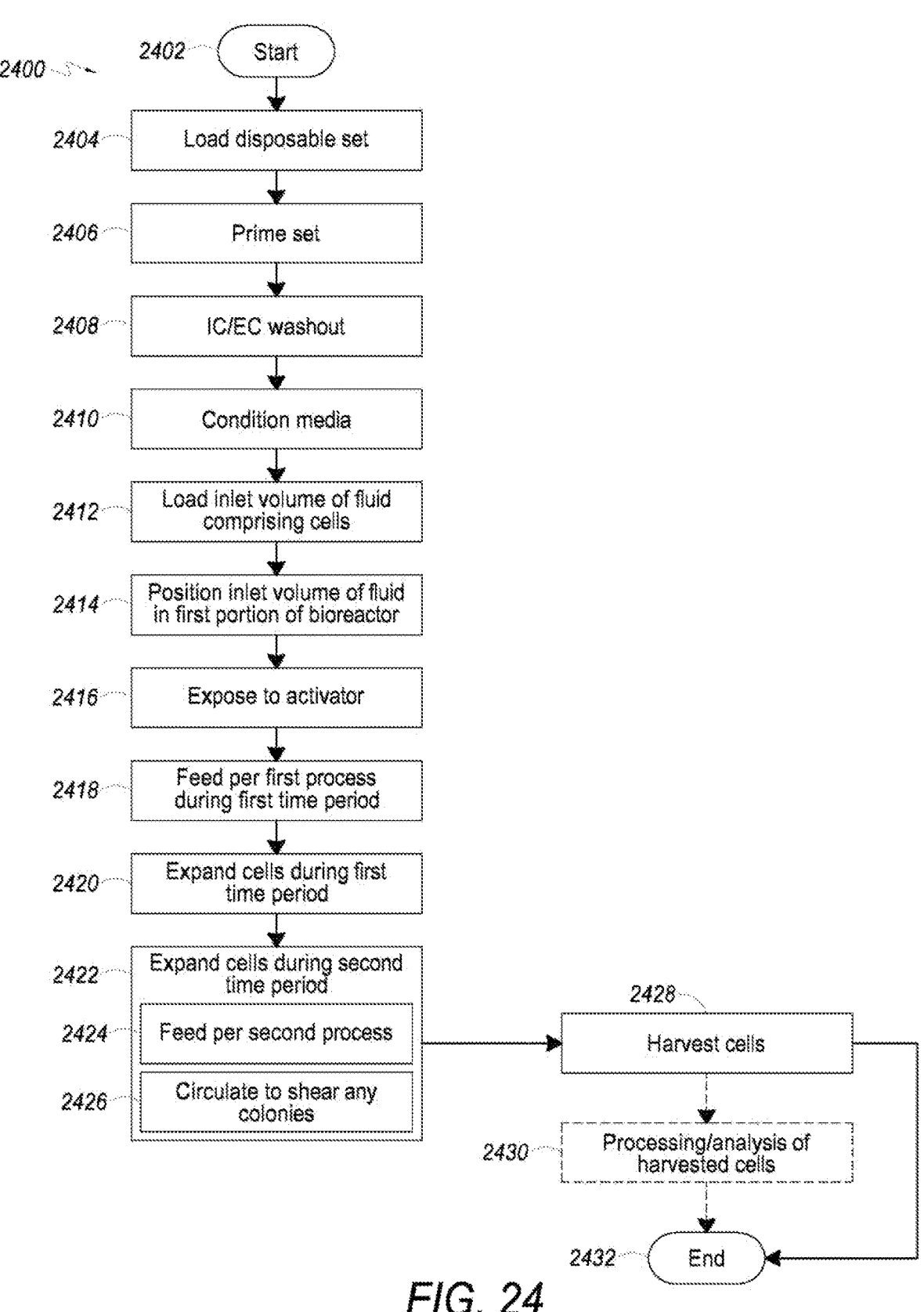
FIG. 24 depicts a flow diagram illustrating the operational characteristics of a process for expanding cells, in accordance with embodiments of the present disclosure.

Turning to FIG. 21 and process 2100, START operation is initiated 2102, and process 2100 proceeds to load a disposable set 1204 onto a cell expansion system, according to embodiments. The disposable set may then be primed 2106, and an IC/EC washout step 2108 may occur. The media may next be conditioned 2110. Next process 2100 proceeds to load cells 2112, e.g., suspension or non-adherent cells, such as T cells, e.g., Tregs. In an embodiment, such cells may be loaded 2112 by a "load cells centrally without circulation" task. In another embodiment, such cells may be loaded 2112 by a "load cells with uniform suspension" task.

Next, process 2100 proceeds with beginning to feed the cells 2114, which may begin on Day 0, according to embodiments. The cells may grow and expand 2116, and by Day 3, for example, it may be desired to add a bolus of a fluid to the IC loop and re-distribute the cells 2118. In an embodiment, such bolus of fluid may comprise a reagent, such as cytokines or other growth factor(s). In another embodiment, such bolus of fluid may comprise a reagent and base media, for example.

Following such bolus addition and re-distribution of cells, process 2100 next proceeds to feeding 2120 the cells again, in which such feeding may occur on Day 3, for example or on Day 2 in some embodiments. With such feeding 2120, the parameters of the system, such as one or more pumps controlling flow rate, may be controlled 2122 to achieve complementary flow and counter-flow settings for fluid moving into the bioreactor from both the IC inlet port and the IC outlet port of the bioreactor. For example, the IC inlet pump 2124 may be adjusted or directed to produce a flow, and the IC circulation pump may be adjusted or directed 2126 to produce a counter-flow. For example, an IC inlet pump rate of 0.1 mL/min may be matched, or closely or substantially matched, to a complementary IC circulation pump rate of −0.1 mL/min to maintain cells in the bioreactor during the growth phase of the cell culture, which may be Days 4-7, for example, in some embodiments, and Days 1-7 in other embodiments. Such control of settings 2122 may allow for counteracting any forces associated with a loss of cells from the IC outlet port of the bioreactor.

Process 2100 next proceeds to query 2128, in which it is determined whether to continue to add reagent or other bolus addition on other days or other time intervals, for example. If it is desired to add additional reagent or other bolus and re-distribute cells, process 2100 branches "yes" to add reagent and re-distribute cells 2118. For example, such bolus addition and re-distribution of calls may next occur on Days 6 and 9, according to embodiments. In other embodiments, the bolus addition and re-distribution may once after two days and then twice daily thereafter.

If, or once, it is not desired to continue adding a bolus, e.g., reagent, and re-distributing the cells, process 2100 proceeds "no" to harvest the cells 2130, in which the ceils may be transferred to a harvest bag(s) or container(s). Process 2100 then terminates at END operation 2136.

Alternatively, from harvest operation 2130, process 2100 may optionally proceed to allow for further processing/ analysis 2132. Such further processing 2132 may include characterization of the phenotype(s), for example, of the harvested cells, e.g., T cells such as Tregs. From optional further processing/analysis step 2132, process 2100 may proceed to optionally reload any remaining cells 2134. Process 2100 may then terminate at END operation 2136.

Process 2200 illustrates operational steps for a process of expanding cells in cell expansion system according to embodiments of the present disclosure. Process 2200 may be used in some embodiments to expand T cells, e.g. Tregs. As illustrated, various steps may be performed over the course of a 14 day protocol to expand the cells. START operation 2202 is initiated and process 2200 proceeds to Day 0, where a disposable set is loaded onto a cell expansion system 2206. The disposable set may then be primed 2208, in which the set may be primed 2208 with PBS (e.g., Lonza Ca2+/Mg2+- free), for example. In preparation for the loading of cells, the priming fluid may be exchanged using an IC/EC washout 2210. For example, the PBS in the system may be exchanged for TexMACS GMP Base Medium, according to one embodiment. The media may next be conditioned 2212. The condition media 2212 may be performed to allow the media to reach equilibrium with provided gas supply before cells are loaded into a bioreactor.

Next on Day 0, process 2200 proceeds to load cells 2214, e.g., suspension of non-adherent cells, such as T cells, e.g., Tregs. In an embodiment, such cells may be loaded 2214 by a "load cells centrally without circulation" task. In another embodiment, such cells may be loaded 2214 by a "load cells with uniform suspension" task.

At Day 3 2216, a bolus of cytokines may be added while the cells are redistributed 2218. In embodiments, the redis- tribution of cells may be performed in combination with the bolus addition to mix the cells and more thoroughly expose the cells to the cytokines (e.g., IL-2) that may be in the bolus addition. In embodiments, the redistribution may also break up colonies or clusters of cells that may have formed. In embodiments, the redistribution may occur first by circulat- ing the cells in a fluid circulation path. The bolus addition may then be added in the process of pushing the cells back into the bioreactor, such as by introducing fluid into a fluid circulation path to push cells back into the bioreactor. After the redistribution and bolus addition 2218, process 2000 proceeds to feed cells 2220.

The cells may again be redistributed with another bolus addition at Day 6 2222. The redistribution may break up colonies or clusters of cells that may have formed during Days 3-5. The bolus addition may expose the cells to additional reagents that promote expansion. Process 2000 proceeds to feed cells 2226 at Day 6. At Day 9 2228, the cells may once again be redistributed 2230 with a bolus addition. The redistribution may break up colonies or clus- ters of cells that may have formed during Days 6-8. The bolus addition may expose the cells to additional supple- ments that promotes expansion. Process 2000 proceeds to feed cells 2232 at Day 9.

At Day 11-13 2234, the cells may again be redistributed 2236 with a bolus addition. The redistribution may break up colonies or clusters of cells that may have formed during Days 9-10. The bolus addition may expose the cells to additional reagents that promote expansion. Process 2000 then proceeds to feed cells 2238. In embodiments, the steps 2236 and 2238 may be performed on each of Day 11, Day 12, and Day 13. This may occur as a result of the cells expanding during Days 0-10 and there being larger numbers of cells in the bioreactor. Performing the redistribution and bolus addition of cells may promote expansion of the cells by breaking up colonies and clusters of cells more often and mixing them with reagents in the bolus addition to promote cell expansion. Process 2200 terminates at END operation 2240.

Process 2300 illustrates operational steps for a process of expanding cells in cell expansion system according to embodiments of the present disclosure. Process 2300 may be used in some embodiments to expand T cells, e.g. effector, helper, memory, naive, combinations thereof, etc. As illustrated, various steps may be performed over the course of an 8-day protocol to expand the cells. START operation 2302 is initiated and process 2300 proceeds to Day 0, where a disposable set is loaded onto a call expansion system 2306. The disposable set may then be primed 2308, in which the set may be primed 2308 with PBS (e.g. Lonza Ca2+/Mg2+-free), for example. In preparation for the loading of cells, the priming fluid may be exchanged using an IC/EC washout 2310. For example, the PBS in the system may be exchanged for TexMACS GMP Base Medium, according to one embodiment. In other embodiments, the PBS may be exchanged for Prime XV Base Media, Advanced RPMI+glutamine Base Media, RPMI 1640+glutamine Base Media, or IMDM+glutamine. The media may next be conditioned 2312. The condition media 2312 may be performed to allow the media to reach equilibrium with provided gas supply before cells are loaded into a bioreactor.

Next on Day 0, process 2300 proceeds to load cells 2314, e.g., suspension of non-adherent cells, such as T cells. In an embodiment, such cells may be loaded 2314 by a "load cells centrally without circulation" task. In another embodiment, such cells may be loaded 2314 by a "load cells with uniform suspension" task. In some embodiments, the cells may be mixed with beads, such as DYNABEADS® Human T-Activator beads. The beads may, in embodiments, be present in ratios such as about 1 bead:about 1 cell, about 2 beads:about 1 cell, about 3 beads:about 1 cell, or even about 4 beads:about 1 cell. The cells may be mononuclear cells (e.g., PBMC's), in some embodiments.

At Day 2 2316, a bolus of cytokines may be added while the cells are redistributed 2318. In embodiments, the redistribution of cells may be performed in combination with the bolus addition to mix the cells and more thoroughly expose the cells to the cytokines (e.g., IL-2) that may be in the bolus addition. In embodiments, the redistribution may also break up colonies or clusters of cells that may have formed. In embodiments, the redistribution may occur first by circulating the cells in a fluid circulation path. The bolus addition may then be added in the process of pushing the cells back into the bioreactor, such as by introducing fluid into a fluid circulation path to push cells back into the bioreactor. After the redistribution and bolus addition 2318, process 2300 proceeds to feed cells 2320.

The cells may again be redistributed 2324 with another bolus addition at Day 3 2322. The redistribution may break up colonies or clusters of cells that may have formed during Days 0-2. The bolus addition may expose the cells to additional reagents that promote expansion. Process 2300 proceeds to feed cells 2326 at Day 3. The cells may once again at Day 3, be redistributed with another bolus addition 2328 at Day 3 2322. As mentioned above, the bolus addition may expose the cells to additional reagents that continue to promote their expansion. Process 2300 may once again proceed to feed cells 2330 at Day 3.

The cells may again be redistributed 2334 with another bolus addition at Day 4 2332. The redistribution may break up colonies or clusters of cells that may have formed during Day 3. The bolus addition may expose the cells to additional reagents that promote expansion. Process 2300 proceeds to feed cells 2336 at Day 4. The cells may once again at Day 4, be redistributed with another bolus addition 2338 at Day 4 2332. As mentioned above, the bolus addition may expose the cells to additional reagents that continue to promote their expansion. Process 2300 may once again proceed to feed cells 2340 at Day 4. In embodiments, the steps 2334, 2336, 2338, and 2340 may be performed on each of Day 5, Day 6, and Day 7. This may occur as a result of the cells expanding during Days 0-4 and there being larger numbers of cells in the bioreactor. Performing the redistribution and bolus addition of cells may promote expansion of the cells by breaking up colonies and clusters of cells more often and mixing them with reagents in the bolus addition to promote cell expansion. Process 2300 terminates at END operation 2342.

Process 2400 illustrates operational steps for a process of expanding cells, e.g., suspension or non-adherent cells, in a cell expansion system according to embodiments of the present disclosure. Process 2400 may be used in some embodiments to expand T cells, such as Tregs. The combination of steps of process 2400 may allow the expansion of the cells to useful clinical amounts using initial low seeding densities.

START operation 2402 is initiated and process 2400 proceeds to load disposable set 2404 onto a cell expansion system. The disposable set may then be primed 2406, in which the set may be primed 2406 with PBS (e.g., Lonza Ca2+/Mg2+-free), for example. In preparation for the loading of cells, the priming fluid may be exchanged using an IC/EC washout 2408. For example, the PBS in the system may be exchanged for TexMACS GMP Base Medium, according to one embodiment. In other embodiments, the base media may be Prime XV, Advanced RPMI+glutamine, RPMI 1640+glutamine, and/or IMDM+glutamine. The media may next be conditioned 2410. The condition media 2410 may be performed to allow the media to reach equilibrium with a provided gas supply before cells are loaded into a bioreactor.

Process 2400 proceeds to 2412 load inlet volume of fluid with cells. In embodiments, the cells may comprise non-adherent cells, such as one or more types of T cells, e.g., Tregs. In one embodiment, the cells comprise Tregs. Embodiments may provide for the inlet volume of fluid with the cells to be loaded through an IC inlet path utilizing an IC inlet pump and into an IC circulation path. In embodiments, the load inlet volume 2412 is loaded without activating an IC circulation pump.

Process 2400 proceeds to positioning the inlet volume in a first portion of a bioreactor 2414. In embodiments, the positioning may be performed by introducing a second volume of fluid, which may comprise media and may be introduced into a portion of the IC circulation path to push the inlet volume with the cells into the first position in the bioreactor. In embodiments, the inlet volume of fluid and the second volume of fluid may be the same. In other embodiments, the inlet volume of fluid and the second volume of fluid may be different. In yet other embodiments, a sum of the inlet volume of fluid and the second volume of fluid may be equal to a percentage of a volume of the IC circulation path.

Following the position inlet volume 2414, process 2400 proceeds to expose cells to activator 2416 in order to activate the cells to expand. The cells may be exposed to an activator 2416 that is soluble in some embodiments. The activator, which may include antibody complexes in some embodiments, may be added to the media and may be included in the inlet volume or added later, such as with the second volume. In embodiments, the activator may be a human antibody CD3/CD28/CD2 cell activator complex, for example. In other embodiments, the activator may be beads with CD3/CD28 antibodies. In embodiments, the cells may be exposed to an activator before the loading 2412.

Process 2400 proceeds to feed the cells per a first process during a first time period 2418. In an embodiment, the cells may be fed at a minimum or low feed rate, for example, where the cell population is beginning to grow/expand for a first time period 2420, and a minimum or low feed rate is able to meet the demands of such population. For example, an IC inlet pump rate of +0.1 mL/min may be used during such first time period. If it is desired to reduce the loss of cells from the hollow fiber membrane bioreactor during such first time period, the IC inlet pump rate of +0.1 mL/min may be matched, or closely or substantially matched, to a complementary IC circulation pump rate of −0.1 mL/min to maintain cells in the bioreactor during the growth phase of the cell culture.

From 2420, process 2400 proceeds to expand cells during a second time period 2422. Expanding during the second period of time 2422 may also involve feeding the cells per a second process during the second time period 2424. In an embodiment, such second process may involve feeding the cells at substantially the same feed rates as during the first time period, for example. In another embodiment, the second process may involve feeding the cells at different feed rates as compared to the feed rates used during the first time period. For example, the feed rates may increase as a result of the expansion of the cells during the first time period.

While expanding the cells during the second time period 2422, the cells may also be circulated to shear cells colonies or cell clusters 2426. Step 2426 may involve circulating the cells in the IC circulation path to shear any colonies or clusters that may have formed during the first time period. The shear colonies or clusters 2426 step may reduce a number of cells in a cell colony or cell cluster. In embodiments, the circulate to shear 2426 may cause cell colonies to incur a shear stress, causing one or more cells in the cell colony to break apart from the cell colony.

Process 2400 may next proceed to harvest operation 2428, in which the cells may be transferred to a harvest bag(s) or container(s). In embodiments, a therapeutic dose of cells may be harvested. In embodiments, the cells harvested at operation 2428 may be on the order of $1 \times 10^9$ cells. The harvested cells may have viabilities between about 75% and about 95%, in embodiments.

Process 2400 may then optionally proceed to allow for further processing/analysis 2430. Such further processing may include characterization of the phenotype(s), for example, of the harvested cells, e.g., T cells such as Tregs. In one embodiment, the harvested cells may express biomarkers consistent with Tregs. For example, the cells may express CD4+, CD25+, and/or FoxP3+ biomarkers. In embodiments, the harvested cells may include the CD4+ CD25+ phenotype at a frequency of above about 80%. In other embodiments, the cells may include the CD4+FoxP3+ phenotype at a frequency of above about 55%. In other embodiments, the cells may express biomarkers consistent with effector, helper, memory, and/or naïve T cells. For example, the cells may express CD3+, CD4+, and/or CD8+ biomarkers. In embodiments, the harvested cells may include the CD3+ phenotype at a frequency of between about 50% and about 100%. The harvested cells may include the CD4+ phenotype at a frequency of above about 25%, above about 30%, above about 35%, above about 40%, above about 45%, above about 50%, above about 55%, or even above about 60%. In other embodiments, the cells may include the CD8+ phenotype at a frequency of between about 30% and about 100%. Process 2400 may then terminate at END operation 2432.

The operational steps depicted in the above figures are offered for purposes of illustration and may be rearranged, combined into other steps, used in parallel with other steps, etc., according to embodiments of the present disclosure. Fewer or additional steps may be used in embodiments without departing from the spirit and scope of the present disclosure. Also, steps (and any sub-steps), such as priming, conditioning media, loading cells, for example, may be performed automatically in some embodiments, such as by a processor executing pre-programmed tasks stored in memory, in which such steps are provided merely for illustrative purposes. Further, the example pump rate settings for feeding cells depicted in FIG. 10B, for example, are offered for purposes of illustration. Other pump rates, flow rates, directions, etc. may be used in accordance with embodiments of the present disclosure.

Examples and further description of tasks and protocols, including custom tasks and pre-program tasks, for use with a cell expansion system are provided in U.S. patent application Ser. No. 13/269,323 ("Configurable Methods and Systems of Growing and Harvesting Cells in a Hollo ow Fiber Bioreactor System," filed Oct. 7, 2011) and U.S. patent application Ser. No. 13/269,351 ("Customizable Methods and Systems of Growing and Harvesting Cells in a Hollow Fiber Bioreactor System," filled Oct. 7, 2011), which are hereby incorporated by reference herein in their entireties for all that they teach and for all purposes.

Figure 25:
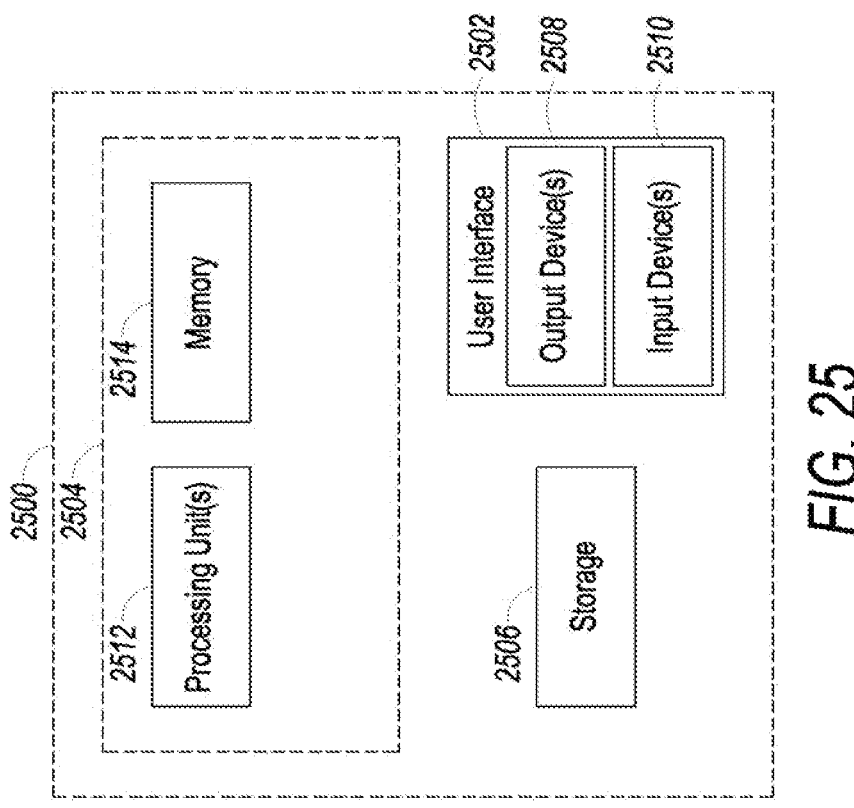
FIG. 25 depicts an example processing system of a cell expansion system upon which embodiments of the present disclosure may be implemented.

Next, FIG. 25 illustrates example components of a computing system 2500 upon which embodiments of the present disclosure may be implemented. Computing system 2500 may be used in embodiments, for example, where a cell expansion system uses a processor to execute tasks, such as custom tasks or pre-programmed tasks performed as part of processes such as processes illustrated and/or described herein. In embodiments, pre-programmed tasks may include, follow "IC/EC Washout" and/or "Feed Cells," for example.

The computing system 2500 may include a user interface 2502, a processing system 2504, and/or storage 2506. The user interface 2502 may include output device(s) 2508, and/or input device(s) 2510 as understood by a person of skill in the art. Output device(s) 2508 may include one or more touch screens, in which the touch screen may comprise a display area for providing one or more application windows. The touch screen may also be an input device 2510 that may receive and/or capture physical touch events from a user or operator, for example. The touch screen may comprise a liquid crystal display (LCD) having a capacitance structure that allows the processing system 2504 to deduce the location(s) of touch event(s), as understood by those of skill in the art. The processing system 2504 may then map the location of touch events to UI elements rendered in predetermined locations of an application window. The touch screen may also receive touch events through one or more other electronic structures, according to embodiments. Other output devices 2508 may include a printer, speaker, etc. Other input devices 2510 may include a keyboard, other touch input devices, mouse, voice input device, etc., as understood by a person of skill in the art.

Processing system 2504 may include a processing unit 2512 and/or a memory 2514, according to embodiments of the present disclosure. The processing unit 2512 may be a general purpose processor operable to execute instructions stored in memory 2514. Processing unit 2512 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 2514 may include any short-term or long-term storage for data and/or processor executable instructions, according to embodiments. The memory 2514 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 2506 may be any long-term data storage device or component. Storage 2506 may include one or more of the systems described in conjunction with the memory 2514, according to embodiments. The storage 2506 may be permanent or removable. In embodiments, storage 2506 stores data generated or provided by the processing system 2504.

EXAMPLES

The following description includes some examples of protocols/methods/processes that may be used with a cell expansion system, such as CES 500 (e.g., FIGS. 5A, 5B, 5C) and/or CES 600 (FIG. 6), for example, that implements aspects of the embodiments. Although specific features may be described in the examples, such examples are provided merely for illustrative and descriptive purposes. For example, while examples may provide for the expansion of T cells and/or Treg cells, other and/or additional cell types and/or combinations thereof may be used in other embodiments. Although specific parameters, features, and/or values are described, e.g., use of a CES, e.g., Quantum® Cell Expansion System, according to some embodiments, these parameters, features, and/or values, etc., are provided merely for illustrative purposes. The present disclosure is not limited to the examples and/or specific details provided herein.

Further, the examples provided herein intended to limit other embodiments, which may include different or additional steps, parameters, or other features. The example methods or protocols, including the steps (and any sub-steps), may be performed automatically in some embodiments, such as by a processor executing pre-programmed tasks stored in memory. In other embodiments, the steps (and any sub-steps) may be performed through the combination of automated and manual execution of operations. In further embodiments, the steps (and any sub-steps) may be performed by an operator(s) or user(s) or through other manual means.

While example data may be provided in such examples, such example data are provided for illustrative purposes and are not intended to limit other embodiments, which may include different steps, parameters, values, materials, or other features.

Example 1

Methods

General Treg Cell Culture

Immunomagnetic-isolated CD4$^+$CD25$^+$ Tregs may be acquired from healthy adult donor peripheral blood by leukapheresis (HemaCare Corporation, Van Nuys, CA) and may be subsequently expanded at Terumo BCT at a concentration of $1.0 \times 10^6$ cells/mL. In sterile-filtered Tex-MACS™ GMP Medium supplemented using three T25 flasks (7 mL/flask) with the recombinant human IL-2 IS Premium grade cytokine at 200 IU/mL (Miltenyi Biotec GmbH, Bergisch Gladbach) and Gibco PSN 100× antibiotic mixture (ThermoFisher Scientific, Waltham, MA). The actively growing Treg cell suspension may be subsequently used as the inoculum in each of the three (3) Quantum® Cell Expansion System experimental runs. Tregs for both the inoculum and the Quantum system expansion may be co-stimulated using a soluble tetrameric Immunocult™ human antibody CD3/CD28/CD2 cell activator complex (Stem Cell Technologies, Vancouver, BC) at 25 μl/ml in the absence of microbeads. Co-stimulation may be performed on Days 0 and 9 for the Treg inoculum and on Day 0 for the Quantum system Treg expansion. The Quantum system HFM bioreactor may be characterized by an intracapillary loop volume of 177.1 mL and surface area of 21,000 cm$^2$.

Quantum System Treg Expansion

According to embodiments, two (21) bags of sterile filtered media may be prepared for the Treg scale up expansion in the Quantum system using the Quantum Media Bag 4 L Set (Cat. 21021). One 2 L bag of complete media containing TexMACS GMP, IL-2 and PSN antibiotics may be used to supply the IC compartment and one 21 of base media containing TexMACS GMP and PSN antibiotics may be used to supply the EC inlet compartment of the bioreactor. After priming the Quantum system with PBS (Lonza Cat. 17-516Q, Walkersville, MD), media bags may be connected to the appropriate IC and EC inlet lines using the TSCD-Q Terumo Sterile Weider. The complete media may be protected from exposure to light.

The total cell load for each run ($4.5$-$6.5 \times 10^7$ Tregs) may be resuspended, using aseptic technique, in 50 mL of complete medium with a Quantum Cell Inlet Bag (Cat. 21020) for introduction into the Quantum system bioreactor. Additional disposable bags, such as the Quantum CES Media Bag 4 L (Cat, 21021) and Waste Bag 4 L (Cat. 21023) may also be used during the Treg scale-up expansion runs.

At the completion of the "Load Cells Centrally without Circulation" Task, the Quantum system runs (n=3) may be seeded with Tregs at a concentration of $2.5$-$3.7 \times 10^5$ calls/mi in 177 mL of complete medium or an average of $2.1$-$3.1 \times 10^3$ cells/cm$^2$ within the lumen or the intracapillary (IC) compartment of the hollow fiber membrane bioreactor.

Day 0-4:

Example Quantum System Custom Task

Feed Cells, Modified.

IC/EC Exchange & Condition Media for Regulatory T Cells, Example.

Attach the TexMACS GMP Complete Medium with IL-2 supplement (200 IU/ml) Media bag to the IC Media line of the Quantum system with the Terumo BCT TSCD-Q sterile welder. Attach TexMACS Base Media to EC Media line.

Perform IC/EC Washout and Condition Media Tasks respectively. Complete Media may be used for IC Exchange of Washout and Base Media may be used for the EC Exchange or Washout to conserve the amount of IL-2 and activator complex.

Place system on modified "Feed Cells" prior to introducing cells. Increase the IC inlet rate ($Q_1$) and IC circulation rate ($Q_2$) in a matched rate to 0.2, 0.3, and 0.4 mL/min on Days 5, 6, and 7, but opposite direction on Days 4, 5, 6 or as needed to keep the lactate level between 5-8 mmol/L.

TABLE 1

Feed Cells, Modified, Example.
Feed Calls

| Setting | Step 1 |
|---|---|
| IC Inlet | IC Media |
| IC Inlet Rate | 0.1 |
| IC Circulation Rate | −0.1 |
| EC Inlet | None |
| EC Inlet Rate | 0.00 |
| EC Circulation Rate | 100 |
| Outlet | EC Waste |
| Rocker Control | No Motion: (0°) |
| Stop Condition | Manual |
| Estimated Paid | Unknown |
| Omit or Include | Include |

Example Quantum System Custom Task:

Load Cells Centrally Without Circulation, Example.

Purpose: This task enables suspension cells to be centrally distributed within the bioreactor membrane while allowing flow on the extracapillary (EC) circulation loop. The pump flow rate to the IC loop may be set to zero.

Prior to loading the cells into the Quantum systems using the Load Cells without Circulation, enter the modifications to the task.

TABLE 2

Load Cells Centrally without Circulation,
Modifications, Example
Solutions for Loading Suspension Cells

| Bag | Solution in Bag | Volume (estimate based on factory default values) |
|---|---|---|
| Cell Inlet | 50 ml | N/A |
| Reagent | None | N/A |
| IC Media | Serum-Free Media | 6 mL/hour |
| Wash | None | N/A |
| EC Media | None | N/A |

TABLE 3

Load Cells Centrally without Circulation, Example
Custom Task 8 Load Cells without Circulation

| Setting | Step 1 | Step 2 |
|---|---|---|
| IC Inlet | Cell | IC Media |
| IC Inlet Rate | 50 | 50 |
| IC Circulation Rate | 0 | 0 |
| EC Inlet | None | None |
| EC Inlet Rate | 0.00 | 0.00 |
| EC Circulation Rate | 30 | 30 |

TABLE 3-continued

Load Cells Centrally without Circulation, Example
Custom Task 8 Load Cells without Circulation

| Setting | Step 1 | Step 2 |
|---|---|---|
| Outlet | IC Waste | IC Waste |
| Rocker Control | In Motion: (−90°, 180°) Dwell Time: 1 sec | In Motion: (−90°, 180°) Dwell Time: 1 sec |
| Stop Condition | Empty Bag | IC Volume: 57.1 mL |
| Estimated Paid | Unknown | <0.1 L |
| Omit or Include | Include | Include |

Return to default cell feeding tasks as needed and continue with the expansion protocol using Feed Cells Task.

TABLE 4

Feed Cells, Modified, Example.
Feed Cells

| Setting | Step 1 |
|---|---|
| IC Inlet | IC Medis |
| IC Inlet Rate | 0.1 |
| IC Circulation Rate | −0.1 |
| EC Inlet | None |
| EC Inlet Rate | 0.00 |
| EC Circulation Rate | 100 |
| Outlet | EC Waste |
| Rocker Control | No Motion: (0°) |
| Stop Condition | Manual |
| Estimated Paid | Unknown |
| Omit or Include | Include |

Day 4 or Later:

Resuspension of Treg Cells During Cell Culture or Prior to Harvest, Example.

A purpose of this modified Circulation Task is to uniformly resuspend those cells that may be loosely adhered during culture or prior to initiating the Harvest Task.

In addition, this task may be used to shear Treg cell colonies every two (2) days during cell culture in order to maintain uniform cell density and nutrient diffusion beginning on or after Day 4. If the task is used to shear colonies during the culture process, the Quantum system may be returned to the modified "Feed Cells" Task.

TABLE 5

Circulation and Resuspension of Cells, Return
Cells to Bioreactor, Feed, Example
Custom Task 6 Settings to Reuspend Settled Cells

| Setting | Step 1 | Step 2 | Step 3 | Step 4 |
|---|---|---|---|---|
| IC Inlet | None | IC Media | IC Media | IC Media |
| IC Inlet Rate | 0 | 0.1 | 100 | 0.1 |
| IC Circulation Rate | 300 | −0.1 | −70 | −0.1 |
| EC Intet | None | None | None | None |
| EC Intet Rate | 0 | 0 | 0 | 0 |
| EC Circulation Rate | 100 | 100 | 100 | 100 |
| Outlet | EC Outlet | EC Outlet | EC Outlet | EC Outlet |
| Rocker Control | In Motion: (−90°, 180°) Dwell Time: 1 sec | Stationary | In Motion: (−90°, 180°) Dwell Time: 1 sec | In Motion: (−90°, 180°) Dwell Time: 1 sec |
| Stop Condition | Time: 4 min | Time: 1 min | IC Volume 150 mL | Manual |

TABLE 5-continued

| Circulation and Resuspension of Cells, Return Cells to Bioreactor, Feed, Example Custom Task 6 Settings to Reuspend Settled Cells | | | | |
|---|---|---|---|---|
| Setting | Step 1 | Step 2 | Step 3 | Step 4 |
| Estimated Fluid | Unknown | 0.1 L | 0.2 L | Unknown |
| Omit or include | Include | Include | Include | Include |

Harvest Quantum System Harvest Task with Modification, Example.

TABLE 6

| Harvest, Modification, Example Harvest, Modified | | |
|---|---|---|
| Setting | Step 1 | Step 2 |
| IC Inlet | None | IC Media |
| IC Inlet Rate | 0 | 400 |
| IC Circulation Rate | 300 | −70 |
| EC Inlet | None | IC Media |
| EC Inlet Rate | 0 | 60 |
| EC Circulation Rate | 100 | 30 |
| Outlet | EC Outlet | Harvest |
| Rocker Control | In Motion: (−90°, 180°) Dwell Time: 1 sec | In Motion: (−90°, 180°) Dwell Time: 1 sec |
| Stop Condition | Time: 4 minutes | IC Volume: 378 mL |
| Estimated Fluid | IC Media: <0.1 L | IC Media: 0.5 L |
| Omit of Include | Include | Include |

Harvested cells may be removed from the Quantum system by RF welding for further evaluation and analysis.

Post-Harvest Analysis

Harvested cells may be enumerated with a Vi-CELL XR 2.04 Cell Viability Analyzer (Beckman Coulter) over a range of 5-50 μm and quantified for membrane integrity by trypan blue dye exclusion.

Metabolism

Regulatory T cell metabolism may be monitored from the Quantum system's EC sample port daily by i-STAT handheld analyzer (Abbott Point of Care, Princeton, NJ) using G Cartridge for glucose and lactations using i-STAT G Cartridge (Cat. 03P83-25) and i-STAT CG4+ Cartridge (Cat. 03P85-50) respectively, Cell Surface Biomarker Expression Humans Regulatory T cells (natural and induced) compose a small subset (2-10%) of all T cells in human cord blood and peripheral blood. Functionally, Tregs are responsible for maintaining immunological homeostasis which includes the modulation of immune tolerance in both innate and adoptive responses. Moreover, the expression of the transcriptional regulator forkhead box P3 (FoxP3) gene product is known to correlate with the CD4$^+$CD25$^+$FoxP3$^+$ CD127$^{low}$ Treg phenotype and the immune suppression of antigen presentation cells (APCs) and effector T cells (T$_{eff}$). IL-2 binding to the CD25/IL-2 receptor (Rα) and the activation of STAT5 transcriptional factor is used for Foxp3 induction. FoxP3 suppression upregulates the activity of several genes such as CTLA-4, TNFRSF18 and IL2RA and downregulates IL-2 via its association with histone acetylase KATS and histone deacetylase HDAC7.

Treg phenotype frequency of the harvested cell surface biomarkers may be quantified by flow cytometry. To this end, the cells may be stained with the following antibody conjugates and gated against viable, unstained cells: Fixable Viability Dye eFluor® 780 (eBioscience 65-0865), mouse anti-human CD4-PE (BD Pharmingen 561844), anti-CD4-Alexa Fluor 647 (BD Pharmingen: 557707), anti-CD4-FITC (BD Pharmingen 561842), anti-CD4-FITC (BD Pharmingen 555346), anti-CD25-PE (BD Pharmingen 555432), anti-CD127-PE (BD Pharmingen 557938), anti-CD45RO-PE (BD Pharmingen 347967), and anti-FoxP3-Alexa Fluor 647 (BD Pharmingen 560045). Specimen data may be acquired on a bead-compensated BD Canto II flow cytometer equipped with FACSDiva v6.1.3 software using 1×106 cells and 20,000 total events per sample.

Possible Results

Preliminary studies with Tregs in static culture may show that these cells tend to form micro-colonies on the order of 100 μm in diameter. Separating these cells during the medium exchange process every two days may help to limit cellular necrosis and return the cells to a high density, single cell suspension by using a 1,000 μL pipet tip that has an ID of 762 μm. Alternatively, the process of maintaining a single cell suspension may be accomplished more efficiently in an automated HFM bioreactor where the fiber lumen ID is on the order of 200 μm, such as in the Quantum system, with the aid of a preprogrammed, daily circulation task. In addition, this automated feeding task may reduce the likelihood of contamination while maintaining continuous nutrient flow to the Treg culture since it may be performed in a functionally closed system.

Possible Treg Cell Density and Viability

TABLE 7

| T25 Flask Possible Harvest | |
|---|---|
| Cell Density | 3.11 × 10$^6$ cells/m 8.71 × 10$^5$ cells/cm2 |
| Viability | 81.90% |
| Stimulation Cycles | 2 |
| Doublings | 4.9 |

TABLE 8

| Quantum System Possible Harvest | |
|---|---|
| Cell Density | |
| Harvest bag | 3.61 × 10$^6$ cells/m |
| Bioreactor | 1.24 × 10$^7$ cells/mL ≥7.33 × 10$^4$ cells/cm2 |
| Viability | 84.80% |
| Stimulations Cycles | 1 |
| Doublings | 4.6 |
| Doubling Time | 41.6 hours |

Preliminary Cell Seeding Density Experiments

In preparation for the expansion of immunomagnetic selected cells from the Donor in the automated bioreactor, a series of static growth experiments may be performed to determine if stimulated Treg s may be cultured at a ding dens than 1.0×10$^6$ cells/mL. This portion of the study may be performed by seeding 18 wells of a 24-well tissue culture plate 1.0×10$^5$ cells/mL or well in TexMACS GMP medium supplemented with IL-2 (200 IU/ml) and PSN antibiotics. These cells may also be co-stimulated with the soluble anti-CD3/CD28/CD2 mAb complex on Day 0 and Day 9 at 25 μL/mL. Cells may be manually harvested and counted on Day 14 by Vi-CELL XR.

TABLE 9

Summary of possible Treg cell seeding ststic plate test.

| Treg Plate Samples (1 mL each) | Average Trge Seeding Day 0 (viable cells/ mL) | Average Treg Harvest Day 14 (viable cells/mL) | Average Treg Harvest Day 14 (cells/ cm²) | Treg Cell DS | Treg Cell DT (hours) | Treg Plate Harvest Cell Viability (Trypan Blue Exclusion) |
|---|---|---|---|---|---|---|
| n = 18 | $1.00 \times 10^5$ | $2.65 \times 10^6$ SE $4.14 \times 10^4$ | $1.33 \times 10^6$ | 4.7 | 71.0 | 61.5% |

Abbreviations:
Doublings (DS),
Doubling Time (DT).

After harvest, the cell samples may be pooled for Treg biomarker analysis by flow cytometry. Possible results may show that the frequencies of CD4⁺C25⁺, CD4⁺CD127, and CD4⁺FoxP3⁺ phenotype may be respectively 90.9%, 79.7%, and 31.6% in static culture. The CD4⁺CD25⁺ phenotype (>70%) is generally the most reliable determinant for Treg biomarker identification since FoxP3+ detection is highly dependent on the permeabilization method and cell viability.

The data from this static plate test may suggest that human Tregs may be expanded, with cell seeding densities on the order of $10^5$ cells/mt, when cultured in the presence of a soluble co-stimulation anti-CD3/CD28/CD2 mAb complex and serum-free medium.

Treg Metabolism

Regulatory T cells are dependent on mitochondrial metabolism and have the ability to oxidize multiple carbon sources, i.e., lipid or glucose. Tregs are known to shift their metabolism from fatty acid oxidation (FAO) to glycolysis when they enter a highly proliferative state as a result of mTOR regulation of glycolysis and fatty acid metabolism. Moreover, it has been shown that glycolysis may be necessary for the generation and suppressive functionality of human inducible Tregs by modulating the expression of FoxP3 variants through IL-2/STAT5/enolase-1 promoter signaling and 2-Deoxy-D-glucose inhibition studies. Accordingly, monitoring the glucose and lactate levels may facilitate the adjustment of Quantum system media flow rates to support Treg expansion in the hollow fiber bioreactor. Initially, the Tregs may be thought to transiently reduce their metabolic rate before they enter the cell cycle and proliferate. This may be supported by the transient reduction of glycolysis and mTOR activity in freshly isolated human Tregs before TCR stimulation. Specifically, mTORC1 may be thought to increase the expression of glucose transporters such as Glut-1-mediated glucose transport as a consequence of the upregulated mTOR pathway.

The possible results of three (3) expansions from three separate Treg cell aliquots may indicate that the glucose consumption and lactate generate may appear to correlate within each Quantum system run. All three of the ex vivo expansion runs may show that glucose consumption in Tregs may increase above background levels by Day 1 and 2 out of 3 runs may show that the lactate generation levels may increase above background levels by Day 2. One run, with reduced cell viability at thaw, may generate a lagging lactate generation rate which may be reflected in the cell harvest yield. Maximum glucose consumption rates for the 2 out of 3 runs, in the most actively growing Treg cultures, may be 1.618 and 2.342 mmol/day on Days 8 and 7 respectively. The maximum lactate generation rates may be 2.406 and 3.156 mmol/day at the same time points.

Throughout the Treg expansion runs, an effort may be made to control the lactate values at ≤7 mmol/L by concurrently increasing both the IC input (+) and IC circulation (−) pump rates from (±0.1 to ±0.4 mL/min) within the lumen of the hollow fiber membrane over Days 4-8. The lowest glucose levels during the course of the Treg cell expansions may range from 264 mg/dL on Day 7 (Q1584) to 279 mg/dL on Day 8 (Q1558). The base glucose concentration, in the cell growth formulated medium for these feasibility expansions, may be 325 to 335 mg/dL which may be found to be supportive when used in conjunction with the Quantum system flow rate adjustments.

Regulatory T Cell Biomarker Expression

The evaluation of the Treg cell harvest by flow cytometry may be centered on the CD4⁺CD25⁺FoxP3⁺ T cell subsets in this feasibility study. In T lymphocytes, the human CD4 gene, on Chromosome 12, encodes for a membrane glycoprotein which interacts with the major histocompatibility complex class II and functions to initiate the early phase of T cell activation. In regulatory T cells, the human CD25 (IL2R) gene, on Chromosome 10, encodes for the IL-2 receptor and functions by sequestering the cytokine IL-2. In regulatory T cells, the forkhead/winged-helix box P3 human gene, on the Chromosome X, encodes for the FoxP3 transcriptional factor which may be essential for Treg suppressor function. FoxP3 gene product binds to the promoter region of CD25, CTLA-4 and IL-2, IL7R, IFN-γ genes thereby upregulating CD25 and CTLA-4 and repressing IL-2, IL7R, and IFN-γ gene transcription. The CD127 gene encodes for the IL-7 receptor and Tregs may be generally characterized by low CD127 (IL-7R) expression when compared to conventional T cells. However, certain Treg subsets are known to express high CD127 levels during in vitro and in vivo activation which may correlate to a higher Treg survival when the cells are incubated with IL-7. The CD45RO gene product is expressed on naive thymus derived Tregs that upon activation lose CD45RA and express CD45RO.

TABLE 10

Possible regulatory T cell biomarker expression as a percent of parent population.

| Quantum System Expansion Run | Seeding Viability | Harvest Viability | CD4⁺CD45RO⁺ | CD4⁺CD25⁺ | CD4⁺CD127$^{low}$ | CD4⁺FoxP3⁺ |
|---|---|---|---|---|---|---|
| Q1558 | 81.9% | 84.8% | 72.4% | 86.7% | 40.1% | 58.2% |
| Q1567* | 49.6% | 69.8% | 55.3% | 79.3% | 74.2% | *5.6% |
| Q1584 | 90.7% | 94.6% | 72.8% | 90.5% | 41.0% | 64.9% |

TABLE 10-continued

| Possible regulatory T cell biomarker expression as a percent of parent population. | | | | | | |
|---|---|---|---|---|---|---|
| Quantum System Expansion Run | Seeding Viability | Harvest Viability | CD4+CD45RO+ | CD4+CD25+ | CD4+CD127low | CD4+FoxP3+ |
| Average (n = 3) | | | | 85.5% | | *42.9% |
| Average (n = 2)* | | | | | | *61.6% |

*Low cell viability at thaw/harvest and incomplete permeabilization on Q1567 cells for FoxP3+ frequency.

The average expression of the CD4+CD25+ Treg phenotype frequency may be 85.5% in the cells harvested from the Quantum system which may compare favorably with the published CD4+CD25+ release criteria of >70%. In the Q1567 Treg expansion, the elevated frequency of the CD4+CD127low population (74.2%) may be a reflection of the low cell viability in this particular thawed cell sample since these cells may be cultured only with IL-2 as a cytokine supplement, according to an embodiment. In cells expanded by the two Quantum system runs with seeding and harvest viability above 80%, the CD4+FoxP3+ expression frequency may be 61.6%. This finding may be consistent with the published release specification of ≥60% for FoxP3+. Furthermore, the results of the two billion cell expansions may compare favorably with the CD3+CD45+ (87.30%), CD25+ (47.76%), and FoxP3+ (59.64%) biomarker expression in the original donor Treg cell specimen which may be received from HemaCare BioResearch Products.

Additional flow cytometry analysis may be performed on cryopreserved Treg cells from the Q1584 expansion run by a third-party laboratory, for example, using fluorescence Minus One (FMO) gating, different stains, and different instrumentation. FMO control is a type of gating control use to interpret cell populations by taking into account the spread of all the fluorochromes in the data plots minus the one used to quantify the frequency of a particular marker. For example, the flow results from the third-party laboratory sample. Although interesting, additional studies may be needed to confirm these observations.

Harvest Yield

The possible average diameter of viable (trypan blue exclusion) Treg cells at Quantum system harvest may be 10.89, 11.04, and 11.06 μm respectively across the Q1558, Q1567, and Q1584 runs over a range of 5-50 μm as defined with 50 samples for each run. This may compare to an average cell diameter of 11.91, 12.40, and 7.83 μm respectively from flasks at the time of bioreactor seeding.

These possible cell diameter data may suggest that there may be more uniformity in the diameter of the cells harvested from the Quantum system than there may be in the diameter of the cells which may be expanded in the inoculum flasks.

The Treg Quant m system possible h vest data are summarized in Table 11. Moreover, the impact of the CD4+CD25+ cell viability at the point of seeding the bioreactor may be evident when comparing the results of Q1554/1584 harvests with the Q1567 harvest. There may be a 32-41% higher viability in the bioreactor inoculum for the Q1554/1584 expansion runs versus the viability for the Q1567 run. This may be due to a variation in the original cell isolation, cryopreservation technique or the length of storage since the cell aliquots that may be used in this study (HemaCare PB425C-2; Lot 14034019) may be derived from the same donor collection on Feb. 11, 2014.

TABLE 11

| | Possible expansion of Treg cells from inoculum flasks to Quantum System harvests. | | | | | |
|---|---|---|---|---|---|---|
| Quantum Run | Treg Viability Flask Inoculum[A] | Treg Viability Quantum Harvest[A] | Tregs Quantum Harvest[A] | Treg DS (11 Days) Quantum Inoculum[B] | Treg DS (7-8 Days) Quantum Harvest[B] | Treg DT (hours) Quantum Harvest[B] |
| Q1554 | 81.9% | 84.8% | 1.82 × 10⁹ | 5.0 | 4.8 | 38.5 |
| Q1567 | 49.6% | 69.8% | 1.59 × 10⁸ | 4.4 | 1.8 | 101.3 |
| Q1584 | 90.7% | 94.6% | 1.30 × 10⁹ | 4.7 | 4.6 | 35.7 |

Abbreviations:
DS—Population Doublings,
DT—Population Doubling Time in hours.
[A]Harvest data may be based on Vi-Cell XR counts with Trypan Blue for membrane integrity.
[B]Note:
the Treg cell inoculum from flasks may receive two (2) rounds costimulation on Days −0 and −9; whereas, the Tregs which may be harvested from the Quantum Systems may receive one (1) round of costimulation on Day-0.

may indicate that the CD4+CD25+ Treg cell population frequency may be 95, from the Q1584 run which may compare favorable with the 90.5% which may be found by the Terumo BCT CES Laboratory. Incomplete staining with the alternative anti-FoxP3-PE clone stain may limit the third party laboratory quantification of this internal biomarker, but the dot-plots may suggest that there may be a subpopulation of high expressing FoxP3+ Tregs in the Q1584 specimen that may not be observed in the Control Treg cell reference The objective of this feasibility study may be to determine if the Quantum system may support the expansion of Tregs in the range of 7.0×10⁷-1.4×10⁹ cells with commercially available supplements. Two of the three bioreactor harvests from Q1554 and Q1584 may generate an average of 1.56× 10⁹ Tregs, using a soluble anti-CD3/CD28/CD2 mAb co-stimulator complex, from a seeding density of <1.0×10⁶ cells/mL in less than eight (8) days. This may translate into an average harvest cell density of 8.81×10⁶ cells/mL or $7.43\times10^4$ cells/cm$^2$ in the IC loop of the Quantum system bioreactor over the Q1554/1584 runs, Possible Conclusions The results of this feasibility study may be exploratory in nature and may not necessarily be designed to cover all technical options. For example, one could consider the reduction of inoculum Treg co-stimulation from two (2) to one (1) activation events. As such, the methods which may be used in the automated Quantum system expansion of immunomagnetic-isolated regulatory T cells may be open to modification. Our attempt here may be to define certain technical aspects of the culture process that may be conducive to further study in the upscale expansion of Tregs within the Quantum system platform. Within this context, the possible study findings may suggest that these possible conclusions or observations may be reasonable and may be helpful in the production of regulatory T cells for research, development, or production purposes.

Human Tregs, as identified as FoxP3$^+$/CD25$^+$, may be cultured and may be expanded with a soluble co-stimulatory anti-CD3/CD28/CD2 monoclonal antibody (mAb) T cell complex, in the absence of co-stimulatory mAb-coated beads, when supplemented with the cytokine IL-2 in the Quantum system automated hollow fiber bioreactor.

Human Tregs may be efficiently expanded in the Quantum system from cell seeding densities of less than $1\times10^6$ cels/mL or less than $6.6\times10^4$ cells/cm$^2$. To this end, the objective of harvesting Tregs within the range of $7.0\times10^8$ to $1.4\times10^9$ cells in less than 14 days may be achieved with an average (n=3) of $1.09\times10^9$ total cells. An average of 85.5% of the cells may express the Treg CD4$^+$CD25$^+$ phenotype and an average of 42.9% may express CD4+FoxP3+ phenotype (n=3). In the two (2) billion cell Quantum system expansions, an average of 61.6% of the total cells may express the CD4$^+$FoxP3$^+$ phenotype. One of the three Quantum system Treg cell expansion runs may be validated for CD4$^+$CD25$^+$ expression by a third-party laboratory human IMSR due to the limited number of cells.

Human Tregs may be successfully cultured and may be expanded in the Quantum system by centrally seeding the cells within the lumen (IC loop) of an automated hollow fiber bioreactor.

Media IC input (+0.1 to +0.4 mL/min) and IC circulation (−0.0 to −0.4 mL/min) may be adjusted in parallel to support the Treg cell expansion process in order to maintain lactate levels ≤7 mmol/L and to maintain the single cell suspension of the Treg culture by shearing cell micro-colonies at an IC circulation rate of 300 mL/min through the lumen of the Quantum system HFM bioreactor under functional closed conditions.

Example 2

The tables below provide example task settings (e.g., flow rates, angular rotation, outlet, etc.) for different components (e.g., pumps, rocker, valves, etc.) of a cell expansion system over several days of performing an example protocol for the expansion of T cells. The protocol may follow the following sequence:

Day 0: Load Set, Prime, Add Media, Load Cells, and begin feeding

Day 3: Add a bolus of cytokines to the IC loop while re-distributing the cells. Begin feeding again.

Day 6: Add a bolus of cytokines to the IC loop while re-distributing the cells. Begin feeding again.

Day 9: Add a bolus of cytokines to the IC loop while re-distributing the cells. Begin feeding again.

Day 11-13: Harvest; reload remaining cells. Harvest (Day 14)

Table(s) of settings: changes made compared to example factory settings are highlighted in bold and underline

TABLE 12

IL-2 Concentration and Amount
In Complete Media, Example
Complete Media

| Volume (mL) | IL-2 (IU/mL) | IL-2 (IU) |
|---|---|---|
| 2000 | 200 | 4E+05 |

TABLE 13

Volumes of Bolus Additions
and IL-2 Amounts, Example
Bolus Additions

| | Volume (mL) | IL-2 (IU) |
|---|---|---|
| Day 0 (cell load) | 100 | 1E+05 |
| Day 3 | 150 | 2E+05 |
| Day 6 | 150 | 2E+05 |
| Day 9 | 150 | 4E+05 |

TABLE 14

Settings Day 0-Day 2, Example

Day 0

| | | Load Cell Expansion | | IC EC washout | Condition media | | Load cells with Uniform Suspension (1e8 lymphocytes) | | | Cells in BR Custom 1 | Feed cells |
| | | Set STEP 1 | Prime STEP 2 | STEP 3 | Step 1 STEP 4 | Step 2 STEP 5 | Step 1 STEP 6 | Step 2 STEP 7 | Step 3 STEP 8 | Step 1 STEP 9 | Step 2 STEP 10 |
|---|---|---|---|---|---|---|---|---|---|---|---|
| Task Settings | IC inlet | Default settings | Default settings | EC media | None | None | Cell | IC Media | None | IC Media | IC Media |
| | IC inlet rate | | | 100 | 0 | 0 | 25 | 25 | 0 | 100 | 0.1 |
| | IC circ rate | | | −17 | 100 | 100 | 150 | 150 | 200 | −70 | 1 |
| | EC inlet | | | EC Media | EC Media | EC Media | None | None | None | None | None |
| | EC inlet rate | | | 148 | 0.1 | 0.1 | 0 | 0 | 0 | 0 | 0 |

TABLE 14-continued

| | | | | | Settings Day 0-Day 2, Example | | | | | |
|---|---|---|---|---|---|---|---|---|---|---|
| | | | | | Day 0 | | | | | |
| | Load Cell Expansion | | IC EC | Condition media | | Load cells with Uniform Suspension (1e8 lymphocytes) | | | Cells in BR | Feed cells |
| | | | | | | | | Custom 1 | | |
| | Set STEP 1 | Prime STEP 2 | washout STEP 3 | Step 1 STEP 4 | Step 2 STEP 5 | Step 1 STEP 6 | Step 2 STEP 7 | Step 3 STEP 8 | Step 1 STEP 9 | Step 2 STEP 10 |
| EC circ rate | | | −1.7 | 250 | 30 | 30 | 30 | 30 | 30 | 100 |
| Outlet | | | IC and EC outlet | EC outlet | EC outlet | EC outlet | EC outlet | EC outlet | EC outlet | EC outlet |
| Rocker | | | In Motion (−90°, 180°, 1 sec) | Stationary (0°) | Stationary (0°) | In Motion (−90°, 180°, 1 sec) | In Motion (−90°, 180°, 1 sec) | In Motion (−90°, 180°, 1 sec) | In Motion (−90°, 180°, 1 sec) | Stationary (0°) |
| Stop condition | | | Exchange (2.5 IC volume; 2.5 EC volume) | Time (10 min) | Manual (20-50 min) | Empty bag | IC volume (22 ml) | Time (2 min) | IC Volume (120 mL) | Manual (4320 min) |
| Extra Information | Necessary volume | NA | 1300 mL EC Media | 6 mL/hr EC Media | | 100 ml | 22 mL IC Media | | 120 mL | 432 mL IC Media |
| | Time | 10 min | 2 L (PBS) 35 min | 5 min | 30-60 min | | 7 min | | 2 min | 3 days |

TABLE 15

| | | | Setting Day 3-Day 5, Example | | | |
|---|---|---|---|---|---|---|
| | | | Day 3 | | | |
| | | | Add Bag Contents | | Cells in BR | Feed cells |
| | | | | | Custom 2 | |
| | | | Step 1 STEP 11 | Step 2 STEP 12 | Step 1 STEP 13 | Step 2 STEP 14 |
| Task Settings | IC inlet | | Reagent | IC Media | IC Media | IC Media |
| | IC inlet rate | | 30 | 30 | 100 | 0.1 |
| | IC circ rate | | 100 | 100 | −70 | −0.1 |
| | EC inlet | | None | None | None | None |
| | EC inlet rate | | 0 | 0 | 0 | 0 |
| | EC circ rate | | 100 | 100 | 30 | 150 |

TABLE 15-continued

| | | Setting Day 3-Day 5, Example | | | |
|---|---|---|---|---|---|
| | | Day 3 | | | |
| | | Add Bag Contents | | Cells in BR | Feed cells |
| | | | | Custom 2 | |
| | | Step 1 STEP 11 | Step 2 STEP 12 | Step 1 STEP 13 | Step 2 STEP 14 |
| | Outlet | EC outlet | EC outlet | EC outlet | EC outlet |
| | Rocker | In Motion (−90°, 180°, 1 sec) | In Motion (−90°, 180°, 1 sec) | In Motion (−90°, 180°, 1 sec) | In Motion (0°, 180°, 3600 sec) |
| | Stop condition | Empty Bag | IC Volume (22 mL) | IC Volume (120 mL) | Manual (4320 min) |
| Extra Information | Necessary volume | 150 mL | 22 mL IC Media | 120 mL | 432 mL IC Media |
| | Time | 5 min | | 2 min | 3 days |

TABLE 16

| | | | Settings Day 6-Day 8, Example | | | | | |
|---|---|---|---|---|---|---|---|---|
| | | | Day 6 | | | | | |
| | | | Add Bag Contents | | Cells in BR | Feed cells | Feed cells | Feed cells |
| | | | | | | Custom 3 | | |
| | | | Step 1 STEP 15 | Step 2 STEP 16 | Step 1 STEP 17 | Step 2 STEP 18 | Step 3 STEP 20 | Step 4 STEP 22 |
| Task Settings | IC inlet | | Reagent | IC Media | IC Media | IC Media | IC Media | IC Media |
| | IC inlet rate | | 30 | 30 | 100 | 0.1 | 0.1 | 0.1 |
| | IC circ rate | | 100 | 100 | −70 | −0.1 | −0.1 | −0.1 |
| | EC inlet | | None | None | None | EC Media | EC Media | EC Media |
| | EC inlet rate | | 0 | 0 | 0 | 0.1 | 0.2 | 0.3 |
| | EC circ rate | | 100 | 100 | 30 | 200 | 200 | 250 |
| | Outlet | | EC outlet | EC outlet | EC outlet | EC outlet | EC outlet | EC outlet |
| | Rocker | | In Motion (−90°, 180°, 1 sec) | In Motion (−90°, 180°, 1 sec) | In Motion (−90°, 180°, 1 sec) | In Motion (0°, 180°, 3600 sec) | In Motion (0°, 180°, 3600 sec) | In Motion (0°, 180°, 3600 sec) |

TABLE 16-continued

Settings Day 6-Day 8, Example

Day 6

| | | Add Bag Contents | | Cells in BR | Feed cells Custom 3 | | Feed cells |
|---|---|---|---|---|---|---|---|
| | | Step 1 STEP 15 | Step 2 STEP 16 | Step 1 STEP 17 | Step 2 STEP 18 | Step 3 STEP 20 | Step 4 STEP 22 |
| Extra Information | Stop condition | Empty Bag | IC Volume (22 mL) | IC Volume (120 mL) | Time (1440 min) | Time (1440 min) | Manual |
| | Necessary volume | 150 ml | 22 mL IC Media | 120 mL | 144 mL IC Media 436 mL EC Media | 144 mL IC Media 436 mL EC Media 3 days | 144 mL IC Media 436 mL EC Media |
| | Time | 4 min | | 2 min | | | |

TABLE 17

Settings Day 9-Day 10, Example

Day 9

| | | Add Bag Contents | | Cells in BR | Feed cells Custom 3 | |
|---|---|---|---|---|---|---|
| | | Step 1 STEP 25 | Step 2 STEP 24 | Step 1 STEP 17 | Step 2 STEP 18 | Step 3 STEP 20 |
| Task Settings | IC inlet | Reagent | IC Media | IC Media | IC Media | IC Media |
| | IC inlet rate | 30 | 30 | 100 | 0.1 | 0.1 |
| | IC circ rate | 100 | 100 | −70 | −0.1 | −0.1 |
| | EC inlet | None | None | None | EC Media | EC Media |
| | EC inlet rate | 0 | 0 | 0 | 0.1 | 0.2 |
| | EC circ rate | 100 | 100 | 30 | 200 | 200 |
| | Outlet | EC outlet | EC outlet | EC outlet | EC outlet | EC outlet |
| | Rocker | In Motion | In Motion | In Motion | In Motion | In Motion |
| | | (−90°, 180°, 1 sec) | (−90°, 180°, 1 sec) | (−90°, 180°, 1 sec) | (0°, 180°, 3600 sec) | (0°, 180°, 3600 sec) |
| Extra Information | Stop condition | Empty Bag | IC Volume (22 mL) | IC Volume (120 mL) | Time (1440 min) | IC Volume (22 mL) |
| | Necessary volume | 150 mL | 22 mL IC Media | 120 mL | 144 mL IC Media 144 mL EC Media | 144 mL IC Media 288 mL EC Media |
| | Time | 4 min | | 2 min | 2 days | |

TABLE 18

Settings Day 11, Example

Harvest

| | | Mix Custom 4 | | Load cells with Uniform Suspension (Harvest Product) | | | Cells in BR | Feed cells Custom 2 |
|---|---|---|---|---|---|---|---|---|
| | | Step 1 STEP 31 | Harvest STEP 32 | Step 1 STEP 33 | Step 2 STEP 34 | Step 3 STEP 35 | Step 1 STEP 13 | Step 2 STEP 14 |
| Task Settings | IC inlet | None | EC Media | Cell | IC Media | None | IC Media | IC Media |
| | IC inlet rate | 0 | 100 | 25 | 25 | 0 | 100 | 0.1 |
| | IC circ rate | 200 | −20 | 150 | 150 | 200 | −70 | −0.1 |
| | EC inlet | None | EC Media | None | None | None | None | None |
| | EC inlet rate | 0 | 100 | 0 | 0 | 0 | 0 | 0 |
| | EC circ rate | 200 | 30 | 30 | 30 | 30 | 30 | 150 |
| | Outlet | EC outlet | Harvest | EC outlet | EC outlet | EC outlet | EC outlet | EC outlet |
| | Rocker | In Motion (−90°, 180°, 1 sec) | In Motion (−90°, 180°, 1 sec) | In Motion (−90°, 180°, 1 sec) | In Motion (−90°, 180°, 1 sec) | In Motion (−90°, 180°, 1 sec) | In Motion (−90°, 180°, 1 sec) | In Motion (0°, 180°, 3600 sec) |
| Extra Information | Stop condition | Time (3 min) | IC Volume (400 ml) | Empty bag (variable) | IC volume (22 ml) | Time (2 min) | IC Volume (120 mL) | Manual (1440 min) |
| | Necessary volume | | 800 mL EC Media | mL | 22 mL IC Media | | 120 mL | 144 mL IC Media |
| | Time | 3 min | 4 min | 10 min | | | 2 min | |

TABLE 19

| | | | Harvest | | | | | |
|---|---|---|---|---|---|---|---|---|
| | | Mix Custom 4 | | Load cells with Uniform Suspension (Harvest Product) | | | Cells in BR Custom 2 | Feed cells |
| | | Step 1 STEP 31 | Harvest STEP 32 | Step 1 STEP 33 | Step 2 STEP 34 | Step 3 STEP 35 | Step 1 STEP 13 | Step 2 STEP 14 |
| Task Settings | IC inlet | None | EC Media | Cell | IC Media | None | IC Media | IC Media |
| | IC inlet rate | 0 | 100 | 25 | 25 | 0 | 100 | 0.1 |
| | IC circ rate | 200 | −20 | 150 | 150 | 200 | −70 | −0.1 |
| | EC inlet | None | EC Media | None | None | None | None | None |
| | EC inlet rate | 0 | 100 | 0 | 0 | 0 | 0 | 0 |
| | EC circ rate | 200 | 30 | 30 | 30 | 30 | 30 | 150 |
| | Outlet | EC outlet | Harvest | EC outlet | EC outlet | EC outlet | EC outlet | EC outlet |
| | Rocker | In Motion (−90°, 180°, 1 sec) | In Motion (−90°, 180°, 1 sec) | In Motion (−90°, 180°, 1 sec) | In Motion (−90°, 180°, 1 sec) | In Motion (−90°, 180°, 1 sec) | In Motion (−90°, 180°, 1 sec) | In Motion (0°, 180°, 3600 sec) |
| | Stop condition | Time (3 min) | IC Volume (400 mL) | Empty bag (variable) | IC volume (22 ml) | Time (2 min) | IC Volume (120 mL) | Manual (1440 min) |
| Extra Information | Necessary volume | | 800 mL EC Media | mL | 22 mL IC Media | | 120 mL | 144 mL IC Media |
| | Time | 3 min | 4 min | | 10 min | | 2 min | 1 days |

TABLE 20

| | | | Harvest | | | | | |
|---|---|---|---|---|---|---|---|---|
| | | Mix Custom 4 | | Load cells with Uniform Suspension (Harvest Product) | | | Cells in BR Custom 2 | Feed cells |
| | | Step 1 STEP 31 | Harvest STEP 32 | Step 1 STEP 33 | Step 2 STEP 34 | Step 3 STEP 35 | Step 1 STEP 13 | Step 2 STEP 14 |
| Task Settings | IC inlet | None | EC Media | Cell | IC Media | None | IC Media | IC Media |
| | IC inlet rate | 0 | 100 | 25 | 25 | 0 | 100 | 0.1 |
| | IC circ rate | 200 | −20 | 150 | 150 | 200 | −70 | −0.1 |
| | EC inlet | None | EC Media | None | None | None | None | None |
| | EC inlet rate | 0 | 100 | 0 | 0 | 0 | 0 | 0 |
| | EC circ rate | 200 | 30 | 30 | 30 | 30 | 30 | 150 |
| | Outlet | EC outlet | Harvest | EC outlet | EC outlet | EC outlet | EC outlet | EC outlet |
| | Rocker | In Motion (−90°, 180°, 1 sec) | In Motion (−90°, 180°, 1 sec) | In Motion (−90°, 180°, 1 sec) | In Motion (−90°, 180°, 1 sec) | In Motion (−90°, 180°, 1 sec) | In Motion (−90°, 180°, 1 sec) | In Motion (0°, 180°, 3600 sec) |
| | Stop condition | Time (3 min) | IC Volume (400 mL) | Empty bag (variable) | IC volume (22 ml) | Time (2 min) | IC Volume (120 mL) | Manual (1440 min) |
| Extra Information | Necessary volume | | 800 mL EC Media | mL | 22 mL IC Media | | 120 mL | 144 mL IC Media |
| | Time | 3 min | 4 min | | 10 min | | 2 min | 1 days |

TABLE 21

| | | Harvest | |
|---|---|---|---|
| | | Mix Custom 4 Step 1 Step 31 | Harvest STEP 32 |
| Task Settings | IC inlet | None | EC Media |
| | IC inlet rate | 0 | 100 |
| | IC circ rate | 200 | −20 |
| | EC inlet | None | EC Media |
| | EC inlet rate | 0 | 100 |
| | EC circ rate | 200 | 30 |

TABLE 21-continued

| | | Harvest | |
|---|---|---|---|
| | | Mix Custom 4 Step 1 Step 31 | Harvest STEP 32 |
| | Outlet Rocker | EC outlet In Motion (−90°, 180°, 1 sec | Harvest In Motion (−90°, 180°, 1 sec |
| | Stop condition | Time (3 min) | IC Volume (400 mL) |

TABLE 21-continued

Settings Day 14, Example

| | | Harvest | |
| --- | --- | --- | --- |
| | | Mix Custom 4 Step 1 Step 31 | Harvest STEP 32 |
| Extra Information | Necessary volume Time | 3 min | 800 mL EC Media 4 min |

Example 3

A first protocol for expanding T-cells using the Quantum system may do so by stimulating CD3+ T-cells using CD3+/CD28+ Dynabeads (Gibco). Dynabeads may mimic in vivo T-cell activation from antigen-presenting cells (APC) by utilizing the two activation signals CD3 and CD28, bound to a three-dimensional bead similar in size to the APC. The Dynabeads may be mixed with 100E+06 lymphocytes from an unprocessed apheresis product.

The cells may be expanded on a Quantum system for 12-13 days using a serum free media (TexMACS, Miltenyi Biotech) for a total of seven runs and three different donors. To the serum free media, cytokines IL-2 and IL-7 may be added to the feed media as well as spiked into the system on Days 3, 6, and 9.

Cell expansion results may average 10E+09±4E+09 T-cells; representing a 261±188 fold expansion and a cell doubling time of 40±4 hours.

The cell phenotype after expansion may be CD3+ =98±3%, CD3+/CD4+=38±13%, CD3+/CD8+=60±12%.

Figure 26:
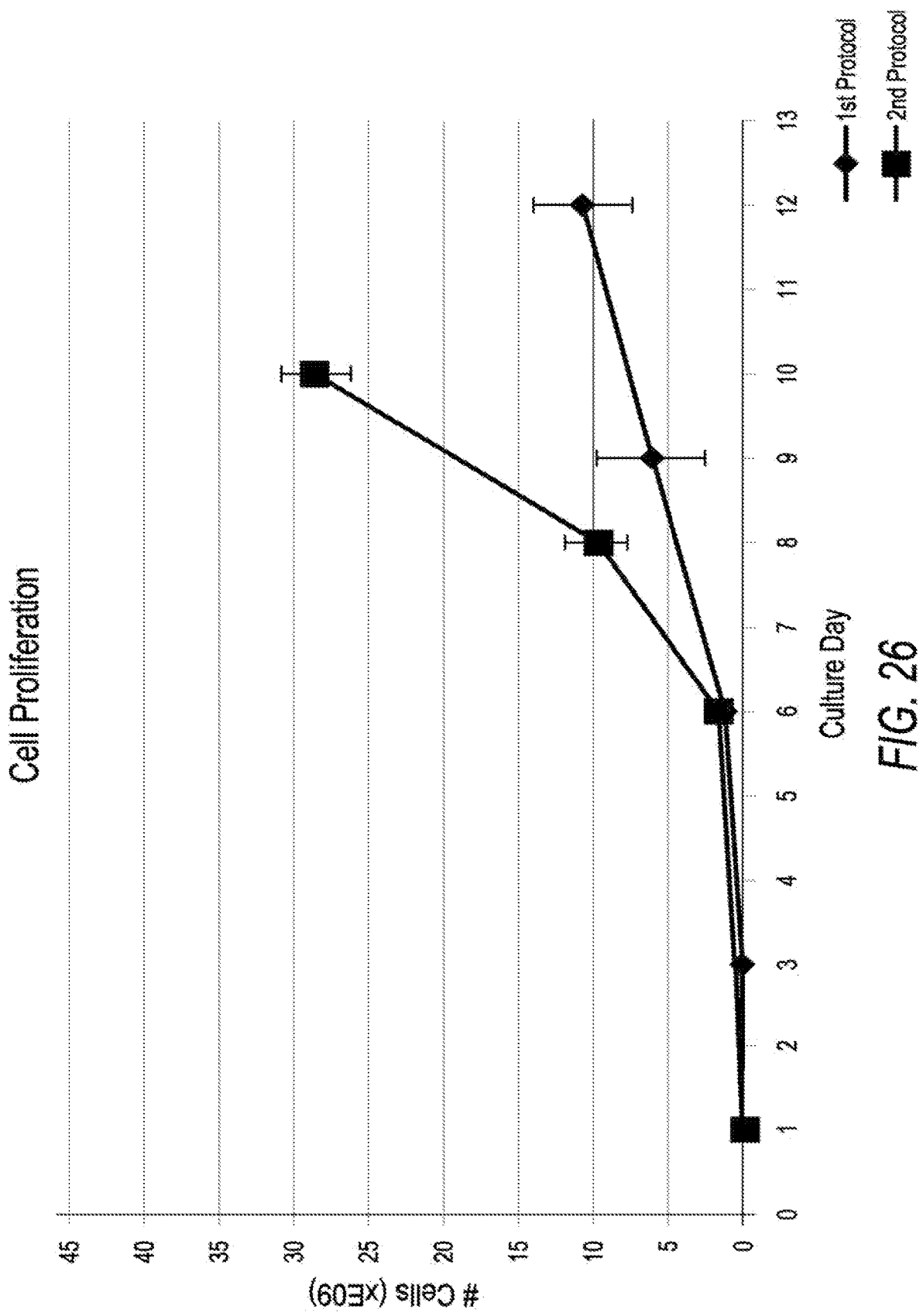
FIG. 26 illustrates a graph of cell numbers versus culture days during cell expansion, in accordance with embodiments of the present disclosure.

Below is a description of some features of a second protocol, with changes made with respect to a first protocol (as described above, for example), to expand T cells. The changes in the second protocol may enhance cell proliferation in accordance with some embodiments. FIG. 26 illustrates a graph of number of cells over culture days comparing the first protocol to the second protocol.

Isolate peripheral blood mononuclear cells (PBMCs) prior to expansion. Isolating PBMCs may allow for fresh or frozen cells to be used as the starting cell product. An additional benefit to PBMC isolation may be found in the process of cell transduction. Manufacturing a CAR-T cell (chimeric antigen receptor-T-cell) may require the transduction of activated T-cell using a retroviral vector. It may be important to this process to minimize the "contaminating" cell population. Contaminating cells may include any cells that are not CD3+ T-cells; including red blood cells, platelets, monocytes, granulocytes, etc.

Keep cells in bioreactor fibers during cell feeding. The hollow fiber bioreactor may be designed such that all gas transfer and nutrient transfer takes place through the semi-permeable membrane of the hollow fibers. It may be an improvement that the cell population be kept in this location to maximize the benefits of this efficient design. Non-adherent cells, like T-cells, can be kept in this space using fluid dynamics. Fluid may constantly be flowing into both the IC inlet and IC outlet headers of the bioreactor at an equal rate.

Improve feed strategy. The improvement in feed strategy may be two-fold. First, traditional cell culturing methodologies may require the culture medium to be replaced at specific time intervals or continuously perfused at specified rates in order to supply the cell population with sufficient nutrients and remove metabolic waste; particularly lactate. The first protocol may allow lactate concentrations to exceed 20 mmol/L and glucose levels to fall to less than ⅓ the starting concentration. By most standard cell culture methods, this may be well below optimal conditions. The second protocol increases feed rates to maintain lactate levels below 15 mmol/L and keep glucose levels greater than 50% of the starting concentration, such as for example above 300 mg/dL.

These feed rate increases may be further specified into independent IC and EC feed rate methods. IC feed rates are determined both for cell culture demands of media constituents having a molecular mass >12 kDa and influencing the physical location of the cells in the bioreactor fibers. Since the hollow fiber membrane may be semi-permeable and feeding with ultrafiltration may be used to keep the cells in the fibers, larger molecular weight constituents contained in the IC medium are retained on the IC side of the bioreactor. As for cell location, the larger the IC feed rate, the more concentrated the cell population may be toward the center of the reactor. EC feed rates may be determined by the glucose demands of the cell culture population and lactate removal needs. This approach provides potential cost benefits. Expensive culture media additives such as cytokines and proteins (their presence may be needed at minimum concentrations) can be added only to the IC medium; conserving them as glucose supply and lactate removal requirements may be typically much higher.

Redistribute cells daily for entire duration of cell expansion. This may minimize the formation of cell aggregates that may commonly observed during T-cell expansion. These aggregates can form necrotic centers (cells in the center of the aggregate may be deprived of oxygen and nutrients).

Figure 27:
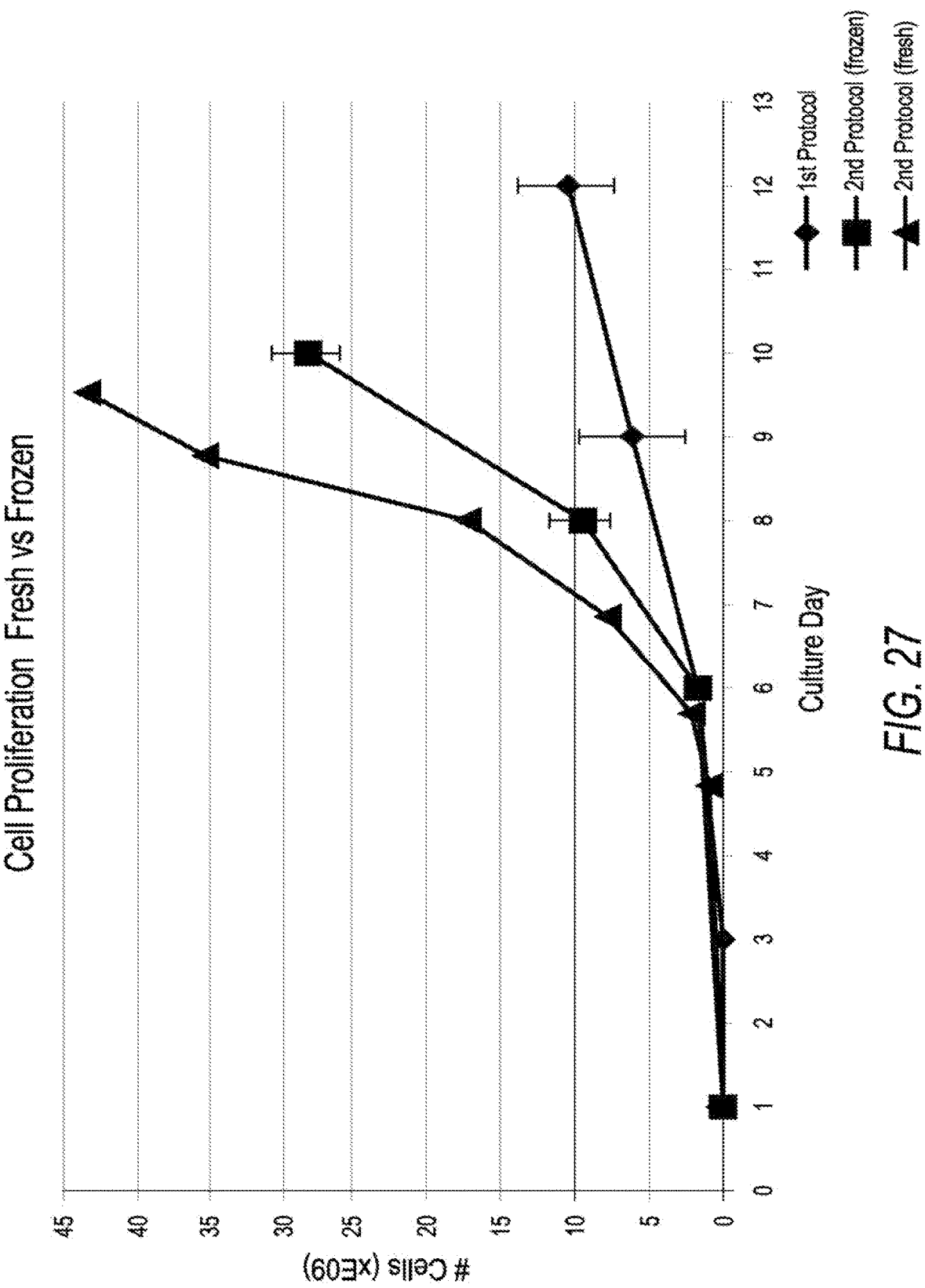
FIG. 27 illustrates a graph of cell numbers versus culture days during cell expansion, in accordance with embodiments of the present disclosure.

Additional improvement may be observed when the starting product is fresh (not cryopreserved). See FIG. 27. Most cell types may proliferate better in the absence of stressors caused by cryopreservation. Typically, cryopreserved cells may remain in lag phase longer than their fresh counterparts, thereafter proliferating at a similar rate. FIG. 27 illustrates a graph of number of cells over culture days comparing the first protocol with the second protocol using both fresh and frozen cells.

Figure 28:
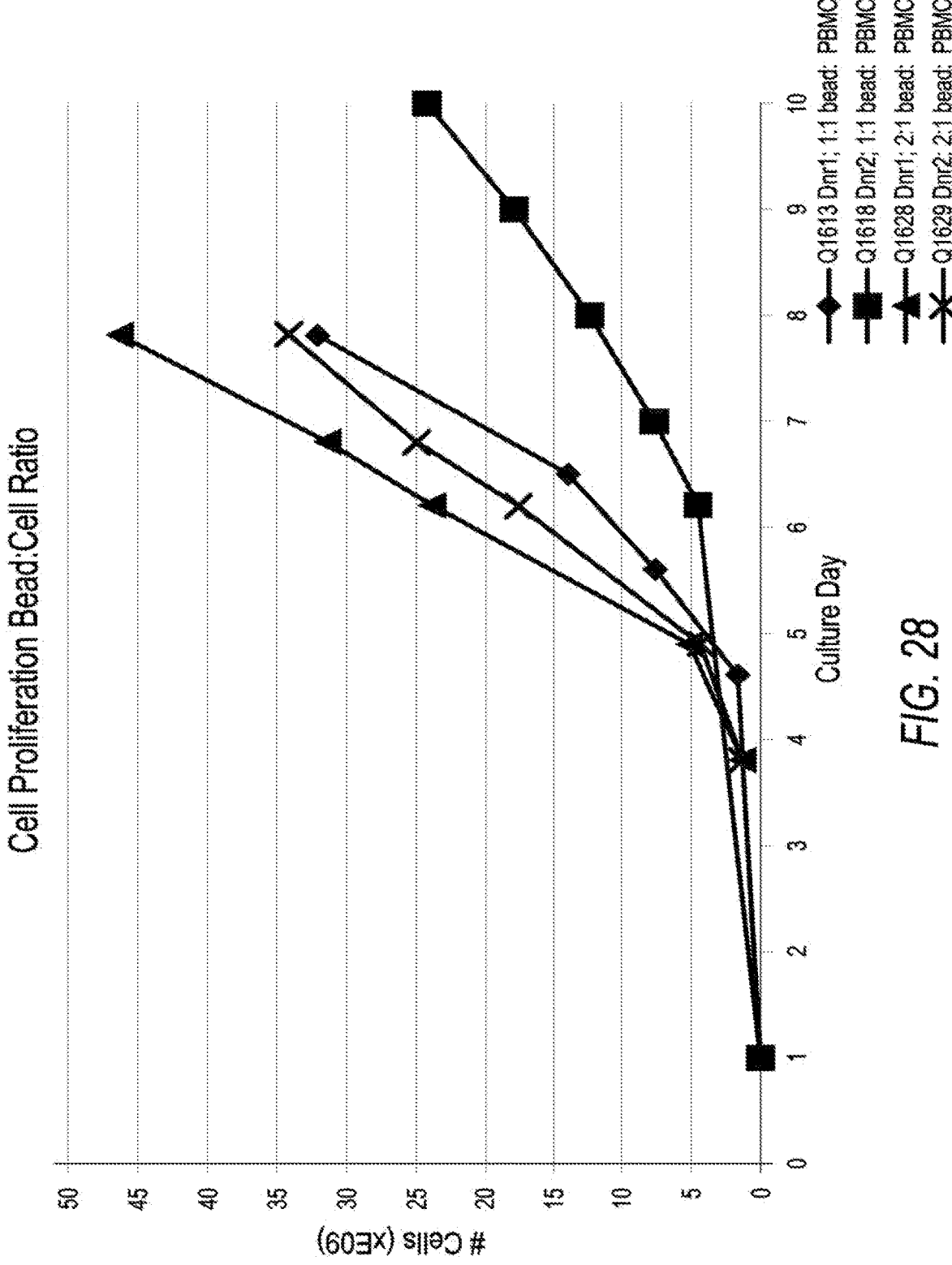
FIG. 28 illustrates a graph of cell numbers versus culture days during cell expansion, in accordance with embodiments of the present disclosure.
Figure 29:
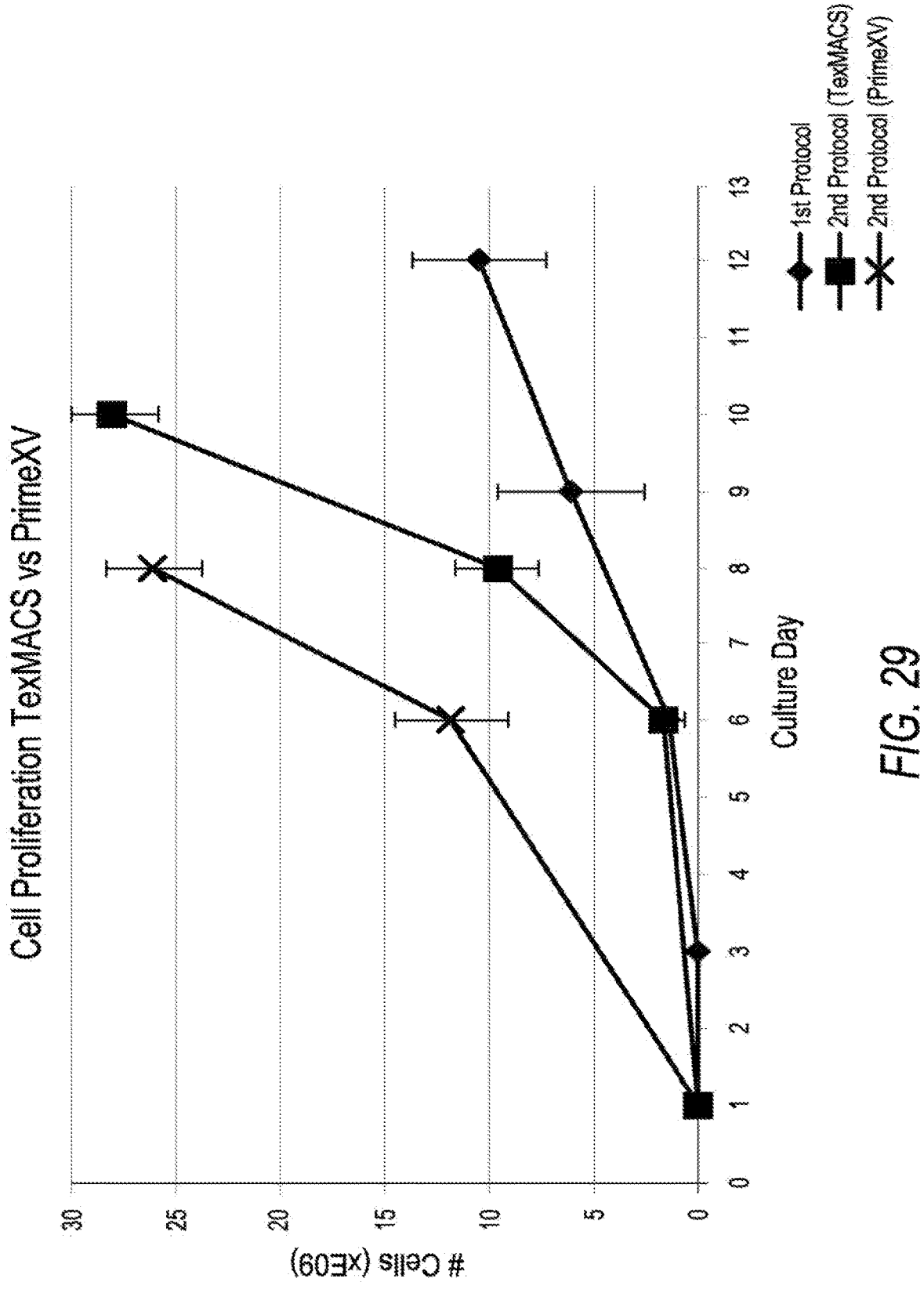
FIG. 29 illustrates a graph of cell numbers versus culture days during cell expansion, in accordance with embodiments of the present disclosure.

Additional protocol enhancements may include increasing the stimulation bead to cell ratio from 1:2 to 2:1 and changing the type of serum free culture medium. Increasing the bead to cell ratio may increases the probability of cell/bead interaction during stimulation and may result in improved proliferation consistency. FIG. 28 illustrates a graph of number of cells over culture days comparing the first protocol with the second protocol using two donors and bead ratios of 1 bead:1 cell and 2 beads:1 cell. The cells may proliferate better using Prime XV (Irvine Scientific) serum free medium compared to TexMACS. FIG. 29 illustrates a graph of number of cells over culture days comparing the first protocol with the second protocol using different media. Since both media formulations are proprietary, the exact reason may not be determined.

Below are some examples that demonstrate Quantum® Cell Expansion System versatility.

The first demonstration of versatility may be to lower the number of cells used to seed the Quantum system. This may allow T-cells to expand if PBMCs are in short supply (e.g. poor collection from a patient) and without the additional requirement of a separate device or flask to perform an initial expansion for the inoculum.

The second demonstration of versatility may be to use a variety of cell culture media types. Serum free media may be becoming more popular for use in cell therapy manufacturing protocols; minimizing variability (chemically defined) and eliminating xeno and human supplements.

Possible Data

PBMCs may be collected via healthy donor apheresis products (AllCells or Key Biologics) or from an IRS chamber during a Trima single platelet collection.

All Quantum system T-cell expansion runs may be seeded with cryopreserved PBMCs isolated from one of two separation methods; fluid gradient separation (ficoll) or elutriation (Elutra).

Figure 30:
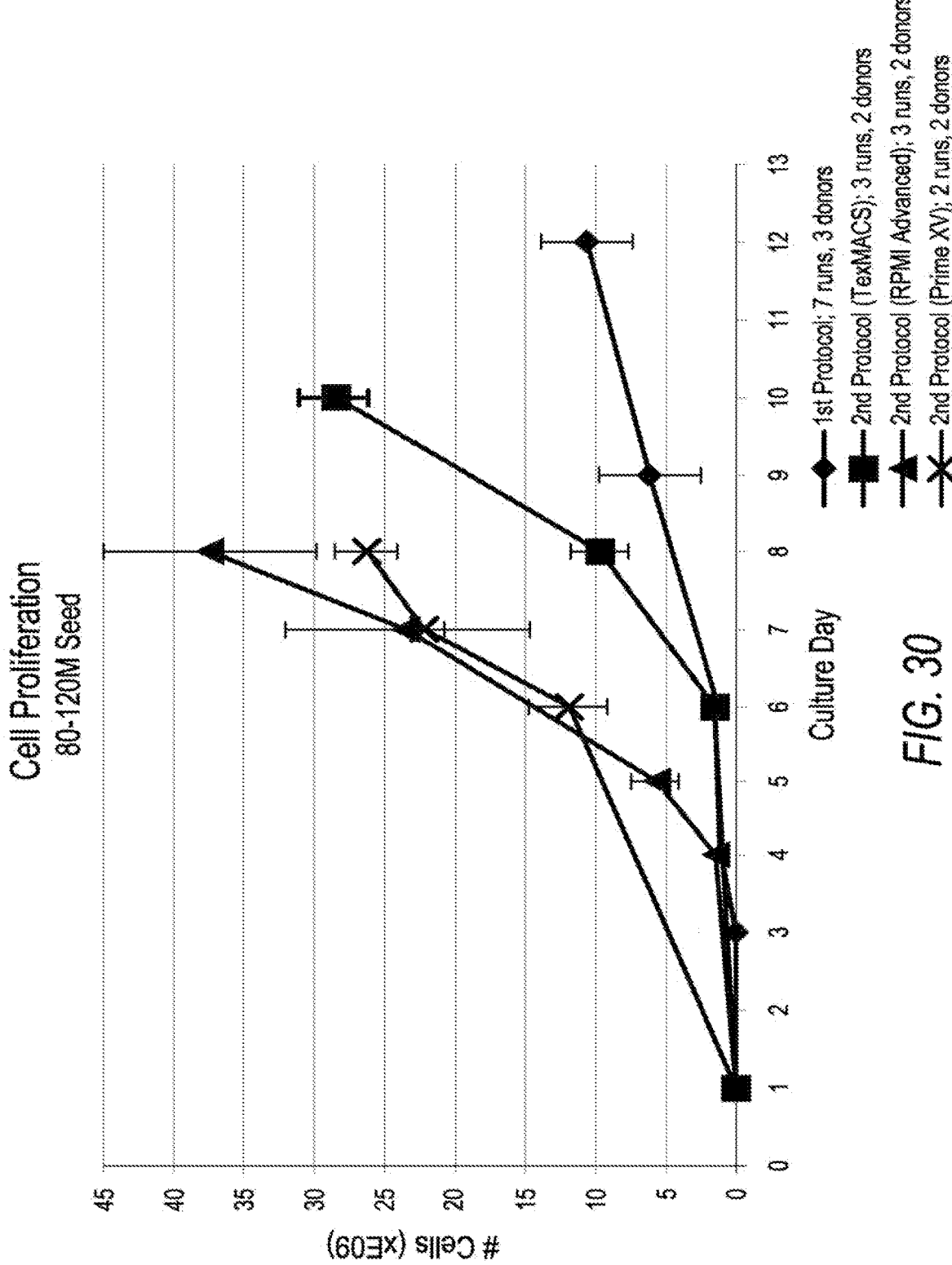
FIG. 30 illustrates a graph of cell numbers versus culture days during cell expansion, in accordance with embodiments of the present disclosure.

Quantum system expansion runs seeded with (80-120)E+06 PBMCs may be summarized in Table 22. FIG. 30 illustrates a graph of number of cells over culture days comparing the first protocol with the second protocol using different media.

Using TexMACS (Miltenyi Biotech) base media, cell expansion may average 28E+09±2E+09 cells; representing a ~550 fold expansion and a doubling time of 26 hours.

Using RPMI Advanced (Gibco) base media, cell expansion may average 37E+09±2E+09 cells; representing a ~750 fold expansion and a doubling time of 20 hours.

Note: RPMI Advanced contains Albumax which is derived from FBS.

Using Prime XV (Irvine Scientific) base media, cell expansion may average 26E+09±2E+09 cells; representing a ~525 fold expansion and a doubling time of 21 hours.

Changing the cell culture doubling time from 37 hours in the original protocol to 21 hours using the new protocol may be highly significant see for example, Table 22. To illustrate this, examples using practical harvest numbers on the Quantum system may be used.

Given 37 hours as the cell culture doubling time, it would require 6.6 days to expand 50E+06 cells to 1E+09 cells.

Given 21 hours as a cell culture doubling time, 10E+09 cells may be expanded from 50E+06 cells during that same 6.6 days. This may be a 10-fold increase in cell proliferation capacity.

TABLE 22

| Cell Proliferation (80-120M Seed) | | | |
|---|---|---|---|
| Base Media | Expansion Time (days) | Cells Harvested (ave. ± s.d.) ×E9 | Fold Expansion (based on ave.) | Doubling Time (hours) |
| TexMACS (1st protocol) | 13 | 11 ± 3 | ~200 | 37 |
| TexMACS | 10 | 28 ± 2 | ~575 | 26 |
| RPMI Advanced | 8 | 37 ± 8 | ~750 | 20 |
| Prime XV | 8 | 26 ± 2 | ~525 | 21 |

Figure 31:
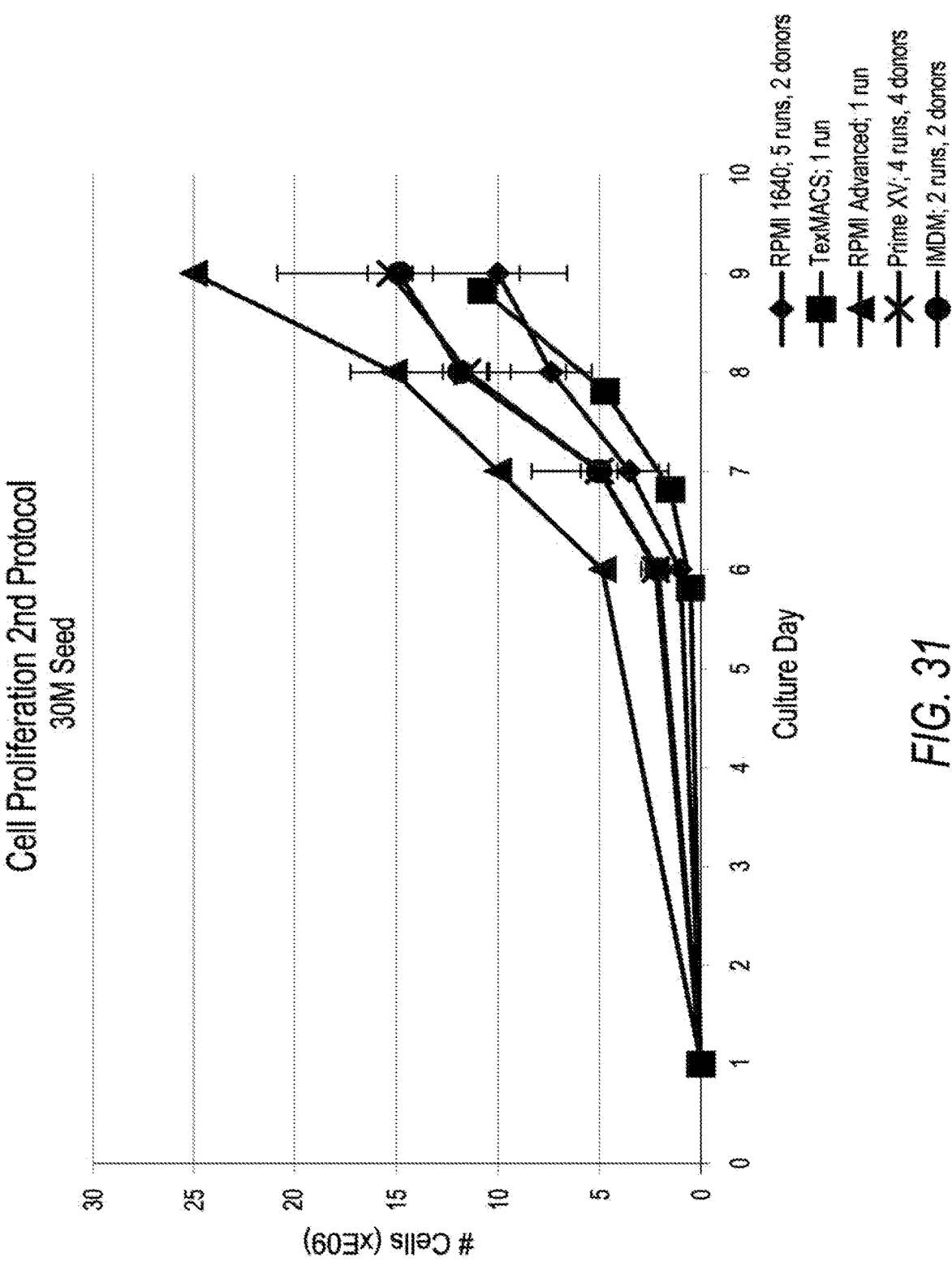
FIG. 31 illustrates a graph of cell numbers versus culture days during cell expansion, in accordance with embodiments of the present disclosure.

Quantum system expansion runs seeded with 30E+06 PBMCs may be summarized in Table 23. FIG. 31 illustrates a graph of number of cells over culture days comparing the second protocol using different media.

Using RPMI 1640 base media cell expansion may result in 10E+09±3E+09 cells; representing a ~850 fold expansion and a doubling time of 22 hours.

Using TexMACS base media cell expansion may result in 11E+09 cells; representing a ~725 fold expansion and a doubling time of 22 hours.

Using RPMI Advanced base media cell expansion may result in 25E+09 cells; representing a ~1675 fold expansion and a doubling time of 20 hours.

Using Prime XV base media cell expansion may result in an average of 15E+09±1E+09 cells; representing a ~1000 fold expansion and a doubling rime of 22 hours.

Using IMDM (Lonza) base media cell expansion may result in an average of 15E+09±6E+09 cells; representing a ~1000 fold expansion and a doubling time of 22 hours.

TABLE 23

| Cell Proliferation (2nd Protocol, 30M Seed) | | | |
|---|---|---|---|
| Base Media | Expansion Time (days) | Cells Harvested (ave. ± s.d.) ×E9 | Fold Expansion (based on ave.) | Doubling Time (hours) |
| RPMI 1640 | 9 | 13 ± 3 | ~850 | 22 |
| TexMACS | 9 | 11 (n = 1) | ~725 | 22 |
| RPMI Advanced | 9 | 25 (n = 1) | ~1675 | 20 |
| Prime XV | 9 | 15 ± 1 | ~1000 | 22 |
| IMDM | 9 | 15 ± 6 | ~1000 | 22 |

Figure 32:
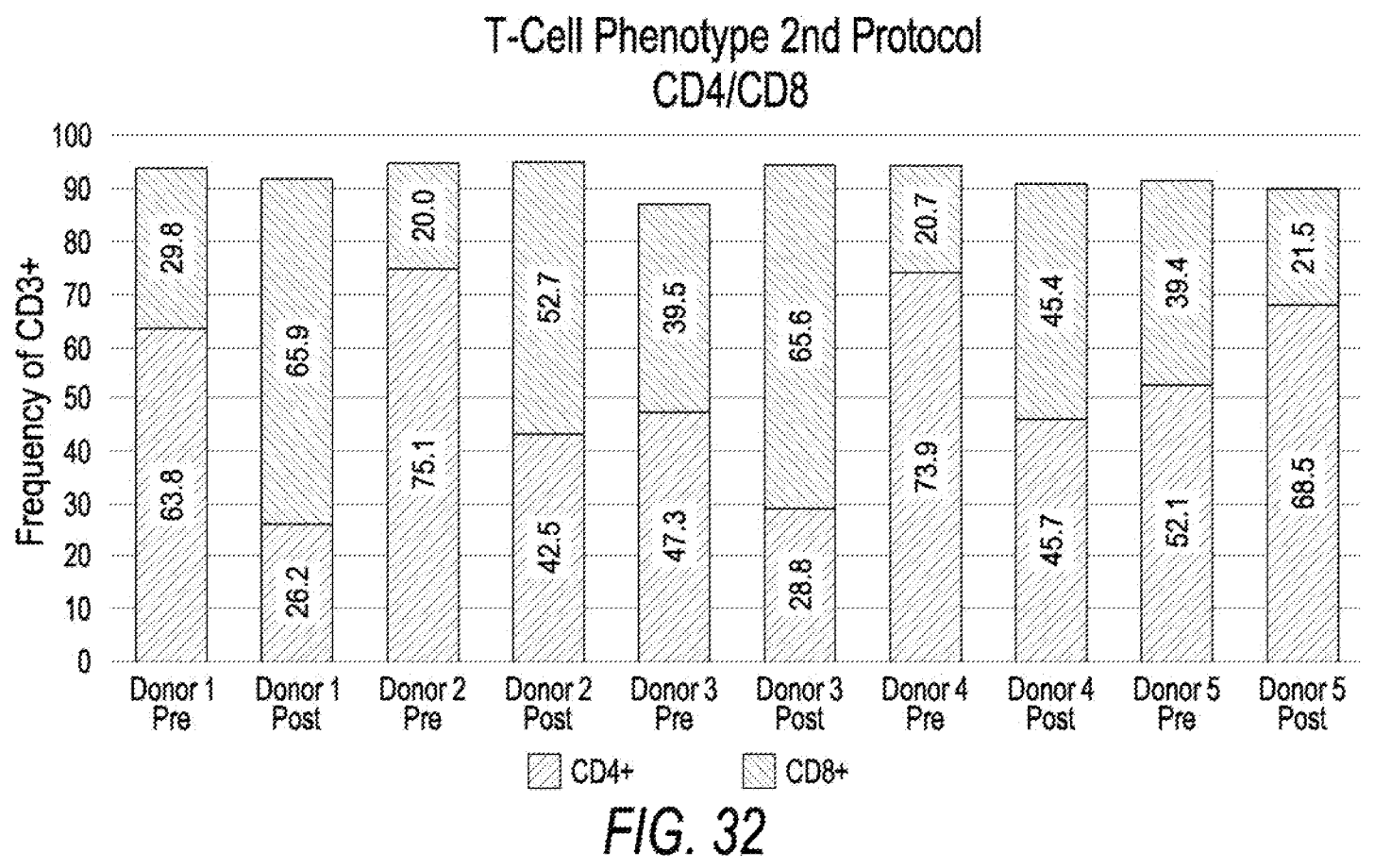
Figure 33:
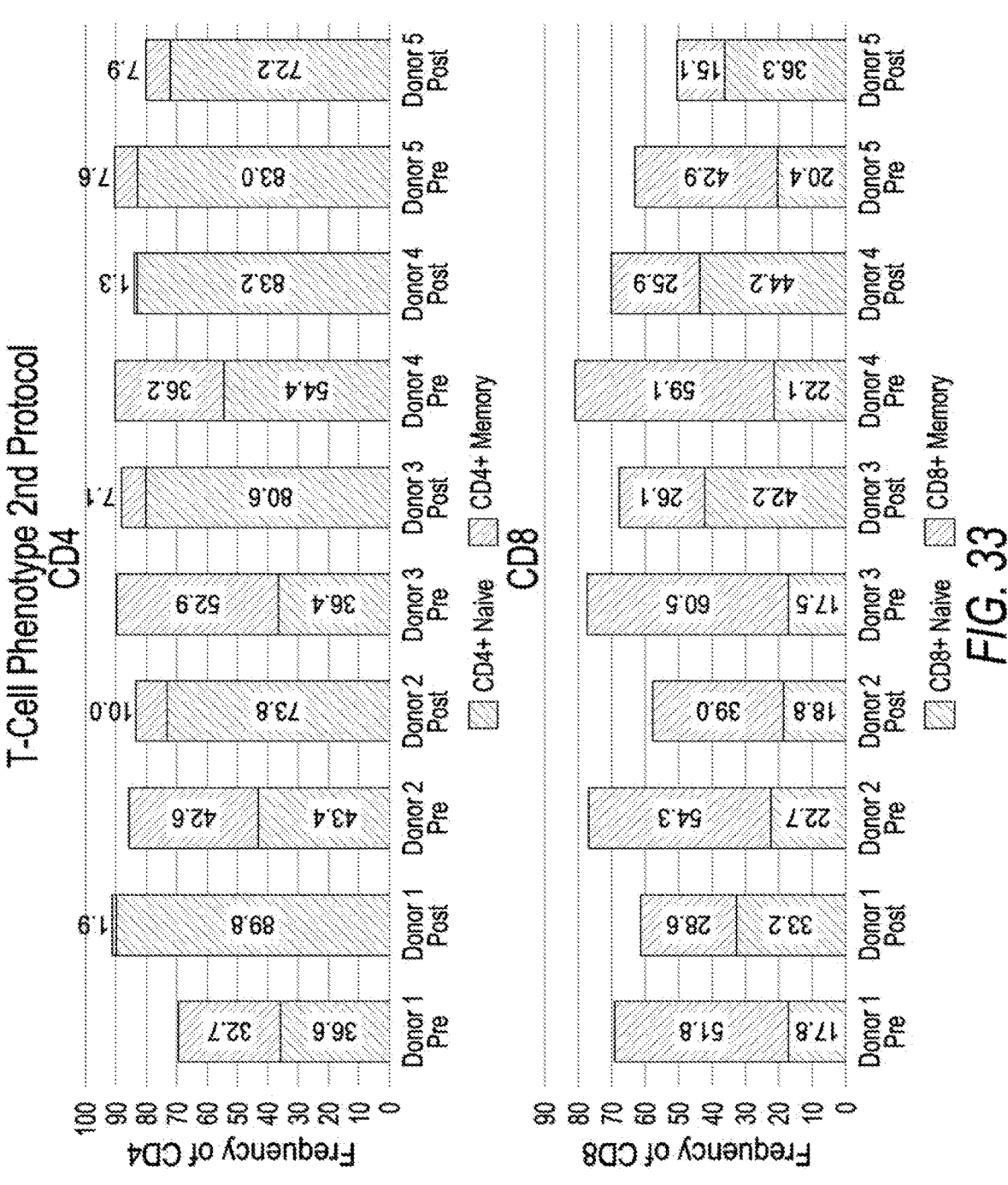
FIG. 33 illustrates a bar graph depicting cell phenotypes, in accordance with embodiments of the present disclosure.

FIGS. 32 and 33 illustrate the cell phenotype of cells expanded using Prime XV medium (Irvine Scientific), 30E+09 PBMCs seeded, and following the protocol described in Example 4. For each donor, "pre" may signify the phenotype of the cell population prior to expansion and "post" may signify the phenotype of the cell population after expansion.

Cell phenotype in the second protocol follows the same general trend as cells expanded using the first protocol T-cell expansion: % CD4+ of CD3+ decreases during expansion and % CD8+ of CD3+ increases during expansion.

The percent of CD4+ and CD8+ T-cells that are memory or naïve phenotype based on CD54RA/RO staining is a phenotype characterization that may not have been obtained for the first protocol and may provide additional granularity in describing the cells (FIG. 33).

At this time, there may be no acceptance criteria for phenotype characterization.

Figures 34, 35, 36:
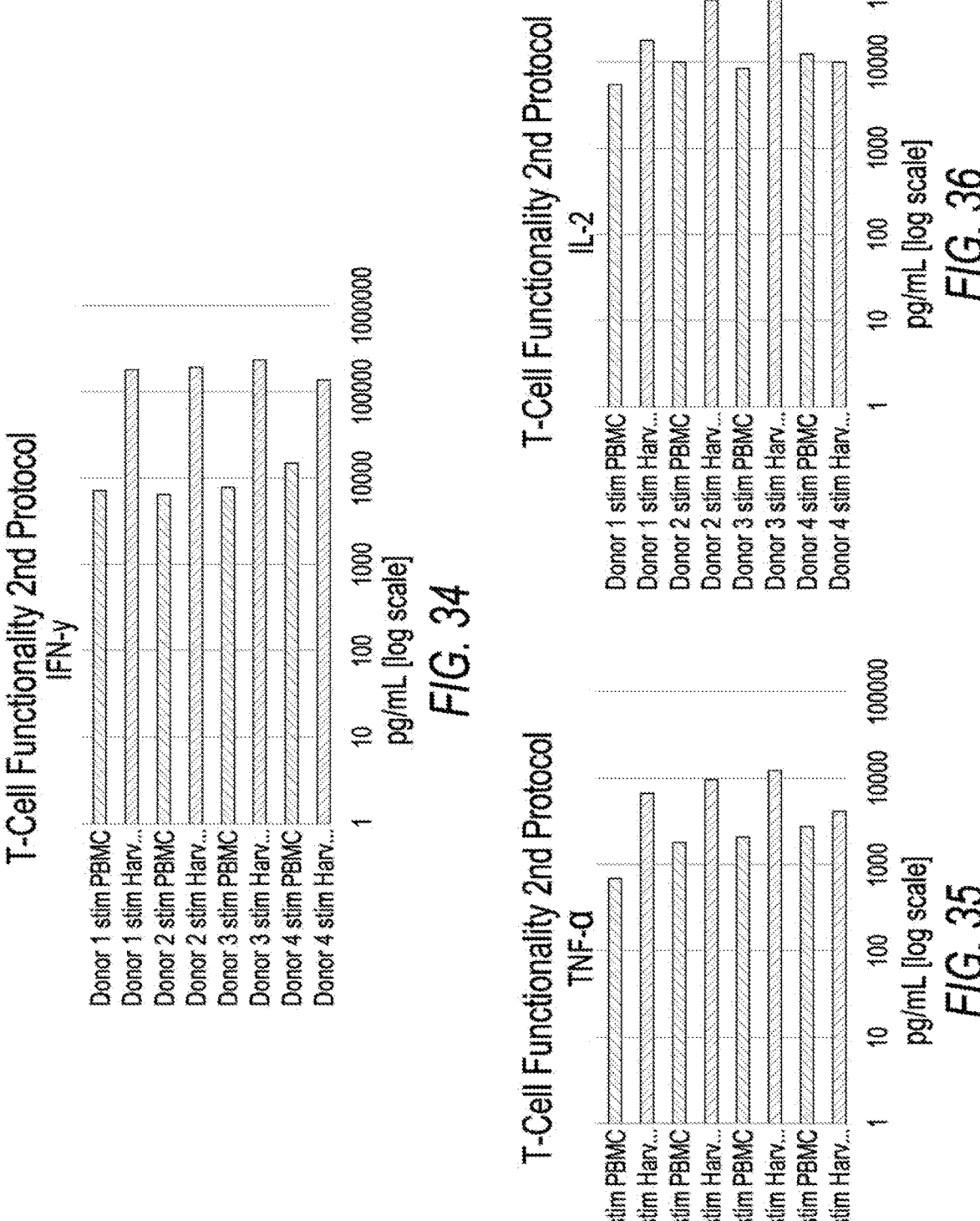
FIGS. 34-36 illustrate bar graphs depicting cell functionality, in accordance with embodiments of the present disclosure.
Figure 37:
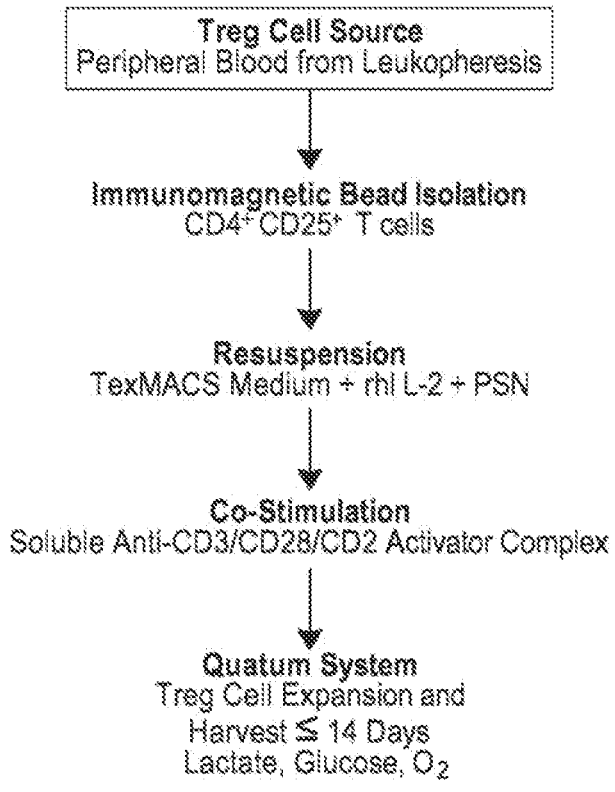
FIG. 37 illustrates an experimental flow example.

FIGS. 34-36 show the functionality of T-cells expanded using Prime XV medium (Irvine Scientific), 30E+09 PBMCs seeded, and following the protocol described in Example 4.

For each donor, "PBMC" may signify the cell population prior to expansion and "Harv" may signify the cell population after expansion.

T-cell functionality associated with a Th1/effector phenotype, is commonly measured by the ability to produce cytokines IFN-$\gamma$, TNF-$\alpha$, and IL-2. These results may demonstrate the T-cell populations produce higher levels of these cytokines after expansion and restimulation.

At this time there is no acceptance criteria for specific cytokine production levels.

Possible Results

T-cell expansion in the Quantum system may be significantly enhanced through process modifications such as maintaining the expanding cell population in the hollow fibers of the bioreactor, keeping lactate concentrations levels <15 mmol/L, and increasing the stimulation bead to cell ratio.

Using similar starting cell numbers, the average T-cell harvest yield may be increased by a factor of three in 40% less time. This is a 10-fold increase in proliferative capacity of the cells (based on comparing cell culture doubling times).

T-cells expanded using the second protocol may have similar phenotypic characteristics as those harvested from the first protocol and may be functionally viable cells.

T-cells can be expanded on the Quantum system using a variety of cell culture medium options; all may result in similar proliferation patterns.

T-cells can be expanded on the Quantum system from small PBMC starting products. 30E+06 PBMCs can be isolated from an average of 20 mL of whole blood from a healthy donor (Leukemia & Lymphoma Society). This may assume a 50% loss of cells during separation and another 50% loss during processing.

Example 4

The purpose of this example procedure may be to prepare T-cells for expansion in the Quantum system according to embodiments.
Equipment
    1. Laminar flow biosafety cabinet
    2. Water Bath
    3 Cell counting equipment (microscope, automated counter)
    4. Centrifuge
    5. Nutator (gentle cell mixing device)
Materials
    1. 50 mL centrifuge tube, polypropylene, sterile
    2. 60 mL syringe with male leur lock
    3. Cell Inlet Bag, 0.5 L, Accessory Set
Reagents
    1. Human AB Serum (hSER)
    2. Phosphate Buffered Saline (PBS)
    3. Dynabeads (CD3+/CD28+).
    4. Peripheral Blood Mononuclear Cells (PBMCs)
    5. Complete Media (see below)
    6. Base Media (see below)
Procedure
    A variety of culture media can be used to expand T-Cells on the Quantum system (see Table 24). This table is not to suggest these are the only possible media formulations that can be used on the Quantum system.

TABLE 24

| Culture Media Options | |
| --- | --- |
| Complete Media | Base Media |
| 1 Prime XV (Irvine Scientific) + 100 IU/mL IL-2 | Prime XV |
| 2 TexMACS (Miltenyl Biotech) + 100 IU/mL IL-2 | TexMACS |
| 3 Advanced RPMI (Gibco) + 2% Human AB Serum (hSER) + 100 IU/mL IL-2 + glutamine | Advances RPMI + glutamine |
| 4 RPMI 1640 + 5% Fetal Bovine Serum (FBS) + 100 IU/mL IL-2 + glutamine | RPMI 1650 + glutamine |
| 5 IMDM + 5% Fetal Bovine Serum (FBS) + 100 IU/mL IL-2 + glutamine | IMDM + glutamine |

Note: All open events must take place in the biosafety cabinet.
Dynabeads
    1. Dynabeads at a 2:1 bead to PBMC ratio for (80-120) E+06 PBMCs may be used.
    1a. Dynabeads at a 3:1 bead to PBMC ratio for 30E+06 PBMCs may be used.
    2. Dynabeads may be washed according to product insert.
    3. Beads may be resuspended in desired base medium.
Thawing PBMCs
    Note: For fresh PBMCs, begin at step 7.
    4. Thaw desired number of PBMCs.
    5. Upon removing cryotube vial(s) from liquid nitrogen, thaw vial(s) at 37° C. in a water bath, 6. Immediately, aseptically transfer cells to 50 mL centrifuge tube containing 10 mL PBS+5% hSER per vial thawed.
    7. Centrifuge at 300×g for 7 minutes.
    8. Discard liquid and resuspend cells in 10 mL PBS+5% hSER and perform cell count.
    9. Combine cells suspended in PBS and beads suspended in base medium to a concentration of (4-6)E+06 cells and beads per ml in a 50 mL centrifuge tube.
    Note: use base medium to dilute cell/bead mixture to proper concentration.
    10. Gently mix (stir, nutate, oscillate, etc.) cell/bead mixture for 10 min. at room temperature.
    11. Dilute cell/bead mixture to 50 mL using base medium.
    12. In biosafety cabinet, open cell inlet bag wrapping.
    13. Open 60 mL syringe wrapping.
    14. Remove syringe plunger and aseptically set aside.
    15. Remove blue luer cap from cell inlet bag line and firmly attach 60 mL syringe with luer-lock tip to cell inlet bag line.
    16. If using syringe as means of measuring, attach hemostat to cell inlet bag line below the syringe,
    17. While holding the syringe above the cell inlet bag, pour cells or reagent into the syringe.
    18. Allow cells to enter cell inlet bag by gravity flow.
    19. Introduce a minimum of 40 mL of air into the bag by gently pushing the plunger into the syringe.
    20. Leave plunger and syringe attached to cell inlet bag line.
    21. Use Quantum system protocol settings in Example 5 for (80-120) E+06 PBMC seed.
    22. Use Quantum system protocol settings in Example 6 for 30E+06 PBMC seed.

Example 5

The tables below provide example task settings (e.g., flow rates, angular rotation, outlet, etc.) for different components (e.g., pumps, rocker, valves, etc.) of a cell expansion system over several days of performing a protocol for the expansion of T cells. The protocol may follow the following sequence:
    Day 0: Load Set, Prime, Add Media, Load Cells, and begin feeding
    Day 2: Add a bolus of cytokines to the IC loop while re-distributing the cells. Begin feeding again.
    Day 3: Add a bolus of cytokines to the IC loop while re-distributing the cells. Begin feeding again. Add another bolus of cytokines to the IC loop while re-distributing the cells. Begin feeding again.
    Day 4: Add a bolus of cytokines to the IC loop while re-distributing the cells. Begin feeding again. Add another bolus of cytokines to the IC loop while re-distributing the cells. Begin feeding again.

Day 5: Add a bolus of cytokines to the IC loop while re-distributing the cells. Begin feeding again. Add another bolus of cytokines to the IC loop while re-distributing the cells. Begin feeding again.

Day 6: Add a bolus of cytokines to the IC loop while re-distributing the cells. Begin feeding again. Add another bolus of cytokines to the IC loop while re-distributing the cells. Begin feeding again.

Day 7: Add a bolus of cytokines to the IC loop while re-distributing the cells. Begin feeding again. Add another bolus of cytokines to the IC loop while re-distributing the cells. Begin feeding again.

Day 8: Harvest cells.

TABLE 25

| Settings Day 0, Example | | | | |
|---|---|---|---|---|
| | Cell Line | PBS | Cell Line | None |
| | IC Media Line | N/A | IC Media Line | Complete |
| | EC Media Line | N/A | EC Media Line | Base |
| | Reagent Line | N/A | Reagent Line | None |
| | Wash Line | N/A | Wash Line | None |

| Day 0 | | | | |
|---|---|---|---|---|
| | Load Expansion Set | Prime | IC EC washout | Condition media |
| | STEP 1 | STEP 2 | STEP 3 | STEP 4 |
| Task Settings | IC inlet | Default settings | Default settings | EC media | None |
| | IC inlet rate | | | 100 | 0 |
| | IC circ rate | | | −17 | 20 |

TABLE 25-continued

| Settings Day 0, Example | | | | | |
|---|---|---|---|---|---|
| | EC inlet | | | EC Media | None |
| | EC inlet rate | | | 148 | 0 |
| | EC circ rate | | | −1.7 | 30 |
| | Outlet | | | IC and EC outlet | EC outlet |
| | Rocker | | | In Motion (−90°, 180°, 1 sec) | Stationary (0°) |
| | Stop condition | | | Exchange (2.5 IC volume; 2.5 EC volume) | Manual (≥10 min) |
| Extra Information | Necessary IC media volume (ml) | 0 | 0 | 0 | 0 |
| | Total IC media consumed (ml) | 0 | 0 | 0 | 0 |
| | Necessary EC media volume (ml) | 0 | 0 | 1300 | |
| | Total EC media consumed (ml) | 0 | 0 | 1300 | 1300 |
| | Necessary reagent volume (ml) | | 1500 ml PBS | | |
| | Time (min) | 10 min | 35 min | 5 min | ≥10 min |

TABLE 26

| Settings Day 0-2, Example | |
|---|---|
| Cell Line | Cells |
| IC Media Line | Comple |
| EC Media Line | Base |
| Reagent Line | None |
| Wash Line | None |

| Day 0-2 | | | |
|---|---|---|---|
| Load cells (3E+07 PBMC) | Condition BR | | Feed cells |
| Custom 1 (load cells and feed for 2 days) | | | |
| Step 1 STEP 5 | Step 2 STEP 6 | Step 3 STEP 7 | Step 4 STEP 8 |

| | | Step 1 STEP 5 | Step 2 STEP 6 | Step 3 STEP 7 | Step 4 STEP 8 |
|---|---|---|---|---|---|
| Task Settings | IC inlet | Cell | IC Media | IC Media | IC Media |
| | IC inlet rate | 50 | 50 | 80 | 0.1 |
| | IC circ rate | 0 | 0 | 40 | −0.1 |
| | EC inlet | None | None | None | None |
| | EC inlet rate | 0 | 0 | 0 | 0 |

TABLE 26-continued

| | | | | | |
|---|---|---|---|---|---|
| | | Settings Day 0-2, Example | | | |
| | EC circ rate | 30 | 30 | 30 | 30 |
| | Outlet Rocker | IC outlet In Motion (−90°, 180°, 1 sec) | IC outlet In Motion (−90°, 180°, 1 sec) | IC outlet In Motion (−90°, 180°, 1 sec) | IC outlet Stationary (0°) |
| | Stop condtion | Empty bag | IC volume (50 mL) | IC Volume (310 mL) | Manual (2880 min) |
| Extra Information | Necessary IC media volume (ml) | 0 | 50 | 310 | 288 |
| | Total IC media consumed (ml) | 0 | 50 | 360 | 648 |
| | Necessary EC media volume (ml) | 0 | 0 | 0 | 0 |
| | Total EC media consumed (ml) | 1300 | 1300 | 1300 | 1300 |
| | Necessary reagent volume (ml) | | | | |
| | Time (min) | 1 min | 1 min | 4 min | 2 days |

TABLE 27

| | | | | |
|---|---|---|---|---|
| | | Settings Day 2, Example | | |
| | Cell Line | None | | |
| | IC Media Line | Complete | | |
| | EC Media Line | Base | | |
| | Reagent Line | None | | |
| | Wash Line | None | | |
| | | Day 2 | | |
| | | Cell Redistribution Custom 2 (1 cell redistribution) | | Feed cells |
| | | Step 1 STEP 9 | Step 2 STEP 10 | Step 3 STEP 11 |
| Task Settings | IC inlet | None | EC Media | IC Media |
| | IC inlet rate | 0 | 50 | 0.1 |
| | IC circ rate | 300 | −30 | −0.1 |
| | EC inlet | None | None | None |
| | EC inlet rate | 0 | 0 | 0 |
| | EC circ rate | 100 | 30 | 100 |
| | Outlet Rocker | EC outlet In Motion (−90°, 180°, 1 sec) | EC outlet In Motion (−90°, 180°, 1 sec) | EC outlet Stationary (0°) |
| | Stop condition | Time (4 min) | IC Volume (150 mL) | Manual (1440 min) |
| Extra Information | Necessary IC media volume (ml) | 0 | 0 | 144 |
| | Total IC media consumed (ml) | 648 | 648 | 792 |
| | Necessary EC media volume (ml) | 0 | 150 | 0 |
| | Total EC media consumed (ml) | 1300 | 1450 | 1450 |
| | Necessary reagent volume (ml) | | | |
| | Time (min) | 4 min | 1.5 min | 1 day |

TABLE 28

| Settings Day 3, Example | |
|---|---|
| Cell Line | None |
| IC Media Line | Complete |
| EC Media Line | Base |
| Reagent Line | None |
| Wash Line | None |

| | | Day 3 | | | | |
|---|---|---|---|---|---|---|
| | | Cell Redistribution | Feed Cells | Cell Redistribution | Feed Cells | |
| | | | Custom 3 (2 cell redistributions) | | | |
| | | STEP 12 | STEP 13 | STEP 14 | STEP 15 | STEP 16 | STEP 17 |

| | | STEP 12 | STEP 13 | STEP 14 | STEP 15 | STEP 16 | STEP 17 |
|---|---|---|---|---|---|---|---|
| Task Settings | IC inlet | None | EC Media | IC Media | None | EC Media | IC Media |
| | IC inlet rate | 0 | 50 | 0.4 | 0 | 50 | 0.4 |
| | IC circ rate | 300 | −30 | −0.2 | −300 | −30 | −0.2 |
| | EC inlet | None | None | EC media | None | None | EC media |
| | EC inlet rate | 0 | 0 | 0.2 | 0 | 0 | 0.2 |
| | EC circ rate | 300 | 30 | 300 | 300 | 30 | 300 |
| | Outlet | EC outlet | EC outlet | EC outlet | EC outlet | EC outlet | EC outlet |
| | Rocker | In Motion (−90°, 180°, 1 sec) | In Motion (−90°, 180°, 1 sec) | Stationary (0°) | In Motion (−90°, 180°, 1 sec) | In Motion (−90°, 180°, 1 sec) | Stationary (0°) |
| | Stop condition | Time (4 min) | IC Volume (150 mL) | Time (720 min) | Time (4 min) | IC Volume (150 mL) | Manual (720 min) |
| Extra Information | Necessary IC media volume (ml) | 0 | 0 | 288 | 0 | 0 | 288 |
| | Total IC media consumed (ml) | 792 | 792 | 1080 | 1080 | 1080 | 1368 |
| | Necessary EC media volume (ml) | 0 | 150 | 144 | 0 | 150 | 144 |
| | Total EC media consumed (ml) | 1450 | 1600 | 1744 | 1744 | 1894 | 2038 |
| | Necessary reagent volume (ml) | | | | | | |
| | Time (min) | 4 min | 1.5 min | 0.5 day | 4 min | 1.5 min | 0.5 day |

TABLE 29

| Settings Day 4, Example | |
|---|---|
| Cell Line | None |
| IC Media Line | Complete |
| EC Media Line | Base |
| Reagent Line | None |
| Wash Line | None |

| | | Day 4 | | | | |
|---|---|---|---|---|---|---|
| | | Cell Redistribution | Feed Cells | Cell Redistribution | Feed Cells | |
| | | | Custom 3 (2 cell redistributions) | | | |
| | | Step 1 STEP 18 | Step 2 STEP 19 | Step 3 STEP 20 | Step 4 STEP 21 | Step 5 STEP 22 | Step 6 STEP 23 |

| | | Step 1 STEP 18 | Step 2 STEP 19 | Step 3 STEP 20 | Step 4 STEP 21 | Step 5 STEP 22 | Step 6 STEP 23 |
|---|---|---|---|---|---|---|---|
| Task Settings | IC inlet | None | EC Media | IC MEdia | None | EC Media | IC Media |
| | IC inlet rate | 0 | 50 | 0.4 | 0 | 50 | 0.4 |
| | IC circ rate | 300 | −30 | −0.2 | −300 | −30 | −0.2 |
| | EC inlet | None | None | EC media | None | None | EC media |
| | EC inlet rate | 0 | 0 | 1.4 | 0 | 0 | 1.4 |
| | EC circ rate | 300 | 30 | 300 | 300 | 30 | 300 |
| | Outlet | EC outlet | EC outlet | EC outlet | EC outlet | EC outlet | EC outlet |
| | Rocker | In Motion (−90°, 180°, 1 sec) | In Motion (−90°, 180°, 1 sec) | Stationary (0°) | In Motion (−90°, 180°, 1 sec) | In Motion (−90°, 180°, 1 sec) | Stationary (0°) |
| | Stop condition | Time (4 min) | IC Volume (150 mL) | Time (720 min) | Time (4 min) | IC Volume (150 mL) | Manual (72 min) |

TABLE 29-continued

| | Settings Day 4, Example | | | | | |
|---|---|---|---|---|---|---|
| Extra Infor-mation | Necessary IC media volume (ml) | 0 | 0 | 288 | 0 | 0 | 288 |
| | Total IC media consumed (ml) | 1368 | 1368 | 1656 | 1656 | 1656 | 1944 |
| | Necessary EC media volume (ml) | 0 | 150 | 1008 | 0 | 150 | 1008 |
| | Total EC media consumed (ml) | 2038 | 2188 | 3196 | 3196 | 3346 | 4354 |
| | Necessary reagent volume (ml) | | | | | | |
| | Time (min) | 4 min | 1.5 min | 0.5 day | 4 min | 1.5 min | 0.5 day |

TABLE 30

| Settings Day 5, Example | |
|---|---|
| Cell Line | None |
| IC Media Line | Complete |
| EC Media Line | Base |
| Reagent Line | None |
| Wash Line | None |

| | | Day 5 | | | | | |
|---|---|---|---|---|---|---|---|
| | | Cell Redistribution | Feed cells | Cell Redistribution | Feed cells | | |
| | | Custom 3 (2 cell redistributions) | | | | | |
| | | Step 1 STEP 24 | Step 2 STEP 25 | Step 3 STEP 26 | Step 4 STEP 27 | Step 5 STEP 28 | Step 6 STEP 29 |
| Task Settings | IC inlet | None | EC Media | IC Media | None | EC Media | IC Media |
| | IC inlet rate | 0 | 50 | 0.4 | 0 | 50 | 0.4 |
| | IC circ rate | 300 | −30 | −0.2 | −300 | −30 | −0.2 |
| | EC inlet | None | None | EC media | None | None | EC media |
| | EC inlet rate | 0 | 0 | 2.8 | 0 | 0 | 2.8 |
| | EC circ rate | 300 | 30 | 300 | 300 | 30 | 300 |
| | Outlet | EC outlet | EC outlet | EC outlet | EC outlet | EC outlet | EC outlet |
| | Rocker | In Motion (−90°, 180°, 1 sec) | In Motion (−90°, 180°, 1 sec) | Stationary (0°) | In Motion (−90°, 180°, 1 sec) | In Motion (−90°, 180°, 1 sec) | Stationary (0°) |
| | Stop condition | Time (4 min) | IC Volume (150 mL) | Time (720 min) | Time (4 min) | IC Volume (150 mL) | |
| Extra Infor-mation | Necessary IC media volume (ml) | 0 | 0 | 288 | 0 | 0 | 288 |
| | Total IC media consumed (ml) | 1944 | 1944 | 2232 | 2232 | 2232 | 2520 |
| | Necessary EC media volume (ml) | 0 | 150 | 2016 | 0 | 150 | 2016 |
| | Total EC media consumed (ml) | 4354 | 4504 | 6520 | 6520 | 6670 | 8686 |
| | Necessary reagent volume (ml) | | | | | | |
| | Time (min) | 4 min | 1.5 min | 0.5 day | 4 min | 1.5 min | 0.5 day |

TABLE 31

| Settings Day 6, Example |
| --- |

| | |
| --- | --- |
| Cell Line | None |
| IC Media Line | Complete |
| EC Media Line | Base |
| Reagent Line | None |
| Wash Line | None |

| Day 6 | | | | | |
| --- | --- | --- | --- | --- | --- |
| Cell Redistribution | | Feed Cells | Cell Redistribution | | Feed Cells |
| Custom 3 (2 cell redistributions) | | | | | |
| Step 1 STEP 30 | Step 2 STEP 31 | Step 3 STEP 32 | Step 4 STEP 33 | Step 5 STEP 34 | Step 6 STEP 35 |

| | | Step 1 STEP 30 | Step 2 STEP 31 | Step 3 STEP 32 | Step 4 STEP 33 | Step 5 STEP 34 | Step 6 STEP 35 |
| --- | --- | --- | --- | --- | --- | --- | --- |
| Task Settings | IC inlet | None | EC Media | IC Media | None | EC Media | IC Media |
| | IC inlet rate | 0 | 50 | 0.4 | 0 | 50 | 0.4 |
| | IC circ rate | 300 | −30 | −0.2 | −300 | −30 | −0.2 |
| | EC inlet | None | None | EC media | None | None | EC media |
| | EC inlet rate | 0 | 0 | 2.8 | 0 | 0 | 2.8 |
| | EC circ rate | 300 | 30 | 300 | 300 | 30 | 300 |
| | Outlet | EC outlet | EC outlet | EC outlet | EC outlet | EC outlet | EC outlet |
| | Rocker | In Motion (−90°, 180°, 1 sec) | In Motion (−90°, 180°, 1 sec) | Stationary (0°) | In Motion (−90°, 180°, 1 sec) | In Motion (−90°, 180°, 1 sec) | Stationary (0°) |
| | Stop condition | Time (4 min) | IC Volume (150 mL) | Time (720 min) | Time (4 min) | IC Volume (150 ml) | Manual (720 min) |
| Extra Information | Necessary IC media volume (ml) | 0 | 0 | 288 | 0 | 0 | 288 |
| | Total IC media consumed (ml) | 2520 | 2520 | 2808 | 2808 | 2808 | 3096 |
| | Necessary EC media volume (ml) | 0 | 150 | 2016 | 0 | 150 | 2016 |
| | Total EC media consumed (ml) | 8686 | 8836 | 10852 | 10852 | 11002 | 13018 |
| | Necessary reagent volume (ml) | | | | | | |
| | Time (min) | 4 min | 1.5 min | 0.5 day | 4 min | 1.5 min | 0.5 day |

TABLE 32

| Settings Day 7, Example |
| --- |

| | |
| --- | --- |
| Cell Line | None |
| IC Media Line | Complete |
| EC Media Line | Base |
| Reagent Line | None |
| Wash Line | None |

| Day 7 | | | | | |
| --- | --- | --- | --- | --- | --- |
| Cell Redistribution | | Feed cells | Cell Redistribution | | Feed cells |
| Custom 3 (2 cell redistributions) | | | | | |
| Step 1 STEP 36 | Step 2 STEP 37 | Step 3 STEP 38 | Step 4 STEP 39 | Step 5 STEP 40 | Step 6 STEP 41 |

| | | Step 1 STEP 36 | Step 2 STEP 37 | Step 3 STEP 38 | Step 4 STEP 39 | Step 5 STEP 40 | Step 6 STEP 41 |
| --- | --- | --- | --- | --- | --- | --- | --- |
| Task Settings | IC inlet | None | EC Media | IC Media | None | EC Media | IC Media |
| | IC inlet rate | 0 | 50 | 0.4 | 0 | 50 | 0.4 |
| | IC circ rate | 300 | −30 | −0.2 | −300 | −30 | −0.2 |
| | EC inlet | None | None | EC media | None | None | EC media |
| | EC inlet rate | 0 | 0 | 2.5 | 0 | 0 | 2.5 |
| | circ rate | 300 | 30 | 300 | 300 | 30 | 300 |

TABLE 32-continued

| | | EC outlet In Motion (−90°, 180°, 1 sec) | EC outlet In Motion (−90°, 180°, 1 sec) | EC outlet Stationary (0°) | EC outlet In Motion (−90°, 180°, 1 sec) | EC outlet In Motion (−90°, 180°, 1 sec) | EC outlet Stationary (0°) |
|---|---|---|---|---|---|---|---|
| | Outlet Rocker | | | | | | |
| | Stop condition | Time (4 min) | IC Volume (150 mL) | Time (720 min) | Time (4 min) | IC Volume (150 mL) | Manual (720 min) |
| Extra Information | Necessary IC media volume (ml) | 0 | 0 | 288 | 0 | 0 | 288 |
| | Total IC media consumed (ml) | 3096 | 3096 | 3384 | 3384 | 3384 | 3672 |
| | Necessary EC media volume (ml) | 0 | 150 | 1800 | 0 | 150 | 1800 |
| | Total EC media consumed (ml) | 13018 | 13168 | 14968 | 14968 | 15118 | 16918 |
| | Necessary reagent volume (ml) | | | | | | |
| | Time (min) | 4 min | 1.5 min | 0.5 day | 4 min | 1.5 min | 0.5 day |

TABLE 33

Settings Day 8, Example

| | |
|---|---|
| Cell Line | None |
| IC Media Line | None |
| EC Media Line | None |
| Reagent Line | None |
| Wash Line | None |

Day 8-Harvest
Harvest
Custom 4 (Harvest)

| | | Step 1 STEP 42 | Step 2 STEP 43 |
|---|---|---|---|
| Task Settings | IC inlet | None | EC media |
| | IC inlet rate | 0 | 100 |
| | IC circ rate | 300 | −20 |
| | EC inlet | None | EC Media |
| | EC inlet rate | 0 | 60 |
| | EC circ rate | 300 | 30 |
| | Outlet | EC outlet | Harvest |
| | Rocker | In Motion (−90°, 180°, 1 sec) | In Motion (−90°, 180°, 1 sec) |
| | Stop condition | Time (4 min) | IC Volume (400 mL) |
| Extra Information | Necessary IC media volume (ml) | 0 | 0 |
| | Total IC media consumed (ml) | 3672 | 3672 |
| | Necessary EC media volume (ml) | 0 | 640 |
| | Total EC media consumed (ml) | 16918 | 17558 |

TABLE 33-continued

Settings Day 8, Example

| | |
|---|---|
| Necessary reagent volume (ml) | |
| Time (min) | 10 min |

Example 6

The tables below provide example task settings (e.g., flow rates, angular rotation, outlet, etc.) for different components (e.g., pumps, rocker, values, etc.) of a cell expansion system over several days of performing another example protocol for the expansion of T cells. The protocol may follow the following sequence:

Day 0: Load Set, Prime, Add Media, Load Cells, and begin feeding

Day 2: Add a bolus of cytokines to the IC loop while re-distributing the cells. Begin feeding again.

Day 3: Add a bolus of cytokines to the IC loop while re-distributing the cells. Begin feeding again.

Day 4: Add a bolus of cytokines to the IC loop while re-distributing the cells. Begin feeding again.

Day 5: Add a bolus of cytokines to the IC loop while re-distributing the cells. Begin feeding again.

Day 6: Add a bolus of cytokines to the IC loop while re-distributing the cells. Begin feeding again. Add another bolus of cytokines to the IC loop while re-distributing the cells. Begin feeding again.

Day 7: Add a bolus of cytokines to the IC loop while re-distributing the cells. Begin feeding again. Add another bolus of cytokines to the IC loop while re-distributing the cells. Begin feeding again.

Day 8: Add a bolus of cytokines to the IC loop while re-distributing the cells Begin feeding again. Add another bolus of cytokines to the IC loop while re-distributing the cells. Begin feeding again.

Day 9: Harvest cells.

TABLE 34

| Settings Day 0, Example | | | |
| --- | --- | --- | --- |
| Cell Line | PBS | Cell Line | None |
| IC Media Line | N/A | IC Media Line | Complete |
| EC Media Line | N/A | EC Media Line | Base |
| Reagent Line | N/A | Reagent Line | None |
| Wash Line | N/A | Wash Line | None |

| Day 0 | | | |
| --- | --- | --- | --- |
| Load Expansion Set | Prime | IC EC washout | Conditon media |

| | | STEP 1 | STEP 2 | STEP 3 | STEP 4 |
| --- | --- | --- | --- | --- | --- |
| Task Settings | IC inlet | Default settings | Default settings | EC media | None |
| | IC inlet rate | | | 100 | 0 |
| | IC circ rate | | | −17 | 20 |
| | EC inlet | | | EC Media | None |
| | EC inlet rate | | | 148 | 0 |
| | EC circ rate | | | −1.7 | 30 |
| | Outlet | | | IC and EC outlet | EC outlet |

TABLE 34-continued

| Settings Day 0, Example | | | | | |
| --- | --- | --- | --- | --- | --- |
| | Rocker | | | In Motion (−90°, 180°, 1 sec) | Stationary (0°) |
| | Stop condition | | | Exchange (2.5 IC volume; 2.5 EC volume) | Manual (≥10 min) |
| Extra Information | Necessary IC media volume (ml) | 0 | 0 | 0 | 0 |
| | Total IC media consumed (ml) | 0 | 0 | 0 | 0 |
| | Necessary EC media volume (ml) | 0 | 0 | 1300 | |
| | Total EC media consumed (ml) | 0 | 0 | 1300 | 1300 |
| | Necessary reagent volume (ml) | | 1500 ml PBS | | |
| | Time (min) | 10 min | 35 min | 5 min | ≥10 min |

TABLE 35

| Settings Day 0-2, Example |
| --- |
| Cell Line    Cells |
| IC Media Line    Complete |
| EC Media Line    Base |
| Reagent Line    None |
| Wash Line    None |

| Day 0-2 | | | |
| --- | --- | --- | --- |
| Load cells (3E+07 PBMC) | | Condition BR | Feed cells |
| Custom 1 (load cells and feed for 2 days) | | | |

| | | Step 1 STEP 5 | Step 2 STEP 6 | Step 3 STEP 7 | Step 4 STEP 8 |
| --- | --- | --- | --- | --- | --- |
| Task Settings | IC inlet | Cell | IC Media | IC Media | IC Media |
| | IC inlet rate | 50 | 50 | 80 | 0.1 |
| | IC circ rate | 0 | 0 | −40 | −0.1 |
| | EC inlet | None | None | None | None |
| | EC inlet rate | 0 | 0 | 0 | 0 |
| | EC circ rate | 30 | 30 | 30 | 30 |
| | Outlet | IC outlet | IC outlet | EC outlet | EC outlet |
| | Rocker | In Motion (−90°, 180°, 1 sec) | In Motion (−90°, 180°, 1 sec) | In Motion (−90°, 180°, 1 sec) | Stationary (0°) |
| | Stop condition | Empty bag | IC volume (65 ml) | IC Volume (295 mL) | Manual (2880 min) |
| Extra Information | Necessary IC media volume (ml) | 0 | 65 | 295 | 288 |
| | Total IC media consumed (ml) | 0 | 65 | 360 | 648 |

TABLE 35-continued

| | | | | | |
|---|---|---|---|---|---|
| | Settings Day 0-2, Example | | | | |
| Necessary EC media volume (ml) | 0 | 0 | 0 | 0 | |
| Total EC media consumed (ml) | 1300 | 1300 | 1300 | 1300 | |
| Necessary reagent volume (ml) | | | | | |
| Time (min) | 1 min | 1 min | 4 min | 2 days | |

TABLE 36

| | | Settings Day 2, Example | | |
|---|---|---|---|---|
| | | Cell Line | None | |
| | | IC Media Line | Complete | |
| | | EC Media Line | Base | |
| | | Reagent Line | None | |
| | | Wash Line | None | |

| | | Day 2 | | |
|---|---|---|---|---|
| | | Cell Redistribution | Feed cells | |
| | | Custom 2 (1 cell redistribution) | | |
| | | Step 1 STEP 9 | Step 2 STEP 10 | Step 3 STEP 11 |
| Task Settings | IC inlet | None | EC Media | IC Media |
| | IC inlet rate | 0 | 50 | 0.1 |
| | IC circ rate | 300 | −30 | −0.1 |
| | EC inlet | None | None | None |
| | EC inlet rate | 0 | 0 | 0 |
| | EC circ rate | 100 | 30 | 100 |
| | Outlet | EC outet | EC outlet | EC outlet |
| | Rocker | In Motion (−90°, 180°, 1 sec) | In Motion (−90°, 180°, 1 sec) | Stationary (0°) |
| | Stop condition | Time (4 min) | IC Volumne (150 mL) | Manual (1440 min) |
| Extra Information | Necessary IC media volume (ml) | 0 | 0 | 144 |
| | Total IC media consumed (ml) | 648 | 648 | 792 |
| | Necessary EC media volume (ml) | 0 | 150 | 0 |
| | Total EC media consumed (ml) | 1300 | 1450 | 1450 |
| | Necessary reagent volume (ml) | | | |
| | Time (min) | 4 min | 1.5 min | 1 day |

TABLE 37

| | | Settings Day 3, Example | | |
|---|---|---|---|---|
| | | Cell Line | None | |
| | | IC Media Line | Complete | |
| | | EC Media Line | Base | |
| | | Reagent Line | None | |
| | | Wash Line | None | |

| | | Day 3 | | |
|---|---|---|---|---|
| | | Cell Redistribution | Feed cells | |
| | | Custom 2 (1 cell redistribution) | | |
| | | Step 1 STEP 12 | Step 2 STEP 13 | Step 3 STEP 14 |
| Task Settings | IC inlet | None | EC Media | IC Media |
| | IC inlet rate | 0 | 50 | 0.1 |
| | IC circ rate | 300 | −30 | −0.1 |
| | EC inlet | None | None | None |
| | EC inlet rate | 0 | 0 | 0 |
| | EC circ rate | 100 | 30 | 100 |
| | Outlet | EC outlet | EC outlet | EC outlet |
| | Rocker | In Motion (−90°, 180°, 1 sec) | In Motion (−90°, 180°, 1 sec) | Stationary (0°) |
| | Stop conditon | Time (4 min) | IC Volume (150 mL) | Manual (1440 min) |
| Extra Information | Necessary IC media volume (ml) | 0 | 0 | 144 |
| | Total IC media consumed (ml) | 792 | 792 | 936 |
| | Necessary EC media volume (ml) | 0 | 150 | 0 |
| | Total EC media consumed (ml) | 1450 | 1600 | 1600 |
| | Necessary reagent volume (ml) | | | |
| | Time (min) | 4 min | 1.5 min | 1 day |

101

TABLE 38

Settings Day 4, Example

| | |
|---|---|
| Cell Line | None |
| IC Media Line | Complete |
| EC Media Line | Base |
| Reagent Line | None |
| Wash Line | None |

| | Day 4 | | |
|---|---|---|---|
| | Cell Redistribution | Feed cells | |
| | Custom 2 (1 cell redistribution) | | |
| | Step 1 STEP 15 | Step 2 STEP 16 | Step 3 STEP 17 |
| Task Settings | | | |
| IC inlet | None | EC Media | IC Media |
| IC inlet rate | 0 | 50 | 0.1 |
| IC circ rate | 300 | −30 | −0.1 |
| EC inlet | None | None | None |
| EC inlet rate | 0 | 0 | 0 |
| EC circ rate | 100 | 30 | 100 |
| Outlet | EC outlet | EC outlet | EC outlet |
| Rocker | In Motion (−90°, 180°, 1 sec) | In Motion (−90°, 180°, 1 sec) | Stationary (0°) |
| Stop condition | Time (4 min) | IC Volumne (150 mL) | Manual (1440 min) |
| Extra Information | | | |
| Necessary IC media volume (ml) | 0 | 0 | 144 |
| Total IC media consumed (ml) | 936 | 936 | 1080 |
| Necessary EC media volume (ml) | 0 | 150 | 0 |
| Total EC media consumed (ml) | 1600 | 1750 | 1750 |
| Necessary reagent volume (ml) | | | |
| Time (min) | 4 min | 1.5 min | 1 day |

102

TABLE 39

Settings Day 5, Example

| | |
|---|---|
| Cell Line | None |
| IC Media Line | Complete |
| EC Media Line | Base |
| Reagent Line | None |
| Wash Line | None |

| | Day 5 | | |
|---|---|---|---|
| | Cell Redistribution | Feed cells | |
| | Custom 2 (1 cell redistribution) | | |
| | Step 1 STEP 18 | Step 2 STEP 19 | Step 3 STEP 20 |
| Task Settings | | | |
| IC inlet | None | EC Media | IC Media |
| IC inlet rate | 0 | 50 | 0.4 |
| IC circ rate | −300 | −30 | −0.2 |
| EC inlet | None | None | None |
| EC inlet rate | 0 | 0 | 0 |
| EC circ rate | 100 | 30 | 100 |
| Outlet | EC outlet | EC outlet | EC outlet |
| Rocker | In Motion (−90°, 180°, 1 sec) | In Motion (−90°, 180°, 1 sec) | Stationary (0°) |
| Stop condition | Time (4 min) | IC Volume (150 mL) | Manual (1440 min) |
| Extra Information | | | |
| Necessary IC media volume (ml) | 0 | 0 | 576 |
| Total IC media consumed (ml) | 1080 | 1080 | 1656 |
| Necessary EC media volume (ml) | 0 | 150 | 0 |
| Total EC media consumed (ml) | 1750 | 1900 | 1900 |
| Necessary reagent volume (ml) | | | |
| Time (min) | 4 min | 1.5 min | 1 day |

TABLE 40

Settings Day 6, Example

| | |
|---|---|
| Cell Line | None |
| IC Media Line | Complete |
| EC Media Line | Base |
| Reagent Line | None |
| Wash Line | None |

| | | Day 6 | | | | |
|---|---|---|---|---|---|---|
| | | Cell Redistribution | Feed cells | Cell Redistribution | Feed cells | |
| | | Custom 3 (2 cell redistributions) | | | | |
| | | Step 1 STEP 21 | Step 2 STEP 22 | Step 3 STEP 23 | Step 4 STEP 24 | Step 5 STEP 25 | Step 6 STEP 26 |
| Task Settings | IC inlet | None | EC Media | IC Media | None | EC Media | IC Media |
| | IC inlet rate | 0 | 50 | 0.4 | 0 | 50 | 0.4 |
| | IC circ rate | 300 | −30 | −0.2 | −300 | −30 | −0.2 |
| | EC inlet | None | None | EC media | None | None | EC media |

TABLE 40-continued

| | | | | | | | |
|---|---|---|---|---|---|---|---|
| | | Settings Day 6, Example | | | | | |
| | EC inlet rate | 0 | 0 | 0.8 | 0 | 0 | 0.8 |
| | EC circ rate | 300 | 30 | 300 | 300 | 30 | 300 |
| | Outlet | EC outlet | EC outlet | EC outlet | EC outlet | EC outlet | EC outlet |
| | Rocker | In Motion (−90°, 180°, 1 sec) | In Motion (−90°, 180°, 1 sec) | Stationary (0°) | In Motion (−90°, 180°, 1 sec) | In Motion (−90°, 180°, 1 sec) | Stationary (0°) |
| | Stop condition | Time (4 min) | IC Volume (150 ml) | Time (720 min) | Time (4 min) | IC Volume (150 mL) | Manual (720 min) |
| Extra Information | Necessary IC media volume (ml) | 0 | 0 | 288 | 0 | 0 | 288 |
| | Total IC media consumed (ml) | 1656 | 1656 | 1944 | 1944 | 1944 | 2232 |
| | Necessary EC media volume (ml) | 0 | 150 | 576 | 0 | 150 | 576 |
| | Total EC media consumed (ml) | 1900 | 2050 | 2626 | 2626 | 2776 | 3352 |
| | Necessary reagent volume (ml) | | | | | | |
| | Time (min) | 4 min | 1.5 min | 0.5 day | 4 min | 1.5 min | 0.5 day |

TABLE 41

| | |
|---|---|
| Settings Day 7, Example | |
| Cell Line | None |
| IC Media Line | Complete |
| EC Media Line | Base |
| Reagent Line | None |
| Wash Line | None |

| | | Day 7 | | | | | |
|---|---|---|---|---|---|---|---|
| | | Cell Redistribution | | Feed cells | Cell Redistribution | | Feed cells |
| | | Custom 3 (2 cell redistributions) | | | | | |
| | | Step 1 STEP 27 | Step 2 STEP 28 | Step 3 STEP 29 | Step 4 STEP 30 | Step 5 STEP 31 | Step 6 STEP 32 |
| Task Settings | IC inlet | None | EC Media | IC Media | None | EC Media | IC Media |
| | IC inlet rate | 0 | 50 | 0.4 | 0 | 50 | 0.4 |
| | IC circ rate | 300 | −30 | −0.2 | −300 | −30 | −0.2 |
| | EC inlet | None | None | EC media | None | None | EC media |
| | EC inlet rate | 0 | 0 | 2 | 0 | 0 | 2 |
| | EC circ rate | 300 | 30 | 300 | 300 | 30 | 300 |
| | Outlet | EC outlet | EC outlet | EC outlet | EC outlet | EC outlet | EC outlet |
| | Rocker | In Motion (−90°, 180°, 1 sec) | In Motion (−90°, 180°, 1 sec) | Stationary (0°) | In Motion (−90°, 180°, 1 sec) | In Motion (−90°, 180°, 1 sec) | Stationary (0°) |
| | Stop condition | Time (4 min) | IC Volume (150 mL) | Time (720 min) | Time (4 min) | IC Volume (150 mL) | Manual (720 min) |
| Extra Information | Necessary IC media volume (ml) | 0 | 0 | 288 | 0 | 0 | 288 |
| | Total IC media consumed (ml) | 2232 | 2232 | 2520 | 2520 | 2520 | 2808 |
| | Necessary EC media volume (ml) | 0 | 150 | 1440 | 0 | 150 | 1440 |
| | Total EC media consumed (ml) | 3352 | 3502 | 4942 | 4942 | 5092 | 6532 |
| | Necessary reagent volume (ml) | | | | | | |
| | Time (min) | 4 min | 1.5 min | 0.5 day | 4 min | 1.5 min | 0.5 day |

TABLE 42

| Settings Day 8, Example | |
|---|---|
| Cell Line | None |
| IC Media Line | Complete |
| EC Media Line | Base |
| Reagent Line | None |
| Wash Line | None |

| | | Day 8 | | | | |
|---|---|---|---|---|---|---|
| | | Cell Redistribution | Feed cells | Cell Redistribution | Feed cells | |
| | | Custom 3 (2 cell redistributions) | | | | |
| | | Step 1 STEP 33 | Step 2 STEP 34 | Step 3 STEP 35 | Step 4 STEP 36 | Step 5 STEP 37 | Step 6 STEP 38 |

| | | Step 1 STEP 33 | Step 2 STEP 34 | Step 3 STEP 35 | Step 4 STEP 36 | Step 5 STEP 37 | Step 6 STEP 38 |
|---|---|---|---|---|---|---|---|
| Task Settings | IC inlet | None | EC Media | IC Media | None | EC Media | IC Media |
| | IC inlet rate | 0 | 50 | 0.4 | 0 | 50 | 0.4 |
| | IC circ rate | 300 | −30 | −0.2 | −300 | −30 | −0.2 |
| | EC inlet | None | None | EC media | None | None | EC media |
| | EC inlet rate | 0 | 0 | 2.5 | 0 | 0 | 2.5 |
| | EC circ rate | 300 | 30 | 300 | 300 | 30 | 300 |
| | Outlet | EC outlet | EC outlet | EC outlet | EC outlet | EC outlet | EC outlet |
| | Rocker | In Motion (−90°, 180°, 1 sec) | In Motion (−90°, 180°, 1 sec) | Stationary (0°) | In Motion (−90°, 180°, 1 sec) | In Motion (−90°, 180°, 1 sec) | Stationary (0°) |
| | Stop condition | Time (4 min) | IC Volume (150 mL) | Time (720 min) | Time (4 min) | IC Volume (150 mL) | Manual (720 min) |
| Extra Information | Necessary IC media volume (ml) | 0 | 0 | 288 | 0 | 0 | 288 |
| | Total IC media consumed (ml) | 2808 | 2808 | 3096 | 3096 | 3096 | 3384 |
| | Necessary EC media volume (ml) | 0 | 150 | 1800 | 0 | 150 | 1800 |
| | Total EC media consumed (ml) | 6532 | 6682 | 8482 | 8482 | 8632 | 10432 |
| | Necessary reagent volume (ml) | | | | | | |
| | Time (min) | 4 min | 1.5 min | 0.5 day | 4 min | 1.5 min | 0.5 day |

TABLE 43

| Settings Day 9, Example | |
|---|---|
| Cell Line | None |
| IC Media Line | Complete |
| EC Media Line | Base |
| Reagent Line | None |
| Wash Line | None |

| | | Day 9-Harvest | |
|---|---|---|---|
| | | Harvest | |
| | | Custom 4 (Harvest) | |
| | | Step 1 STEP 39 | Step 2 STEP 40 |
| Task Settings | IC inlet | None | EC media |
| | IC inlet rate | 0 | 100 |
| | IC circ rate | 300 | −20 |
| | EC inlet | None | EC Media |
| | EC inlet rate | 0 | 60 |
| | EC circ rate | 300 | 30 |
| | Outlet | EC outlet | Harvest |
| | Rocker | In Motion (−90°, 180°, 1 sec) | In Motion (−90°, 180°, 1 sec) |

TABLE 43-continued

| Settings Day 9, Example | | | |
|---|---|---|---|
| Extra Information | Stop condition | Time (4 min) | IC Volume (400 mL) |
| | Necessary IC media volume (ml) | 0 | 0 |
| | Total IC media consumed (ml) | 3384 | 3384 |
| | Necessary EC media volume (ml) | 0 | 640 |
| | Total EC media consumed (ml) | 10432 | 11072 |
| | Necessary reagent volume (ml) | | |
| | Time (min) | | 10 min |

It will be apparent to those skilled in the art that various modifications and variations may be made to the methods and structure of the present invention without departing from its scope. Thus, it should be understood that the invention is not to be limited to the specific examples given. Rather, the invention is intended to cover modifications and variations within the scope of the following claims and their equivalents.

What is claimed is:

1. A cell expansion system comprising:
a bioreactor having a first port and a second port, the first port and the second port being positioned on opposing ends of the bioreactor;
a first fluid flow path having a first end fluidly associated with the first port of the bioreactor and a second end fluidly associated with the second port of the bioreactor;
a first pump configured to circulate fluid in the first fluid flow path;
a first fluid circulation path fluidly associated with the first fluid flow path and with the bioreactor;
a second pump configured to circulate fluid in the first fluid circulation path; and
a controller configured to:
direct a loading of cells into the bioreactor;
control a first feeding of the fluid to the cells in the bioreactor, the fluid including media;
after the first feeding, control activation of the second pump to circulate the cells at a first circulation rate for a first time period to cause a first redistribution of the cells;
control a second feeding of the fluid to the cells in the bioreactor, the fluid including media;
after the second feeding, control activation of the second pump to circulate the cells at the first circulation rate for a second time period to cause a second redistribution of the cells; and
control a harvesting of expanded cells,
wherein the first feeding of the fluid to the cells includes:
controlling activation of the first pump to move a first portion of the fluid in a first direction and at a first fluid flow rate; and
controlling activation of the second pump to move a second portion of the fluid in a second direction and at a second fluid flow rate, the second direction being opposite the first direction, and
wherein the second feeding of the fluid to the cells includes:
controlling activation of the first pump to move a third portion of the fluid in the first direction and at a third fluid flow rate; and
controlling activation of the second pump to move a fourth portion of the fluid in the second direction and at a fourth fluid flow rate.

2. The cell expansion system of claim 1, wherein the controller is configured to control a third feeding of the fluid to the cells in the bioreactor.

3. The cell expansion system of claim 1, wherein the cells include peripheral blood mononuclear cells (PBMC).

4. The cell expansion system of claim 1, wherein the expanded cells include one or more subpopulations of T cells including effector, memory, helper, naïve, and combinations thereof.

5. The cell expansion system of claim 1, wherein at least 90% of the expanded cells include cells that express CD3+.

6. The cell expansion system of claim 1, wherein at least 50% of the expanded cells include cells that express CD4+.

7. The cell expansion system of claim 1, wherein at least 30% of the expanded cells include cells that express CD8+.

8. The cell expansion system of claim 1, wherein the cells are exposed to an activator prior to the loading of the cells into the bioreactor.

9. The cell expansion system of claim 8, wherein the activator is located on beads.

10. The cell expansion system of claim 1, wherein the fluid includes glucose.

11. The cell expansion system of claim 10, wherein the glucose in the fluid is maintained at a level that is at least 50% of a starting concentration in the fluid.

12. A cell expansion system comprising:
a bioreactor having a first port and a second port, the first port and the second port being positioned on opposing ends of the bioreactor;
a first fluid flow path having a first end fluidly associated with the first port of the bioreactor and a second end fluidly associated with the second port of the bioreactor;
a first pump configured to circulate fluid in the first fluid flow path;
a first fluid circulation path fluidly associated with the first fluid flow path and with the bioreactor;
a second pump configured to circulate fluid in the first fluid circulation path; and
a controller configured to:
control the first pump to load a first volume of fluid comprising a plurality of cells into the first fluid flow path;
control the second pump to load a second volume of fluid including media into a portion of the first fluid flow path to position the first volume of fluid in a first portion of the bioreactor;
control activation of the first pump and the second pump to move a third volume of fluid in the first direction and a fourth volume of fluid in the second direction and control feeding of the plurality of cells during a first time period and cause expanding the plurality of cells during the first time period;
after the first time period, control activation of the first pump or the second pump to circulate the plurality of cells at a first circulation rate through an intracapillary space of the bioreactor during a second time period to break up cells therein and reduce a size of a first cell cluster formed at least in part while expanding the plurality of cells for the first time period,
control activation of the first pump and the second pump to move fluid in a first direction and a second direction and control feeding of the plurality of cells during the second time period,
control activation of the first pump and the second pump to expand the plurality of cells during a third time period,
after the third time period, control activation of the first pump or the second pump to circulate the plurality of cells at a second circulation rate through the intracapillary space of the bioreactor during a fourth time period to break up cells therein and reduce a size of a second cell cluster formed at least in part during the third time period; and
harvesting expanded cells.

13. The cell expansion system of claim 12, wherein the first cell cluster has a reduced size of between about 25 microns and about 300 microns after circulating the plurality of cells at the first circulation rate.

14. The cell expansion system of claim 12, wherein the first direction of the third volume of fluid is opposite the second direction of the fourth volume of fluid.

15. The cell expansion system of claim 12, wherein the plurality of cells includes T cells.

16. The cell expansion system of claim 12, wherein the plurality of cells include peripheral blood mononuclear cells (PBMC).

17. The cell expansion system of claim 12, wherein the plurality of cells include from about $1 \times 10^6$ to about $500 \times 10^6$ PBMC.

18. The cell expansion system of claim 12, wherein the first volume of fluid includes human serum.

19. The cell expansion system of claim 12, wherein the expanded cells include between about $1 \times 10^9$ cells to about $100 \times 10^9$ cells.

20. The cell expansion system of claim 12, wherein the activator is located on beads.

\* \* \* \* \*